(12) United States Patent
Akioka et al.

(10) Patent No.: US 9,730,448 B2
(45) Date of Patent: *Aug. 15, 2017

(54) TETRAZOLINONE COMPOUND AND USE OF SAME

(71) Applicant: Sumitomo Chemical Company, Limited, Tokyo (JP)

(72) Inventors: Yuki Akioka, Takarazuka (JP); Sadayuki Arimori, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/914,183

(22) PCT Filed: Aug. 25, 2014

(86) PCT No.: PCT/JP2014/072845
§ 371 (c)(1),
(2) Date: Feb. 24, 2016

(87) PCT Pub. No.: WO2015/030217
PCT Pub. Date: Mar. 5, 2015

(65) Prior Publication Data
US 2016/0205935 A1 Jul. 21, 2016

(30) Foreign Application Priority Data

Aug. 29, 2013 (JP) .................... 2013-177630

(51) Int. Cl.
| | |
|---|---|
| *A01N 43/713* | (2006.01) |
| *C07D 257/04* | (2006.01) |
| *C07D 401/12* | (2006.01) |
| *C07D 403/12* | (2006.01) |
| *A01N 43/76* | (2006.01) |
| *A01N 43/78* | (2006.01) |
| *C07D 405/12* | (2006.01) |
| *C07D 409/12* | (2006.01) |
| *C07D 413/12* | (2006.01) |
| *C07D 417/12* | (2006.01) |
| *A01N 43/80* | (2006.01) |
| *A01N 43/82* | (2006.01) |

(52) U.S. Cl.
CPC ........... *A01N 43/713* (2013.01); *A01N 43/76* (2013.01); *A01N 43/78* (2013.01); *A01N 43/80* (2013.01); *A01N 43/82* (2013.01); *C07D 257/04* (2013.01); *C07D 403/12* (2013.01); *C07D 405/12* (2013.01); *C07D 409/12* (2013.01); *C07D 413/12* (2013.01); *C07D 417/12* (2013.01)

(58) Field of Classification Search
CPC .. A01N 43/713; C07D 257/04; C07D 401/12; C07D 403/12
See application file for complete search history.

(56) References Cited

U.S. PATENT DOCUMENTS

| | | |
|---|---|---|
| 5,798,316 A | 8/1998 | Theodoridis |
| 6,583,090 B1 | 6/2003 | Gewehr et al. |
| 2015/0031733 A1 | 1/2015 | Yoshimoto et al. |
| 2015/0051171 A1 | 2/2015 | Yoshimoto et al. |
| 2015/0299146 A1 | 10/2015 | Hasegawa et al. |
| 2015/0336908 A1 | 11/2015 | Shioda et al. |
| 2016/0081339 A1 | 3/2016 | Yoshimoto et al. |
| 2016/0081340 A1 | 3/2016 | Arimori et al. |
| 2016/0150787 A1 | 6/2016 | Azuma et al. |
| 2016/0157489 A1 | 6/2016 | Shioda et al. |
| 2016/0159755 A1 | 6/2016 | Shioda et al. |
| 2016/0174558 A1 | 6/2016 | Hou et al. |
| 2016/0235065 A1 | 8/2016 | Shioda et al. |

FOREIGN PATENT DOCUMENTS

| | | |
|---|---|---|
| JP | H08501774 A | 2/1996 |
| JP | H09208565 A | 8/1997 |

(Continued)

OTHER PUBLICATIONS

English translation of International Search Report issued Nov. 25, 2014 in International Application No. PCT/JP2014/072845.

(Continued)

*Primary Examiner* — Yong Chong
(74) *Attorney, Agent, or Firm* — Panitch Schwarze Belisario & Nadel LLP

(57) ABSTRACT

A tetrazolinone compound represented by formula (1):

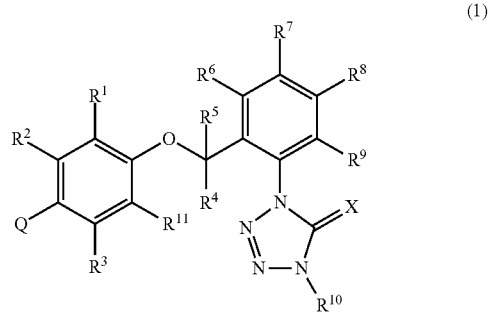

wherein $R^1$, $R^2$, $R^3$, $R^6$, $R^7$, $R^8$, $R^9$, $R^{10}$, and $R^{11}$ each independently represents a C1-C6 alkyl group optionally having one or more halogen atoms, etc.; $R^4$, and $R^5$ each independently represents a hydrogen atom, etc.; Q represents any one group selected from Group $P^2$ (provided that the group optionally has one or more atoms or groups selected from Group $P^1$); and X represents an oxygen atom or a sulfur atom, has excellent control activity against pests.

12 Claims, No Drawings

(56) References Cited

FOREIGN PATENT DOCUMENTS

| | | |
|---|---|---|
| JP | 2002506060 A | 2/2002 |
| WO | 9636229 A1 | 11/1996 |
| WO | 2013092224 A1 | 6/2013 |
| WO | 2013162072 A1 | 10/2013 |
| WO | 2013162077 A1 | 10/2013 |
| WO | 2014051161 A1 | 4/2014 |
| WO | 2014051165 A1 | 4/2014 |
| WO | 2014084223 A1 | 6/2014 |
| WO | 2014104268 A1 | 7/2014 |
| WO | 2014104382 A1 | 7/2014 |
| WO | 2014104384 A1 | 7/2014 |
| WO | 2014175465 A1 | 10/2014 |
| WO | 2014192953 A1 | 12/2014 |
| WO | 2015005499 A1 | 1/2015 |
| WO | 2015016335 A1 | 2/2015 |
| WO | 2015016372 A1 | 2/2015 |
| WO | 2015016373 A1 | 2/2015 |
| WO | 2015041360 A1 | 3/2015 |
| WO | 2015046480 A1 | 4/2015 |
| WO | 2015056806 A1 | 4/2015 |
| WO | 2015056811 A1 | 4/2015 |
| WO | 2015060461 A1 | 4/2015 |
| WO | 2015064727 A1 | 5/2015 |
| WO | 2015088038 A1 | 6/2015 |

OTHER PUBLICATIONS

English translation of Written Opinion issued Nov. 25, 2014 in International Application No. PCT/JP2014/072845.

Theodoridis et al., "Synthesis and Structure—Activity Relationships of 1-Aryl-4-substituted-1, 4-dihydro-5H-tetrazol-5-ones, a Novel Class of Pre- and Post-emergence Herbicides," Pesticide Science, vol. 30, pp. 259-274 (1990).

Office Action issued on Dec. 27, 2016 in CN Application No. 201480047082.3.

Extended European Search Report dated Mar. 24, 2017 in EP Application No. 14839897.7.

TETRAZOLINONE COMPOUND AND USE OF SAME

CROSS-REFERENCE TO RELATED APPLICATION

This application is a Section 371 of International Application No. PCT/JP2014/072845, filed Aug. 25, 2014, which was published in the Japanese language on Mar. 5, 2015, under International Publication No. WO 2015/030217A1, and the disclosure of which is incorporated herein by reference.

TECHNICAL FIELD

The present invention relates to a tetrazolinone compound and use of same.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by formula (A):

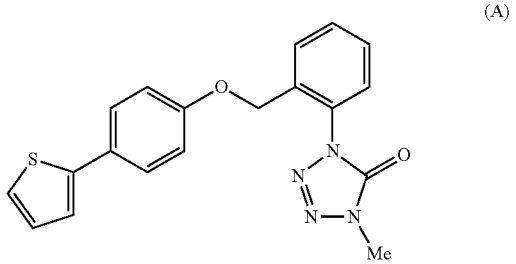 [SMILES: Cn1nnn(-c2ccccc2COc2ccc(-c3cccs3)cc2)c1=O]

(see WO 96/36229 A).

The present invention provides compounds having excellent control activity against pests.

DISCLOSURE OF THE INVENTION

The present inventors have intensively studied so as to find compounds having excellent control activity against pests, and found that a tetrazolinone compound represented by the following formula (1) has excellent control activity against pests, thus completing the present invention.

The present invention includes the followings [1] to [13].
[1] A tetrazolinone compound represented by formula (1):

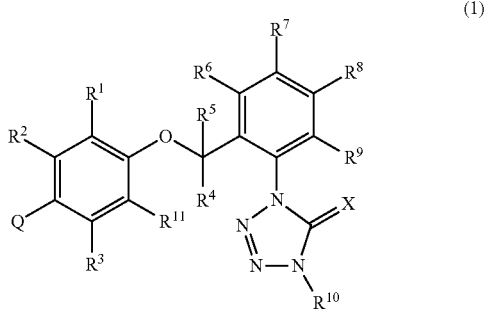

wherein $R^1$, $R^2$, $R^3$, and $R^{11}$ each independently represents a C1-C6 alkyl group optionally having one or more atoms or groups selected from Group $P^3$, a C3-C6 cycloalkyl group optionally having one or more atoms or groups selected from Group $P^3$, a halogen atom, a hydrogen atom, a C1-C6 alkoxy group optionally having one or more halogen atoms, a cyano group, a nitro group, an amino group, a hydroxy group, a sulfanyl group, a C2-C6 alkenyl group optionally having one or more halogen atoms, a C2-C6 alkynyl group optionally having one or more halogen atoms, a C1-C8 alkylamino group optionally having one or more halogen atoms, a C1-C6 alkylthio group optionally having one or more halogen atoms, a C1-C6 alkylsulfinyl group optionally having one or more halogen atoms, a C1-C6 alkylsulfonyl group optionally having one or more halogen atoms, a pentafluorosulfanyl group, a C3-C9 trialkylsilyl group, a C2-C6 alkylcarbonyl group, a C2-C6 alkoxycarbonyl group, or an aminocarbonyl group optionally having one or more C1-C6 alkyl groups;

$R^4$ and $R^5$ each independently represents a hydrogen atom, a halogen atom, or a C1-C3 alkyl group;

$R^6$ represents a C1-C6 alkyl group optionally having one or more halogen atoms, a C3-C6 cycloalkyl group optionally having one or more halogen atoms, a halogen atom, a C2-C6 alkenyl group optionally having one or more halogen atoms, a C1-C6 alkoxy group optionally having one or more halogen atoms, a C1-C6 alkylthio group optionally having one or more halogen atoms, a C2-C6 alkynyl group optionally having one or more halogen atoms, a nitro group, a cyano group, an aminocarbonyl group optionally having one or more C1-C6 alkyl groups, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group, a C2-C6 alkylcarbonylthio group, a C2-C6 alkoxycarbonyl group, a hydroxy group, a sulfanyl group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group optionally having one or more halogen atoms, a C1-C4 alkylsulfinyl group optionally having one or more halogen atoms, a C2-C5 alkoxyalkyl group, or a C2-C5 alkylthioalkyl group;

$R^7$, $R^8$, and $R^9$ each independently represents a hydrogen atom, a halogen atom, a C1-C3 alkyl group optionally having one or more halogen atoms, a C2-C3 alkenyl group optionally having one or more halogen atoms, or a C1-C3 alkoxy group optionally having one or more halogen atoms;

$R^{10}$ represents a C1-C3 alkyl group optionally having one or more halogen atoms, a C2-C3 alkenyl group optionally having one or more halogen atoms, a C2-C3 alkynyl group optionally having one or more halogen atoms, or a C3-C5 cycloalkyl group optionally having one or more halogen atoms;

Q represents any one group selected from Group $P^2$ (provided that the group optionally has one or more atoms or groups selected from Group $P^1$); and X represents an oxygen atom or a sulfur atom:

Group $P^1$: Group consisting of a C1-C6 alkyl group optionally having one or more halogen atoms, a halogen atom, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C6-C16 aryl group optionally having one or more halogen atoms, a C6-C16 aryloxy group optionally having one or more halogen atoms, a C6-C16 arylthio group optionally having one or more halogen atoms, a C7-C18 aralkyl group optionally having one or more halogen atoms, a C7-C18 arylalkoxy group optionally having one or more halogen atoms, a sulfanyl group, a pentafluorosulfanyl group, a C3-C12 trialkylsilyl group, a C5-C14 trialkylsilylethynyl group, a C1-C6 alkylsulfonyl group optionally having one or more halogen atoms, a C6-C16 arylsulfonyl group optionally having one or more halogen atoms, a C1-C6 alkylsulfinyl group optionally having one or more halogen atoms, a C6-C16 arylsulfinyl group optionally having one or more halogen atoms, an aminosulfonyl group optionally having a C1-C6 alkyl group and/or a C6-C12 aryl group, and an aminocarbonyl group optionally having one or more C1-C6 alkyl groups:

Group $P^2$: Group consisting of a thiazolyl group, a thiazolinyl group, an oxazolyl group, an oxazolinyl group, a triazolyl group, a tetrazolyl group, a furyl group, a thienyl group, a thiadiazolyl group, an oxadiazolyl group, an isoxazolyl group, an isothiazolyl group, a tetrahydrofuryl group, a butenolidyl group, a γ-butyrolactonyl group, a tetrahydrothienyl group, a pyrrolyl group, a pyrrolinyl group, a pyrrolidinyl group, a pyrrolidonyl group, an oxazolidinyl group, an oxazolidonyl group, a thiazolidinyl group, a thiazolidonyl group, an isoxazolinyl group, an isoxazolidinyl group, an isoxazolidonyl group, an isothiazolinyl group, an isothiazolidinyl group, an isothiazolidonyl group, a dioxolanyl group, a floxanil group, a tetrazolinyl group, a tetrazolidinyl group, a tetrazolinonyl group, a triazolinyl group, a triazolidinyl group, a triazolinonyl group, a urazolyl group, an imidazolyl group, an imidazolinyl group, an imidazolidinyl group, an imidazolidonyl group, a hydantoinyl group, a thiohydantoinyl group, a dithiohydantoinyl group, a pyrazolinyl group, a pyrazolidinyl group, a pyrazolidonyl group, a pyrazolonyl group, a succinimidyl group, a maleimidyl group, and a dioxazolyl group; and Group $P^3$: Group consisting of a halogen atom, a cyano group, a C3-C6 cycloalkyl group optionally having one or more halogen atoms, a C1-C4 alkoxy group optionally having one or more halogen atoms, and a C1-C4 alkylthio group optionally having one or more halogen atoms.

[2] The tetrazolinone compound according to [1], wherein $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms; $R^2$, $R^4$, $R^5$, $R^7$, $R^8$, $R^9$, and $R^{11}$ are hydrogen atoms; $R^3$ is a hydrogen atom, a halogen atom, or a C1-C3 alkyl group optionally having one or more halogen atoms; $R^6$ is a C1-C3 alkyl group optionally having one or more halogen atoms, a halogen atom, a C3-C5 cycloalkyl group optionally having one or more halogen atoms, a C1-C3 alkoxy group optionally having one or more halogen atoms, a C2-C4 alkenyl group optionally having one or more halogen atoms, or a C2-C4 alkynyl group optionally having one or more halogen atoms; $R^{10}$ is a C1-C3 alkyl group; and X is an oxygen atom.

[3] The tetrazolinone compound according to [1] or [2], wherein $R^1$ is a C1-C3 alkyl group optionally having one or more halogen atoms, a halogen atom, a C2-C3 alkenyl group optionally having one or more halogen atoms, a C3-C5 cycloalkyl group optionally having one or more halogen atoms, or a C1-C3 alkoxy group optionally having one or more halogen atoms; $R^3$ is a hydrogen atom or a methyl group; Q is any one group selected from Group $P^8$ (provided that the group optionally has one or more atoms or groups selected from Group $P^4$): Group $P^4$: Group consisting of a C1-C3 alkyl group optionally having one or more halogen atoms, a halogen atom, a cyano group, a nitro group, a C3-C6 cycloalkyl group optionally having one or more halogen atoms, a C2-C3 alkenyl group optionally having one or more halogen atoms, a C1-C4 alkoxy group optionally having one or more halogen atoms, and a C1-C4 alkylthio group optionally having one or more halogen atoms; and Group $P^8$: Group consisting of a thiazolyl group, an oxazolyl group, a thiazolinyl group, an oxazolinyl group, a furyl group, a thienyl group, a 1,3,4-thiadiazolyl group, a 1,3,4-oxadiazolyl group, a 1,2,3-triazolyl group, a tetrazolyl group, a dioxolanyl group, a tetrahydrofuryl group, a pyrazolonyl group, a pyrrolyl group, an imidazolyl group, and a 1,2,4-triazolyl group.

[4] The tetrazolinone compound according to [1] or [2], wherein $R^1$ is a C1-C3 alkyl group optionally having one or more halogen atoms;

$R^3$ is a hydrogen atom or a methyl group;

$R^6$ is a C1-C3 alkyl group optionally having one or more halogen atoms, a halogen atom, a C3-C5 cycloalkyl group optionally having one or more halogen atoms, or a C1-C3 alkoxy group optionally having one or more halogen atoms; and Q is any one group selected from Group $P^9$ (provided that the group optionally has one or more atoms or groups selected from Group $P^{11}$):

Group $P^9$: Group consisting of a thiazolyl group, an oxazolyl group, a thiazolinyl group, an oxazolinyl group, a furyl group, a thienyl group, a 1,3,4-oxadiazolyl group, a 1,2,3-triazolyl group, a dioxolanyl group, a tetrahydrofuryl group, a pyrrolyl group, an imidazolyl group, a 1,2,4-triazolyl group, a 1,2,4-thiadiazolyl group, an isothiazolyl group, a pyrrolidinyl group, and a pyrrolidonyl group; and Group P¹¹: Group consisting of a C1-C3 alkyl group optionally having one or more halogen atoms, a halogen atom, a cyano group, a C1-C4 alkoxy group optionally having one or more halogen atoms, a C1-C4 alkylthio group optionally having one or more halogen atoms, a C2-C6 alkylcarbonyl group optionally having one or more halogen atoms, and a C2-C6 alkylcarbonyloxy group.

[5] The tetrazolinone compound according to any one of claims 1, 2, or 4, wherein Q is any one group selected from Group P¹⁰ (provided that the group optionally has one or more atoms or groups selected from Group P¹¹):
Group P¹⁰: Group consisting of a thiazolyl group, an oxazolyl group, a thiazolinyl group, an oxazolinyl group, a furyl group, and a thienyl group.

[6] The tetrazolinone compound according to any one of [1], [2], [4] or [5], wherein Q is any one group selected from Group P¹⁰ (provided that the group optionally has one or more atoms or groups selected from Group P¹²):
Group P¹²: Group consisting of a halogen atom, a cyano group, and a C1-C3 alkyl group optionally having one or more halogen atoms.

[7] The tetrazolinone compound according to any one of [1], [2], or [4], wherein Q is a thiazolyl or thienyl group optionally having one or more atoms or groups selected from Group P¹¹.

[8] The tetrazolinone compound according to any one of [1], [2], [4], or [7], wherein Q is a thiazolyl or thienyl group optionally having one or more atoms or groups selected from Group P¹².

[9] The tetrazolinone compound according to any one of [1], [2], [4], or [7], wherein Q is a thiazolyl group optionally having one or more atoms or groups selected from Group P¹¹.

[10] The tetrazolinone compound according to any one of [1], [2], [4], [7], or [8], wherein Q is a thienyl group optionally having one or more atoms or groups selected from Group P¹².

[11] A pest control agent comprising the tetrazolinone compound according to any one of [1] to [10].

[12] A method for controlling pests, which comprises treating plants or soil with an effective amount of the tetrazolinone compound according to any one of [1] to [10].

[13] Use of the tetrazolinone compound according to any one of [1] to [10] for controlling pests.

According to the present invention, pests can be controlled.

MODE FOR CARRYING OUT THE INVENTION

A compound of the present invention is a tetrazolinone compound represented by formula (1):

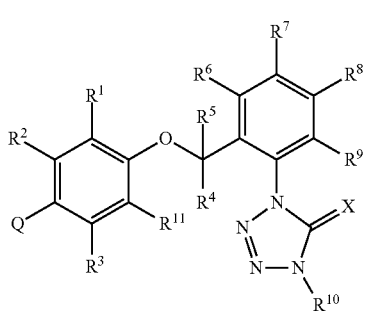

(1)

wherein $R^1$ to $R^{11}$, Q, and X are the same as defined above (hereinafter sometimes referred to as the present compound).

Hereinafter, a pest control agent containing the present compound is sometimes referred to as the present control agent.

Substituents as used herein will be mentioned in detail below.

Examples of the halogen atom include fluorine atom, a chlorine atom, a bromine atom, and an iodine atom.

Q represents any one group selected from the Group P².

Any of groups mentioned in Group P² is a 5-membered ring group.

Among groups mentioned in Group P², any of a triazolyl group, a tetrazolyl group, a pyrrolyl group, a pyrrolinyl group, a pyrrolidinyl group, a pyrrolidonyl group, a tetrazolinyl group, a tetrazolidinyl group, a tetrazolinonyl group, a triazolinyl group, a triazolidinyl group, a triazolinonyl group, a urazolyl group, an imidazolyl group, an imidazolinyl group, an imidazolidinyl group, an imidazolidonyl group, a hydantoinyl group, a thiohydantoinyl group, a dithiohydantoinyl group, a pyrazolinyl group, a pyrazolidinyl group, a pyrazolidonyl group, a pyrazolonyl group, a succinimidyl group, and a maleimidyl group is a 5-membered heterocyclic group, and is a group having only a nitrogen atom as a ring-constituent heteroatom.

Among groups mentioned in Group P², any of an oxazolyl group, an oxazolinyl group, a thiazolyl group, a thiazolinyl group, a furyl group, a thienyl group, a thiadiazolyl group, an oxadiazolyl group, an isoxazolyl group, an isothiazolyl group, a tetrahydrofuryl group, a butenolidyl group, a γ-butyrolactonyl group, a tetrahydrothienyl group, an oxazolidinyl group, an oxazolidonyl group, a thiazolidinyl group, a thiazolidonyl group, an isoxazolinyl group, an isoxazolidinyl group, an isoxazolidonyl group, an isothiazolinyl group, an isothiazolidinyl group, an isothiazolidonyl group, a dioxolanyl group, a floxanil group, and a dioxazolyl group is a 5-membered heterocyclic group, and is a group having one or more chalcogen atoms as a ring-constituent atom.

Among groups mentioned in Group P², any of a pyrrolidinyl group, a pyrrolidonyl group, a tetrazolidinyl group, a tetrazolinonyl group, a triazolidinyl group, a triazolinonyl group, a urazolyl group, an imidazolidinyl group, an imidazolidonyl group, a hydantoinyl group, a thiohydantoinyl group, a dithiohydantoinyl group, a pyrazolidinyl group, a pyrazolidonyl group, and a succinimidyl group is a saturated 5-membered heterocyclic group, and is a group having only a nitrogen atom as a ring-constituent heteroatom.

Among groups mentioned in Group P², any of a triazolyl group, a tetrazolyl group, a pyrrolyl group, a pyrrolinyl group, a tetrazolinyl group, a triazolinyl group, an imidazolyl group, an imidazolinyl group, a pyrazolinyl group, a pyrazolonyl group, and a maleimidyl group is an unsaturated 5-membered heterocyclic group, and is a group having only a nitrogen atom as a ring-constituent heteroatom.

Among groups mentioned in Group P², any of a tetrahydrofuryl group, a γ-butyrolactonyl group, a tetrahydrothienyl group, an oxazolidinyl group, an oxazolidonyl group, a thiazolidinyl group, a thiazolidonyl group, an isoxazolidinyl group, an isoxazolidonyl group, an isothiazolidinyl group, an isothiazolidonyl group, and a dioxolanyl group is a saturated 5-membered heterocyclic group, and is a group having one or more chalcogen atoms as a ring-constituent atom.

Among groups mentioned in Group P², any of an oxazolyl group, an oxazolinyl group, a thiazolyl group, a thiazolinyl group, a furyl group, a thienyl group, a thiadiazolyl group, an oxadiazolyl group, an isoxazolyl group, an isothiazolyl group, a butenolidyl group, an isoxazolinyl group, an isothiazolinyl group, and a floxanil group is an unsaturated 5-membered heterocyclic group, and is a group having one or more chalcogen atoms as a ring-constituent atom.

The C1-C6 alkyl group optionally having one or more atoms or groups selected from Group $P^3$ represents a C1-C6 alkyl group in which one or more hydrogen atoms bound to a carbon atom are optionally substituted with one or more atoms or groups selected from Group $P^3$ and, when the C1-C6 alkyl group has two or more atoms or groups selected from Group $P^3$, those atoms or groups may be the same or different to each other.

Examples of the C1-C6 alkyl group optionally having a group selected from Group $P^3$ include a trifluoromethyl group, a trichloromethyl group, a tribromomethyl group, a 2,2,2-trifluoroethyl group, a 2,2,2-trichloroethyl group, a difluoromethyl group, a 2,2-difluoroethyl group, a 1,1-difluoroethyl group, a pentafluoroethyl group, a 1,1,2,2-tetrafluoroethyl group, a 2,2,3,3,3-pentafluorobutyl group, a cyclopropylmethyl group, a 2-cyclopropylethyl group, a cyclobutylmethyl group, a 2-cyclobutylethyl group, a 3-cyclobutylpropyl group, a cyclopentylmethyl group, a (1-fluorocyclopropyl)methyl group, a 2-(1-fluorocyclopropyl)ethyl group, a 3-(1-fluorocyclopropyl)propyl group, a (2,2-difluorocyclopropyl)methyl group, a 2-(2,2-difluorocyclopropyl)ethyl group, a (1-chlorocyclopropyl)methyl group, a 2-(1-chlorocyclopropyl)ethyl group, a 2-(1-chlorocyclopropyl)propyl group, a (2,2-dichlorocyclopropyl)methyl group, a 2-(2,2-dichlorocyclopropyl)ethyl group, a (pentachlorocyclopropyl)methyl group, a (1-fluorocyclobutyl)methyl group, a (2,2-difluorocyclobutyl)methyl group, a (1-chlorocyclobutyl)methyl group, a (2,2-dichlorocyclobutyl)methyl group, a (1-fluorocyclopentyl)methyl group, a (2,2-difluorocyclopentyl)methyl group, a methoxymethyl group, an ethoxymethyl group, an isopropoxymethyl group, a tert-butoxymethyl group, a 2-methoxyethyl group, a 2-ethoxyethyl group, a 3-methoxypropyl group, a (trifluoromethoxy)methyl group, a 4-(trifluoromethoxy)butyl group, a (difluoromethoxy)methyl group, a methylthiomethyl group, a 2-methylthioethyl group, an ethylthiomethyl group, a 2-ethylthioethyl group, a 2-(tert-butylthio)ethyl group, a 3-(tert-butylthio)propyl group, a (trifluoromethylthio)methyl group, a 2-(trifluoromethylthio)ethyl group, a cyanomethyl group, a 2-cyanoethyl group, a 1-cyanoethyl group, and a 2-cyanopropyl group.

The C3-C6 cycloalkyl group optionally having one or more atoms or groups selected from Group $P^3$ represents a C3-C6 cycloalkyl group in which one or more hydrogen atoms bound to a carbon atom are optionally substituted with one or more atoms or groups selected from Group $P^3$ and, when the C3-C6 cycloalkyl group has two or more atoms or groups selected from Group $P^3$, those atoms or groups selected from Group $P^3$ may be the same or different to each other.

Examples of the C3-C6 cycloalkyl group optionally having a group selected from Group $P^3$ include a cyclopropyl group, a 1-fluorocyclopropyl group, a 2,2-dichloro-1-methylcyclopropyl group, a 2-chlorocyclopentyl group, a 3-chlorocyclopentyl group, a 1-cyclopropylcyclopropyl group, a 1-methoxycyclopropyl group, a 1-methoxycyclopentyl group, a 1-methoxycyclohexyl group, a 2-methoxycyclopropyl group, a 2-methoxycyclohexyl group, a 2-ethoxycyclopropyl group, a 1-ethoxycyclopropyl group, a 1-isopropoxycyclopropyl group, a 1-trifluoromethoxycyclopropyl group, a 2-trifluoromethoxycyclopropyl group, a 1-difluoromethoxycyclopropyl group, a 2-difluoromethoxycyclopropyl group, a 1-(2,2-difluoroethoxy)-cyclopropyl group, a 2-(2,2-difluoroethoxy)cyclopropyl group, a 1-methylthiocyclopropyl group, a 1-ethylthiocyclopropyl group, a 2-methylthiocyclopropyl group, a 2-ethylthiocyclopropyl group, a 1-trifluoromethylthiocyclopropyl group, a 2-trifluoromethylthiocyclopropyl group, a 1-cyanocyclopropyl group, and a 2-cyanocyclopropyl group.

The C1-C6 alkoxy group optionally having one or more halogen atoms represents a group in which one or more hydrogen atoms are optionally substituted with a halogen atom among straight or branched alkoxy groups having 1-6 carbon atoms and, when the C1-C6 alkoxy group has two or more halogen atoms, the halogen atoms may be the same or different to each other. Examples of the C1-C6 alkoxy group optionally having one or more halogen atoms include a methoxy group, an ethoxy group, a propoxy group, an isopropoxy group, a butoxy group, an isobutoxy group, a sec-butoxy group, a tert-butoxy group, a pentyloxy group, a 2-pentyloxy group, a 2-methylbutoxy group, a hexyloxy group, an isohexyloxy group, a trifluoromethoxy group, a chloromethoxy group, a dichloromethoxy group, a fluoromethoxy group, a difluoromethoxy group, a chlorofluoromethoxy group, a pentafluoroethoxy group, a 2,2,2-trifluoroethoxy group, a 2,2,2-tribromoethoxy group, a 2-fluoroethoxy group, a 2-chloroethoxy group, a 2,2-difluoroethoxy group, a 2-chloro-2-fluoroethoxy group, a heptafluoropropoxy group, a 3,3,3-trifluoropropoxy group, a 3,3,3-trichloropropoxy group, a 2-fluoropropoxy group, a 3-fluoropropoxy group, a 2,2-difluoropropoxy group, a 2-chloropropoxy group, a 3-chloropropoxy group, a 2,3-dichloropropoxy group, a 3-bromopropoxy group, a 3,3,3-trifluoropropoxy group, a nonafluorobutoxy group, a perfluoropentyloxy group, a perfluorohexyloxy group, and a perchlorohexyloxy group.

The C2-C6 alkenyl group optionally having one or more halogen atoms represents a group in which one or more hydrogen atoms are optionally substituted with one or more halogen atoms among straight or branched alkenyl groups having 2-6 carbon atoms and, when the C2-C6 alkenyl group has two or more halogen atoms, the halogen atoms may be the same or different to each other. Examples of the C2-C6 alkenyl group optionally having one or more halogen atoms include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 1,3-butadienyl group, a 1-pentenyl group, a 2-pentenyl group, a 1-methyl-2-butenyl group, a 4-pentenyl group, a 3-methyl-1-butenyl group, a 1,2-dimethyl-2-propenyl group, a 1,1-dimethyl-2-propenyl group, a 2-methyl-2-butenyl group, a 1,2-dimethyl-1-propenyl group, a 2-methyl-3-butenyl group, a 1-hexenyl group, a 5-hexenyl group, a 2-chlorovinyl group, a 2-bromovinyl group, a 2-iodovinyl group, a 3-chloro-2-propenyl group, a 3-bromo-3,3-difluoro-1-propenyl group, a 1-trifluoromethyl-2,2-difluorovinyl group, a 2-chloro-2-propenyl group, a 3,3-difluoro-2-methyl-2-propenyl group, a 3,3,3-trifluoro-2-methyl-1-propenyl group, a 3,3,3-trifluoro-1-methyl-1-propenyl group, and a 3,4,4-trifluoro-1,3-butadienyl group.

The C2-C6 alkynyl group optionally having one or more halogen atoms represents a group in which one or more hydrogen atoms are optionally substituted with one or more halogen atoms among straight or branched alkynyl groups having 2-6 carbon atoms and, when the C2-C6 alkynyl group has two or more halogen atoms, the halogen atoms may be the same or different to each other. Examples of the C2-C6 alkynyl group optionally having one or more halogen atoms include an ethynyl group, a propargyl group, a 1-butyn-3-yl group, a 3-methyl-1-butyn-3-yl group, a 2-butynyl group, a 3-butynyl group, a 2-pentynyl group, a 3-pentynyl group, a 4-pentynyl group, a 1-hexynyl group, a 5-hexynyl group, a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3-fluoro-2-propynyl group, a perfluoro-2-butynyl group, a perfluoro-2-pentynyl group, a perfluoro-3-pentynyl group, and a perfluoro-1-hexynyl group.

The C1-C8 alkylamino group optionally having one or more halogen atoms represents an amino group in which one or two hydrogen atoms on nitrogen are substituted with the same or different straight and/or branched alkyl groups, and represents an amino group in which the total number of carbon atoms of an alkyl group on nitrogen is within a range of 1 to 8, and one or more hydrogen atoms of an alkyl group are optionally substituted with a halogen atom. When the alkyl group on nitrogen has two or more halogen atoms, the halogen atoms may be the same or different to each other. Examples of the C1-C8 alkylamino group optionally having one or more halogen atoms include a methylamino group, an ethylamino group, a propylamino group, an isopropylamino group, an N,N-dimethylamino group, an N,N-diethylamino group, an N-ethyl-N-methylamino group, a butylamino group, a pentylamino group, a hexylamino group, an N,N-dibutylamino group, an N-sec-butyl-N-methylamino group, a 2,2,2-trifluoroethylamino group, an N,N-(2,2-difluoroethyl)-amino group, an N,N-(2,2-ditrichloroethyl)-amino group, and a pentafluoropropylamino group.

The C1-C6 alkylthio group optionally having one or more halogen atoms represents a straight or branched alkylthio group having 1-6 carbon atoms in which one or more hydrogen atoms are optionally substituted with a halogen atom and, when the C1-C6 alkylthio group has two or more halogen atoms, the halogen atoms may be the same or different to each other. Examples of the C1-C6 alkylthio group optionally having one or more halogen atoms include a methylthio group, an ethylthio group, an n-propylthio group, an isopropylthio group, an n-butylthio group, a tert-butylthio group, a neopentylthio group, an n-hexylthio group, a sec-hexylthio group, a fluoromethylthio group, a difluoromethylthio group, a trifluoromethylthio group, a tribromomethylthio group, a chlorofluoromethylthio group, a pentafluoroethylthio group, a 2,2,2-trichloroethylthio group, a 2,2,2-trifluoroethylthio group, a 2,2-difluoroethylthio group, a heptafluoropropylthio group, a heptabromopropylthio group, a heptaiodopropylthio group, a 3,3,3-trifluoropropylthio group, a 3,3,3-trichloropropylthio group, a 2,2-difluoropropylthio group, a nonafluorobutylthio group, a nonachlorobutylthio group, a perfluoropentylthio group, a perfluorohexylthio group, and a periodohexylthio group.

The C1-C6 alkylsulfinyl group optionally having one or more halogen atoms represents a straight or branched alkylsulfinyl group having 1-6 carbon atoms in which one or more hydrogen atoms are optionally substituted with a halogen atom and, when the C1-C6 alkylsulfinyl group has two or more halogen atoms, the halogen atoms may be the same or different to each other. Examples of the C1-C6 alkylsulfinyl group optionally having one or more halogen atoms include a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, a neopentylsulfinyl group, a 2-pentylsulfinyl group, a 2-methylbutylsulfinyl group, a hexylsulfinyl group, a 3-methylpentylsulfinyl group, a trifluoromethylsulfinyl group, a trichloromethylsulfinyl group, a pentafluoroethylsulfinyl group, a 2,2,2-trichloroethylsulfinyl group, a 2,2,2-trifluoroethylsulfinyl group, a heptachloropropylsulfinyl group, a heptabromopropylsulfinyl group, a 3,3,3-trichloropropylsulfinyl group, a nonafluorobutylsulfinyl group, a perfluoropentylsulfinyl group, a perfluorohexylsulfinyl group, and a perchlorohexylsulfinyl group.

The C1-C6 alkylsulfonyl group optionally having one or more halogen atoms represents a straight or branched alkylsulfonyl group having 1-6 carbon atoms in which one or more hydrogen atoms are optionally substituted with a halogen atom and, when the C1-C6 alkylsulfonyl group has two or more halogen atoms, the halogen atoms may be the same or different to each other. Examples of the C1-C6 alkylsulfonyl group optionally having one or more halogen atoms include a methylsulfonyl group, an ethylsulfonyl group, a propylsulfonyl group, an isopropylsulfonyl group, a butylsulfonyl group, a sec-butylsulfonyl group, a pentylsulfonyl group, an isoamylsulfonyl group, a 2-pentylsulfonyl group, a 3-pentylsulfonyl group, a hexylsulfonyl group, an isohexylsulfonyl group, a 3-methylpentylsulfonyl group, a 4-methylpentylsulfonyl group, a trifluoromethylsulfonyl group, a chloromethylsulfonyl group, a bromomethylsulfonyl group, an iodomethylsulfonyl group, a 2-fluoroethylsulfonyl group, a 2-chloroethylsulfonyl group, a 2-bromoethylsulfonyl group, a 2-iodoethylsulfonyl group, a 2,2,2-trifluoroethylsulfonyl group, a 2,2,2-tribromoethylsulfonyl group, a heptafluoropropylsulfonyl group, a heptachloropropylsulfonyl group, a 3,3,3-trifluoropropylsulfonyl group, a 3,3,3-trichloropropylsulfonyl group, a nonafluorobutylsulfonyl group, a perfluoropentylsulfonyl group, a perchloropentylsulfonyl group, and a perfluorohexylsulfonyl group.

The C3-C9 trialkylsilyl group represents an alkylsilyl group in which three hydrogen atoms on a silyl group are substituted with the same or different straight or branched alkyl groups, and represents a group in which the total number of carbon atoms of an alkyl group on a silyl group is within a range of 3 to 9. Examples of the C3-C9 trialkylsilyl group include a trimethylsilyl group, a tert-butyldimethylsilyl group, a triethylsilyl group, an isopropyldimethylsilyl group, and a triisopropylsilyl group.

The C2-C6 alkylcarbonyl group represents a group in which a straight or branched alkyl group having 1-5 carbon atoms and a carbonyl group are bound to each other, and examples thereof include a methylcarbonyl group, an ethylcarbonyl group, an n-propylcarbonyl group, an isopropylcarbonyl group, a pivaloyl group, an n-butylcarbonyl group, and an n-pentylcarbonyl group.

The C2-C6 alkoxycarbonyl group represents a group in which a straight or branched alkoxy group having 1-5 carbon atoms and a carbonyl group are bound to each other, and examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutoxycarbonyl group.

The aminocarbonyl group optionally having one or more C1-C6 alkyl groups represents an aminocarbonyl group in which one or two hydrogen atoms on nitrogen are optionally substituted with the same or different C1-C6 alkyl groups, and examples thereof include an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, a dipropylaminocarbonyl group, a diisopropylaminocarbonyl group, a pentylaminocarbonyl group, and a hexylaminocarbonyl group, and examples of the C1-C3 alkyl group include a methyl group, an ethyl group, a propyl group, and an isopropyl group.

The C1-C6 alkyl group optionally having one or more halogen atoms represents a straight or branched alkyl group having 1-6 carbon atoms, which optionally has one or more halogen atoms and, when the C1-C6 alkyl group has two or more halogen atoms, the halogen atoms may be the same or different to each other. Examples of the C1-C6 alkyl group optionally having one or more halogen atoms include a methyl group, an ethyl group, a propyl group, an isopropyl group, a butyl group, an isobutyl group, a sec-butyl group, a tert-butyl group, a pentyl group, a hexyl group, a fluoromethyl group, a chloromethyl group, a dichloromethyl group, a difluoromethyl group, a trifluoromethyl group, a trichloromethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2,2-difluoropropyl group, a 4-fluorobutyl group, and a 2,2-difluorohexyl group.

The C3-C6 cycloalkyl group optionally having one or more halogen atoms also includes a cycloalkyl group having an alkyl group, and represents a group in which one or more hydrogen atoms are optionally substituted with a halogen atom, and examples thereof include a cyclopropyl group, a cyclobutyl group, a cyclopentyl group, a cyclohexyl group, a 2-methylcyclopropyl group, a 2,2-dimethylcyclopropyl group, a 2,3-dimethylcyclopropyl group, a 2-fluorocyclopropyl group, a 2,2-difluorocyclopropyl group, a 2-chloro-2-fluorocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2-chlorocyclopentyl group, and a 3-chlorocyclopentyl group.

The C3-C6 cycloalkyloxy group optionally having one or more halogen atoms represents a group in which one or more hydrogen atoms of a cycloalkyloxy group having 3-6 carbon atoms are optionally substituted with a halogen atom, and examples thereof include a cyclopropoxy group, a cyclobutoxy group, a cyclopentyloxy group, a cyclohexyloxy group, a 2-fluorocyclopropoxy group, a 2,2-difluorocyclopropoxy group, a 2-chloro-2-fluorocyclopropoxy group, a 2,2-dichlorocyclopropoxy group, a 2,2-dibromocyclopropoxy group, a 2,2,3,3-tetrafluorocyclobutoxy group, a 2-chlorocyclohexyloxy group, a 4,4-difluorocyclohexyloxy group, and a 4-chlorocyclohexyloxy group.

The C3-C6 cycloalkylthio group optionally having one or more halogen atoms represents a group in which one or more hydrogen atoms of a cycloalkylthio group having 3-6 carbon atoms are optionally substituted with a halogen atom, and examples thereof include a cyclopropylthio group, a cyclobutylthio group, a cyclopentylthio group, a cyclohexylthio group, a 2-fluorocyclopropylthio group, a 2,2-difluorocyclopropylthio group, a 2-chloro-2-fluorocyclopropylthio group, a 2,2-dichlorocyclopropylthio group, a 2,2-dibromocyclopropylthio group, a 2,2,3,3-tetrafluorocyclobutylthio group, a 2-chlorocyclohexylthio group, a 4,4-difluorocyclohexylthio group, and a 4-chlorocyclohexylthio group.

The C3-C6 alkenyloxy group optionally having one or more halogen atoms represents a straight or branched alkenyloxy group having 3-6 carbon atoms, which optionally has one or more halogen atoms, and examples thereof include a 2-propenyloxy group, a 2-butenyloxy group, a 3-butenyloxy group, a 2-methyl-2-propenyloxy group, a 2-pentenyloxy group, a 3-pentenyloxy group, a 4-pentenyloxy group, a 1,2-dimethyl-2-propenyloxy group, a 1,1-dimethyl-2-propenyloxy group, a 3-methyl-2-butenyloxy group, a 2-methyl-3-butenyloxy group, a 3-methyl-3-butenyloxy group, a 1-vinyl-2-propenyloxy group, a 5-hexenyloxy group, a 3-chloro-2-propenyloxy group, a 3-bromo-2-propenyloxy group, a 2-chloro-2-propenyloxy group, a 3,3-difluoro-2-propenyloxy group, a 3,3-dichloro-2-propenyloxy group, a 3-fluoro-3-chloro-2-propenyloxy group, a 3-chloro-2-butenyloxy group, a 4,4,4-trifluoro-2-butenyloxy group, a 3-bromo-3-butenyloxy group, a 4,4-difluoro-3-methyl-3-butenyloxy group, and a 5,5-difluoro-4-pentenyloxy group.

The C3-C6 alkynyloxy group optionally having one or more halogen atoms represents a straight or branched alkynyloxy group having 3-6 carbon atoms, which optionally has one or more halogen atoms, and examples thereof include a propargyloxy group, a 1-butyn-3-yloxy group, a 3-methyl-1-butyn-3-yloxy group, a 2-butynyloxy group, a 3-butynyloxy group, a 2-pentynyloxy group, a 3-pentynyloxy group, a 4-pentynyloxy group, a 5-hexynyloxy group, a 3-chloro-2-propynyloxy group, a 3-bromo-2-propynyloxy group, a 3-iodo-2-propynyloxy group, a 5-chloro-4-pentynyloxy group, a 3-fluoro-2-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group.

The C3-C6 alkenylthio group optionally having one or more halogen atoms represents a straight or branched alkenylthio group having 3-6 carbon atoms, which optionally has one or more halogen atoms, and examples thereof include a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, a 5-hexenylthio group, a 3-chloro-2-propenylthio group, a 3-bromo-2-propenylthio group, a 2-chloro-2-propenylthio group, a 3,3-difluoro-2-propenylthio group, a 3,3-dichloro-2-propenylthio group, a 3,3-dibromo-2-propenylthio group, a 1-bromomethyl-2-propenylthio group, a 3-chloro-2-butenylthio group, a 4,4,4-trifluoro-2-butenylthio group, a 3-bromo-3-butenylthio group, a 3-bromo-2-methyl-2-propenylthio group, a 3,3-difluoro-2-methyl-2-propenylthio group, a 4,4-difluoro-3-methyl-3-butenylthio group, a 5,5-difluoro-4-pentenylthio group, a 4,4,4-trifluoro-3-methyl-2-butenylthio group, and a 3,5,5-trifluoro-2,4-pentadienylthio group.

The C3-C6 alkynylthio group optionally having one or more halogen atoms represents a straight or branched alkynylthio group having 3-6 carbon atoms, which optionally has one or more halogen atoms, and examples thereof include a propargylthio group, a 1-butyn-3-ylthio group, a 3-methyl-1-butyn-3-ylthio group, a 2-butynylthio group, a 3-butynylthio group, a 2-pentynylthio group, a 3-pentynylthio group, a 4-pentynylthio group, a 5-hexynylthio group, a 3-chloro-2-propynylthio group, a 3-bromo-2-propynylthio group, a 3-iodo-2-propynylthio group, a 5-chloro-4-pentynylthio group, a 3-fluoro-2-propynylthio group, a perfluoro- 2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group.

The C2-C6 alkylcarbonyl group optionally having one or more halogen atoms represents a straight or branched alkylcarbonyl group having 2-6 carbon atoms, which optionally has one or more halogen atoms, and examples thereof include an acetyl group, a propionyl group, a butanoyl group, a pentanoyl group, or a hexanoyl group, a trichloroacetyl group, a fluoroacetyl group, a difluoroacetyl group, a trifluoroacetyl group, a pentafluoropropionyl group, a 3,3,3-trichloropropionyl group, a 3,3,3-trifluoropropionyl group, a 3-bromopropionyl group, a 3-iodopropionyl group, a 4,4,4-trifluorobutanoyl group, a 4,4,4-trichlorobutanoyl group, a nonafluoropentanoyl group, and a perfluorohexanoyl group.

The C2-C6 alkylcarbonyloxy group represents a group in which a straight or branched alkyl group having 1-5 carbon atoms and a carbonyloxy group are bound to each other, and examples thereof include an acetyloxy group, a propionyloxy group, and a butanoyloxy group.

The C2-C6 alkylcarbonylthio group represents a group in which a straight or branched alkyl group having 1-5 carbon atoms and a carbonylthio group are bound to each other, and examples thereof include an acetylthio group, a propionylthio group, and a butanoylthio group.

The amino group optionally having a C1-C6 alkyl group represents an amino group in which one or two hydrogen atoms on nitrogen are substituted with the same or different C1-C6 alkyl groups, and examples thereof include an amino group, an N-methylamino group, an N-ethylamino group, an N-propylamino group, an N-isopropylamino group, an N-butylamino group, an N,N-dimethylamino group, an N,N-diethylamino group, an N,N-dipropylamino group, an N-ethyl-N-methylamino group, and an N-propyl-N-methylamino group.

The C5-C14 trialkylsilylethynyl group represents an ethynyl group in which three hydrogen atoms on a silyl group are bound to a trialkylsilyl group substituted with the same or different alkyl groups, and the alkyl group is either straight or branched, and examples thereof include a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tri(n-butyl)silylethynyl group.

The C1-C4 alkylsulfonyl group optionally having one or more halogen atoms represents a straight or branched alkylsulfonyl group having 1-4 carbon atoms in which one or more hydrogen atoms are optionally substituted with one or more halogen atoms, and examples thereof include a methylsulfonyl group, an ethylsulfonyl group, a propylsulfonyl group, an isopropylsulfonyl group, a butylsulfonyl group, an isobutylsulfonyl group, a sec-butylsulfonyl group, a trifluoromethylsulfonyl group, a chloromethylsulfonyl group, a bromomethylsulfonyl group, an iodomethylsulfonyl group, a 2-chloroethylsulfonyl group, a 2,2-difluoroethylsulfonyl group, a 2-bromoethylsulfonyl group, a 2-iodoethylsulfonyl group, a heptafluoropropylsulfonyl group, a 3,3,3-trifluoropropylsulfonyl group, a 3,3,3-trichloropropylsulfonyl group, a 3,3,3-tribromopropylsulfonyl group, a 3-iodopropylsulfonyl group, and a 4-fluorobutylsulfonyl group.

The C1-C4 alkylsulfinyl group optionally having one or more halogen atoms represents a straight or branched alkylsulfinyl group having 1-6 carbon atoms in which one or more hydrogen atoms are optionally substituted with a halogen atom, and examples thereof include a methylsulfinyl group, an ethylsulfinyl group, a propylsulfinyl group, an isopropylsulfinyl group, a butylsulfinyl group, an isobutylsulfinyl group, or a sec-butylsulfinyl group, a trifluoromethylsulfinyl group, a chloromethylsulfinyl group, a bromomethylsulfinyl group, an iodomethylsulfinyl group, a pentafluoroethylsulfinyl group, a pentachloroethylsulfinyl group, a pentabromoethylsulfinyl group, a pentaiodoethylsulfinyl group, a 2-chloroethylsulfinyl group, a 2,2,2-trifluoroethylsulfinyl group, a 2-bromoethylsulfinyl group, a heptafluoropropylsulfinyl group, a 3,3,3-trifluoropropylsulfinyl group, a 3-chloropropylsulfinyl group, a 3-bromopropylsulfinyl group, a 3-iodopropylsulfinyl group, and a nonafluorobutylsulfinyl group.

The C2-C5 alkoxyalkyl group means that it has 2 to 5 carbon atom as the total number of carbon atoms of the alkoxy moiety and the alkyl moiety, and may be either straight or branched, and examples thereof include a methoxymethyl group, an ethoxymethyl group, a propoxymethyl group, an isopropoxymethyl group, a butoxymethyl group, an isobutoxymethyl group, a sec-butoxymethyl group, a 1-methoxyethyl group, a 2-methoxyethyl group, a 2-propoxyethyl group, a 2-isopropoxyethyl group, a 3-methoxypropyl group, a 3-ethoxypropyl group, a 3-methoxybutyl group, and a 4-methoxybutyl group.

The C2-C5 alkylthioalkyl group means that it has 2 to 5 carbon atoms as the total number of carbon atoms of an alkylthioalkyl group, and may be either straight or branched, and examples thereof include a methylthiomethyl group, an ethylthiomethyl group, a propylthiomethyl group, an isopropylthiomethyl group, a butylthiomethyl group, an isobutylthiomethyl group, a sec-butylthiomethyl group, a 1-methylthioethyl group, a 2-methylthioethyl group, a 2-propylthioethyl group, a 2-isopropylthioethyl group, a 3-methylthiopropyl group, a 3-ethylthiopropyl group, a 3-methylthiobutyl group, and a 4-methylthiobutyl group.

Examples of the C3-C4 cycloalkyl group include a cyclopropyl group and a cyclobutyl group.

The C1-C3 alkyl group optionally having one or more halogen atoms represents a straight or branched alkyl group having 1-3 carbon atoms, which optionally has one or more halogen atoms, and examples thereof include a methyl group, an ethyl group, a propyl group, an isopropyl group, a fluoromethyl group, a chloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, and a 3,3,3-trifluoropropyl group.

The C2-C3 alkenyl group optionally having one or more halogen atoms represents a straight or branched alkenyl group having 2-3 carbon atoms, which optionally has one or more halogen atoms, and examples thereof include a vinyl group, a 1-propenyl group, a 2-propenyl group, a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, and a 2,3,3-trichloro-2-propenyl group.

The C1-C3 alkoxy group optionally having one or more halogen atoms represents a straight or branched alkyl group having 1-3 carbon atoms, which optionally has one or more halogen atoms, and examples thereof include a methoxy group, an ethoxy group, a propoxy group, an isopropoxy group, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, and a 3,3,3-trifluoropropoxy group.

The C2-C3 alkynyl group optionally having one or more halogen atoms represents an alkynyl group having 2-3 carbon atoms, which optionally has one or more halogen atoms, and examples thereof include an ethynyl group, a propargyl group, a fluoroethynyl group, a 3-chloro-2-propynyl group, a 3-bromo-2-propynyl group, a 3-iodo-2-propynyl group, and a 3-chloro-1-propynyl group.

The C3-C5 cycloalkyl group optionally having one or more halogen atoms also includes a cycloalkyl group having an alkyl group, and represents a group in which one or more hydrogen atoms are optionally substituted with a halogen atom, and examples thereof include a cyclopropyl group, a cyclobutyl group, a cyclopentyl group, a 2-methylcyclopropyl group, a 2,2-dimethylcyclopropyl group, a 2,3-dimethylcyclopropyl group, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2-chlorocyclopentyl group, and a 3-chlorocyclopentyl group.

The C6-C16 aryl group optionally having one or more halogen atoms represents an aryl group having 6-16 carbon atoms in which one or more hydrogen atoms are optionally substituted with a halogen atom and, when the C6-C16 aryl group has two or more halogen atoms, the halogen atoms may be the same or different to each other. Examples of the C6-C16 aryl group optionally having one or more halogen atoms include a phenyl group, a 1-naphthyl group, a 2-naphthyl group, a 1-acenaphthyl group, a 1-phenanthryl group, a 9-anthryl group, a 1-pyrenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a pentafluorophenyl group, a 2-bromo-3-fluorophenyl group, a 2-chloro-4-fluorophenyl group, a 2-fluoro-1-naphthyl group, a 4-chloro-2-naphthyl group, a 3-fluoro-1-acenaphthyl group, a 9-fluoro-1-phenanthryl group, a 10-fluoro-9-anthryl group, and a 6-fluoro-1-pyrenyl group.

The C6-C16 aryloxy group optionally having one or more halogen atoms represents a group in which one or more hydrogen atoms of an aryloxy group having 6-16 carbon atoms are optionally substituted with a halogen atom and, when the C6-C16 aryloxy group has two or more halogen atoms, the halogen atoms may be the same or different to each other. Examples of the C6-C16 aryloxy group optionally having one or more halogen atoms include a phenyloxy group, a 1-naphthyloxy group, a 2-naphthyloxy group, a 1-acenaphthyloxy group, a 1-phenanthryloxy group, a 9-anthryloxy group, a 1-pyrenyloxy group, a 2-fluorophenyloxy group, a 3-fluorophenyloxy group, a 4-fluorophenyloxy group, a 2-chlorophenyloxy group, a 3-chlorophenyloxy group, a 4-chlorophenyloxy group, a 2-bromophenyloxy group, a 3-bromophenyloxy group, a 4-bromophenyloxy group, a 2-iodophenyloxy group, a 3-iodophenyloxy group, a 4-iodophenyloxy group, a 2,4-difluorophenyloxy group, a 2,5-dichlorophenyloxy group, a 2,4,6-trifluorophenyloxy group, a 2,3,4-trichlorophenyloxy group, a pentafluorophenyloxy group, a pentachlorophenyloxy group, a 2-bromo-4-fluorophenyloxy group, a 2-chloro-3-fluorophenyloxy group, a 2-fluoro-1-naphthyloxy group, a 3-chloro-1-naphthyloxy group, a 3-fluoro-1-acenaphthyloxy group, a 9-fluoro-1-phenanthryloxy group, a 10-fluoro-9-anthryloxy group, and a 6-fluoro-1-pyrenyloxy group.

The C6-C16 arylthio group optionally having one or more halogen atoms represents a group in which one or more hydrogen atoms of an arylthio group having 6-16 carbon atoms are optionally substituted with a halogen atom and, when the C6-C16 arylthio group has two or more halogen atoms, the halogen atoms may be the same or different to each other. Examples of the C6-C16 arylthio group optionally having one or more halogen atoms include a phenylthio group, a 1-naphthylthio group, a 2-naphthylthio group, a 1-acenaphthylthio group, a 1-phenanthrylthio group, a 9-anthrylthio group, a 1-pyrenylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, a 2-iodophenylthio group, a 3-iodophenylthio group, a 4-iodophenylthio group, a 2,4-difluorophenylthio group, a 2,5-dichlorophenylthio group, a 2,3,4-trifluorophenylthio group, a pentachlorophenylthio group, a 2-bromo-3-fluorophenylthio group, a 2-chloro-4-fluorophenylthio group, a 3-chloro-4-fluorophenylthio group, a 3-fluoro-1-naphthylthio group, a 4-chloro-1-naphthylthio group, a 1-fluoro-2-naphthylthio group, a 1-chloro-2-naphthylthio group, a heptafluoro-2-naphthylthio group, a 3-fluoro-1-acenaphthylthio group, a 9-fluoro-1-phenanthrylthio group, a 10-fluoro-9-anthrylthio group, and a 6-fluoro-1-pyrenylthio group.

The C7-C18 aralkyl group optionally having one or more halogen atoms represents a group in which one or more hydrogen atoms of a C7-C18 aralkyl group are optionally substituted with a halogen atom and, when the C7-C18 aralkyl group has two or more halogen atoms, the halogen atoms may be the same or different to each other. Examples of the C7-C18 aralkyl group optionally having one or more halogen atoms include a benzyl group, a phenethyl group, a 3-phenylpropyl group, a 4-phenylbutyl group, a 9-phenylnonyl group, a 12-phenyldodecyl group, a 1-naphthylmethyl group, a 2-(1-naphthyl)ethyl group, a 3-(1-naphthyl)propyl group, a 4-(1-naphthyl)butyl group, a 8-(1-naphthyl)octyl group, a 2-naphthylmethyl group, a 2-(2-naphthyl)ethyl group, a 3-(2-naphthyl)propyl group, a 8-(2-naphthyl)octyl group, a 1-anthrylmethyl group, a 2-(1-anthryl)ethyl group, a 3-(1-anthryl)propyl group, a 2-anthrylmethyl group, a 2-(2-anthryl)ethyl group, a 4-(2-anthryl)butyl group, a 9-anthrylmethyl group, a 2-(9-anthryl)ethyl group, a 2-fluorobenzyl group, a 4-fluorobenzyl group, a 2-chlorobenzyl group, a 3-chlorobenzyl group, a 2-bromobenzyl group, a 3-bromobenzyl group, a 4-bromobenzyl group, a 2-iodobenzyl group, a 3-iodobenzyl group, a 2,4-difluorobenzyl group, a 2,5-dichlorobenzyl group, a 2,4,6-trifluorobenzyl group, a 2,3,4-trichlorobenzyl group, a pentafluorobenzyl group, a 2-bromo-3-fluorobenzyl group, a 2-chloro-4-fluorobenzyl group, a 3-(4-iodophenyl)propyl group, a 4-(4-fluorophenyl)butyl group, a 5-(4-chlorophenyl)pentyl group, a 6-(4-bromophenyl)hexyl group, a 12-(4-fluorophenyl)dodecyl group, a (6-fluoro-1-naphthyl)methyl group, a (4-chloro-2-naphthyl)methyl group, a 2-(5-chloro-1-naphthyl)ethyl group, a 3-(6-bromo-2-naphthyl)propyl group, a 6-(6-chloro-2-naphthyl)octyl group, a (9-fluoro-1-phenanthryl)methyl group, and a difluoro(phenyl)methyl group.

The C7-C18 arylalkoxy group optionally having one or more halogen atoms represents a group in which the total number of carbon atoms of the aryl moiety and the alkoxy moiety is within a range of 7 to 18, and represents a group in which one or more hydrogen atoms of the aryl moiety are optionally substituted with a halogen atom and, when the C7-C18 arylalkoxy group has two or more halogen atoms, the halogen atoms may be the same or different to each other. Examples of the C7-C18 arylalkoxy group optionally having one or more halogen atoms include a benzyloxy group, a phenethyloxy group, a 3-phenylpropoxy group, a 4-phenylbutoxy group, a 5-phenylpentyloxy group, a 6-phenylhexyloxy group, a 7-phenylheptyloxy group, a 8-phenyloctyloxy group, a 9-phenylnonyloxy group, a 10-phenyldecyloxy group, a 11-phenylundecyloxy group, a 12-phenyldodecyloxy group, a naphthylmethyloxy group, a naphthylethyloxy group, a naphthylpropoxy group, a naphthylbutoxy group, a naphthylpentyloxy group, a naphthylhexyloxy group, a naphthylheptyloxy group, a naphthyloctyloxy group, an anthrylmethyloxy group, an anthrylethyloxy group, an anthrylpropoxy group, an anthrylbutoxy group, a 4-fluorobenzyloxy group, a 2-chlorobenzyloxy group, a 3-bromobenzyloxy group, a 4-iodobenzyloxy group, a 2,4-difluorobenzyloxy group, a 2,5-dichlorobenzyloxy group, a 3,4,5-trifluorobenzyloxy group, a 2,3,4-trichlorobenzyloxy group, a pentafluorobenzyloxy group, a 4-bromo-2-fluorobenzyloxy group, a 2-chloro-3-fluorobenzyloxy group, a 6-chloro-2-fluorobenzyloxy group, a 2-(4-fluorophenyl)ethyloxy group, a 2-(3-chlorophenyl)ethyloxy group, a 2-(2-bromophenyl)ethyloxy group, a 3-(4-iodophenyl)propoxy group, a 3-(3-fluorophenyl)propoxy group, a 3-(2-chlorophenyl)propoxy group, a 4-(4-bromophenyl)butoxy group, a 5-(4-fluorophenyl)pentyloxy group, a 6-(4-chlorophenyl)hexyloxy group, a 7-(4-fluorophenyl)heptyloxy group, a 8-(4-chlorophenyl)octyloxy group, a 9-(4-bromophenyl)nonyloxy group, a 10-(4-fluorophenyl)decyloxy group, a 11-(4-chlorophenyl)undecyloxy group, a 12-(4-bromophenyl)dodecyloxy group, a 4-fluoro-1-naphthylmethyloxy group, a 1-chloro-2-naphthylmethyloxy group, a 2-(5-fluoro-1-naphthyl)ethyloxy group, a 3-(6-chloro-2-naphthyl)propoxy group, a 4-(5-bromo-1-naphthyl)butoxy group, a 5-(6-fluoro-2-naphthyl)pentyloxy group, a 6-(6-bromo-2-naphthyl)octyloxy group, a 3-fluoro-1-acenaphthylmethyloxy group, a 9-fluoro-1-phenanthrylmethyloxy group, a 10-fluoro-9-anthrylmethyloxy group, a 6-fluoro-1-pyrenylmethyloxy group, and a 1,1-difluoro-1-phenylmethyloxy group.

The C6-C16 arylsulfonyl group optionally having one or more halogen atoms represents an arylsulfonyl group having 6-16 carbon atoms, which optionally has one or more halogen atoms, and examples thereof include a phenylsulfonyl group, a 1-naphthylsulfonyl group, a 2-naphthylsulfonyl group, a 1-acenaphthylsulfonyl group, a 1-phenanthrylsulfonyl group, a 9-anthrylsulfonyl group, a 1-pyrenylsulfonyl group, a 2-fluorophenylsulfonyl group, a 3-fluorophenylsulfonyl group, a 4-fluorophenylsulfonyl group, a 2-chlorophenylsulfonyl group, a 3-chlorophenylsulfonyl group, a 4-chlorophenylsulfonyl group, a 2-bromophenylsulfonyl group, a 3-bromophenylsulfonyl group, a 4-bromophenylsulfonyl group, a 4-iodophenylsulfonyl group, a 2,4-difluorophenylsulfonyl group, a 2,4-dichlorophenylsulfonyl group, a 2,6-dichlorophenylsulfonyl group, a 2,4,6-trifluorophenylsulfonyl group, a 3,4,5-trifluorophenylsulfonyl group, a 2,4,6-trichlorophenylsulfonyl group, a 3,4,5-trichlorophenylsulfonyl group, a pentafluorophenylsulfonyl group, a 3-bromo-4-fluorophenylsulfonyl group, a 4-bromo-3-fluorophenylsulfonyl group, a 4-bromo-2-fluorophenylsulfonyl group, a 2-bromo-6-fluorophenylsulfonyl group, a 2-chloro-4-fluorophenylsulfonyl group, a 2-chloro-6-fluorophenylsulfonyl group, a 2-fluoro-1-naphthylsulfonyl group, a 3-chloro-1-naphthylsulfonyl group, a 4-bromo-1-naphthylsulfonyl group, a 5-fluoro-2-naphthylsulfonyl group, a 1-chloro-2-naphthylsulfonyl group, a 3-bromo-2-naphthylsulfonyl group, a 3-fluoro-1-acenaphthylsulfonyl group, a 9-fluoro-1-phenanthrylsulfonyl group, a 10-fluoro-9-anthrylsulfonyl group, and a 6-fluoro-1-pyrenylsulfonyl group.

The C6-C16 arylsulfinyl group optionally having one or more halogen atoms represents an arylsulfinyl group having 6-16 carbon atoms, which optionally has one or more halogen atoms, and examples thereof include a phenylsulfinyl group, a 1-naphthylsulfinyl group, a 2-naphthylsulfinyl group, a 1-acenaphthylsulfinyl group, a 1-phenanthrylsulfinyl group, a 9-anthrylsulfinyl group, a 1-pyrenylsulfinyl group, a 2-fluorophenylsulfinyl group, a 3-fluorophenylsulfinyl group, a 4-fluorophenylsulfinyl group, a 2-chlorophenylsulfinyl group, a 3-chlorophenylsulfinyl group, a 4-chlorophenylsulfinyl group, a 2-bromophenylsulfinyl group, a 3-bromophenylsulfinyl group, a 4-bromophenylsulfinyl group, a 2-iodophenylsulfinyl group, a 3-iodophenylsulfinyl group, a 4-iodophenylsulfinyl group, a 2,4-difluorophenylsulfinyl group, a 2,5-difluorophenylsulfinyl group, a 2,6-difluorophenylsulfinyl group, a 3,5-difluorophenylsulfinyl group, a 2,4-dichlorophenylsulfinyl group, a 3,4,5-trifluorophenylsulfinyl group, a 2-bromo-5-fluorophenylsulfinyl group, a 2-chloro-4-fluorophenylsulfinyl group, a 4-chloro-2-fluorophenylsulfinyl group, a 2-fluoro-1-naphthylsulfinyl group, a 3-fluoro-1-naphthylsulfinyl group, a 4-fluoro-1-naphthylsulfinyl group, a 5-fluoro-1-naphthylsulfinyl group, a 6-fluoro-1-naphthylsulfinyl group, a 1-fluoro-2-naphthylsulfinyl group, a 3-fluoro-1-acenaphthylsulfinyl group, a 9-fluoro-1-phenanthrylsulfinyl group, a 10-fluoro-9-anthrylsulfinyl group, and a 6-fluoro-1-pyrenylsulfinyl group.

The aminosulfonyl group optionally having a C1-C6 alkyl group and/or a C6-C12 aryl group represents an aminosulfonyl group in which one or two hydrogen atoms on nitrogen are optionally substituted with the same or different C1-C6 alkyl groups and/or C6-C12 aryl groups, and examples thereof include an aminosulfonyl group, an N-methylaminosulfonyl group, an N-ethylaminosulfonyl group, an N-propylaminosulfonyl group, an N-isopropylaminosulfonyl group, an N-butylaminosulfonyl group, an N-pentylaminosulfonyl group, an N-hexylaminosulfonyl group, an N,N-dimethylaminosulfonyl group, an N,N-diethylaminosulfonyl group, an N,N-dipropylaminosulfonyl group, an N,N-diisopropylaminosulfonyl group, an N-ethyl-N-methylaminosulfonyl group, an N-propyl-N-methylaminosulfonyl group, an N-butyl-N-methylaminosulfonyl group, an N-pentyl-N-methylaminosulfonyl group, an N-phenylaminosulfonyl group, an N,N-diphenylaminosulfonyl group, an N-methyl-N-phenylaminosulfonyl group, an N-ethyl-N-phenylaminosulfonyl group, an N-propyl-N-phenylaminosulfonyl group, an N-butyl-N-phenylaminosulfonyl group, an N-pentyl-N-phenylaminosulfonyl group, an N-hexyl-N-phenylaminosulfonyl group, an N-(1-naphthyl)aminosulfonyl group, an N-(1-naphthyl) N-methylaminosulfonyl group, an N-(2-naphthyl)aminosulfonyl group, and an N-(2-naphthyl) N-methylaminosulfonyl group.

The "any one group selected from Group $P^2$, provided that the group optionally has one or more atoms or groups selected from Group $P^1$" means that a hydrogen atom or atoms possessed by any one group selected from Group $P^2$ are optionally substituted with one or more atoms or groups selected from Group P and, when the number of atoms or groups selected from Group $P^1$ is 2 or more, the atoms or groups may be the same or different to each other, and examples thereof include a furan-2-yl group, a furan-3-yl group, a thiophen-2-yl group, a thiophen-3-yl group, a 3-methylthiophen-2-yl group, a 5-methylthiophen-2-yl group, a 5-chlorothiophen-2-yl group, a 5-cyanothiophen-2-yl group, a 1-methylpyrrol-2-yl group, an oxazol-2-yl group, a 5-methylthiazol-2-yl group, a 2-methylthiazol-4-yl group, a 4,5-dimethylthiazol-2-yl group, a 4-methylthiazol-5-yl group, a thiazol-2-yl group, an imidazol-1-yl group, a 1,4,5-trimethylimidazol-2-yl group, a 5-methyl-1,2,4-oxadiazol-2-yl group, a 3-bromo-1,2,4-thiadiazol-2-yl group, a 1,2,3-triazol-2-yl group, a 1,2,3-triazol-3-yl group, a 1,2,4-triazol-2-yl group, a tetrazol-2-yl group, a 2-oxazolin-2-yl group, a 4,4-dimethyl-2-oxazolin-2-yl group, a 2-thiazolin-2-yl group, and a 2-methyldioxolan-2-yl group.

The thiazol-2-yl group optionally having one or more atoms or groups selected from Group $P^4$ (Group $P^4$: Group consisting of a C1-C3 alkyl group optionally having one or more halogen atoms, a halogen atom, a cyano group, a nitro group, a C3-C6 cycloalkyl group optionally having one or more halogen atoms, a C2-C3 alkenyl group optionally having one or more halogen atoms, a C1-C4 alkoxy group optionally having one or more halogen atoms, and a C1-C4 alkylthio group optionally having one or more halogen atoms) represents a thiazol-2-yl group in which hydrogen atoms of a thiazol-2-yl group are optionally substituted with one or more atoms or groups selected from Group $P^4$ and, when the number of atoms or groups selected from Group $P^4$ is 2 or more, those atoms or groups may be the same or different to each other. Examples of the thiazol-2-yl group optionally having one or more atoms or groups selected from Group $P^4$ include a thiazol-2-yl group, a 4-methylthiazol-2-yl group, a 5-methylthiazol-2-yl group, a 4-ethylthiazol-2-yl group, a 5-ethylthiazol-2-yl group, a 4,5-dimethylthiazol-2-yl group, a 4-fluorothiazol-2-yl group, a 5-fluorothiazol-2-yl group, a 4-chlorothiazol-2-yl group, a 5-chlorothiazol-2-yl group, a 4-bromothiazol-2-yl group, a 5-bromothiazol-2-yl group, a 4-methyl-5-chlorothiazol-2-yl group, a 4-cyanothiazol-2-yl group, a 5-cyanothiazol-2-yl group, a 4-methoxythiazol-2-yl group, and a 5-methoxythiazol-2-yl group.

The thiazol-4-yl group optionally having one or more atoms or groups selected from Group $P^4$ represents a thiazol-4-yl group in which hydrogen atoms of a thiazol-4-yl group are optionally substituted with one or more atoms or groups selected from Group $P^4$ and, when the number of atoms or groups selected from Group $P^4$ is 2 or more, those atoms or groups may be the same or different to each other. Examples of the thiazol-4-yl group optionally having one or more atoms or groups selected from Group $P^4$ include a thiazol-4-yl group, a 2-methylthiazol-4-yl group, a 5-methylthiazol-4-yl group, a 2-ethylthiazol-4-yl group, a 5-ethylthiazol-4-yl group, a 2,5-dimethylthiazol-4-yl group, a 2-fluorothiazol-4-yl group, a 5-fluorothiazol-4-yl group, a 2-chlorothiazol-4-yl group, a 5-chlorothiazol-2-yl group, a 2-bromothiazol-4-yl group, a 5-bromothiazol-4-yl group, a 2-methyl-5-chlorothiazol-4-yl group, a 2-cyanothiazol-4-yl group, a 5-cyanothiazol-4-yl group, a 2-methoxythiazol-4-yl group, and a 5-methoxythiazol-4-yl group.

The thiazol-5-yl group optionally having one or more atoms or groups selected from Group $P^4$ represents a thiazol-5-yl group in which hydrogen atoms of a thiazol-5-yl group are optionally substituted with one or more atoms or groups selected from Group $P^4$ and, when the number of atoms or groups selected from Group $P^4$ is 2 or more, those atoms or groups may be the same or different to each other. Examples of the thiazol-5-yl group optionally having one or more atoms or groups selected from Group $P^4$ include a thiazol-5-yl group, a 4-methylthiazol-5-yl group, a 2-methylthiazol-5-yl group, a 4-ethylthiazol-5-yl group, a 2-ethylthiazol-5-yl group, a 2,4-dimethylthiazol-5-yl group, a 4-fluorothiazol-5-yl group, a 2-fluorothiazol-5-yl group, a 4-chlorothiazol-5-yl group, a 2-chlorothiazol-5-yl group, a 4-bromothiazol-5-yl group, a 2-bromothiazol-5-yl group, a 2-chloro-4-methylthiazol-5-yl group, a 4-cyanothiazol-5-yl group, a 2-cyanothiazol-5-yl group, a 4-methoxythiazol-5-yl group, and a 2-methoxythiazol-5-yl group.

The oxazol-2-yl group optionally having one or more atoms or groups selected from Group $P^4$ represents an oxazol-2-yl group in which hydrogen atoms of an oxazol-2-yl group are optionally substituted with one or more atoms or groups selected from Group $P^4$ and, when the number of atoms or groups selected from Group $P^4$ is 2 or more, those atoms or groups may be the same or different to each other. Examples of the oxazol-2-yl group optionally having one or more atoms or groups selected from Group $P^4$ include an oxazol-2-yl group, a 4-methyloxazol-2-yl group, a 5-methyloxazol-2-yl group, a 4-ethyloxazol-2-yl group, a 5-ethyloxazol-2-yl group, a 4,5-dimethyloxazol-2-yl group, a 4-fluorooxazol-2-yl group, a 5-fluorooxazol-2-yl group, a 4-chlorooxazol-2-yl group, a 5-chlorooxazol-2-yl group, a 4-bromooxazol-2-yl group, a 5-bromooxazol-2-yl group, a 4-methyl-5-chlorooxazol-2-yl group, a 4-cyanooxazol-2-yl group, a 5-cyanooxazol-2-yl group, a 4-methoxyoxazol-2-yl group, and a 5-methoxyoxazol-2-yl group.

The oxazol-4-yl group optionally having one or more atoms or groups selected from Group $P^4$ represents an oxazol-4-yl group in which hydrogen atoms of an oxazol-4-yl group are optionally substituted with one or more atoms or groups selected from Group $P^4$ and, when the number of atoms or groups selected from Group $P^4$ is 2 or more, those atoms or groups may be the same or different to each other. Examples of the oxazol-4-yl group optionally having one or more atoms or groups selected from Group $P^4$ include an oxazol-4-yl group, a 2-methyloxazol-4-yl group, a 5-methyloxazol-4-yl group, a 2-ethyloxazol-4-yl group, a 5-ethyloxazol-4-yl group, a 2,5-dimethyloxazol-4-yl group, a 2-fluorooxazol-4-yl group, a 5-fluorooxazol-4-yl group, a 2-chlorooxazol-4-yl group, a 5-chlorooxazol-2-yl group, a 2-bromooxazol-4-yl group, a 5-bromooxazol-4-yl group, a 2-methyl-5-chlorooxazol-4-yl group, a 2-cyanooxazol-4-yl group, a 5-cyanooxazol-4-yl group, a 2-methoxyoxazol-4-yl group, and a 5-methoxyoxazol-4-yl group.

The oxazol-5-yl group optionally having one or more atoms or groups selected from Group $P^4$ represents an oxazol-5-yl group in which hydrogen atoms of an oxazol-5-yl group are optionally substituted with one or more atoms or groups selected from Group $P^4$ and, when the number of atoms or groups selected from Group $P^4$ is 2 or more, those atoms or groups may be the same or different to each other. Examples of the oxazol-5-yl group optionally having one or more atoms or groups selected from Group $P^4$ include an oxazol-5-yl group, a 4-methyloxazol-5-yl group, a 2-methyloxazol-5-yl group, a 4-ethyloxazol-5-yl group, a 2-ethyloxazol-5-yl group, a 2,4-dimethyloxazol-5-yl group, a 4-fluorooxazol-5-yl group, a 2-fluorooxazol-5-yl group, a 4-chlorooxazol-5-yl group, a 2-chlorooxazol-5-yl group, a 4-bromooxazol-5-yl group, a 2-bromooxazol-5-yl group, a 2-chloro-4-methyloxazol-5-yl group, a 4-cyanooxazol-5-yl group, a 2-cyanooxazol-5-yl group, a 4-methoxyoxazol-5-yl group, and a 2-methoxyoxazol-5-yl group.

The 2-oxazolin-2-yl group optionally having one or more atoms or groups selected from Group $P^4$ represents a 2-oxazolin-2-yl group in which hydrogen atoms of a 2-oxazolin-2-yl group are optionally substituted with one or more atoms or groups selected from Group $P^4$ and, when the number of atoms or groups selected from Group $P^4$ is 2 or more, those atoms or groups may be the same or different to each other. Examples of the 2-oxazolin-2-yl group optionally having one or more atoms or groups selected from Group $P^4$ include a 2-oxazolin-2-yl group, a 4-methyl-2-oxazolin-2-yl group, a 5-methyl-2-oxazolin-2-yl group, a 4-ethyl-2-oxazolin-2-yl group, a 5-ethyl-2-oxazolin-2-yl group, a 4,5-dimethyl-2-oxazolin-2-yl group, a 4,4-dimethyl-2-oxazolin-2-yl group, a 5,5-dimethyl-2-oxazolin-2-yl group, a 4-fluoro-2-oxazolin-2-yl group, a 5-fluoro-2-oxazolin-2-yl group, a 4-chloro-2-oxazolin-2-yl group, a 5-chloro-2-oxazolin-2-yl group, a 4-bromo-2-oxazolin-2-yl group, a 5-bromo-2-oxazolin-2-yl group, a 4-methyl-5-chloro-2-oxazolin-2-yl group, a 4-cyano-2-oxazolin-2-yl group, a 5-cyano-2-oxazolin-2-yl group, a 4-methoxy-2-oxazolin-2-yl group, and a 5-methoxy-2-oxazolin-2-yl group.

The 2-thiazolin-2-yl group optionally having one or more atoms or groups selected from Group $P^4$ represents a 2-thiazolin-2-yl group in which hydrogen atoms of a 2-thiazolin-2-yl group are optionally substituted with one or more atoms or groups selected from Group $P^4$ and, when the number of atoms or groups selected from Group $P^4$ is 2 or more, those atoms or groups may be the same or different to each other. Examples of the 2-thiazolin-2-yl group optionally having one or more atoms or groups selected from Group $P^4$ include a 2-thiazolin-2-yl group, a 4-methyl-2-thiazolin-2-yl group, a 5-methyl-2-thiazolin-2-yl group, a 4-ethyl-2-thiazolin-2-yl group, a 5-ethyl-2-thiazolin-2-yl group, a 4,5-dimethyl-2-thiazolin-2-yl group, a 4,4-dimethyl-2-thiazolin-2-yl group, a 5,5-dimethyl-2-thiazolin-2-yl group, a 4-fluoro-2-thiazolin-2-yl group, a 5-fluoro-2-thiazolin-2-yl group, a 4-chloro-2-thiazolin-2-yl group, a 5-chloro-2-thiazolin-2-yl group, a 4-bromo-2-thiazolin-2-yl group, a 5-bromo-2-thiazolin-2-yl group, a 4-methyl-5-chloro-2-thiazolin-2-yl group, a 4-cyano-2-thiazolin-2-yl group, a 5-cyano-2-thiazolin-2-yl group, a 4-methoxy-2-thiazolin-2-yl group, and a 5-methoxy-2-thiazolin-2-yl group.

The thiophen-2-yl group optionally having one or more atoms or groups selected from Group $P^4$ represents a thiophen-2-yl group in which hydrogen atoms of a thiophen-2-yl group are optionally substituted with one or more atoms or groups selected from Group $P^4$ and, when the number of atoms or groups selected from Group $P^4$ is 2 or more, those atoms or groups may be the same or different to each other. Examples of the thiophen-2-yl group optionally having one or more atoms or groups selected from Group $P^4$ include a thiophen-2-yl group, a 4-methylthiophen-2-yl group, a 3-methylthiophen-2-yl group, a 4-ethylthiophen-2-yl group, a 5-ethylthiophen-2-yl group, a 4,5-dimethylthiophen-2-yl group, a 3,4,5-trimethylthiophen-2-yl group, a 3-fluorothiophen-2-yl group, a 5-fluorothiophen-2-yl group, a 4-chlorothiophen-2-yl group, a 5-chlorothiophen-2-yl group, a 4-bromothiophen-2-yl group, a 3-bromothiophen-2-yl group, a 5-chloro-4-methylthiophen-2-yl group, a 3-cyanothiophen-2-yl group, a 5-cyanothiophen-2-yl group, a 4-methoxythiophen-2-yl group, a 4-cyanothiophen-2-yl group, and a 5-methoxythiophen-2-yl group.

The thiophen-3-yl group optionally having one or more atoms or groups selected from Group $P^4$ represents a thiophen-3-yl group in which hydrogen atoms of a thiophen-3-yl group are optionally substituted with one or more atoms or groups selected from Group $P^4$ and, when the number of atoms or groups selected from Group $P^4$ is 2 or more, those atoms or groups may be the same or different to each other. Examples of the thiophen-3-yl group optionally having one or more atoms or groups selected from Group $P^4$ include a thiophen-3-yl group, a 4-methylthiophen-3-yl group, a 2-methylthiophen-3-yl group, a 4-ethylthiophen-3-yl group, a 5-ethylthiophen-3-yl group, a 4,5-dimethylthiophen-2-yl group, a 2,4,5-trimethylthiophen-2-yl group, a 2-fluorothiophen-2-yl group, a 5-fluorothiophen-3-yl group, a 4-chlorothiophen-3-yl group, a 5-chlorothiophen-3-yl group, a 4-bromothiophen-3-yl group, a 2-bromothiophen-3-yl group, a 5-chloro-4-methylthiophen-3-yl group, a 2-cyanothiophen-3-yl group, a 5-cyanothiophen-3-yl group, a 4-methoxythiophen-3-yl group, a 4-cyanothiophen-3-yl group, and a 5-methoxythiophen-3-yl group.

The furan-2-yl group optionally having one or more atoms or groups selected from Group $P^4$ represents a furan-2-yl group in which hydrogen atoms of a furan-2-yl group are optionally substituted with one or more atoms or groups selected from Group $P^4$ and, when the number of atoms or groups selected from Group $P^4$ is 2 or more, those atoms or groups may be the same or different to each other. Examples of the furan-2-yl group optionally having one or more atoms or groups selected from Group $P^4$ include a furan-2-yl group, a 4-methylfuran-2-yl group, a 3-methylfuran-2-yl group, a 4-ethylfuran-2-yl group, a 5-ethylfuran-2-yl group, a 4,5-dimethylfuran-2-yl group, a 3,4,5-trimethylfuran-2-yl group, a 3-fluorofuran-2-yl group, a 5-fluorofuran-2-yl group, a 4-chlorofuran-2-yl group, a 5-chlorofuran-2-yl group, a 4-bromofuran-2-yl group, a 3-bromofuran-2-yl group, a 5-chloro-4-methylfuran-2-yl group, a 3-cyanofuran-2-yl group, a 5-cyanofuran-2-yl group, a 4-methoxyfuran-2-yl group, a 4-cyanofuran-2-yl group, and a 5-methoxyfuran-2-yl group.

The furan-3-yl group optionally having one or more atoms or groups selected from Group $P^4$ represents a furan-3-yl group in which hydrogen atoms of a furan-3-yl group are optionally substituted with one or more atoms or groups selected from Group $P^4$ and, when the number of atoms or groups selected from Group $P^4$ is 2 or more, those atoms or groups may be the same or different to each other. Examples of the furan-3-yl group optionally having one or more atoms or groups selected from Group $P^4$ include a furan-3-yl group, a 4-methylfuran-3-yl group, a 2-methylfuran-3-yl group, a 4-ethylfuran-3-yl group, a 5-ethylfuran-3-yl group, a 4,5-dimethylfuran-2-yl group, a 2,4,5-trimethylfuran-3-yl group, a 2-fluorofuran-3-yl group, a 5-fluorofuran-3-yl group, a 4-chlorofuran-3-yl group, a 5-chlorofuran-3-yl group, a 4-bromofuran-3-yl group, a 2-bromofuran-3-yl group, a 5-chloro-4-methylfuran-3-yl group, a 2-cyanofuran-3-yl group, a 5-cyanofuran-3-yl group, a 4-methoxyfuran-3-yl group, a 4-cyanofuran-3-yl group, and a 5-methoxyfuran-3-yl group.

The C1-C6 alkyl group represents a straight or branched alkyl group having 1-6 carbon atoms, and examples thereof include a methyl group, an ethyl group, a propyl group, an isopropyl group, a butyl group, a pentyl group, and a hexyl group.

Examples of the aspect of the present compound are compounds in which the substituent in formula (1) is shown below.

A tetrazolinone compound in which $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$. Group $P^4$: Group consisting of a C1-C3 alkyl group optionally having one or more halogen atoms, a halogen atom, a cyano group, a nitro group, a C3-C6 cycloalkyl group optionally having one or more halogen atoms, a C2-C3 alkenyl group optionally having one or more halogen atoms, a C1-C4 alkoxy group optionally having one or more halogen atoms, and a C1-C4 alkylthio group optionally having one or more halogen atoms), $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms:

Group $P^6$: Group consisting of an oxazol-2-yl group, an oxazol-4-yl group, an oxazol-5-yl group, a 2-oxazolin-2-yl group, a thiazol-2-yl group, a thiazol-4-yl group, a thiazol-5-yl group, a 2-thiazolin-2-yl group, a furan-2-yl group, a furan-3-yl group, a thiophen-2-yl group, a thiophen-3-yl group, a 1,2,4-thiadiazol-3-yl group, a 1,3,4-thiadiazol-2-yl group, a 1,3,4-oxadiazol-2-yl group, a 1,2,3-triazol-2-yl group, a tetrazol-2-yl group, a 1,2,3-triazol-1-yl group, a pyrrol-2-yl group, a 5-pyrazolon-3-yl, an isoxazol-3-yl group, an isoxazol-4-yl group, an isoxazol-5-yl group, an isothiazol-3-yl group, an isothiazol-4-yl group, an isothiazol-5-yl group, an isoxazolin-5-yl group, an isoxazolin-3-yl group, an isothiazolin-5-yl group, an isothiazolin-3-yl group, a pyrrolidon-5-yl, a dioxolan-2-yl group, a tetrahydrofuran-2-yl group, a maleimid-3-yl group, and maleimid-1-yl group.

A tetrazolinone compound in which Q is any one group selected from Group $P^5$ (provided that the group optionally has one or more atoms or groups selected from Group $P^4$), $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, $R^{10}$ is a C1-C3 alkyl group optionally having one or more halogen atoms:

Group $P^5$: Group consisting of an oxazol-2-yl group, an oxazol-4-yl group, an oxazol-5-yl group, an oxazolin-2-yl group, a thiazol-2-yl group, a thiazol-4-yl group, a thiazol-5-yl group, a thiazolin-2-yl group, a furan-2-yl group, a furan-3-yl group, a thiophen-2-yl group, a thiophen-3-yl group, a 1,2,4-thiadiazol-5-yl group, a 1,3,4-thiadiazol-2-yl group, a 1,3,4-oxadiazol-2-yl group, a 1,2,3-triazol-2-yl group, a 2-methyldioxolan-2-yl group, a tetrazol-2-yl group, a 1,2,3-triazol-1-yl group, a pyrrol-2-yl group, an imidazol-1-yl group, an imidazol-2-yl group, and a 1,2,4-triazol-1-yl group.

A tetrazolinone compound in which $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^5$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, X is an oxygen atom or a sulfur atom, and $R^{10}$ is a C1-C3 alkyl group optionally having one or more halogen atoms.

A tetrazolinone compound in which Q is any one group selected from Group $P^2$ (provided that the group optionally has one or more atoms or groups selected from Group $P^1$), $R^1$ is a methyl group, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$), $R^1$ is a methyl group, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^5$ (provided that the group optionally has one or more atoms or groups selected from Group $P^4$), $R^1$ is a methyl group, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$), $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^5$ (provided that the group optionally has one or more atoms or groups selected from Group $P^4$), $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $XR^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^5$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which $R^1$ is a methyl group, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$), $R^1$ is a methyl group, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^5$ (provided that the group optionally has one or more atoms or groups selected from Group $P^4$), $R^1$ is a methyl group, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$), $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^5$ (provided that the group optionally has one or more atoms or groups selected from Group $P^4$), $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, X is an oxygen atom or a sulfur atom, and $R^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^5$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, X is an oxygen atom or a sulfur atom, and $R^{10}$ is a C1-C3 alkyl group optionally having one or more halogen atoms.

A tetrazolinone compound in which $R^1$ is a methyl group, $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^6$ (provided that the group optionally has one or more atoms or groups selected from Group $P^4$), $R^1$ is a methyl group, $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which Q is any one group selected from Group $P^5$ (provided that the group optionally has one or more atoms or groups selected from Group $P^4$), $R^1$ is a methyl group, $R^6$ is a methyl group, an ethyl group, a cyclopropyl group, a methoxy group, a trifluoromethyl group, or a chlorine atom, $R^2$, $R^3$, $R^4$, $R^5$, $R^7$, $R^8$, $R^9$, and $R^{11}$ each independently represents a hydrogen atom, a halogen atom, or a C1-C3 alkyl group, and $R^{10}$ is a C1-C3 alkyl group optionally having one or more halogen atoms.

A tetrazolinone compound in which $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is any one group selected from Group $P^6$ (provided that the group optionally has one or more atoms or groups selected from Group $P^4$), $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is any one group selected from Group $P^5$ (provided that the group optionally has one or more atoms or groups selected from Group $P^4$), $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is any one group selected from Group $P^5$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which $R^1$ is a methyl group, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is any one group selected from Group $P^6$ (provided that the group optionally has one or more atoms or groups selected from Group $P^4$), $R^1$ is a methyl group, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is any one group selected from Group $P^5$ (provided that the group optionally has one or more atoms or groups selected from Group $P^4$), $R^1$ is a methyl group, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is any one group selected from Group $P^6$ (provided that the group optionally has one or more atoms or groups selected from Group $P^4$), $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is any one group selected from Group $P^5$ (provided that the group optionally has one or more atoms or groups selected from Group $P^4$), $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolyl group, a thiazolinyl group, an oxazolyl group, an oxazolinyl group, a triazolyl group, a furyl group, a thienyl group, a thiadiazolyl group, an oxadiazolyl group, a pyrrolyl group, a dioxolanyl group, or an imidazolyl group (provided that the thiazolyl group, the thiazolinyl group, the oxazolyl group, the oxazolinyl group, the triazolyl group, the furyl group, the thienyl group, the thiadiazolyl group, the oxadiazolyl group, the pyrrolyl group, the dioxolanyl group, and the imidazolyl group optionally have one or more halogen atoms and/or C1-C3 alkyl groups), $R^1$ is a C1-C3 alkyl group, $R^6$ is a C1-C3 alkyl group, a C3-C4 cycloalkyl group, or a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolyl group (provided that the thiazolyl group optionally has one or more halogen atoms and/or C1-C3 alkyl groups), $R^1$ is a C1-C3 alkyl group, $R^6$ is a C1-C3 alkyl group, a C3-C4 cycloalkyl group, or a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolyl group (provided that the thiazolyl group optionally has one or more halogen atoms and/or C1-C3 alkyl groups), $R^1$ is a C1-C3 alkyl group, $R^6$ is a C1-C3 alkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolyl group (provided that the thiazolyl group optionally has one or more halogen atoms and/or C1-C3 alkyl groups), $R^1$ is a C1-C3 alkyl group, $R^6$ is a C3-C4 cycloalkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolyl group (provided that the thiazolyl group optionally has one or more halogen atoms and/or C1-C3 alkyl groups), $R^1$ is a C1-C3 alkyl group, $R^6$ is a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolinyl group (provided that the thiazolinyl group optionally has one or more halogen atoms and/or C1-C3 alkyl groups), $R^1$ is a C1-C3 alkyl group, $R^6$ is a C1-C3 alkyl group, a C3-C4 cycloalkyl group, or a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolinyl group (provided that the thiazolinyl group optionally has one or more halogen atoms and/or C1-C3 alkyl groups), $R^1$ is a C1-C3 alkyl group, $R^6$ is a C1-C3 alkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolinyl group (provided that the thiazolinyl group optionally has one or more halogen atoms and/or C1-C3 alkyl groups), $R^1$ is a C1-C3 alkyl group, $R^6$ is a C3-C4 cycloalkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thiazolinyl group (provided that the thiazolinyl group optionally has one or more halogen atoms and/or C1-C3 alkyl groups), $R^1$ is a C1-C3 alkyl group, $R^6$ is a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is an oxazolyl group (provided that the oxazolyl group optionally has one or more halogen atoms and/or C1-C3 alkyl groups), $R^1$ is a C1-C3 alkyl group, $R^6$ is a C1-C3 alkyl group, a C3-C4 cycloalkyl group, or a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is an oxazolyl group (provided that the oxazolyl group optionally has one or more halogen atoms and/or C1-C3 alkyl groups), $R^1$ is a C1-C3 alkyl group, $R^6$ is a C1-C3 alkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is an oxazolyl group (provided that the oxazolyl group optionally has one or more halogen atoms and/or C1-C3 alkyl groups), $R^1$ is a C1-C3 alkyl group, $R^6$ is a C3-C4 cycloalkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is an oxazolyl group (provided that the oxazolyl group optionally has one or more halogen atoms and/or C1-C3 alkyl groups), $R^1$ is a C1-C3 alkyl group, $R^6$ is a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is an oxazolinyl group (provided that the oxazolinyl group optionally has one or more halogen atoms and/or C1-C3 alkyl groups), $R^1$ is a C1-C3 alkyl group, $R^6$ is a C1-C3 alkyl group, a C3-C4 cycloalkyl group, or a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is an oxazolinyl group (provided that the oxazolinyl group optionally has one or more halogen atoms and/or C1-C3 alkyl groups), $R^1$ is a C1-C3 alkyl group, $R^6$ is a C1-C3 alkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is an oxazolinyl group (provided that the oxazolinyl group optionally has one or more halogen atoms and/or C1-C3 alkyl groups), $R^1$ is a C1-C3 alkyl group, $R^6$ is a C3-C4 cycloalkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is an oxazolinyl group (provided that the oxazolinyl group optionally has one or more halogen atoms and/or C1-C3 alkyl groups), $R^1$ is a C1-C3 alkyl group, $R^6$ is a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a 1,2,3-triazolyl group (provided that the 1,2,3-triazolyl group optionally has one or more halogen atoms and/or C1-C3 alkyl groups), $R^1$ is a C1-C3 alkyl group, $R^6$ is a C1-C3 alkyl group, a C3-C4 cycloalkyl group, or a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a 1,2,3-triazolyl group (provided that the 1,2,3-triazolyl group optionally has one or more halogen atoms and/or C1-C3 alkyl groups), $R^1$ is a C1-C3 alkyl group, $R^6$ is a C1-C3 alkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a 1,2,3-triazolyl group (provided that the 1,2,3-triazolyl group optionally has one or more halogen atoms and/or C1-C3 alkyl groups), $R^1$ is a C1-C3 alkyl group, $R^6$ is a C3-C4 cycloalkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a 1,2,3-triazolyl group (provided that the 1,2,3-triazolyl group optionally has one or more halogen atoms and/or C1-C3 alkyl groups), $R^1$ is a C1-C3 alkyl group, $R^6$ is a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thienyl group (provided that the thienyl group optionally has one or more halogen atoms and/or C1-C3 alkyl groups), $R^1$ is a C1-C3 alkyl group, $R^6$ is a C1-C3 alkyl group, a C3-C4 cycloalkyl group, or a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thienyl group (provided that the thienyl group optionally has one or more halogen atoms and/or C1-C3 alkyl groups), $R^1$ is a C1-C3 alkyl group, $R^6$ is a C1-C3 alkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thienyl group (provided that the thienyl group optionally has one or more halogen atoms and/or C1-C3 alkyl groups), $R^1$ is a C1-C3 alkyl group, $R^6$ is a C3-C4 cycloalkyl group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which Q is a thienyl group (provided that the thienyl group optionally has one or more halogen atoms and/or C1-C3 alkyl groups), $R^1$ is a C1-C3 alkyl group, $R^6$ is a C1-C3 alkoxy group, $R^2$, $R^3$, $R^4$, $R^5$, $R^7$, $R^8$, $R^9$, and $R^{11}$ are hydrogen atoms, X is an oxygen atom, and $R^{10}$ is a C1-C3 alkyl group.

A tetrazolinone compound in which $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ are hydrogen atoms, X is an oxygen atom, and $R^{10}$ is a methyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, $R^7$, $R^8$, $R^9$, and $R^{11}$ are hydrogen atoms, X is an oxygen atom, and $R^{10}$ is a methyl group.

A tetrazolinone compound in which Q is any one group selected from Group $P^5$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, $R^2$, $R^3$, $R^4$, $R^5$, R$^7$, R$^8$, R$^9$, and R$^{11}$ are hydrogen atoms, X is an oxygen atom, and R$^{10}$ is a methyl group.

A tetrazolinone compound in which R$^1$ is a methyl group, R$^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^6$ (provided that the group optionally has one or more atoms or groups selected from Group P$^4$), R$^1$ is a methyl group, R$^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^5$ (provided that the group optionally has one or more atoms or groups selected from Group P$^4$), R$^1$ is a methyl group, R$^6$ is a C1-C3 alkyl group optionally having one or more halogen atoms, a C3-C4 cycloalkyl group optionally having one or more halogen atoms, a C1-C3 alkoxy group optionally having one or more halogen atoms, or a halogen atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^6$ (provided that the group optionally has one or more atoms or groups selected from Group P$^4$), R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^5$ (provided that the group optionally has one or more atoms or groups selected from Group P$^4$), R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which R$^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^6$ (provided that the group optionally has one or more atoms or groups selected from Group P$^4$), R$^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^5$ (provided that the group optionally has one or more atoms or groups selected from Group P$^4$), R$^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which R$^1$ is a methyl group, R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^6$ (provided that the group optionally has one or more atoms or groups selected from Group P$^4$), R$^1$ is a methyl group, R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^5$ (provided that the group optionally has one or more atoms or groups selected from Group P$^4$), R$^1$ is a methyl group, R$^6$ is a methyl group, an ethyl group, a cyclopropyl group, a methoxy group, a trifluoromethyl group, or a chlorine atom, R$^2$, R$^3$, R$^4$, R$^5$, R$^7$, R$^8$, R$^9$, and R$^{11}$ are hydrogen atoms, X is an oxygen atom, and R$^{10}$ is a methyl group.

A tetrazolinone compound in which Q is any one group selected from Group P$^6$ (provided that the group optionally has one or more atoms or groups selected from Group P$^4$), R$^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, R$^6$ is a C1-C3 alkyl group optionally having one or more halogen atoms, R$^2$ and R$^3$ each represents a hydrogen atom, a halogen atom, or a C1-C3 alkyl group optionally having a halogen atom, R$^4$, R$^5$, R$^7$, R$^8$, R$^9$, and R$^{11}$ are hydrogen atoms, and R$^{10}$ is a methyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C3-C5 cycloalkyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkoxy group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a halogen atom, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C1-C3 alkoxy group optionally having one or more halogen atoms, or a halogen atom, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C1-C3 alkyl group optionally having one or more halogen atoms, a C3-C5 cycloalkyl group optionally having one or more halogen atoms, or a halogen atom, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C3-C5 cycloalkyl group optionally having one or more halogen atoms, a C1-C3 alkoxy group optionally having one or more halogen atoms, or a halogen atom, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is any one group selected from Group $P^6$ (provided that the group optionally has one or more atoms or groups selected from Group $P^4$), $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms, $R^6$ is a C3-C5 cycloalkyl group optionally having 11 or more halogen atoms, a C1-C3 alkoxy group optionally having one or more halogen atoms, or a halogen atom, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is any one group selected from Group $P^6$ (provided that the group optionally has one or more atoms or groups selected from Group $P^7$), $R^1$ is a C1-C3 alkyl group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group:

Group $P^7$: Group consisting of a C1-C3 alkyl group optionally having one or more halogen atoms, a halogen atom, a cyano group, a C2-C3 alkenyl group optionally having one or more halogen atoms, a C1-C4 alkoxy group optionally having one or more halogen atoms, and a C1-C4 alkylthio group optionally having one or more halogen atoms.

A tetrazolinone compound in which Q is any one group selected from Group $P^6$ (provided that the group optionally has one or more atoms or groups selected from Group $P^7$), $R^1$ is a C1-C3 alkyl group optionally having a halogen atom, a halogen atom, or a C3-C5 cycloalkyl group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is a thiazol-2-yl group optionally having one or more atoms or groups selected from Group $P^7$, $R^1$ is a C1-C3 alkyl group optionally having a halogen atom, a halogen atom, or a C3-C5 cycloalkyl group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is a thiazol-4-yl group optionally having one or more atoms or groups selected from Group $P^7$, $R^1$ is a C1-C3 alkyl group optionally having a halogen atom, a halogen atom, or a C3-C5 cycloalkyl group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is a thiazol-5-yl group optionally having one or more atoms or groups selected from Group $P^7$, $R^1$ is a C1-C3 alkyl group optionally having a halogen atom, a halogen atom, or a C3-C5 cycloalkyl group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is thiazol-2-yl group optionally having one or more atoms or groups selected from Group $P^7$, a thiazol-4-yl group optionally having one or more atoms or groups selected from Group $P^7$, or a thiazol-5-yl group optionally having one or more atoms or groups selected from Group $P^7$, $R^1$ is a C1-C3 alkyl group optionally having a halogen atom, a halogen atom, or a C3-C5 cycloalkyl group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is an oxazol-2-yl group optionally having one or more atoms or groups selected from Group $P^7$, $R^1$ is a C1-C3 alkyl group optionally having a halogen atom, a halogen atom, or a C3-C5 cycloalkyl group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a C1-C3 alkyl group.

A tetrazolinone compound in which Q is an oxazol-4-yl group optionally having one or more atoms or groups selected from Group $P^7$, $R^1$ is a C1-C3 alkyl group optionally having a halogen atom, a halogen atom, or a C3-C5 cycloalkyl group optionally having one or more halogen atoms, $R^6$ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, $R^2$ and $R^3$ each independently represents a hydrogen atom, a halogen atom, or a C1-C3 alkyl group optionally having a halogen atom, $R^4$, $R^5$, $R^7$, $R^8$, $R^9$, and $R^{11}$ are hydrogen atoms, and $R^{10}$ is a methyl group.

A tetrazolinone compound in which Q is oxazol-5-yl group optionally having one or more atoms or groups selected from Group P⁷, R¹ is a C1-C3 alkyl group optionally having a halogen atom, a halogen atom, or a C3-C5 cycloalkyl group optionally having one or more halogen atoms, R⁶ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, R² and R³ each independently represents a hydrogen atom, a halogen atom, or a C1-C3 alkyl group optionally having a halogen atom, R⁴, R⁵, R⁷, R⁸, R⁹, and R¹¹ are hydrogen atoms, and R¹⁰ is a C1-C3 alkyl group.

A tetrazolinone compound in which Q is an oxazol-2-yl group optionally having one or more atoms or groups selected from Group P⁷, an oxazol-4-yl group optionally having one or more atoms or groups selected from Group P⁷, or an oxazol-5-yl group optionally having one or more atoms or groups selected from Group P⁷, R¹ is a C1-C3 alkyl group optionally having a halogen atom, a halogen atom, or a C3-C5 cycloalkyl group optionally having one or more halogen atoms, R⁶ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, R² and R³ each independently represents a hydrogen atom, a halogen atom, or a C1-C3 alkyl group optionally having a halogen atom, R⁴, R⁵, R⁷, R⁸, R⁹, and R¹¹ are hydrogen atoms, and R¹⁰ is a C1-C3 alkyl group.

A tetrazolinone compound in which Q is a 2-oxazolin-2-yl group optionally having one or more atoms or groups selected from Group P⁷, a 2-thiazolin-2-yl group optionally having one or more atoms or groups selected from Group P⁴, a thiophen-2-yl group optionally having one or more atoms or groups selected from Group P⁷, a thiophen-3-yl group optionally having one or more atoms or groups selected from Group P⁷, a furan-2-yl group optionally having one or more atoms or groups selected from Group P⁷, or a furan-3-yl group optionally having one or more atoms or groups selected from Group P⁷, R¹ is a C1-C3 alkyl group optionally having a halogen atom, a halogen atom, or a C3-C5 cycloalkyl group optionally having one or more halogen atoms, R⁶ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, R² and R³ each independently represents a hydrogen atom, a halogen atom, or a C1-C3 alkyl group optionally having a halogen atom, R⁴, R⁵, R⁷, R⁸, R⁹, and R¹¹ are hydrogen atoms, and R¹⁰ is a methyl group.

A tetrazolinone compound in which Q is a thiazol-2-yl group optionally having one or more atoms or groups selected from Group P⁷, a thiazol-4-yl group optionally having one or more atoms or groups selected from Group P⁷, a thiazol-5-yl group optionally having one or more atoms or groups selected from Group P⁷, an oxazol-2-yl group optionally having one or more atoms or groups selected from Group P⁷, an oxazol-4-yl group optionally having one or more atoms or groups selected from Group P⁷, or an oxazol-5-yl group optionally having one or more atoms or groups selected from Group P⁷, R¹ is a C1-C3 alkyl group optionally having a halogen atom, a halogen atom, or a C3-C5 cycloalkyl group optionally having one or more halogen atoms, R⁶ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, R² and R³ each independently represents a hydrogen atom, a halogen atom, or a C1-C3 alkyl group optionally having a halogen atom, R⁴, R⁵, R⁷, R⁸, R⁹, and R¹¹ are respectively hydrogen atoms, and R¹⁰ is a methyl group.

A tetrazolinone compound in which Q is a thiazol-2-yl group optionally having one or more atoms or groups selected from Group P⁷, a thiazol-4-yl group optionally having one or more atoms or groups selected from Group P⁷, a thiazol-5-yl group optionally having one or more atoms or groups selected from Group P⁷, an oxazol-2-yl group optionally having one or more atoms or groups selected from Group P⁷, an oxazol-4-yl group optionally having one or more atoms or groups selected from Group P⁷, an oxazol-5-yl group optionally having one or more atoms or groups selected from Group P⁷, a 2-oxazolin-2-yl group optionally having one or more atoms or groups selected from Group P⁷, a 2-thiazolin-2-yl group optionally having one or more atoms or groups selected from Group P⁷, a thiophen-2-yl group optionally having one or more atoms or groups selected from Group P⁷, a thiophen-3-yl group optionally having one or more atoms or groups selected from Group P⁷, a furan-2-yl group optionally having one or more atoms or groups selected from Group P⁷, or a furan-3-yl group optionally having one or more atoms or groups selected from Group P⁷, R¹ is a C1-C3 alkyl group optionally having a halogen atom, a halogen atom, or a C3-C5 cycloalkyl group optionally having one or more halogen atoms, R⁶ is a C1-C3 alkyl group optionally having one or more halogen atoms, a C3-C5 cycloalkyl group optionally having one or more halogen atoms, a C1-C3 alkoxy group optionally having one or more halogen atoms, a C2-C4 alkenyl group optionally having one or more halogen atoms, a halogen atom, or a C2-C4 alkynyl group optionally having one or more halogen atoms, R² and R³ each independently represents a hydrogen atom, a halogen atom, or a C1-C3 alkyl group optionally having a halogen atom, R⁴, R⁵, R⁷, R⁸, R⁹, and R¹¹ are hydrogen atoms, and R¹⁰ is a methyl group.

Next, a process for producing the present compound will be described.

The present compound can be produced, for example, by the following Production Processes.

(Production Process A)

The present compound can be produced by reacting a compound represented by formula (A1) (hereinafter referred to as the compound (A1)) with a compound represented by formula (A2) (hereinafter referred to as the compound (A2)) in the presence of a base:

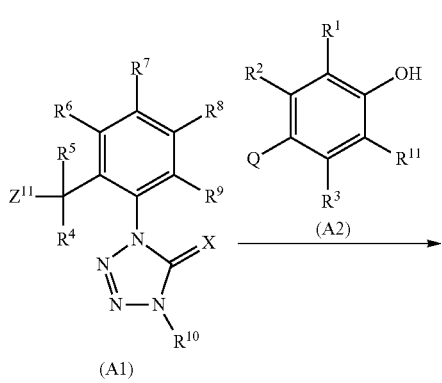

(A1)  (A2) →

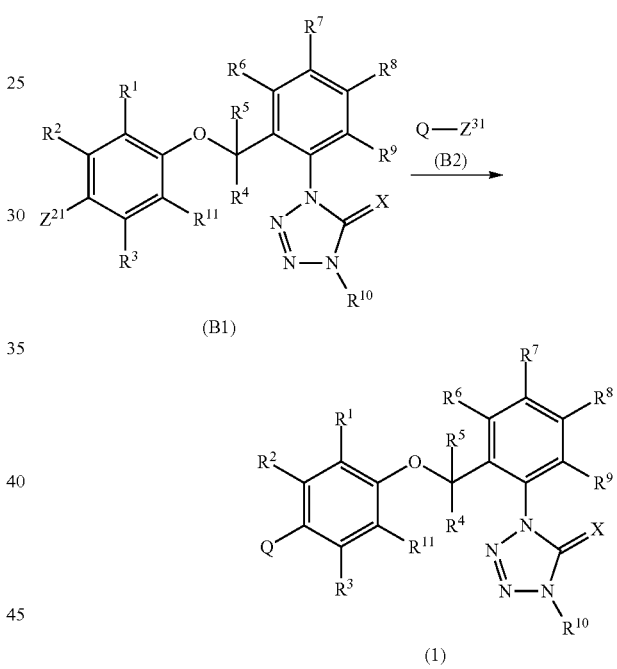

(1)

wherein $R^1$, $R^2$, $R^3$, $R^4$, $R^5$, $R^6$, $R^7$, $R^8$, $R^9$, $R^{10}$, $R^{11}$, Q, and X are the same as defined above, and Z represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion within a range of 0.001 to 1.2 mols, based on 1 mol of the compound (A1).

After completion of the reaction, the present compound represented by formula (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

The present compound can be produced by subjecting a compound represented by formula (B1) (hereinafter referred to as the compound (B1)) and a compound represented by formula (B2) (hereinafter referred to as the compound (B2)) to a coupling reaction in the presence of a base and a catalyst:

wherein $R^1$, $R^2$, $R^3$, $R^4$, $R^5$, $R^6$, $R^7$, $R^8$, $R^9$, $R^{10}$, $R^{11}$, Q, and X are the same as defined above, $Z^{21}$ represents a chlorine atom, a bromine atom, or an iodine atom, and $Z^{31}$ represents $B(OH)_2$, an alkoxyboranyl group, or a trifluoroborate $BF_3K^+$.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. It is possible to produce, as the compound (B2) to be used in the reaction, a boric acid ester derivative by reacting an iodine compound (Q-I), a bromo compound (Q-Br), or a chloro compound with an alkyllithium such as butyllithium, followed by a reaction with a boric acid ester. It is possible to produce a boric acid derivative by optionally hydrolyzing the boric acid ester derivative obtained in the above-mentioned reaction. It is also possible to produce a trifluoroborate $BF_3^-K^+$ by fluorinating the boric acid ester with potassium hydrogen fluoride in accordance with a known method mentioned in Molander et al. Acc. Chem. Res., 2007, 40, 275.

Examples of the catalyst to be used in the reaction include palladium (II) acetate, dichlorobis(triphenylphosphine)palladium, tetrakistriphenylphosphinepalladium(0), palladium (II) acetate/triscyclohexylphosphine, bis(diphenylphosphaneferrocenyl)palladium (II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time is usually within a range of 0.1 to 24 hours.

After completion of the reaction, the present compound represented by formula (1) can be isolated by performing post-treatment operations such as extraction of the reaction mixture with an organic solvent, and drying and concentration of the organic layer. The isolated present compound can be further purified by chromatography, recrystallization, and the like.

(Production Process C)

The present compound can be produced by subjecting a compound represented by formula (C1) (hereinafter referred to as the compound (C1)) and a compound represented by formula (C2) (hereinafter referred to as the compound (C2)) to a coupling reaction in the presence of a base and a catalyst:

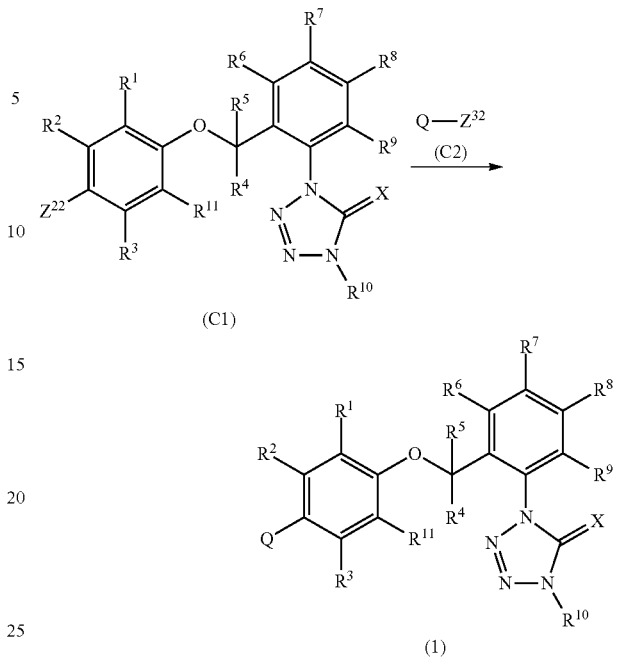

wherein $R^1$, $R^2$, $R^3$, $R^4$, $R^5$, $R^6$, $R^7$, $R^8$, $R^9$, $R^{10}$, $R^{11}$, Q, and X are the same as defined above, $Z^{22}$ represents $B(OH)_2$, an alkoxyboranyl group, or a trifluoroborate $BF_3^-K^+$, and $Z^{32}$ represents a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is possible to usually use, as the compound (C2) to be used in the reaction, commercially available products. Specific examples thereof include bromobenzene, iodobenzene, 1-bromo-2-methylbenzene, and the like.

Examples of the catalyst to be used in the reaction include palladium (II) acetate, dichlorobis(triphenylphosphine)palladium, tetrakistriphenylphosphanepalladium(0), palladium (II) acetate/triscyclohexylphosphine, bis(diphenylphosphaneferrocenyl)palladium (II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time is usually within a range of 0.1 to 24 hours.

After completion of the reaction, the present compound represented by formula (1) can be isolated by performing post-treatment operations such as extraction of the reaction mixture with an organic solvent, and drying and concentration of the organic layer. The isolated present compound can be further purified by chromatography, recrystallization, and the like.

(Production Process D)

Among the present compounds, a compound represented by formula (1-3) in which $R^{10}$ is a hydrogen atom (hereinafter referred to as the compound (1-3)) can be produced by reacting a compound represented by formula (D1) (hereinafter referred to as the compound (D1)) with an azidation agent:

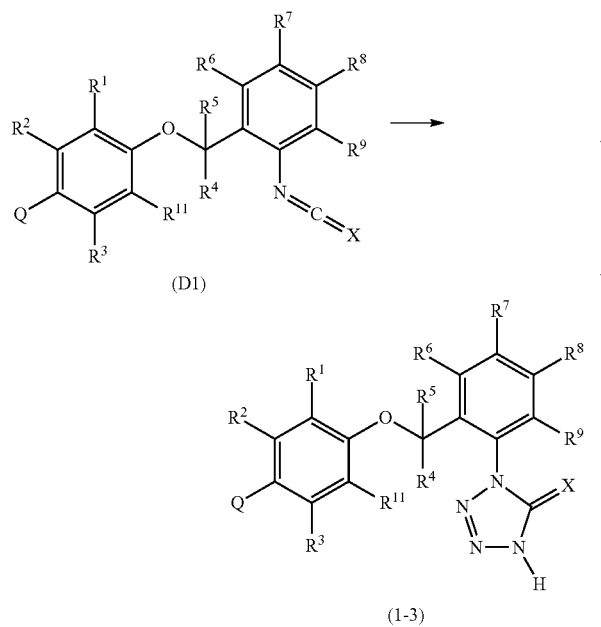

wherein $R^1$, $R^2$, $R^3$, $R^4$, $R^5$, $R^6$, $R^7$, $R^8$, $R^9$, $R^{11}$, Q, and X are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (D1).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (D1).

After completion of the reaction, the present compound represented by formula (1-3) can be isolated by performing post-treatment operations such as extraction of the reaction mixture with an organic solvent, and drying and concentration of the organic layer. The isolated present compound can be further purified by chromatography, recrystallization, and the like.

(Production Process E)

The present compound can be produced by reacting the compound (1-3) with a compound represented by formula (E1) (hereinafter referred to as the compound (E1)) in the presence of a base:

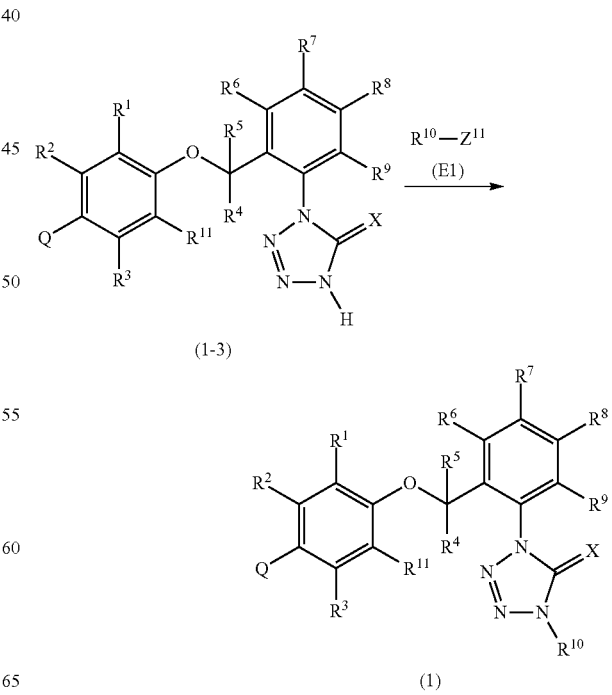

wherein $R^1$, $R^2$, $R^3$, $R^4$, $R^5$, $R^6$, $R^7$, $R^8$, $R^9$, $R^{10}$, $R^{11}$, Q, $Z^{11}$, and X are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is possible to usually use, as the compound (E1) to be used in the reaction, commercially available compounds. Specific examples thereof include alkyl halides such as chlorodifluoromethane, methyl bromide, ethyl bromide, n-propyl bromide, methyl iodide, ethyl iodide, n-propyl bromide, allyl bromide, cyclopropyl bromide, and 1,1-difluoro-2-iodoethane; dialkyl sulfates such as dimethyl sulfate; and sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide and potassium tert-butoxide.

In the reaction, the compound (E1) is usually used in the proportion within a range of 1 to 10 mols, and the base is usually used in the proportion within a range of 1 to 10 mols, based on 1 mol of the compound (1-3).

The reaction temperature of the reaction is usually within a range of −20 to 150° C. The reaction time is usually within a range of 0.1 to 24 hours.

After completion of the reaction, the present compound represented by formula (1) can be isolated by performing post-treatment operations such as extraction of the reaction mixture with an organic solvent, and drying and concentration of the organic layer. The isolated present compound can be further purified by chromatography, recrystallization, and the like.

(Production Process F)

Among the present compounds, a compound in which X is a sulfur atom (hereinafter referred to as the compound (1-S)) can be produced from a compound in which X is an oxygen atom (hereinafter referred to as the compound (1-O)) among the present compounds represented by formula (1) by a known sulfidation reaction using a sulfurizing agent:

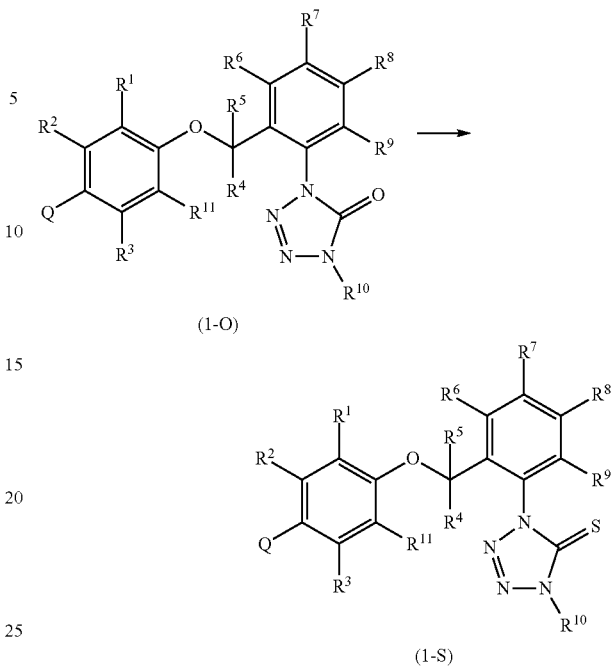

wherein $R^1$, $R^2$, $R^3$, $R^4$, $R^5$, $R^6$, $R^7$, $R^8$, $R^9$, $R^{10}$, $R^{11}$, and Q are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (1-0).

The reaction temperature of the reaction is usually within a range of −20 to 150° C. The reaction time is usually within a range of 0.1 to 24 hours.

In the reaction, if necessary, organic bases such as pyridine and triethylamine; and inorganic bases such as alkali metal hydroxides and alkali metal carbonates may be added, and the amount of the base to be added is within a range of 0.5 to 1.5 mols based on the compound (1-O).

After completion of the reaction, the present compound represented by formula (1-S) can be isolated by performing post-treatment operations such as extraction of the reaction mixture with an organic solvent, and drying and concentration of the organic layer. The isolated present compound can be further purified by chromatography, recrystallization, and the like.

(Production Process G)

Among the present compounds, a compound represented by formula (1-4) in which $R^6$ is $R^{71}$ (hereinafter referred to as the compound (1-4)) can be produced by subjecting a compound represented by formula (G1) (hereinafter referred to as the compound (G1)) and a compound represented by formula (G21) (hereinafter referred to as the compound (G21)) to a coupling reaction in the presence of a base and a catalyst:

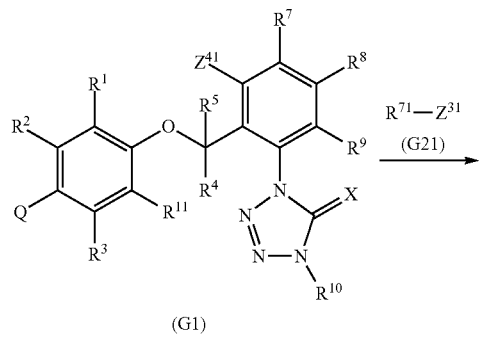

(G1)

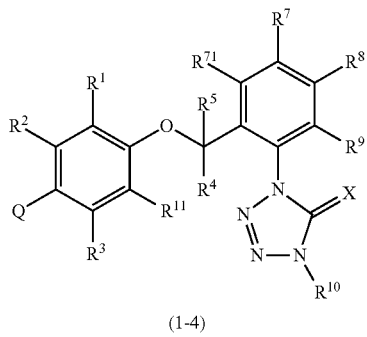

(1-4)

wherein $R^1$, $R^2$, $R^3$, $R^4$, $R^5$, $R^7$, $R^8$, $R^9$, $R^{10}$, $R^{11}$, Q, and $Z^{31}$ are the same as defined above, $Z^{41}$ represents a chlorine atom, a bromine atom, an iodine atom, or a trifluoromethanesulfonyloxy group, $R^{71}$ represents a C1-C6 alkyl group optionally having one or more halogens, a C2-C6 alkenyl group optionally having one or more halogens, a C2-C6 alkynyl group optionally having one or more halogens, or a C3-C6 cycloalkyl group optionally having one or more halogens.

The reaction can be carried out in accordance with Production Process B.

Among the present compounds, a compound represented by formula (1-5) in which $R^7$ is $R^{72}$ (hereinafter referred to as the compound (1-5)) can be produced by subjecting a compound represented by formula (G2) (hereinafter referred to as the compound (G2)) and a compound represented by formula (G22) (hereinafter referred to as the compound (G22)) to a coupling reaction in the presence of a base and a catalyst:

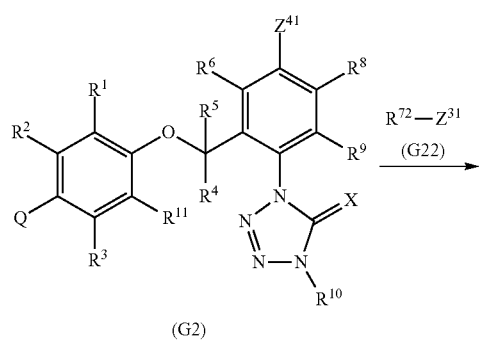

(G2)

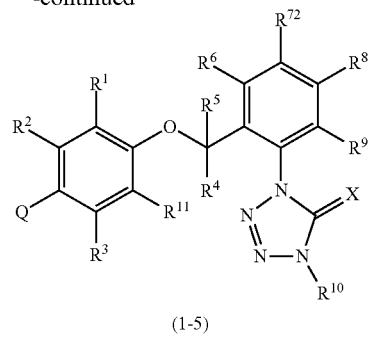

(1-5)

wherein $R^1$, $R^2$, $R^3$, $R^4$, $R^5$, $R^6$, $R^8$, $R^9$, $R^{10}$, $R^{11}$, Q, $Z^{31}$, and $Z^{41}$ are the same as defined above, $R^{72}$ represents a C1-C4 alkyl group optionally having one or more halogens, or a C3-C5 cycloalkyl group optionally having one or more halogens.

The reaction can be carried out in accordance with Production Process B.

Among the present compounds, a compound represented by formula (1-6) in which $R^8$ is $R^{72}$ (hereinafter referred to as the compound (1-6)) can be produced by subjecting a compound represented by formula (G3) (hereinafter referred to as the compound (G3)) and the compound (G22) to a coupling reaction in the presence of a base and a catalyst:

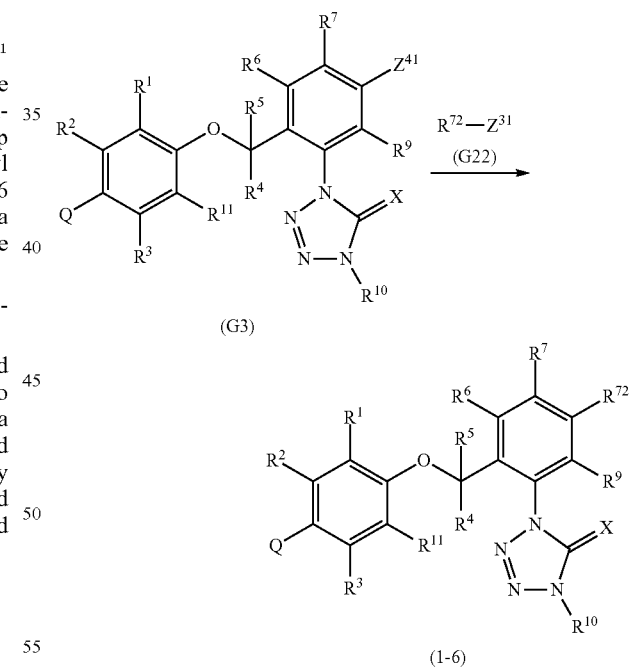

(G3)

(1-6)

wherein $R^1$, $R^2$, $R^3$, $R^4$, $R^5$, $R^6$, $R^7$, $R^9$, $R^{10}$, $R^{11}$, Q, $R^{72}$, $Z^{31}$, and $Z^{41}$ are the same as defined above.

The reaction can be carried out in accordance with Production Process B.

Among the present compounds, a compound represented by formula (1-7) in which $R^9$ is $R^{72}$ (hereinafter referred to as the compound (1-7)) can be produced by subjecting a compound represented by formula (G4) (hereinafter referred to as the compound (G4)) and the compound (G22) to a coupling reaction in the presence of a base and a catalyst:

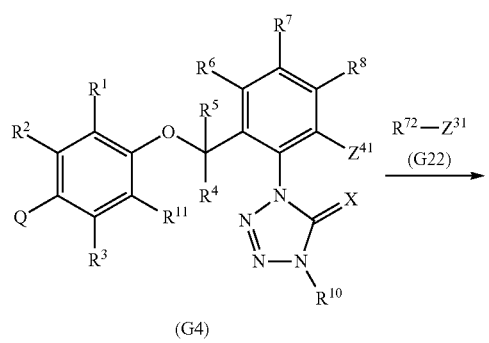

(G4)

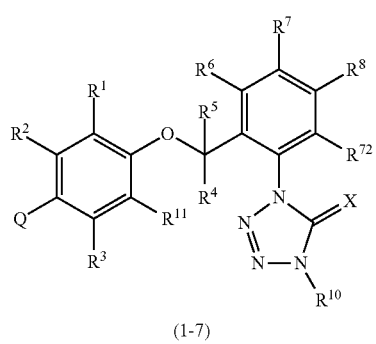

(1-7)

wherein $R^1$, $R^2$, $R^3$, $R^4$, $R^5$, $R^6$, $R^7$, $R^8$, $R^{10}$, $R^{11}$, Q, $R^{72}$, $Z^{31}$, and $Z^{41}$ are the same as defined above.

The reaction can be carried out in accordance with Production Process B.

In accordance with Production Process B, it is possible to produce a compound in which two or more substituents selected from $R^6$, $R^7$, $R^8$, and $R^9$ are either $R^{71}$ or $R^{72}$, among the present compounds.

It is also possible to produce the present compound by using the other known coupling reaction in place of the coupling reaction of the Production Process B.

(Production Process H)

Among the present compounds, a compound represented by formula (1-8) in which $R^1$ is $R^{73}$ (hereinafter referred to as the compound (1-8)) can be produced by subjecting a compound represented by formula (H1) (hereinafter referred to as the compound (H1)) and a compound represented by formula (H21) (hereinafter referred to as the compound (H21)) to a coupling reaction in the presence of a base and a catalyst:

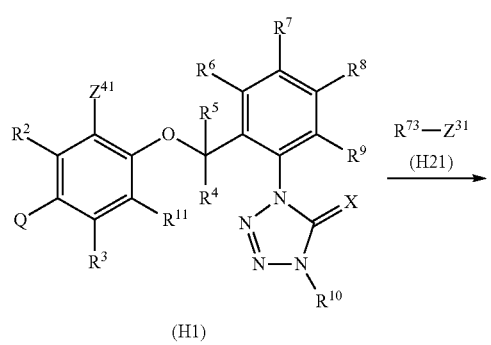

(H1)

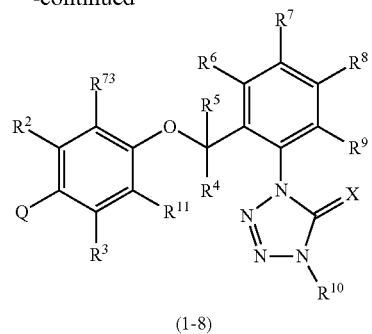

(1-8)

wherein $R^2$, $R^3$, $R^4$, $R^5$, $R^6$, $R^7$, $R^8$, $R^9$, $R^{10}$, $R^{11}$, Q, $Z^{31}$, and $Z^{41}$ are the same as defined above, and $R^{73}$ represents a C1-C6 alkyl group optionally having one or more atoms or groups selected from Group $P^1$; a C3-C6 cycloalkyl group one or more atoms or groups selected from Group $P^1$; a C2-C6 alkenyl group optionally having one or more halogens; or a C2-C6 alkynyl group optionally having one or more halogens.

The reaction can be carried out in accordance with Production Process B.

Among the present compounds, a compound represented by formula (1-9) in which $R^2$ is $R^{73}$ (hereinafter referred to as the compound (1-9)) can be produced by subjecting a compound represented by formula (H2) (hereinafter referred to as the compound (H2)) and the compound (H21) to a coupling reaction in the presence of a base and a catalyst:

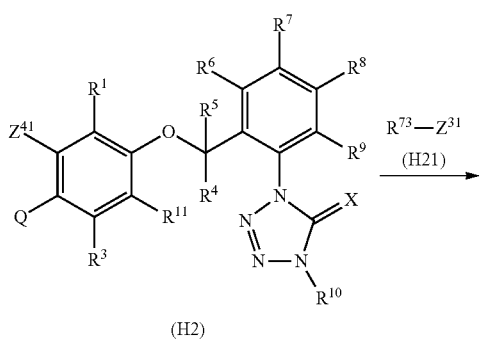

(H2)

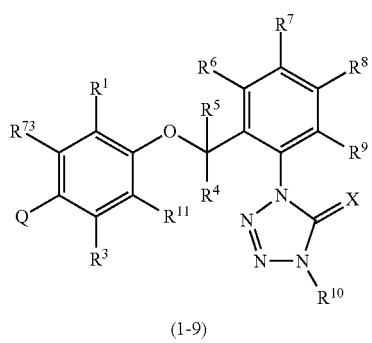

(1-9)

wherein $R^1$, $R^3$, $R^4$, $R^5$, $R^6$, $R^7$, $R^8$, $R^9$, $R^{10}$, $R^{11}$, Q, $Z^{31}$, and $Z^{41}$ are the same as defined above.

The reaction can be carried out in accordance with Production Process B.

Among the present compounds, a compound represented by formula (1-10) in which $R^3$ is $R^{73}$ (hereinafter referred to as the compound (1-10)) can be produced by subjecting a compound represented by formula (H3) (hereinafter referred to as the compound (H3)) and the compound (H21) to a coupling reaction in the presence of a base and a catalyst:

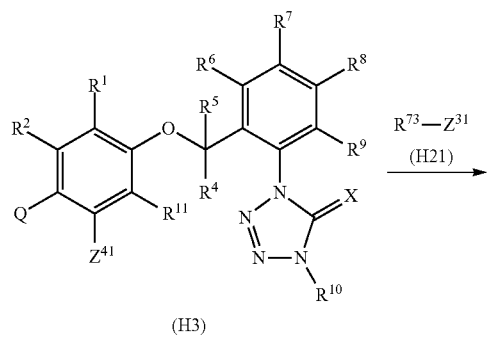

(H3)

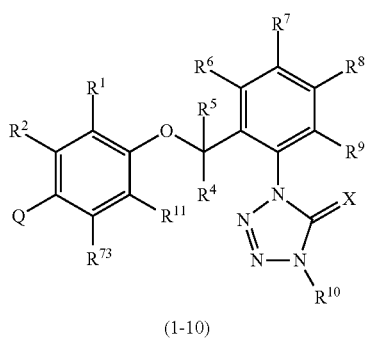

(1-10)

wherein $R^1$, $R^2$, $R^4$, $R^5$, $R^6$, $R^7$, $R^8$, $R^9$, $R^{10}$, $R^{11}$, Q, $Z^{31}$, and $Z^{41}$ are the same as defined above.

The reaction can be carried out in accordance with Production Process B.

Among the present compounds, a compound represented by formula (1-11) in which Q is Q2 and $R^{11}$ is $R^{73}$ (hereinafter referred to as the compound (1-11)) can be produced by subjecting a compound represented by formula (H4) (hereinafter referred to as the compound (H4)) and the compound (H21) to a coupling reaction in the presence of a base and a catalyst:

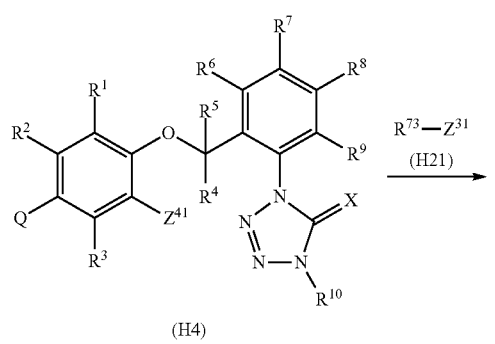

(H4)

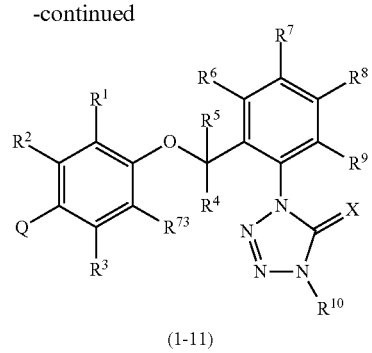

(1-11)

wherein $R^1$, $R^2$, $R^3$, $R^4$, $R^5$, $R^6$, $R^7$, $R^8$, $R^9$, $R^{10}$, Q, $Z^{31}$, and $Z^{41}$ are the same as defined above.

The reaction can be carried out in accordance with Production Process B.

In accordance with Production Process B, it is possible to produce a compound represented by formula (1) in which two or more substituents selected from $R^1$, $R^2$, $R^3$, and $R^{11}$ are $R^{73}$, among the present compounds.

It is also possible to produce the present compound by using the other known coupling reaction in place of the coupling reaction of the Production Process B.

(Production Process I)

A compound represented by the following formula (I2) (hereinafter referred to as the compound (I2)) can be produced by reacting a compound represented by the following formula (I1) (hereinafter referred to as the compound (I1)), a base, and a compound represented by formula (I3) (hereinafter referred to as the compound (I3), the compound (I3) may be a salt with hydrogen chloride or hydrogen bromide):

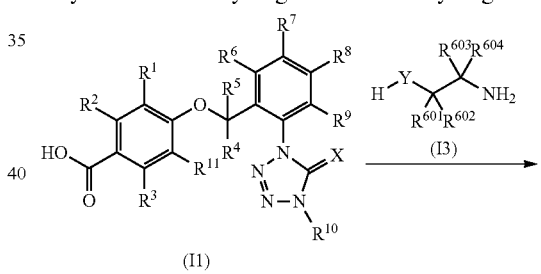

(I1) (I3)

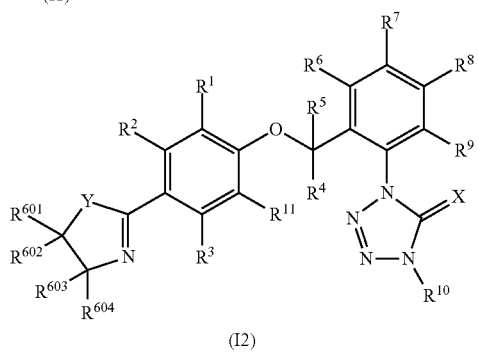

(I2)

wherein $R^1$, $R^2$, $R^3$, $R^4$, $R^5$, $R^6$, $R^7$, $R^8$, $R^9$, $R^{10}$, $R^{11}$, and X are the same as defined above, $R^{601}$, $R^{602}$, $R^{603}$, and $R^{604}$ represent a hydrogen atom, a C1-C6 alkyl group optionally having one or more halogen atoms, a C1-C6 alkoxy group optionally having one or more halogen atoms, or a cyano group, and Y represents an oxygen atom, N—H, or a sulfur atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (I3) is usually used in the proportion within a range of 1 to 10 mols, and the base is usually used in an excess amount, based on 1 mol of the compound (I1).

The reaction temperature of the reaction is usually within a range of −20 to 200° C. The reaction time of the reaction is usually within a range of 0.1 to 100 hours.

After completion of the reaction, the compound (I2) can be isolated by performing post-treatment operations such as extraction of the reaction mixture with an organic solvent, and drying and concentration of the organic layer. Alternatively, the compound (I2) can be isolated by performing post-treatment operations such as concentration of the reaction mixture. The isolated compound can be further purified by chromatography, recrystallization, and the like.

(Production Process J)

A compound represented by the following formula (J2) (hereinafter referred to as the compound (J2)) can be produced by reacting the compound (XAC2) with a halogenating agent:

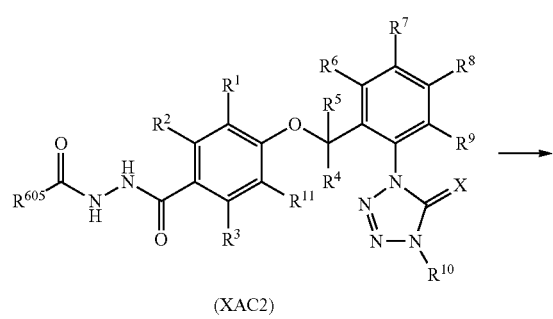

(XAC2)

-continued

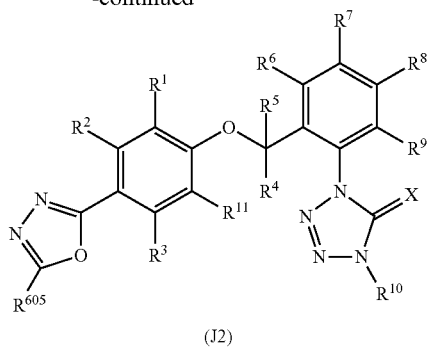

(J2)

wherein $R^1$, $R^2$, $R^3$, $R^4$, $R^5$, $R^6$, $R^7$, $R^8$, $R^9$, $R^{10}$, $R^{11}$, and X are the same as defined above, and $R^{605}$ represents a hydrogen atom or a C1-C6 alkyl group optionally having one or more halogen atoms.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water, and mixtures thereof.

Examples of the halogenating agent to be used in the reaction include phosphorous oxychloride, phosphorus oxybromide, and the like.

In the reaction, the halogenating agent is usually used in the proportion within a range of 1 to 10 mols based on 1 mol of the compound (XAC2).

The reaction temperature of the reaction is usually within a range of −20 to 150° C. The reaction time is usually within a range of 0.1 to 24 hours.

After completion of the reaction, the compound (J2) can be isolated by performing post-treatment operations such as extraction of the reaction mixture with an organic solvent, and drying and concentration of the organic layer. The isolated compound can be further purified by chromatography, recrystallization, and the like.

(Production Process K)

A compound represented by the following formula (K2) (hereinafter referred to as the compound (K2)) can be produced by subjecting a compound represented by the following formula (K1) (hereinafter referred to as the compound (K1)) and the compound (B1) to a coupling reaction in the presence of a base and a catalyst:

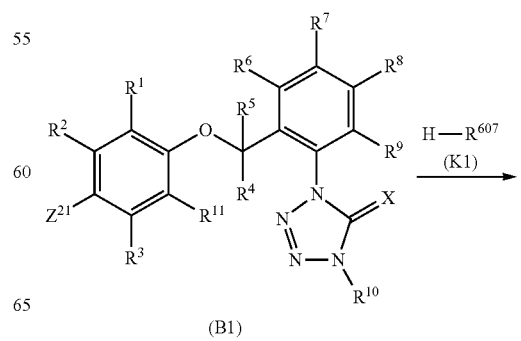

(B1)

-continued

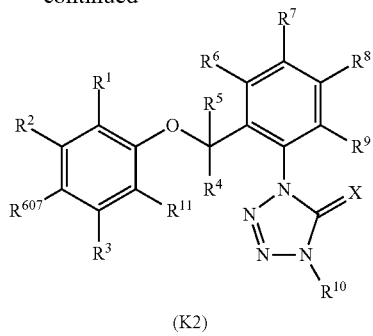

(K2)

wherein $R^1$, $R^2$, $R^3$, $R^4$, $R^5$, $R^6$, $R^7$, $R^8$, $R^9$, $R^{10}$, $R^{11}$, $Z^{21}$, and X are the same as defined above, and $R^{607}$ represents an indol-2-yl group, an indol-3-yl group, a pyrrol-2-yl group, or a furan-2-yl group (provided that the indol-2-yl group, the indol-3-yl group, the pyrrol-2-yl group, and the furan-2-yl group optionally have one or more atoms or groups selected from Group $P^4$).

The reaction is usually performed in a solvent. Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; N,N'-dimethylpropylene urea (hereinafter referred to as DMPU), hexamethylphosphoric triamide (HMPA); water; and mixtures thereof.

Examples of the catalyst to be used in the reaction include palladium (II) acetate, dichlorobis(triphenylphosphine)palladium, tetrakistriphenylphosphinepalladium(0), palladium (II) acetate/triscyclohexylphosphine, bis(diphenylphosphaneferrocenyl)palladium (II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (K1) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 200° C. The reaction time is usually within a range of 0.1 to 24 hours.

After completion of the reaction, the compound (K2) can be isolated by performing post-treatment operations such as extraction of the reaction mixture with an organic solvent, and drying and concentration of the organic layer. Alternatively, the compound (K2) can be isolated by performing post-treatment operations such as concentration of the reaction mixture. The isolated compound can be further purified by chromatography, recrystallization, and the like.

(Production Process L)

A compound represented by the following formula (L2) (hereinafter referred to as the compound (L2)) can be produced by subjecting the compound (B1) and a compound represented by the following formula (L1) (hereinafter referred to as the compound (L1)) to a coupling reaction in the presence of a base and a catalyst:

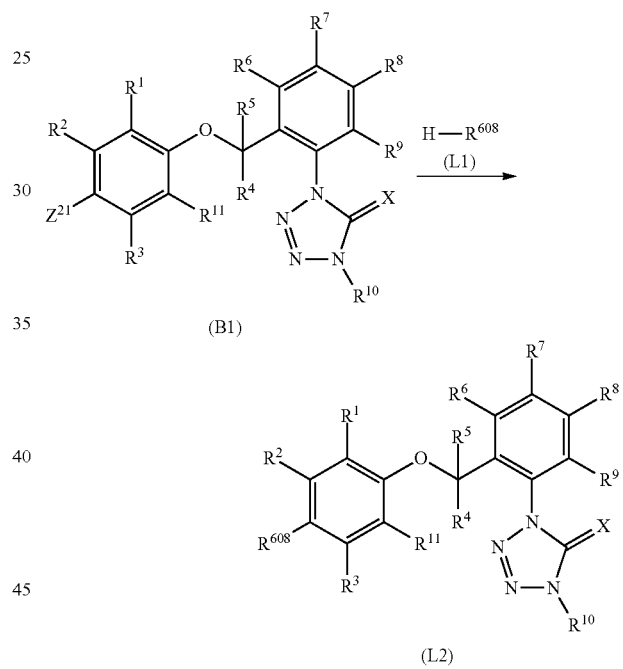

wherein $R^1$, $R^2$, $R^3$, $R^4$, $R^5$, $R^6$, $R^7$, $R^8$, $R^9$, $R^{10}$, $R^{11}$, $Z^{21}$, and X are the same as defined above, and $R^{608}$ represents an imidazol-1-yl group, a 1,2,3-triazol-1-yl group, a 1,2,3-triazol-2-yl group, a 1,2,4-triazol-1-yl group, a tetrazol-2-yl group, a 2-pyrrolidon-1-yl group, a pyrrolidin-1-yl group, or a pyrrol-1-yl group (provided that the imidazol-1-yl group, the 1,2,3-triazol-1-yl group, the 1,2,3-triazol-2-yl group, the 1,2,4-triazol-1-yl group, the tetrazol-2-yl group, the 2-pyrrolidon-1-yl group, the pyrrolidin-1-yl group, and the pyrrol-1-yl group optionally have one or more atoms or groups selected from Group $P^4$).

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the catalyst to be used in the reaction include copper(I) iodide, copper(II) acetate, palladium (II) acetate/triscyclohexylphosphine, bis(diphenylphosphaneferrocenyl)palladium (II) dichloride, palladium (II) acetate/dicyclohexyl(2',4',6'-triisopropylbiphenyl-2-yl)phosphine, tris(dibenzylideneacetone)dipalladium/xantphos, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (L1) is usually used in the proportion within a range of 1 to 10 mols, the catalyst is usually used in the proportion within a range of 0.001 to 5 mols, and the base is usually used in the proportion within a range of 0.5 to 10 mols, based on 1 mol of the compound (B1).

In the reaction, if necessary, ligands such as 1,10-phenanthroline, tetramethylethylenediamine, and L-proline may be added, and these compounds are usually used in the proportion within a range of 0.001 to 5 mols based on 1 mol of the compound (B1).

The reaction temperature of the reaction is usually within a range of −20 to 200° C. The reaction time is usually within a range of 0.1 to 24 hours.

After completion of the reaction, the compound (L2) can be isolated by performing post-treatment operations such as extraction of the reaction mixture with an organic solvent, and drying and concentration of the organic layer. Alternatively, the compound (L2) can be isolated by performing post-treatment operations such as concentration of the reaction mixture. The isolated compound can be further purified by chromatography, recrystallization, and the like.

(Production Process M)

A compound represented by the following formula (M2) (hereinafter referred to as the compound (M2)) can be produced by reacting the compound (XAE1) with a compound represented by the following formula (M1) (hereinafter referred to as the compound (M1)) in the presence of a base:

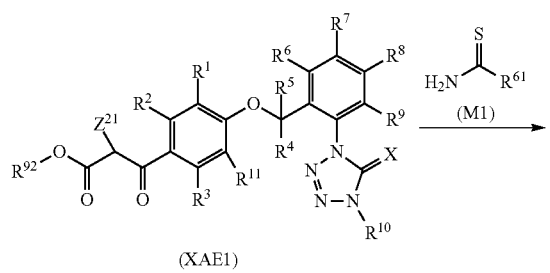

(XAE1)

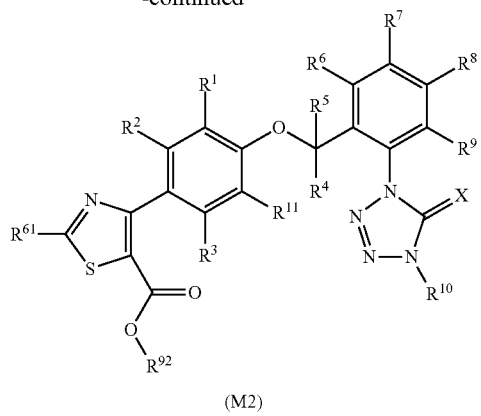

(M2)

wherein $R^1$, $R^2$, $R^3$, $R^4$, $R^5$, $R^6$, $R^7$, $R^8$, $R^9$, $R^{10}$, $R^{11}$, $Z^{21}$, and X are the same as defined above, $R^{92}$ represents a C1-C5 alkyl group, and $R^{61}$ represents a hydrogen atom, a C1-C6 alkyl group optionally having one or more halogen atoms, a C1-C6 alkoxy group optionally having one or more halogen atoms, a C6-C16 aryl group optionally having one or more halogen atoms, or a C6-C16 aryloxy group optionally having one or more halogen atoms.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (M1) is usually used in the proportion within a range of 1 to 10 mols, the catalyst is usually used in the proportion within a range of 0.001 to 5 mols, and the base is usually used in the proportion within a range of 0.5 to 10 mols, based on 1 mol of the compound (XAE1).

The reaction temperature of the reaction is usually within a range of −20 to 200° C. The reaction time is usually within a range of 0.1 to 24 hours.

After completion of the reaction, the compound (M2) can be isolated by performing post-treatment operations such as extraction of the reaction mixture with an organic solvent, and drying and concentration of the organic layer. Alternatively, the compound (M2) can be isolated by performing post-treatment operations such as concentration of the reaction mixture. The isolated compound can be further purified by chromatography, recrystallization, and the like.
(Production Process N)

The compound (N1) can be produced by reacting the compound (XAF1) with a dehydrating agent:

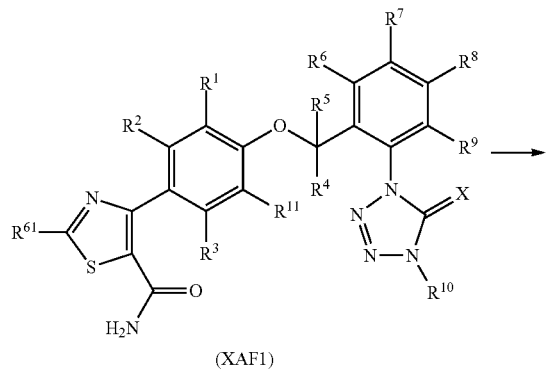

(XAF1)

(N1)

wherein $R^1$, $R^2$, $R^3$, $R^4$, $R^5$, $R^6$, $R^7$, $R^8$, $R^9$, $R^{10}$, $R^{11}$, $R^{61}$, and X are the same as defined above.

The reaction is usually performed in a solvent.

Examples of the solvent to be used in the reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile, organic acids such as formic acid, acetic acid, and trifluoroacetic acid; water; and mixtures thereof.

Examples of the halogenating agent to be used in the reaction include phosphorus oxychloride, diphosphorus pentaoxide, phosphorus oxybromide, oxalyl dichloride, N-chlorosuccinimide, N-bromosuccinimide, and the like.

In the reaction, the halogenating agent is usually used in the proportion within a range of 1 to 10 mols based on 1 mol of the compound (XAF1).

The reaction temperature of the reaction is usually within a range of −20 to 150° C. The reaction time is usually within a range of 0.1 to 24 hours.

After completion of the reaction, the compound (N1) can be isolated by performing post-treatment operations such as extraction of the reaction mixture with an organic solvent, and drying and concentration of the organic layer. The isolated compound may be further purified by operations such as distillation, chromatography, and recrystallization.

The process for synthesis of an intermediate compound will be described in detail below.
(Reference Production Process A)

A compound represented by the following formula (XA3) (hereinafter referred to as the compound (XA3)) can be produced by reacting a compound represented by the following formula (XA1) (hereinafter referred to as the compound (XA1)) or a compound represented by formula (XA2) (hereinafter referred to as the compound (XA2)) with an azidation agent:

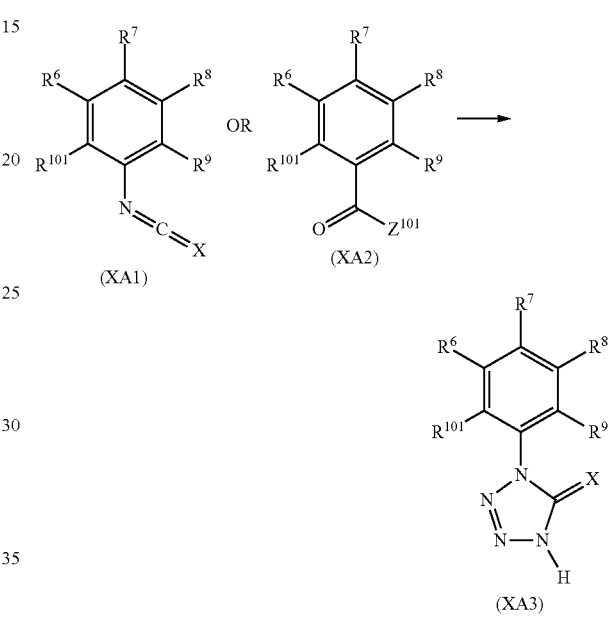

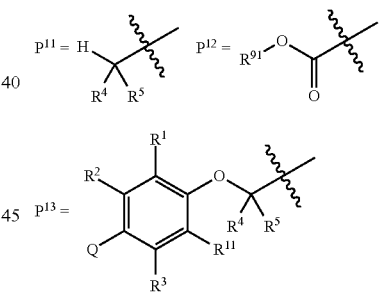

wherein $R^1$, $R^2$, $R^3$, $R^4$, $R^5$, $R^6$, $R^7$, $R^8$, $R^9$, $R^{10}$, $R^{11}$, Q, and X are the same as defined above, $R^{101}$ represents $P^{11}$, $P^{12}$, or $P^{13}$, $R^{91}$ represents a C1-C12 alkyl group, $Z^{101}$ represents a chlorine atom or a bromine atom, and the wavy line represents a binding site.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

(Reference Production Process B)

The compound (XA1) can be produced by reacting a compound represented by the following formula (XB1) (hereinafter referred to as the compound (XB1)) with an isocyanating agent:

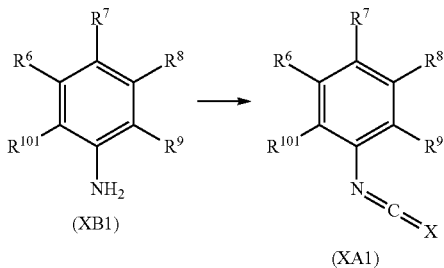

wherein $R^6$, $R^7$, $R^8$, $R^9$, $R^{101}$, and X are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols, based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

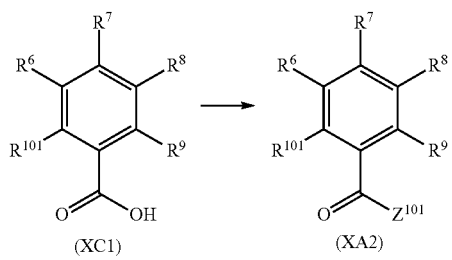

wherein $R^6$, $R^7$, $R^8$, $R^9$, $R^{101}$, and $Z^{101}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of −20 to 150° C. The reaction time is usually within a range of 0.1 to 24 hours.

In the reaction, a catalyst may be added and N,N-dimethylformamide, or the like is used. The amount of the catalyst to be used is usually in the proportion within a range of 0.001 to 1 mol based on 1 mol of the compound (XC1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by the following formula (XD1) (hereinafter referred to as the compound (XD1)), and then reacting the compound (XD1) with an isocyanating agent:

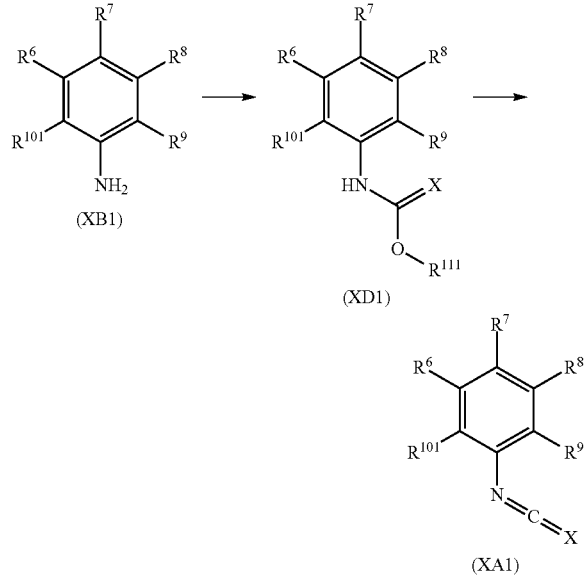

wherein $R^6$, $R^7$, $R^8$, $R^9$, $R^{101}$, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; aromatic hydrocarbons such as toluene and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

It is possible to use, as the isocyanating agent to be used in the reaction, for example, phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by the following formula (XE2) (hereinafter referred to as the compound (XE2)) can be produced by reacting a compound represented by the following formula (XE1) (hereinafter referred to as the compound (XE1)) with hydrogen in the presence of a catalyst:

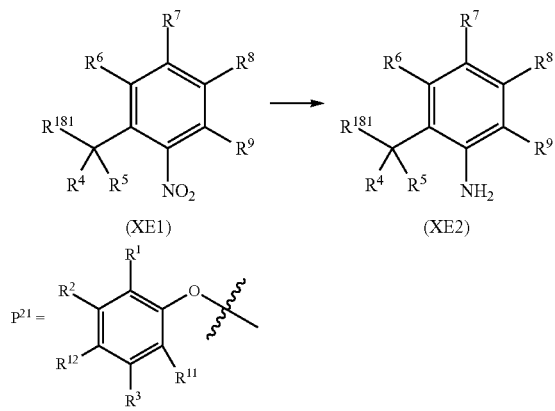

wherein $R^1$, $R^2$, $R^3$, $R^4$, $R^5$, $R^6$, $R^7$, $R^8$, $R^9$, $R^{10}$, $R^{11}$, and Q are the same as defined above, $R^{181}$ represents a hydrogen atom or $P^{21}$, and the wavy line represents a binding site.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; water; and mixtures thereof.

Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), Raney nickel, and the like.

In the reaction, the catalyst is usually used in the proportion within a range of 0.0001 to 1 mol based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process F)

The compound (XE2) can be produced by reacting the compound (XE1) with a reducing agent in the presence of an acid:

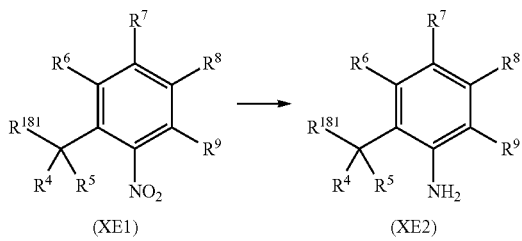

wherein $R^4$, $R^5$, $R^6$, $R^7$, $R^8$, $R^9$, and $R^{181}$ are the same as defined above.

The reaction is usually performed in a solvent.

Examples of the solvent to be used in the reaction include solvent include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, an aqueous ammonium chloride solution, and the like.

In the reaction, the reducing agent is usually used in the proportion within a range of 1 to 30 mols based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by the following formula (XG2) (hereinafter referred to as the compound (XG2)) can be produced by reacting a compound represented by the following formula (XG1) (hereinafter referred to as the compound (XG1)) with the compound (E1) in the presence of a base:

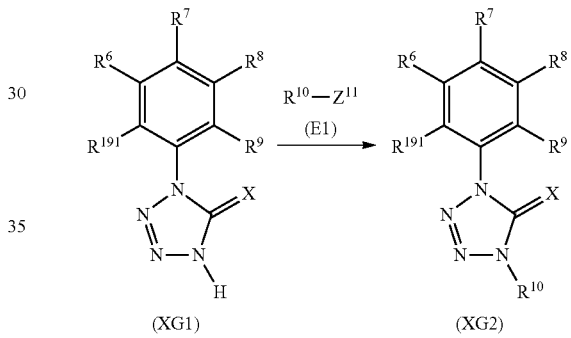

wherein $R^6$, $R^7$, $R^8$, $R^9$, $R^{10}$, and $Z^{11}$ are the same as defined above, and $R^{191}$ represents $P^{11}$ or $P^{12}$.

The reaction can be carried out in accordance with Production Process E.

(Reference Production Process H)

A compound represented by the following formula (XH2) (hereinafter referred to as the compound (XH2)) can be produced by reacting a compound represented by the following formula (XH1) (hereinafter referred to as the compound (XH1)) with a halogenating agent:

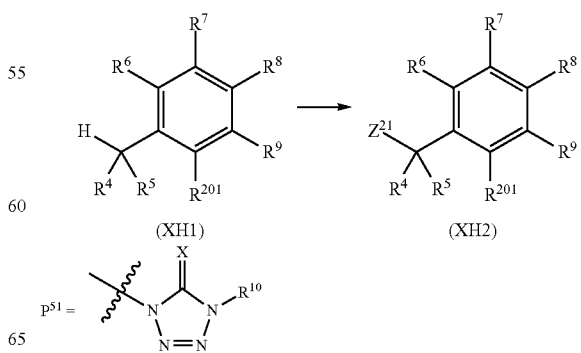

wherein $R^4, R^5, R^6, R^7, R^8, R^9, R^{10}, Z^{21}$, and X are the same as defined above, and $R^{201}$ represents $P^{51}$ or a nitro group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, and N-bromophthalimide.

In the reaction, a radical initiator can also be used.

Examples of the radical initiator to be used in the reaction include benzoyl peroxide, azobisisobutyronitrile (AIBN), diacyl peroxide, dialkylperoxydicarbonate, tert-alkylperoxyester, monoperoxycarbonate, di(tert-alkylperoxy)ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by the following formula (XJ2) (hereinafter referred to as the compound (XJ2)) can be produced by reacting the compound (XH2) with a compound represented by the following formula (XJ1) (hereinafter referred to as the compound (XJ1))

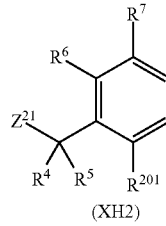
(XH2)

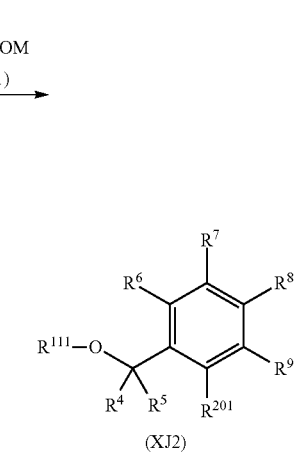
(XJ2)

wherein $R^4, R^5, R^6, R^7, R^8, R^9, R^{111}$, and $Z^{21}$ are the same as defined above, and M represents sodium, potassium, or lithium.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) usable in the reaction include sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide, sodium phenoxide, and the like.

In the reaction, the compound (XJ1) is usually used in the proportion within a range of 1 to 10 mols based on 1 mol of the compound (XH2).

The reaction temperature of the reaction is usually within a range of −20 to 150° C. The reaction time is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by the following formula (XK1) (hereinafter referred to as the compound (XK1)) can be produced by reacting the compound (XH2) with water in the presence of a base:

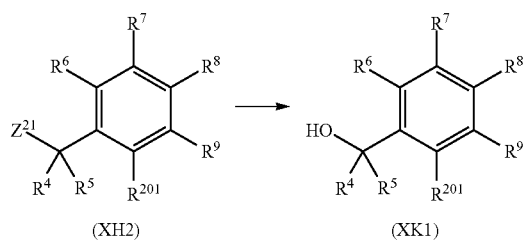

wherein $R^4, R^5, R^6, R^7, R^8, R^9, R^{201}$, and $Z^{21}$ are the same as defined above.

The reaction is usually performed in water, or a solvent containing water.

Examples of the solvent to be used in the reaction include ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, 4-dimethylaminopyridine, diisopropylethylamine, and diazabicycloundecene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to large excess based on 1 mol of the compound (XH2).

The reaction temperature of the reaction is usually within a range of −20 to 150° C. The reaction time is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

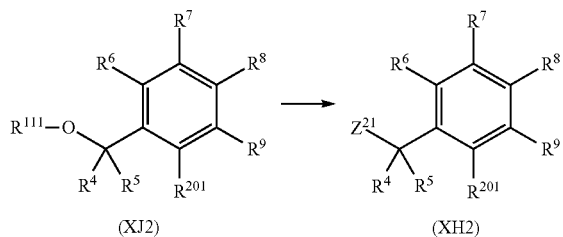

(XJ2)                (XH2)

wherein $R^4$, $R^5$, $R^6$, $R^7$, $R^8$, $R^9$, $R^{111}$, $R^{201}$, and $Z^{21}$ are the same as defined above.

The reaction is usually performed in a solvent.

Examples of the solvent to be used in the reaction include hydrocarbons such as n-hexane, cyclohexane, toluene, and xylene; halogenated hydrocarbons such as chloroform, 1,2-dichloroethane, and chlorobenzene; ketones such as acetone, methyl ethyl ketone, and methyl isobutyl ketone; nitriles such as acetonitrile; organic acids such as formic acid, acetic acid, and trifluoroacetic acid; water, and mixtures thereof.

Examples of the halogenating agent to be used in the reaction include hydrochloric acid, hydrobromic acid, hydroiodic acid, and hydrogen bromide.

Examples of the halogenating agent to be used in the reaction include hydrochloric acid, hydrobromic acid, and hydroiodic acid.

In the reaction, the halogenating agent is usually used in the proportion of 1 mol or more based on 1 mol of the compound (XJ2).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can be produced by reacting the compound (XK1) with a halogenating agent:

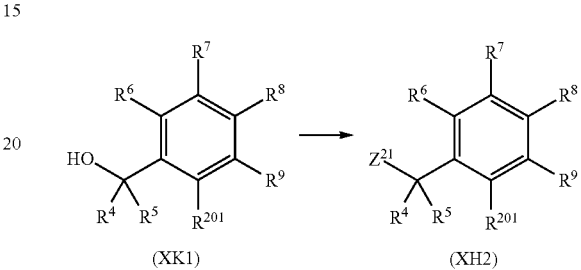

(XK1)                (XH2)

wherein $R^4$, $R^5$, $R^6$, $R^7$, $R^8$, $R^9$, $R^{201}$, and $Z^{21}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water, and mixtures thereof.

Examples of the halogenating agent to be used in the reaction include hydrobromic acid, hydrogen bromide, thionyl chloride, thionyl bromide, phosphorus oxychloride, phosphorus trichloride, phosphorous pentachloride, phosphorous oxybromide, phosphorous pentabromide, phosphorous triiodide, oxalyl dichloride, oxalyl dibromide, and the like.

In the reaction, the halogenating agent is usually used in the proportion within a range of 1 to 10 mols based on 1 mol of the compound (XK1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by the following formula (XM3) (hereinafter referred to as the compound (XM3)) can be produced by reacting the compound (XK1) with a compound represented by the following formula (XM2) (hereinafter referred to as the compound (XM2)) in the presence of a base:

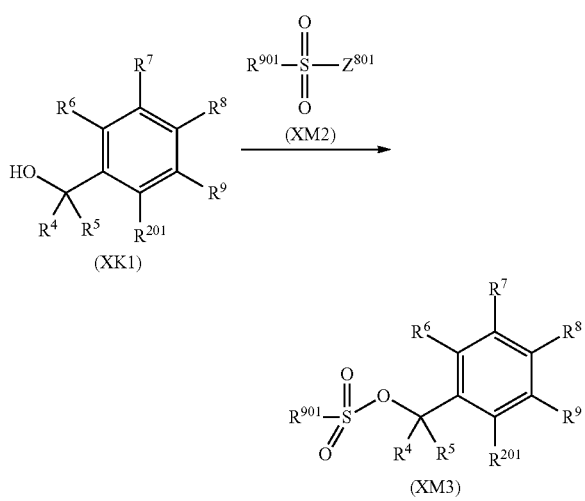

wherein $R^4$, $R^5$, $R^6$, $R^7$, $R^8$, $R^9$, and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

In the reaction, the compound (XM2) is usually used in the proportion within a range of 1 to 10 mols, and the base is usually used in the proportion within a range of 1 to 5 mols, based on 1 mol of the compound (XK1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer.

The isolated compound may be further purified by operations such as distillation, chromatography, and recrystallization.

(Reference Production Process N)

A compound represented by the following formula (XN12) (hereinafter referred to as the compound (XN12)) can be produced by subjecting a compound represented by the following formula (XN11) (hereinafter referred to as the compound (XN11)) and the compound (G21) to a coupling reaction in the presence of a base and a catalyst:

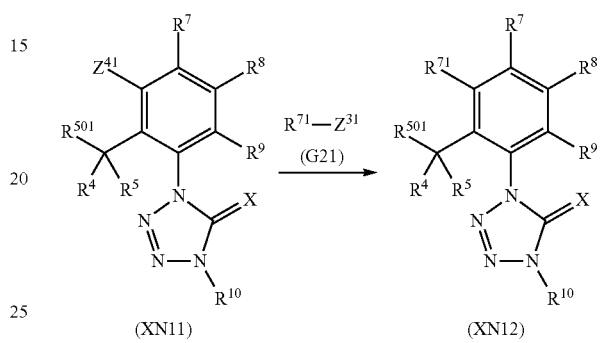

wherein $R^{501}$ represents a hydrogen atom or an $OR^{111}$ group, and $R^{111}$, $R^4$, $R^5$, $R^7$, $R^8$, $R^9$, $R^{10}$, $R^{71}$, X, $Z^{31}$, and $Z^{41}$ are the same as defined above.

The reaction can be carried out in accordance with Production Process B.

A compound represented by the following formula (XN22) (hereinafter referred to as the compound (XN22)) can be produced by subjecting a compound represented by the following formula (XN21) (hereinafter referred to as the compound (XN21)) and the compound (G22) to a coupling reaction in the presence of a base and a catalyst:

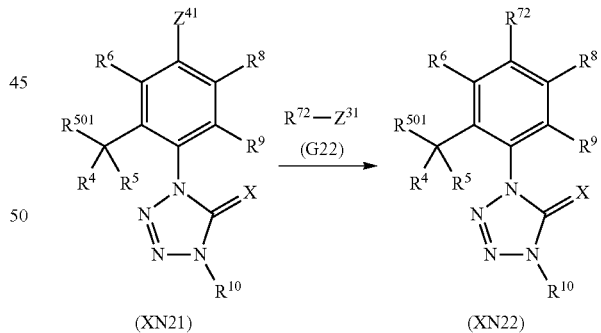

wherein $R^4$, $R^5$, $R^6$, $R^8$, $R^9$, $R^{10}$, $R^{72}$, $R^{501}$, X, $Z^{31}$, and $Z^{41}$ are the same as defined above.

The reaction can be carried out in accordance with Production Process B.

A compound represented by the following formula (XN32) (hereinafter referred to as the compound (XN32)) can be produced by subjecting a compound represented by the following formula (XN31) (hereinafter referred to as the compound (XN31)) and the compound (G22) to a coupling reaction in the presence of a base and a catalyst:

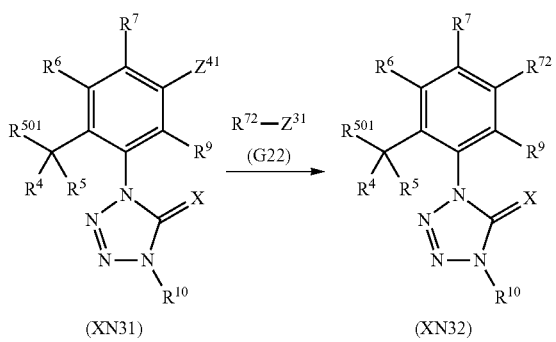

(XN31) → (XN32)

wherein $R^4$, $R^5$, $R^6$, $R^7$, $R^9$, $R^{10}$, $R^{72}$, $R^{501}$, X, $Z^{31}$, and $Z^{41}$ are the same as defined above.

The reaction can be carried out in accordance with Production Process B.

A compound represented by the following formula (XN42) (hereinafter referred to as the compound (XN42)) can be produced by subjecting a compound represented by the following formula (XN41) (hereinafter referred to as the compound (XN41)) and the compound (G22) to a coupling reaction in the presence of a base and a catalyst:

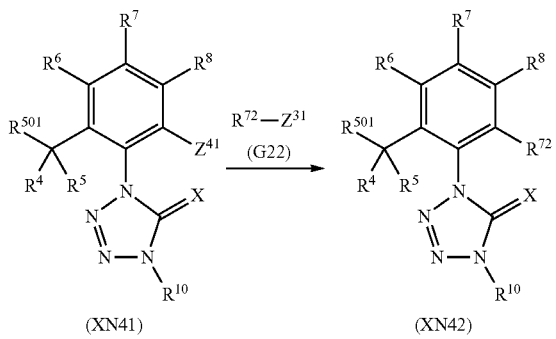

(XN41) → (XN42)

wherein $R^4$, $R^5$, $R^6$, $R^7$, $R^8$, $R^{10}$, $R^{72}$, $R^{501}$, X, $Z^{31}$, and $Z^{41}$ are the same as defined above.

The reaction can be carried out in accordance with Production Process B.

In accordance with Production Process B, it is possible to produce a compound in which two or more substituents selected from $R^6$, $R^7$, $R^8$, and $R^9$ are $R^{71}$ and/or $R^{72}$, among Group of compounds represented by the following formula (XN50):

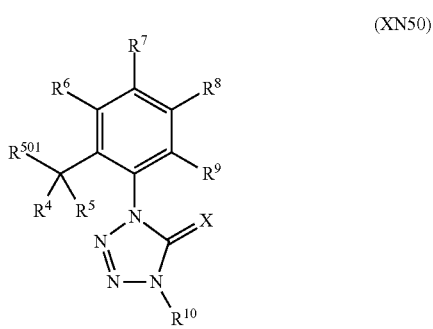

(XN50)

wherein $R^4$, $R^5$, $R^6$, $R^7$, $R^8$, $R^9$, $R^{10}$, $R^{501}$, and X are the same as defined above.

It is also possible to produce the compound (XN50) by using the other known coupling reaction in place of the coupling reaction mentioned in the Production Process B.
(Reference Production Process O)

A compound represented by the following formula (XW2) (hereinafter referred to as the compound (XW2)) can be produced by reacting a compound represented by the following formula (XW1) (hereinafter referred to as the compound (XW1)) with a compound represented by the following formula (XW3) (hereinafter referred to as the compound (XW3)) in the presence of a reaction accelerator:

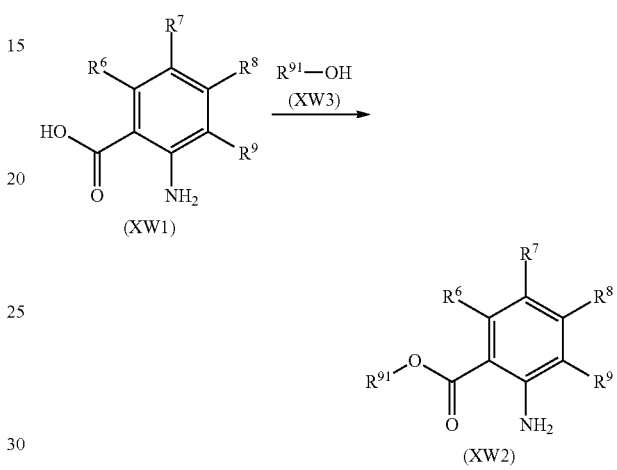

wherein $R^6$, $R^7$, $R^8$, $R^9$, and $R^{91}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) usable in the reaction include methanol, ethanol, propanol, isopropanol, n-butanol, sec-butanol, t-butanol, n-pentanol, and the like.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, the reaction accelerator is usually used in the proportion within a range of 0.01 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 0.001 to 5 mols based on 1 mol of the compound (XW1).

In the reaction, an excess amount of the compound (XW3) is used based on the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by the following formula (XV1) (hereinafter referred to as the compound (XV1)), followed by a reaction with the compound (XW3):

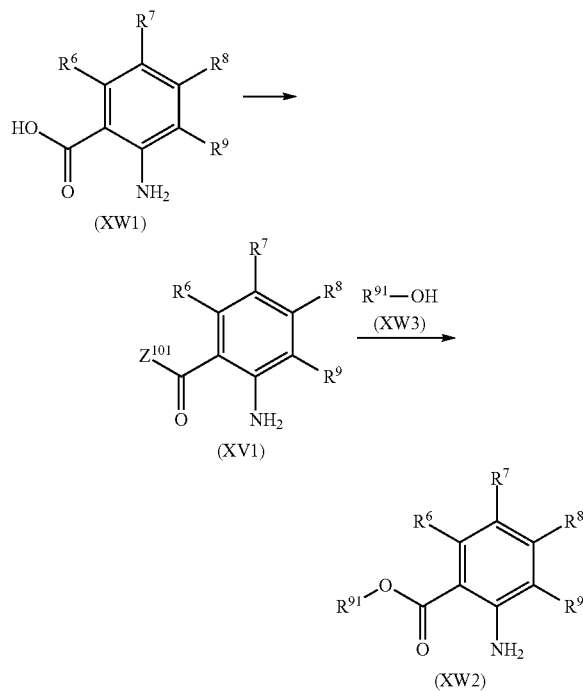

wherein $R^6$, $R^7$, $R^8$, $R^9$, $R^{91}$, and $Z^{101}$ are the same as defined above.

The process for producing the compound (XV1) by reacting the compound (XW1) with a halogenating agent can be carried out in accordance with Reference Production Process C.

The process for producing the compound (XW2) from the compound (XV1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) usable in the reaction include methyl alcohol, ethyl alcohol, propyl alcohol, isopropyl alcohol, n-butyl alcohol, sec-butyl alcohol, n-pentanol, and the like.

In the reaction, an excess amount of the compound (XW3) is used based on the compound (XV1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

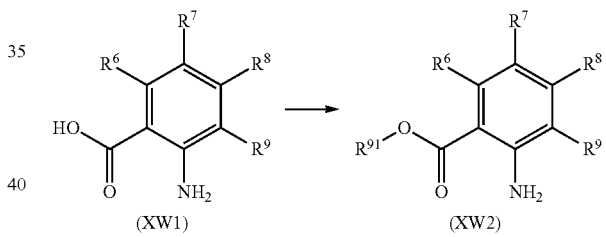

wherein $R^6$, $R^7$, $R^8$, $R^9$, and $R^{91}$ are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the alkylating agent usable in the reaction include diazomethane, trimethylsilyldiazomethane; halogenated alkyls such as methyl bromide, ethyl bromide, n-propyl bromide, methyl iodide, ethyl iodide, n-propyl bromide, and cyclopropyl bromide; sulfuric acid dialkyls such as dimethyl sulfate, diethyl sulfate, and di-n-propyl sulfate; and alkyl or arylsulfonic acid esters, such as methyl p-toluenesulfonate, ethyl p-toluenesulfonate, n-propyl p-toluenesulfonate, methyl methanesulfonate, ethyl methanesulfonate, and n-propyl methanesulfonate.

In the reaction, the alkylating agent is usually used in the proportion within a range of 1 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; and quaternary ammonium salts such as tetra(n-butyl)ammonium hydroxide may be added, and these compounds are usually used in the proportion within a range of 0.001 to 5 mols based on 1 mol of the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

A compound represented by the following formula (XS2) (hereinafter referred to as the compound (XS2)) can be produced by reacting a compound represented by the following formula (XS1) (hereinafter referred to as the compound (XS1)) with the compound (A2) in the presence of a base:

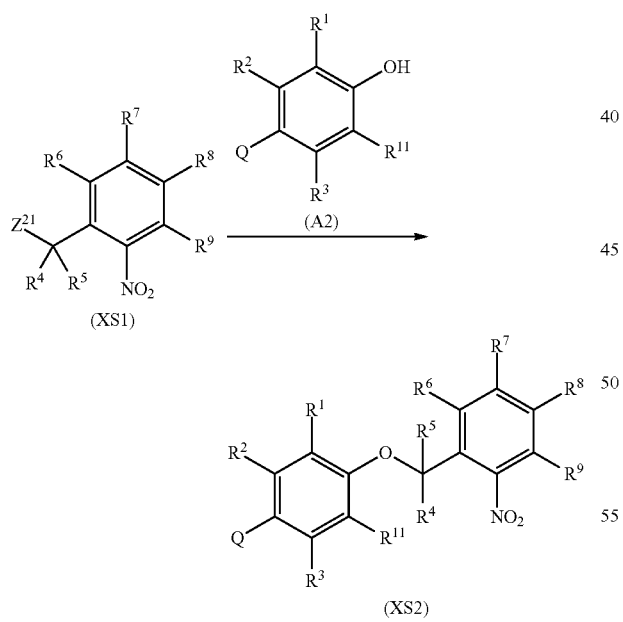

wherein $R^1$, $R^2$, $R^3$, $R^4$, $R^5$, $R^6$, $R^7$, $R^8$, $R^9$, $R^{11}$, Q, and $Z^{21}$ are the same as defined above.

The reaction can be carried out in accordance with the Production Process A.

(Reference Production Process U)

A compound represented by the following formula (XU2) (hereinafter referred to as the compound (XU2)) can be produced by subjecting a compound represented by the following formula (XU1) (hereinafter referred to as the compound (XU1)) and the compound (B2) to a coupling reaction in the presence of a base and a catalyst:

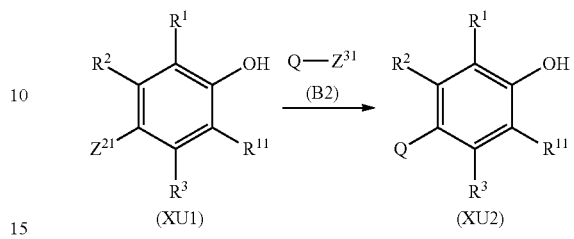

wherein $R^1$, $R^2$, $R^3$, $R^{11}$, $Z^{21}$, $Z^{31}$, and Q are the same as defined above.

The reaction can be carried out in accordance with the Production Process B.

(Reference Production Process V)

The compound (B1) can be produced by reacting a compound represented by the following formula (XO1) (hereinafter referred to as the compound (XO1)) with the compound (XU1) in the presence of a base:

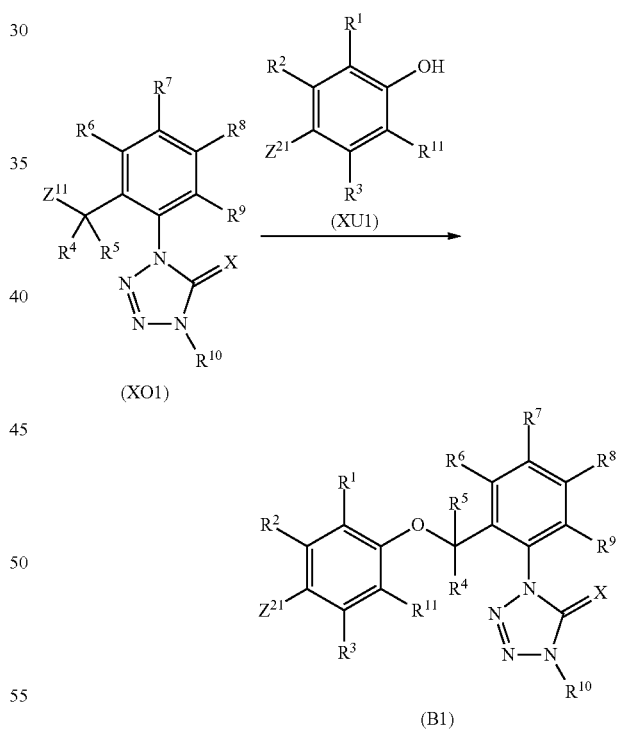

wherein $R^1$, $R^2$, $R^3$, $R^4$, $R^5$, $R^6$, $R^7$, $R^8$, $R^9$, $R^{10}$, $R^{11}$, $Z^{11}$, and $Z^{21}$ are the same as defined above.

The reaction can be carried out in accordance with the Production Process A.

(Reference Production Process W)

The compound (C21) can be produced by reacting the compound (B1) with a Borylation reagent in the presence of a catalyst and a base:

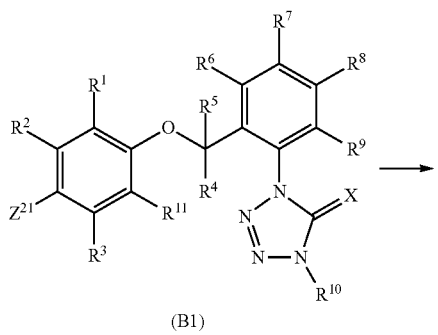

(B1)

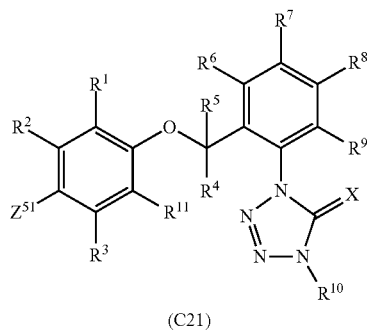

(C21)

wherein $R^1$, $R^2$, $R^3$, $R^4$, $R^5$, $R^6$, $R^7$, $R^8$, $R^9$, $R^{10}$, $R^{11}$, and $Z^{21}$ are the same as defined above, and $Z^{51}$ represents an alkoxyboranyl group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the Borylation reagent to be used in the reaction include bis(pinacolato)diboron, pinacolborane, and the like.

Examples of the catalyst to be used in the reaction include palladium (II) acetate, dichlorobis(triphenylphosphine)palladium, tetrakistriphenylphosphinepalladium(0), palladium (II) acetate/tricyclohexylphosphine, bis(diphenylphosphaneferrocenyl)palladium (II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the Borylation reagent is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time is usually within a range of 0.1 to 24 hours.

After completion of the reaction, the compound (C21) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process X)

A compound represented by the following formula (XX2) (hereinafter referred to as the compound (XX2)) can be produced by reacting a compound represented by the following formula (XX1) (hereinafter referred to as the compound (XX1)) with the compound (X1) in the presence of a base:

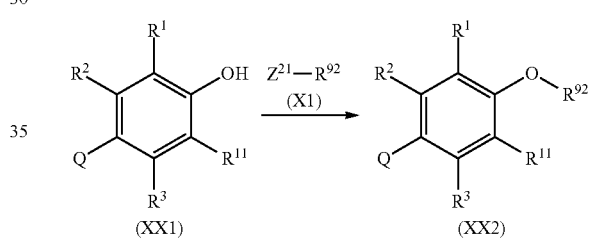

wherein $R^1$, $R^2$, $R^3$, $R^{11}$, $R^{92}$, Q, and $Z^{21}$ are the same as defined above.

The reaction can be carried out in accordance with the Production Process A.

(Reference Production Process Y)

A compound represented by the following formula (XY2) formula (hereinafter referred to as the compound (XY2)) can be produced by subjecting a compound represented by the following formula (XY1) (hereinafter referred to as the compound (XY1)) and the compound (Y1) to a coupling reaction in the presence of a base and a catalyst:

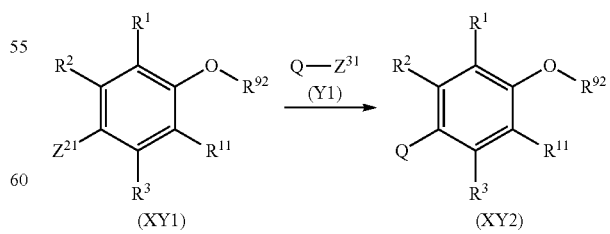

wherein $R^1$, $R^2$, $R^3$, $R^{11}$, $Z^{21}$, $Z^{31}$, $R^{92}$, and Q are the same as defined above.

The reaction can be carried out in accordance with the Production Process B.

(Reference Production Process Z)

A compound represented by the following formula (XZ2) (hereinafter referred to as the compound (XZ2)) can be produced by reacting a compound represented by the following formula (XZ1) (hereinafter referred to as the compound (XZ1)) with an acid:

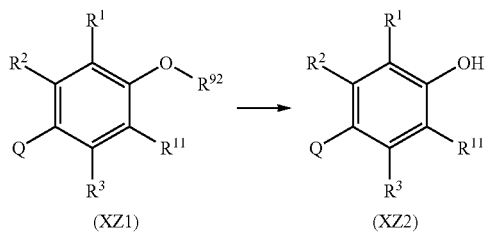

wherein $R^1$, $R^2$, $R^3$, $R^{11}$, $R^{92}$, and Q are the same as defined above.

The reaction is usually performed in a solvent.

Examples of the solvent to be used in the reaction include alcohols such as methanol, ethanol, propanol, and butanol; water; acetic acid; and mixtures thereof.

Examples of the acid to be used in the reaction include acetic acid, hydrochloric acid, hydrobromic acid, and the like, and aqueous solutions thereof can also be used as the solvent.

In the reaction, an excess amount of the acid is usually used based on 1 mol of the compound (XZ1).

The reaction temperature of the reaction is usually within a range of −20 to 150° C. The reaction time is usually within a range of 0.1 to 100 hours.

After completion of the reaction, the compound (XZ2) can be isolated by performing post-treatment operations such as extraction of the reaction mixture with an organic solvent, and drying and concentration of the organic layer.

Alternatively, the compound (XZ2) can be isolated by performing post-treatment operations such as concentration of the reaction mixture. The isolated compound can be further purified by chromatography, recrystallization, and the like.

(Reference Production Process AA)

A compound represented by the following formula (XAA2) can be produced by reacting a compound represented by formula (XAA1) with a reducing agent:

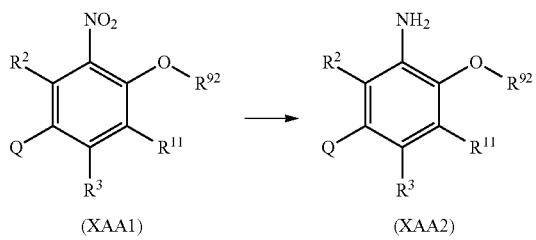

wherein $R^2$, $R^3$, $R^{11}$, $R^{92}$, and Q are the same as defined above.

The reaction can be carried out in accordance with the Production Process F.

(Reference Production Process AB)

A compound represented by the following formula (XAB2) (hereinafter referred to as the compound (XAB2)) can be produced by reacting a compound represented by formula (XAB1) (hereinafter referred to as the compound (XAB1)) with an acid, a diazotizing agent, and a compound represented by formula (AB1) (hereinafter referred to as the compound (AB1)):

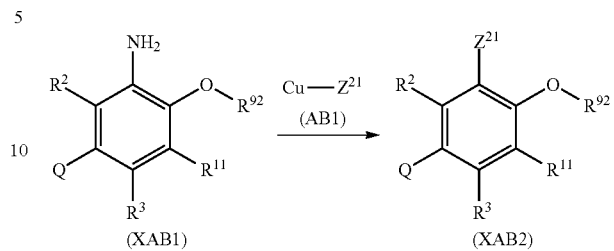

wherein $R^2$, $R^3$, $R^{11}$, $R^{92}$, $Z^{21}$, and Q are the same as defined above.

The reaction is usually performed in a solvent.

Examples of the solvent to be used in the reaction include water, ethers such as tetrahydrofuran, 1,4-dioxane, ethylene glycol dimethyl ether, methyl tert-butyl ether, and diisopropyl ether; nitriles such as acetonitrile; and mixtures thereof.

Examples of the acid to be used in the reaction include hydrochloric acid, hydrobromic acid, and the like, and aqueous solutions thereof can also be used as the solvent.

Examples of the diazotizing agent to be used in the reaction include sodium nitrite, tert-butyl nitrite, and the like.

In the reaction, an excess amount of the acid is usually used, the diazotizing agent is usually used in the proportion within a range of 1 to 10 mols, and the compound (AB1) is used in the proportion within a range of 1 to 10 mols, based on 1 mol of the compound (XAB1).

The reaction temperature of the reaction is usually within a range of −20 to 60° C. The reaction time is usually within a range of 0.1 to 100 hours.

After completion of the reaction, the compound (XAB2) can be isolated by performing post-treatment operations such as extraction of the reaction mixture with an organic solvent, and drying and concentration of the organic layer.

Alternatively, the compound (XAB2) can be isolated by performing post-treatment operations such as concentration of the reaction mixture. The isolated compound can be further purified by chromatography, recrystallization, and the like.

(Reference Production Process AC)

A compound represented by the following formula (XAC2) (hereinafter referred to as the compound (XAC2)) can be produced by reacting a compound represented by the following formula (XAC1) (hereinafter referred to as the compound (XAC1)) with a condensing agent and a compound represented by formula (XAC3) (hereinafter referred to as the compound (XAC3)):

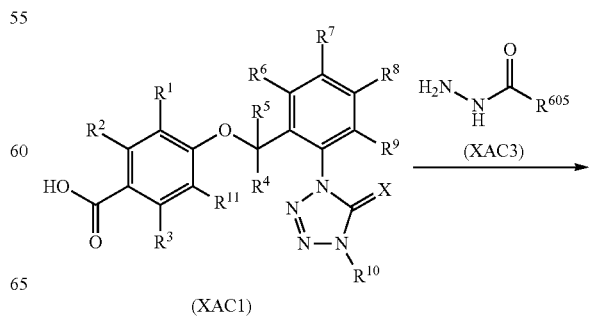

-continued

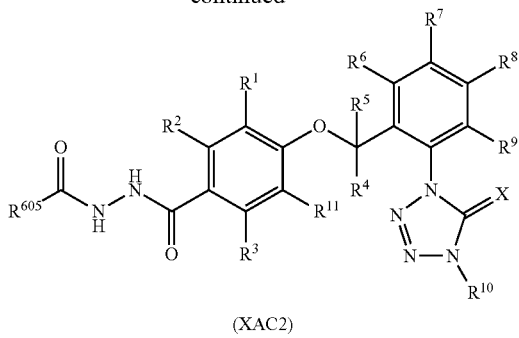

(XAC2)

wherein $R^1$, $R^2$, $R^3$, $R^4$, $R^5$, $R^6$, $R^7$, $R^8$, $R^9$, $R^{10}$, $R^{11}$, $R^{605}$, and X are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile; and mixtures thereof.

Examples of the condensing agent to be used as the reaction include N,N'-dicyclohexylcarbodiimide (DCC), N,N'-diisopropylcarbodiimide (DIC), 1-ethyl-3-(3-dimethylaminopropyl)carbodiimide (EDC), 1-ethyl-3-(3-dimethylaminopropyl)carbodiimide hydrochloride (EDC.HCl), 1H-benzotriazol-1-yloxytris(dimethylamino)phosphonium hexafluorophosphate (BOP), 1H-benzotriazol-1-yloxytripyrrolidinophosphonium hexafluorophosphate (PyBOP), O-(benzotriazol-1-yl)-N,N,N,N',N'-tetramethyluronium hexafluorophosphate (HBTU), O-(benzotriazol-1-yl)-N,N,N',N'-tetramethyluronium tetrafluoroborate (TBTU), O-(7-azabenzotriazol-1-yl)-N,N,N,N'-tetramethyluronium hexafluorophosphate (HATU), O-(7-azabenzotriazol-1-yl)-N,N,N',N'-tetramethyluronium tetrafluoroborate (TATU), 1,1'-carbonylbis-1H-imidazole (CDI), 4-(4,6-dimethoxy-1,3,5-trizin-2-yl)-4-methylmorpholinium chloride (hereinafter referred to as DMT-MM), and the like.

In the reaction, the compound (XAC3) is usually used in the proportion within a range of 1 to 10 mols, and the condensing agent is usually used in the proportion within a range of 1 to 10 mols, based on 1 mol of the compound (XAC1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate may be added, and these compounds are usually used in the proportion within a range of 1 to 5 mols based on 1 mol of the compound (XAC1).

The reaction temperature of the reaction is usually within a range of −20 to 150° C. The reaction time is usually within a range of 0.1 to 24 hours.

After completion of the reaction, the compound (XAC2) can be isolated by performing post-treatment operations such as extraction of the reaction mixture with an organic solvent, and drying and concentration of the organic layer. The isolated compound can be further purified by chromatography, recrystallization, and the like.

(Reference Production Process AD)

The compound (XAD2) can be produced by reacting the compound (XAD1) with a compound represented by formula (XAD3) formula (hereinafter referred to as the compound (XAD3)) in the presence of a base:

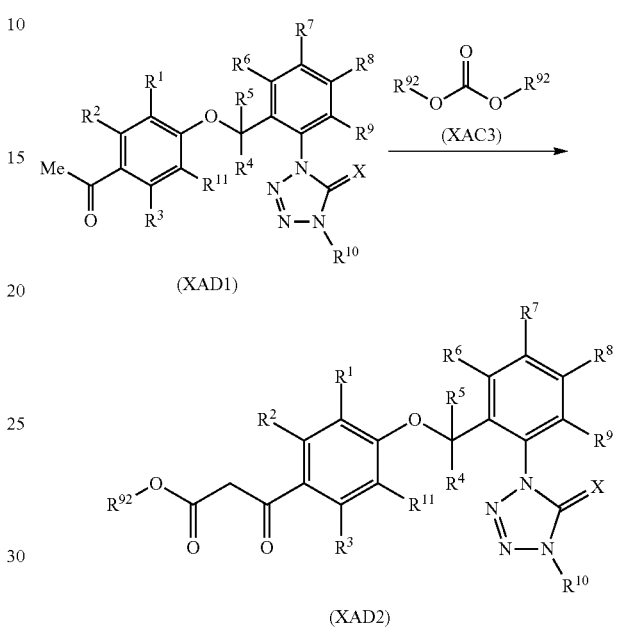

wherein $R^1$, $R^2$, $R^3$, $R^4$, $R^5$, $R^6$, $R^7$, $R^8$, $R^9$, $R^{10}$, $R^{11}$, $R^{92}$, and X are the same as defined above.

The reaction is usually performed in a solvent.

Examples of the solvent to be used in the reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include alkali metal carbonates such as lithium carbonate, sodium carbonate, potassium carbonate, and cesium carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the compound (XAD3) is usually used in the proportion within a range of 1 to 10 mols, and the base is usually used in the proportion within a range of 1 to 10 mols, based on 1 mol of the compound (XAD1).

The reaction temperature of the reaction is usually within a range of −20 to 150° C. The reaction time is usually within a range of 0.1 to 24 hours.

In the reaction, if necessary, additives may be added, and examples of the additive include 18-crown-6-ether, dibenzo-18-crown-6-ether, and the like. These additives are usually in the proportion within a range of 0.001 to 1.2 mols based on 1 mol of the compound (XAD1).

After completion of the reaction, the compound (XAD2) can be isolated by performing post-treatment operations such as extraction of the reaction mixture with an organic solvent, and drying and concentration of the organic layer. The isolated compound can be further purified by chromatography, recrystallization, and the like.

(Reference Production Process AE)

The compound (XAE1) can be produced by reacting the compound (XAD2) with a halogenating agent:

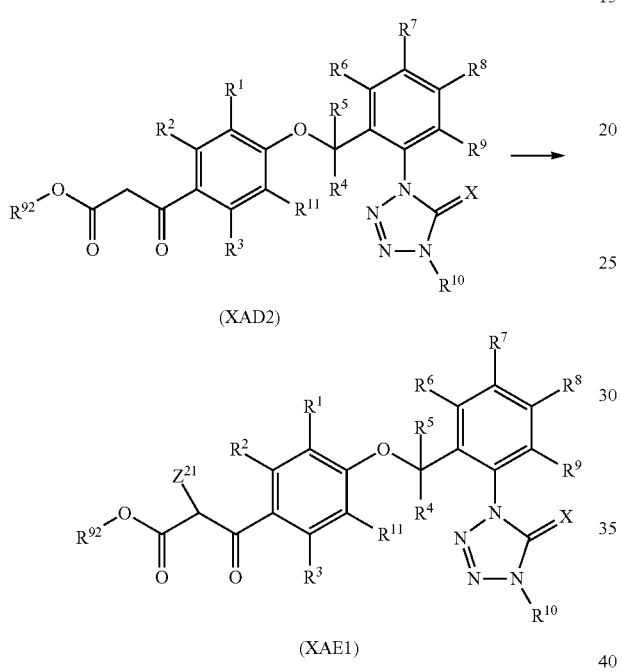

(XAD2)

(XAE1)

wherein $R^1$, $R^2$, $R^3$, $R^4$, $R^5$, $R^6$, $R^7$, $R^8$, $R^9$, $R^{10}$, $R^{11}$, $R^{92}$, $Z^{21}$ and X are the same as defined above.

The reaction is usually performed in a solvent.

Examples of the solvent to be used in the reaction include hydrocarbons such as heptane, hexane, cyclohexane, pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include bromine, thionyl chloride, thionyl bromide, N-bromosuccinimide, N-bromosuccinimide, N-bromosuccinimide, and the like.

In the reaction, the halogenating agent is usually used in the proportion within a range of 1 to 10 mols based on 1 mol of the compound (XAD2).

The reaction temperature of the reaction is usually within a range of −20 to 150° C. The reaction time is usually within a range of 0.1 to 24 hours.

After completion of the reaction, the compound (XAE1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process AF)

The compound (XAF1) can be produced by reacting the compound (M2) with an amidating agent:

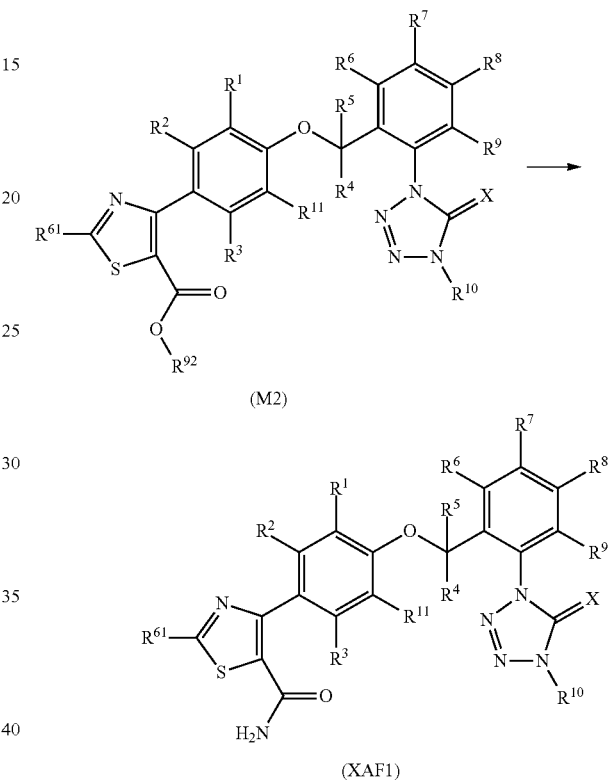

(M2)

(XAF1)

wherein $R^1$, $R^2$, $R^3$, $R^4$, $R^5$, $R^6$, $R^7$, $R^8$, $R^9$, $R^{10}$, $R^{11}$, $R^{92}$, $R^{61}$, and X are the same as defined above.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as heptane, hexane, cyclohexane, pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; alcohols such as methanol, ethanol, propanol, and butanol; water; and mixtures thereof.

It is possible to use, as the amidating agent to be used in the reaction, aqueous ammonium solution, ammonia hydrochloride, ammonia sulfate, ammonia gas, and the like. The amidating agent can also be used as the solvent.

In the reaction, the amidating agent is usually used in the proportion within a range of 1 mol to large excess based on 1 mol of the compound (M2).

The reaction temperature of the reaction is usually within a range of −20 to 150° C. The reaction time is usually within a range of 0.1 to 72 hours.

After completion of the reaction, the compound (XAF1) can be isolated by performing post-treatment operations such as extraction of the reaction mixture with an organic solvent, and drying and concentration of the organic layer. When the precipitate is formed, the compound (XAF1) can be isolated by filtering the precipitate. The isolated compound may be further purified by operations such as distillation, chromatography, and recrystallization.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexane, and kerosene), esters (for example, ethyl acetate and butyl acetate), nitriles (for example, acetonitrile and isobutyronitrile), ethers (for example, dioxane and diisopropylether), acid amides (for example, N,N-dimethylformamide and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or esters thereof, and the like.

The method for applying the present control agent is not particularly limited, as long as the applying form is a form by which the present control agent may be applied substantially, and includes, for example, an application to plants such as a foliage application; an application to area for cultivating plants such as a submerged treatment; and an application to soil such as seed disinfection.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present compound can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), apiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers; Ornamental foliage plants:

Fruits: pomaceous fruits (for example, apple, pear, Japanese pear, Chinese quince, and quince), stone fruits (for example, peach, plum, nectarine, Prunus mume, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese medlar, banana, coffee, date palm, coconuts, and the like.

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir tree, hemlock, juniper, *Pinus, Picea*, and *Taxus cuspidate*); and the like.

The above-mentioned "plants" include genetically modified crops.

The pests which can be controlled by the present control agent include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), yellow spot (*Pyrenophora tritici-repentis*), seeding blight caused by rhizoctonia fungus (*Rhizoctonia solani*), and take-all disease (*Gaeumannomyces graminis*); Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and seeding blight caused by rhizoctonia fungus (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum gfaminicola*), gray leaf spot (*Cercospora zeae-maydis*), eyespot (*Kabatiella zeae*), and phaeosphaeria leaf spot (*Phaeosphaeria maydis*); Cotton diseases: anthracnose (*Colletotrichum gossypii*), grey mildew (*Ramuraria areola*), and alternaria leaf spot (*Alternaria macrospora, A. gossypii*);

Coffee diseases: rust (*Hemileia vastatrix*); Rape seed diseases: *sclerotinia* rot (*Sclerotinia sclerotiorum*), gray leaf spot (*Alternaria brassicae*), and root rot (*Phoma lingam*); Citrus diseases: melanose (*Diaporthe citri*), scab (*Elsinoe fawcetti*), and green mold (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*);

Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora parasitica*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia rot (*Rhizoctonia solani*), septoria brown spot (*Septoria glycines*), and frog eye leaf spot (*Cercospora sojina*); Kidney bean diseases: anthracnose (*Colletotrichum lindemuthianum*); Peanut diseases: early leaf spot (*Cercospora personata*), brown leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and verticillium wilt (*verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces sochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: *botrytis* leaf blight (*Botrytis cinerea, B. byssoidea, B. squamosa*), gray-mold neck rot (*Botrytis allii*), and small sclerotial rot (*Botrytis squamosa*); various crops diseases: gray mold (*Botrytis cinerea*) and *sclerotinia* rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as Calformia red scale (*Aonidiella aurantii*), San Jose scale (*Comstockaspis perniciosa*), citrus north scale (*Unaspis citri*), red wax scale (*Ceroplastes rubens*), and cottonycushion scale (*Icerya purchasi*); lace bugs (Tingidae); and jumping plant lice (Homoptera, Psylloidea).

Lepidoptera: pyralid moths (Pyralidae) such as rice stem borer (*Chilo suppressalis*), yellow rice borer (*Tryporyza*

*incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), Thoricoplusia spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit *tortrix* (*Adoxophyes orana fasciata*), smaller tea *tortrix* (*Adoxophyes* sp.), oriental tea *tortrix* (*Homona magnanima*), apple *tortrix* (*Archips fuscocupreanus*), and codling moth (*Cydia pomonella*); leafblotch miners (Gracillariidae) such as tea leafroller (*Caloptilia theivora*) and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutella xylostella*); gelechild moths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: *thrips* such as yellow citrus thrip (*Frankliniella occidentalis*), melon thrip (*Thrips palmi*), yellow tea thrip (*Scirtothrips dorsalis*), onion *thrips* (*Thrips tabaci*), flower thrip (*Frankliniella intonsa*), and tobacco thrip (*Frankliniella fusca*).

Diptera: houseflies (*Musca domestica*), common mosquito (*Culex pipiens pallens*), horsefly (*Tabanus trigonus*), onion maggot (*Hylemya anitqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Meditteranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leaf-cutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta America*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides ptrenyssnus*)); Cheyletidae (for example, cheyletid mite (*Cheyletus eruditus*), *Cheyletus malaccensis*, and *Cheyletus moorei*; and Dermanyssidae.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, goat, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *dermacentor* spp., *Ornithodoros* spp. (for example, *Ornithodoros moubata*), red mite (*Dermahyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp.), *Linognathus* spp., *Haematopinus* spp., *Ctenocephalides* spp. (for example, cat flea (*Ctenocephalides felis*)) *Xenosylla* spp., Pharaoh's ant (*monomorium pharaonis*) and nematodes [for example, hairworm (for example, *Nippostrongylus brasiliensis*, *Trichostrongylus axei, Trichostrongylus colubriformis*), *Trichinella* spp. (for example, *Trichinella* spiriralis), barber pole worm (*Haemonchus contortus*), *Nematodirus* spp. (for example, *Nematodirus battus*), *Ostertagia circumcincta*, *Cooperia* spp., *Hymenolepis nana*, and the like.

EXAMPLES

The present invention will be described in more detail below by way of Production Examples, Formulation Examples, and Test Examples, but the present invention is not limited to these Examples.

Names of intermediates used in Production Examples are shown by names given to intermediates produced in the below-mentioned Reference Production Examples, for example, C4A.

When the numeral part of the name of this intermediate is the number of Reference Production Example and the title of the intermediate is C4A, it means an intermediate to be produced in Reference Production Example 4.

First, Production Examples will be shown.

Production Example 1

A mixture of 0.43 g of C27A, 0.21 g of 2-bromothiophene, 0.02 g of 1,1'-bis(diphenylphosphino)ferrocene]palladium (II) dichloride dichloromethane adduct, 0.70 g of tripotassium phosphate, 4 mL of 1,2-dimethoxyethane, and 0.4 ml of water was stirred at 80° C. for 4 hours. After cooling, the reaction mixture was concentrated and the residue thus obtained was subjected to silica gel column chromatography to obtain 0.35 g of 1-{3-methyl-[2-[2-methyl-4-(thiophen-2-yl)phenoxy]methyl]phenyl}-4-methyl-1,4-dihydrotetrazol-5-one (hereinafter referred to as the present compound 1).

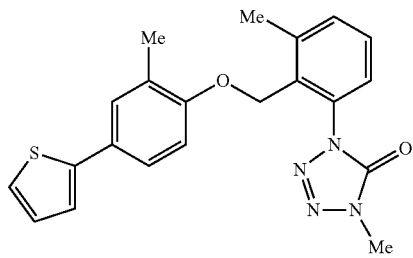 [SMILES: Cc1cc(-c2cccs2)ccc1OCc1c(C)cccc1-n1nnn(C)c1=O]

$^1$H-NMR (CDCl$_3$) δ: 7.45-7.36 (4H, m), 7.28 (1H, dd, J=7.0, 2.2 Hz), 7.21 (1H, dd, J=5.0, 0.9 Hz), 7.18 (1H, dd, J=3.7, 0.9 Hz), 7.04 (1H, dd, J=5.0, 3.7 Hz), 6.84 (1H, d, J=8.0 Hz), 5.06 (2H, s), 3.63 (3H, s), 2.51 (3H, s), 2.12 (3H, s).

Production Example 2

Using the compounds mentioned in Reference Production Examples, the following present compounds were synthesized in the same manner as in Production Example 1. Structural formulas of the thus obtained present compounds and $^1$H-NMR data thereof are shown below.

Present Compound 2

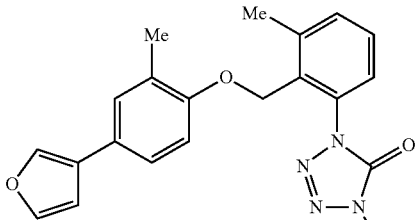

Present Compound 3

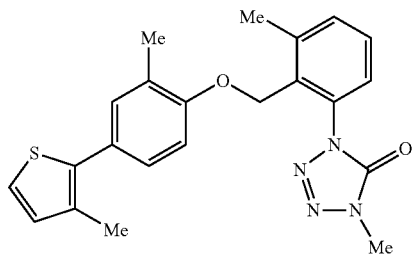

Present Compound 4

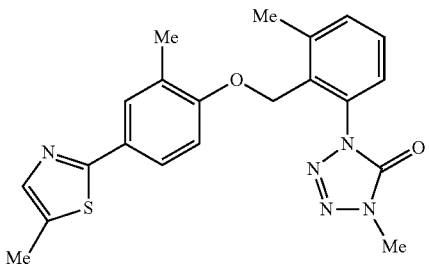

Present Compound 5

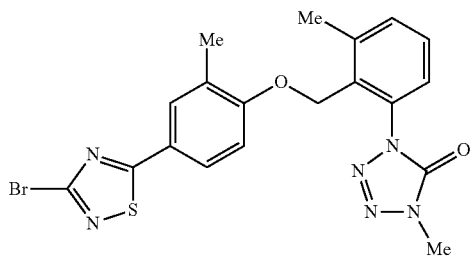

Present Compound 6

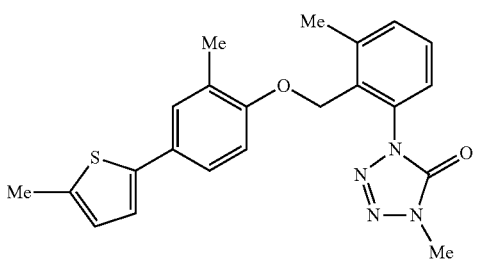

Present Compound 7

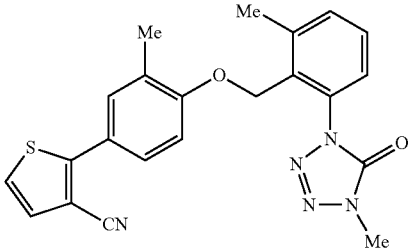

Present Compound 8

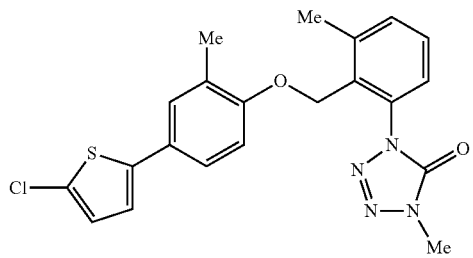

Present Compound 9
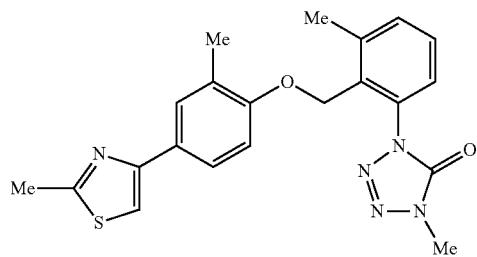
Present Compound 37
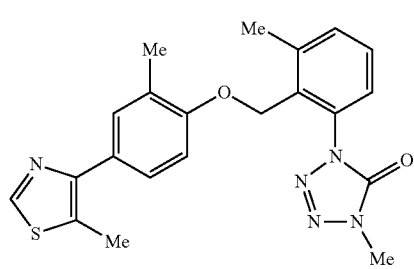
Present Compound 10
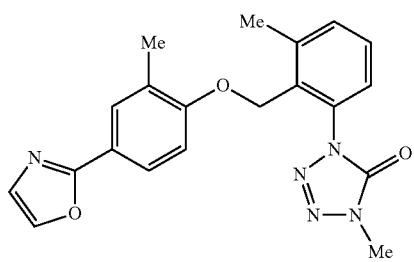
Present Compound 38
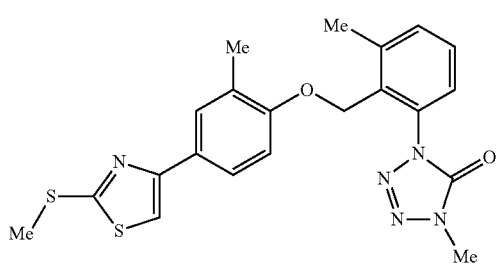
Present Compound 25
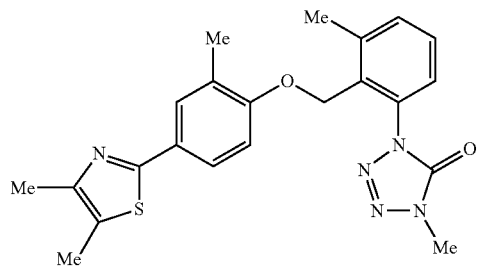
Present Compound 39
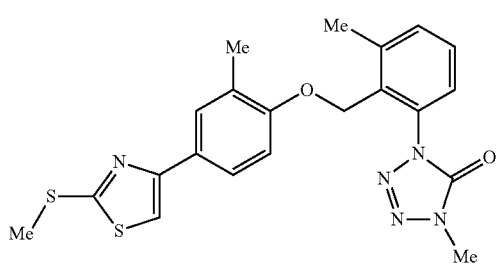
Present Compound 26
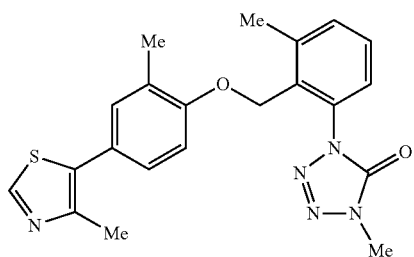
Present Compound 40
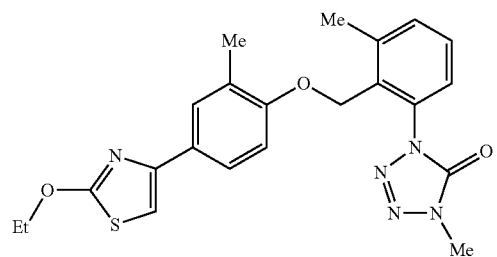
Present Compound 27
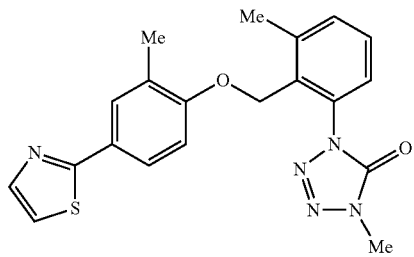
Present Compound 41
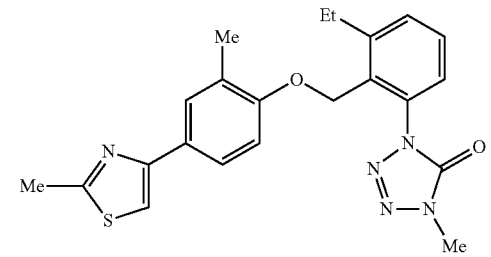

Present Compound 42
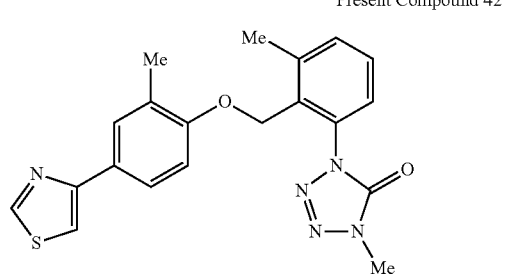
Present Compound 43
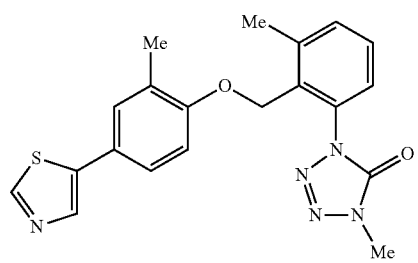
Present Compound 44
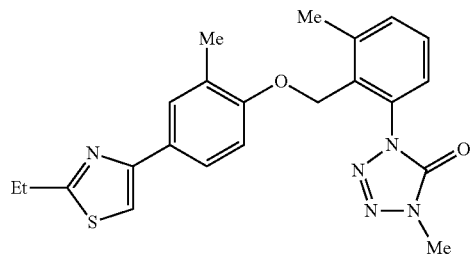
Present Compound 45
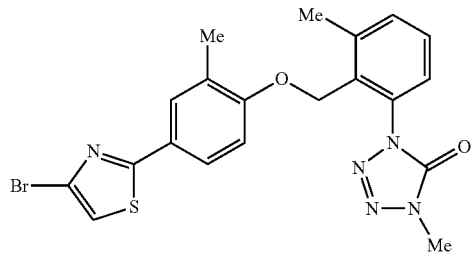
Present Compound 46
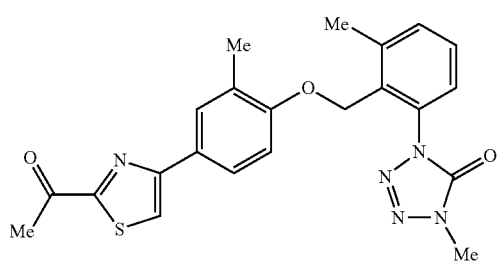
Present Compound 47
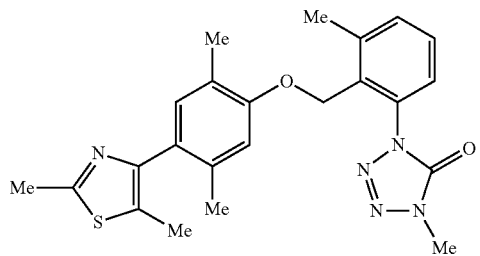
Present Compound 48
Present Compound 49
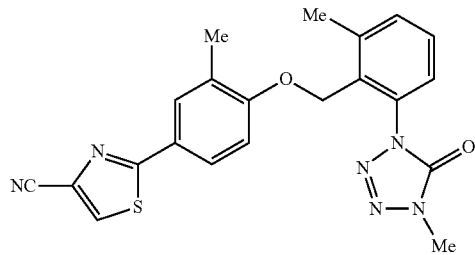
Present Compound 50
Present Compound 51
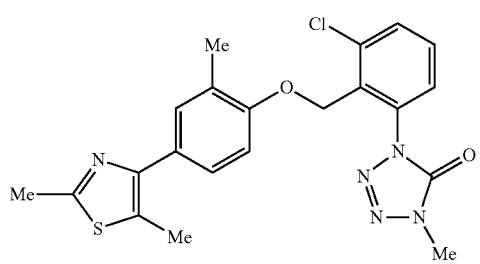

-continued

Present Compound 52

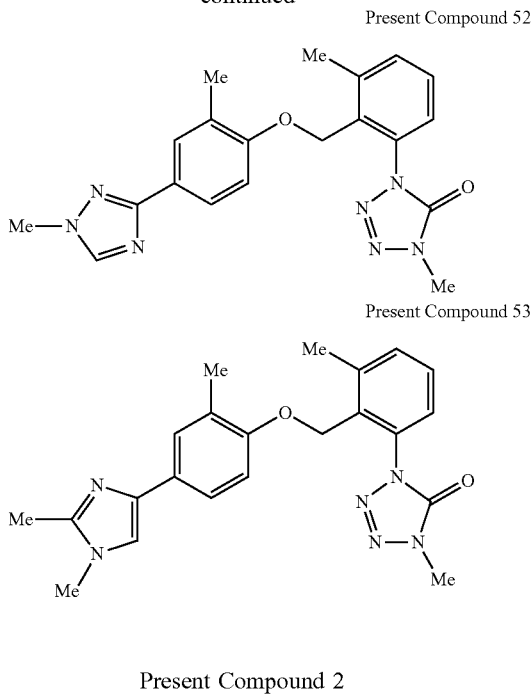

Present Compound 53

Present Compound 2

¹H-NMR (CDCl₃) δ: 7.63 (1H, s), 7.44 (1H, t, J=1.7 Hz), 7.42-7.38 (2H, m), 7.28-7.24 (3H, m), 6.84 (1H, d, J=8.9 Hz), 6.64-6.63 (1H, m), 5.05 (2H, s), 3.62 (3H, s), 2.51 (3H, s), 2.11 (3H, s).

Present Compound 3

¹H-NMR (CDCl₃) δ: 7.45-7.40 (2H, m), 7.28 (1H, dd, J=6.7, 2.4 Hz), 7.24-7.21 (2H, m), 7.14 (1H, d, J=5.2 Hz), 6.90-6.87 (2H, m), 5.06 (2H, s), 3.63 (3H, s), 2.52 (3H, s), 2.29 (3H, s), 2.13 (3H, s).

Present Compound 4

¹H-NMR (CDCl₃) δ: 7.67-7.64 (2H, m), 7.46-7.40 (3H, m), 7.29 (1H, dd, J=7.1, 1.9 Hz), 6.87 (1H, d, J=8.2 Hz), 5.08 (2H, s), 3.63 (3H, s), 2.51 (3H, s), 2.49 (3H, d, J=1.1 Hz), 2.13 (3H, s).

Present Compound 5

¹H-NMR (CDCl₃) δ: 7.76 (1H, dd, J=8.6, 2.4 Hz), 7.72 (1H, d, J=2.4 Hz), 7.48-7.42 (2H, m), 7.30 (1H, dd, J=7.4, 1.9 Hz), 6.92 (1H, d, J=8.6 Hz), 5.12 (2H, s), 3.64 (3H, s), 2.51 (3H, s), 2.15 (3H, s).

Present Compound 6

¹H-NMR (CDCl₃) δ: 7.45-7.39 (2H, m), 7.32-7.26 (3H, m), 6.97 (1H, d, J=3.4 Hz), 6.82 (1H, d, J=8.6 Hz), 6.69-6.68 (1H, m), 5.05 (2H, s), 3.62 (3H, s), 2.51 (3H, s), 2.49 (3H, d, J=0.9 Hz), 2.11 (3H, s).

Present Compound 7

¹H-NMR (CDCl₃) δ: 7.58 (1H, dd, J=8.2, 2.3 Hz), 7.48-7.47 (1H, m), 7.45-7.41 (2H, m), 7.29 (1H, dd, J=7.0, 2.0 Hz), 7.24 (2H, s), 6.93 (1H, d, J=8.6 Hz), 5.09 (2H, s), 3.65 (3H, s), 2.52 (3H, s), 2.15 (3H, s).

Present Compound 8

¹H-NMR (CDCl₃) δ: 7.45-7.40 (2H, m), 7.29-7.26 (3H, m), 6.93 (1H, d, J=3.9 Hz), 6.85-6.82 (2H, m), 5.05 (2H, s), 3.63 (3H, s), 2.51 (3H, s), 2.11 (3H, s).

Present Compound 9

¹H-NMR (CDCl₃) δ: 7.64-7.62 (2H, m), 7.45-7.40 (2H, m), 7.28 (1H, dd, J=7.2, 2.7 Hz), 7.16 (1H, s), 6.87 (1H, d, J=9.3 Hz), 5.07 (2H, s), 3.62 (3H, s), 2.76 (3H, s), 2.51 (3H, s), 2.13 (3H, s).

Present Compound 10

¹H-NMR (CDCl₃) δ: 7.85-7.82 (2H, m), 7.66 (1H, d, J=0.9 Hz), 7.46-7.41 (2H, m), 7.30-7.28 (1H, m), 7.18 (1H, d, J=0.7 Hz), 6.91 (1H, d, J=8.4 Hz), 5.10 (2H, s), 3.62 (3H, s), 2.51 (3H, s), 2.14 (3H, s).

Present Compound 25

¹H-NMR (CDCl₃) δ: 7.65-7.60 (2H, m), 7.45-7.39 (2H, m), 7.28 (1H, dd, J=7.1, 2.2 Hz), 6.84 (1H, d, J=8.6 Hz), 5.07 (2H, s), 3.62 (3H, s), 2.50 (3H, s), 2.37 (3H, s), 2.36 (3H, s), 2.12 (3H, s).

Present Compound 26

¹H-NMR (CDCl₃) δ: 8.64 (1H, s), 7.46-7.40 (2H, m), 7.29 (1H, dd, J=6.8, 2.5 Hz), 7.23-7.18 (2H, m), 6.89 (1H, d, J=8.4 Hz), 5.07 (2H, s), 3.65 (3H, s), 2.53 (3H, s), 2.51 (3H, s), 2.14 (3H, d, J=3.4 Hz).

Present Compound 27

¹H-NMR (CDCl₃) δ: 7.80 (1H, d, J=3.4 Hz), 7.75-7.73 (2H, m), 7.46-7.41 (2H, m), 7.29 (1H, dd, J=7.1, 2.2 Hz), 7.26 (1H, d, J=5.2 Hz), 6.89 (1H, d, J=9.1 Hz), 5.09 (2H, s), 3.63 (3H, s), 2.52 (3H, s), 2.15 (3H, s).

Present Compound 37

¹H-NMR (CDCl₃) δ: 7.46-7.41 (2H, m), 7.30-7.27 (1H, m), 7.19-7.14 (2H, m), 6.87 (1H, d, J=8.4 Hz), 5.06 (2H, s), 3.64 (3H, s), 2.67 (3H, s), 2.52 (3H, s), 2.43 (3H, s), 2.13 (3H, s).

Present Compound 38

¹H-NMR (CDCl₃) δ: 8.62 (1H, s), 7.46-7.40 (4H, m), 7.28 (1H, dd, J=6.6, 2.5 Hz), 6.91 (1H, d, J=8.4 Hz), 5.08 (2H, s), 3.63 (3H, s), 2.57 (3H, s), 2.52 (3H, s), 2.14 (3H, s).

Present Compound 39

¹H-NMR (CDCl₃) δ: 7.67-7.64 (2H, m), 7.45-7.39 (2H, m), 7.29-7.27 (1H, m), 7.19 (1H, s), 6.86 (1H, d, J=8.2 Hz), 5.07 (2H, s), 3.62 (3H, s), 2.75 (3H, s), 2.51 (3H, s), 2.13 (3H, s).

Present Compound 40

¹H-NMR (CDCl₃) δ: 7.60-7.56 (2H, m), 7.45-7.39 (2H, m), 7.29-7.26 (1H, m), 6.84 (1H, d, J=8.4 Hz), 6.69 (1H, s), 5.06 (2H, s), 4.52 (2H, q, J=7.1 Hz), 3.62 (3H, s), 2.51 (3H, s), 2.12 (3H, s), 1.47 (3H, t, J=7.1 Hz).

Present Compound 41

¹H-NMR (CDCl₃) δ: 7.66-7.61 (2H, m), 7.50-7.44 (2H, m), 7.30-7.27 (1H, m), 7.16 (1H, s), 6.88 (1H, d, J=9.1 Hz), 5.09 (2H, s), 3.58 (3H, s), 2.85 (2H, q, J=7.6 Hz), 2.76 (3H, s), 2.12 (3H, s), 1.28 (3H, t, J=7.6 Hz).

Present Compound 42

¹H-NMR (CDCl₃) δ: 8.85 (1H, d, J=2.0 Hz), 7.72-7.68 (2H, m), 7.45-7.39 (3H, m), 7.28 (1H, dd, J=6.7, 2.6 Hz), 6.90 (1H, d, J=9.1 Hz), 5.09 (2H, s), 3.63 (3H, s), 2.52 (3H, s), 2.15 (3H, s).

Present Compound 43

¹H-NMR (CDCl₃) δ: 8.69 (1H, d, J=0.7 Hz), 7.96 (1H, d, J=0.7 Hz), 7.46-7.41 (2H, m), 7.37-7.32 (2H, m), 7.29 (1H, dd, J=7.0, 2.0 Hz), 6.86 (1H, d, J=8.4 Hz), 5.07 (2H, s), 3.64 (3H, s), 2.52 (3H, s), 2.13 (3H, s).

Present Compound 44

¹H-NMR (CDCl₃) δ: 7.66-7.62 (2H, m), 7.45-7.39 (2H, m), 7.29-7.27 (1H, m), 7.18 (1H, s), 6.87 (1H, d, J=9.3 Hz), 5.07 (2H, s), 3.62 (3H, s), 3.09 (2H, q, J=7.6 Hz), 2.51 (3H, s), 2.13 (3H, s), 1.43 (3H, t, J=7.6 Hz).

Present Compound 45

¹H-NMR (CDCl₃) δ: 7.73-7.69 (2H, m), 7.47-7.40 (2H, m), 7.31-7.27 (1H, m), 7.13 (1H, s), 6.87 (1H, d, J=9.3 Hz), 5.09 (2H, s), 3.63 (3H, s), 2.51 (3H, s), 2.13 (3H, s).

Present Compound 46

¹H-NMR (CDCl₃) δ: 7.74-7.68 (2H, m), 7.67 (1H, s), 7.46-7.40 (2H, m), 7.29 (1H, dd, J=6.9, 2.2 Hz), 6.91 (1H, d, J=8.4 Hz), 5.10 (2H, s), 3.63 (3H, s), 2.79 (3H, s), 2.52 (3H, s), 2.17 (3H, s).

Present Compound 47

¹H-NMR (CDCl₃) δ: 7.45-7.39 (3H, m), 7.35 (1H, dd, J=8.4, 2.3 Hz), 7.30-7.27 (1H, m), 6.88 (1H, d, J=8.4 Hz), 5.07 (2H, s), 3.64 (3H, s), 2.66 (3H, s), 2.51 (3H, s), 2.48 (3H, s), 2.13 (3H, s).

Present Compound 48

¹H-NMR (CDCl₃) δ: 8.67 (1H, d, J=4.8 Hz), 7.78-7.76 (1H, m), 7.73 (1H, dd, J=8.5, 2.4 Hz), 7.54 (1H, d, J=4.5 Hz), 7.46-7.40 (2H, m), 7.29 (1H, dd, J=6.9, 2.4 Hz), 6.91 (1H, d, J=8.4 Hz), 5.10 (2H, s), 3.62 (3H, s), 2.52 (3H, s), 2.15 (3H, s).

Present Compound 49

¹H-NMR (CDCl₃) δ: 7.45-7.39 (2H, m), 7.29-7.27 (1H, m), 6.98 (1H, s), 6.72 (1H, s), 5.04 (2H, s), 3.66 (3H, s), 2.66 (3H, s), 2.51 (3H, s), 2.24 (3H, s), 2.16 (3H, s), 2.05 (3H, s).

Present Compound 50

¹H-NMR (CDCl₃) δ: 7.89 (1H, s), 7.76-7.71 (2H, m), 7.48-7.41 (2H, m), 7.30 (1H, dd, J=7.2, 1.9 Hz), 6.90 (1H, d, J=8.5 Hz), 5.11 (2H, s), 3.64 (3H, s), 2.52 (3H, s), 2.15 (3H, s).

Present Compound 51

¹H-NMR (CDCl₃) δ: 7.62 (1H, d, J=8.2 Hz), 7.47 (1H, t, J=8.0 Hz), 7.43-7.37 (2H, m), 7.34 (1H, d, J=8.4 Hz), 6.88 (1H, d, J=8.4 Hz), 5.35 (2H, s), 3.61 (3H, s), 2.66 (3H, s), 2.47 (3H, s), 2.06 (3H, s).

Present Compound 52

¹H-NMR (CDCl₃) δ: 8.01 (1H, s), 7.89-7.84 (2H, m), 7.45-7.39 (2H, m), 7.28 (1H, dd, J=6.9, 2.3 Hz), 6.90 (1H, d, J=8.2 Hz), 5.08 (2H, s), 3.95 (3H, s), 3.62 (3H, s), 2.51 (3H, s), 2.14 (3H, s).

Present Compound 53

¹H-NMR (CDCl₃) δ: 7.50 (1H, d, J=1.4 Hz), 7.46 (1H, dd, J=8.3, 2.2 Hz), 7.43-7.38 (2H, m), 7.27 (1H, dd, J=6.1, 3.2 Hz), 6.97 (1H, s), 6.82 (1H, d, J=8.4 Hz), 5.04 (2H, s), 3.61 (3H, s), 3.58 (3H, s), 2.50 (3H, s), 2.42 (3H, s), 2.10 (3H, s).

Production Example 3

A mixture of 0.13 g of C21A, 0.13 g of 2-furylboronic acid, 0.03 g of [1,1'-bis(diphenylphosphino) ferrocene]palladium (II) dichloride dichloromethane adduct, 0.65 g of tripotassium phosphate, 4 mL of 1,2-dimethoxyethane, and 0.4 ml of water was stirred at 80° C. for 6 hours. After cooling, the reaction mixture was concentrated and the residue thus obtained was subjected to silica gel column chromatography to obtain 0.13 g of 1-{3-methyl-2-[[2-methyl-4-(furan-2-yl)phenoxy]methyl]phenyl}-4-methyl-1,4-dihydrotetrazol-5-one (hereinafter referred to as the present compound 11).

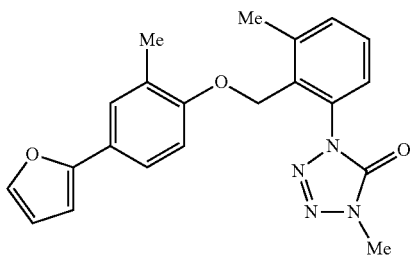 [SMILES: Cc1cc(-c2ccco2)ccc1OCc1c(C)cccc1-n1nnn(C)c1=O]

¹H-NMR (CDCl₃) δ: 7.46-7.41 (5H, m), 7.29-7.26 (1H, m), 6.85 (1H, d, J=8.2 Hz), 6.50 (1H, d, J=3.2 Hz), 6.44-6.43 (1H, m), 5.06 (2H, s), 3.62 (3H, s), 2.51 (3H, s), 2.12 (3H, s).

Production Example 4

The following compounds were synthesized in the same manner as in Production Example 3. Structural formulas of the thus obtained present compounds and ¹H-NMR data thereof are shown below.

Present Compound 12

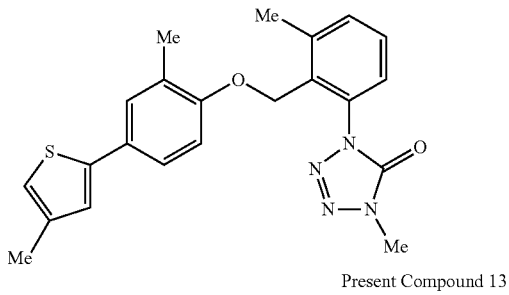

Present Compound 13

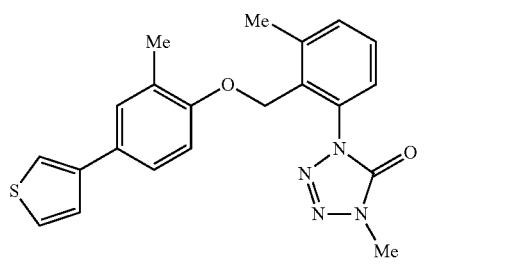

Present Compound 14

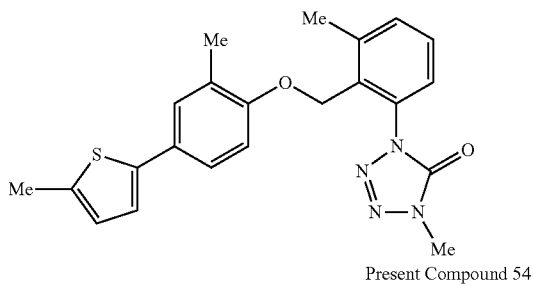

Present Compound 54

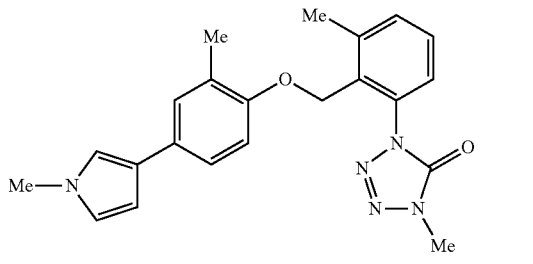

Present Compound 12

¹H-NMR (CDCl₃) δ: 7.45-7.40 (2H, m), 7.36-7.33 (2H, m), 7.29-7.26 (1H, m), 7.00 (1H, d, J=1.4 Hz), 6.83 (1H, d, J=8.2 Hz), 6.78-6.78 (1H, m), 5.05 (2H, s), 3.62 (3H, s), 2.51 (3H, s), 2.27 (3H, s), 2.11 (3H, s).

Present Compound 13

¹H-NMR (CDCl₃) δ: 7.45-7.40 (2H, m), 7.38-7.35 (3H, m), 7.33-7.32 (2H, m), 7.28 (1H, dd, J=6.7, 2.4 Hz), 6.86 (1H, d, J=9.1 Hz), 5.06 (2H, s), 3.63 (3H, s), 2.52 (3H, s), 2.13 (3H, s).

Present Compound 14

¹H-NMR (CDCl₃) δ: 7.46 (1H, t, J=8.2 Hz), 7.29-7.25 (1H, m), 7.10-7.06 (2H, m), 6.94 (1H, d, J=3.4 Hz), 6.85 (1H, d, J=8.2 Hz), 6.68-6.66 (1H, m), 5.27 (2H, s), 3.93 (3H, s), 3.58 (3H, s), 2.48 (3H, d, J=1.1 Hz), 2.01 (3H, s).

Present Compound 54

¹H-NMR (CDCl₃) δ: 7.43-7.39 (2H, m), 7.28-7.21 (3H, m), 6.82-6.80 (2H, m), 6.60 (1H, s), 6.35 (1H, s), 5.03 (2H, s), 3.67 (3H, s), 3.61 (3H, s), 2.51 (3H, s), 2.10 (3H, s).

Production Example 5

To a mixture of 0.44 g of C31A and 0.1 mL of 1,2,3-triazole, 0.04 g of copper(I) iodide and 0.43 g of tripotassium phosphate were added, followed by stirring at 100° C. for 7 hours. The reaction mixture was concentrated under reduced pressure and the residue thus obtained was subjected to silica gel column chromatography to obtain 0.08 g of 1-{3-methyl-2-[[2-methyl-4-(1,2,3-triazol-2-yl)phenoxy]methyl]phenyl}-4-methyl-1,4-dihydrotetrazol-5-one (hereinafter referred to as the present compound 15) and 0.04 g of 1-{3-methyl-2-[[2-methyl-4-(1,2,3-triazol-1-yl)phenoxy]methyl]phenyl}-4-methyl-1,4-dihydrotetrazol-5-one (hereinafter referred to as the present compound 16).

Present Compound 15

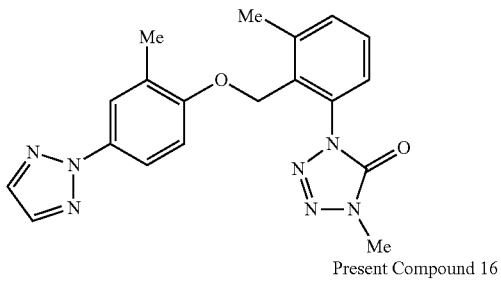

Present Compound 16

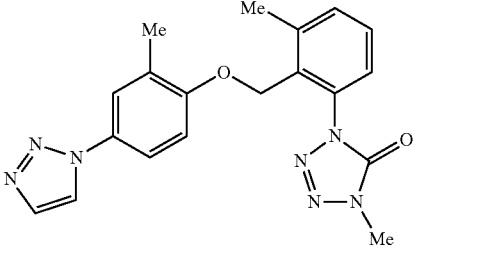

Present Compound 15

¹H-NMR (CDCl₃) δ: 7.84-7.80 (2H, m), 7.77 (2H, s), 7.46-7.41 (2H, m), 7.29 (1H, dd, J=7.0, 2.3 Hz), 6.92 (1H, d, J=8.6 Hz), 5.09 (2H, s), 3.63 (3H, s), 2.52 (3H, s), 2.17 (3H, s).

Present Compound 16

¹H-NMR (CDCl₃) δ: 7.90 (1H, s), 7.82 (1H, s), 7.49-7.42 (4H, m), 7.30 (1H, dd, J=6.9, 2.2 Hz), 6.94 (1H, d, J=8.4 Hz), 5.10 (2H, s), 3.65 (3H, s), 2.53 (3H, s), 2.17 (3H, s).

Production Example 6

To a mixture of 0.44 g of C31A and 0.07 g of 1,2,4-triazole, 0.01 g of copper(II) acetate monohydrate, 0.67 g of cesium carbonate, and 2 ml of N,N-dimethylformamide were added, followed by stirring at 135° C. for 14 hours. The reaction mixture was concentrated under reduced pressure and the residue thus obtained was subjected to silica gel column chromatography to obtain 0.25 g of 1-{3-methyl-2-[[2-methyl-4-(1,2,4-triazol-1-yl)phenoxy]methyl]phenyl}-4-methyl-1,4-dihydrotetrazol-5-one (hereinafter referred to as the present compound 17).

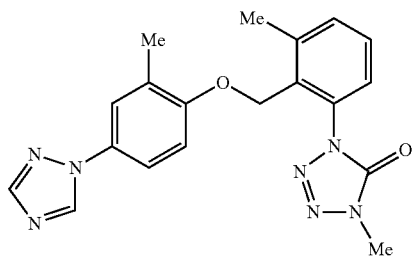 [SMILES: Cc1cc(-n2cncn2)ccc1OCc1c(C)cccc1-n1nnn(C)c1=O]

$^1$H-NMR (CDCl$_3$) δ: 8.43 (1H, s), 8.07 (1H, s), 7.47-7.38 (4H, m), 7.30 (1H, dd, J=7.0, 2.3 Hz), 6.92 (1H, d, J=8.4 Hz), 5.09 (2H, s), 3.64 (3H, s), 2.52 (3H, s), 2.16 (3H, s).

Production Example 7

The following compounds were synthesized in the same manner as in Production Example 6. Structural formulas of the thus obtained present compounds and $^1$H-NMR data thereof are shown below.

Present Compound 18

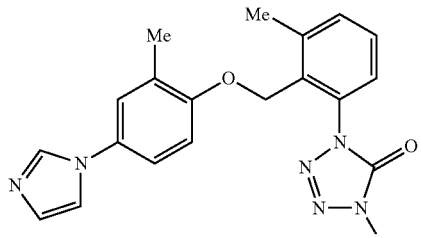

Present Compound 19

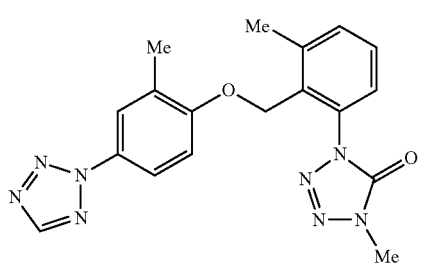

Present Compound 18

$^1$H-NMR (CDCl$_3$) δ: 8.04-8.00 (1H, m), 7.76 (1H, br s), 7.47-7.41 (2H, m), 7.29 (1H, dd, J=7.0, 1.9 Hz), 7.16-7.14 (3H, br m), 6.89 (1H, d, J=9.2 Hz), 5.07 (2H, s), 3.65 (3H, s), 2.52 (3H, s), 2.15 (3H, s).

Present Compound 19

$^1$H-NMR (CDCl$_3$) δ: 8.61 (1H, s), 7.91-7.88 (2H, m), 7.48-7.41 (2H, m), 7.30 (1H, dd, J=7.1, 1.9 Hz), 6.97 (1H, d, J=9.5 Hz), 5.12 (2H, s), 3.64 (3H, s), 2.53 (3H, s), 2.19 (3H, s).

Production Example 8

A mixture of 0.20 g of C14A, 0.16 g of C38A, 0.20 g of potassium carbonate, and 10 mL of acetonitrile was stirred with heating under reflux for 4 hours. The mixture was concentrated under reduced pressure and the residue thus obtained was subjected to silica gel column chromatography to obtain 0.11 g of 1-{3-methyl-2-[[2-methyl-4-(1,4,5-trimethylimidazol-2-yl)phenoxy]methyl]phenyl}-4-methyl-1,4-dihydrotetrazol-5-one (hereinafter referred to as the present compound 20).

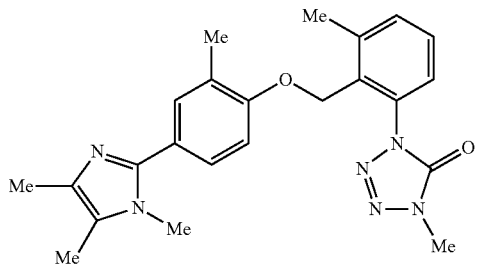 [SMILES: Cc1cc(-c2nc(C)c(C)n2C)ccc1OCc1c(C)cccc1-n1nnn(C)c1=O]

$^1$H-NMR (CDCl$_3$) δ: 2.10 (3H, s), 2.17 (3H, s), 2.20 (3H, s), 2.50 (3H, s), 3.51 (3H, s), 3.63 (3H, s), 5.06 (2H, s), 6.87 (1H, d, J=8.2 Hz), 7.27-7.45 (5H, m).

Production Example 9

A mixture of 0.40 g of C21A, 0.48 ml of 1-methylpyrrole, 0.02 g of palladium acetate, 0.04 g of (2-biphenylyl)dicyclohexylphosphine, 0.42 g of tripotassium phosphate, and 2 ml of DMPU was stirred at 125° C. for 2 hours. The reaction mixture was filtered through Celite (registered trademark) and then concentrated under reduced pressure. The residue thus obtained was subjected to silica gel column chromatography to obtain 0.06 g of 1-{3-methyl-2-[[2-methyl-4-(1-methylpyrrol-2-yl)phenoxy]methyl]phenyl}-4-methyl-1,4-dihydrotetrazol-5-one (hereinafter referred to as the present compound 22).

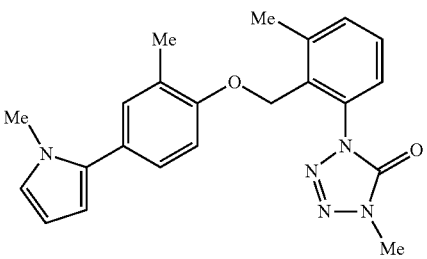 [SMILES: Cc1cc(-c2cccn2C)ccc1OCc1c(C)cccc1-n1nnn(C)c1=O]

$^1$H-NMR (CDCl$_3$) δ: 7.45-7.40 (2H, m), 7.28 (1H, dd, J=6.8, 2.4 Hz), 7.17-7.15 (2H, m), 6.87 (1H, d, J=8.9 Hz), 6.68-6.67 (1H, m), 6.17 (1H, dd, J=3.5, 2.6 Hz), 6.13 (1H, dd, J=3.5, 1.8 Hz), 5.05 (2H, s), 3.64 (3H, s), 3.63 (3H, s), 2.52 (3H, s), 2.12 (3H, s).

Production Example 10

A mixture of 0.37 g of C35A, 0.27 g of 2-bromoethylamine hydrobromide, 0.33 g of DMT-MM, 0.13 g of N-methylmorpholine, and 10 ml of methanol was stirred at room temperature for 17 hours, followed by the addition of 0.21 g of DMT-MM and further stirring at room temperature 4 hours. To the reaction solution, a methanol solution (4.2 ml) of 0.24 g of potassium hydroxide was added, followed by stirring at 70° C. for 1 hour. After cooling, the solvent was concentrated under reduced pressure. The residue was subjected to silica gel chromatography to obtain 0.36 g of 1-{3-methyl-2-[[2-methyl-4-(2-oxazolin-2-yl)phenoxy]methyl]phenyl}-4-methyl-1,4-dihydrotetrazol-5-one (hereinafter referred to as the present compound 23).

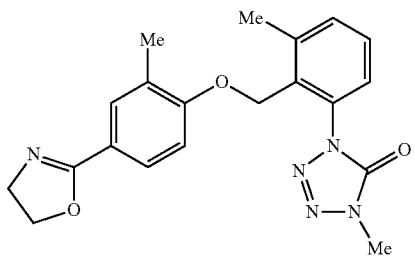 [SMILES: Cc1cc(C2=NCCO2)ccc1OCc1c(C)cccc1-n1nnn(C)c1=O]

$^1$H-NMR (CDCl$_3$) δ: 7.75-7.72 (2H, m), 7.46-7.40 (2H, m), 7.28 (1H, dd, J=7.2, 2.0 Hz), 6.85 (1H, d, J=9.3 Hz), 5.08 (2H, s), 4.41 (2H, t, J=9.4 Hz), 4.05-4.00 (2H, m), 3.62 (3H, s), 2.50 (3H, s), 2.10 (3H, s).

Production Example 11

A mixture of 0.35 g of C35A, 0.30 g of 2-aminoethanethiol hydrochloride, 0.35 ml of diisopropylethylamine, 0.03 g of 3-nitrophenylboronic acid, 15 ml of xylene, and 0.3 g of 4AMS was stirred at 150° C. for 20 hours. After cooling, the solvent was concentrated under reduced pressure and the residue was subjected to silica gel chromatography to obtain 0.12 g of 1-{3-methyl-2-[[2-methyl-4-(2-thiazolin-2-yl)phenoxy]methyl]phenyl}-4-methyl-1,4-dihydrotetrazol-5-one (hereinafter referred to as the present compound 24).

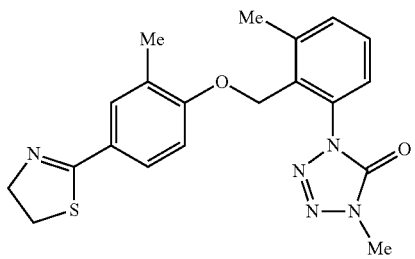 [SMILES: Cc1cc(C2=NCCS2)ccc1OCc1c(C)cccc1-n1nnn(C)c1=O]

$^1$H-NMR (CDCl$_3$) δ: 7.64-7.59 (2H, m), 7.46-7.40 (2H, m), 7.30-7.27 (1H, m), 6.84 (1H, d, J=8.4 Hz), 5.08 (2H, s), 4.42 (2H, t, J=8.3 Hz), 3.62 (3H, s), 3.39 (2H, t, J=8.3 Hz), 2.50 (3H, s), 2.10 (3H, s).

Production Example 12

A mixture of 0.25 g of C36A and 2.5 ml of phosphorus oxychloride was stirred at 110° C. for 10 hours. After cooling, the reaction solution was concentrated under reduced pressure and the residue was subjected to silica gel chromatography to obtain 0.11 g of 1-{3-methyl-2-[[2-methyl-4-(5-methyl-1,3,4-oxadiazol-2-yl)phenoxy]methyl]phenyl}-4-methyl-1,4-dihydrotetrazol-5-one (hereinafter referred to as the present compound 28).

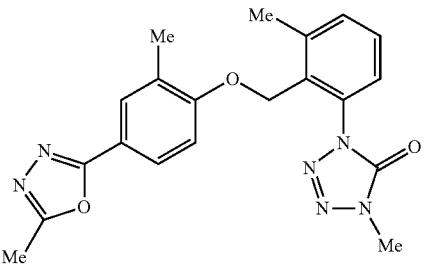 [SMILES: Cc1nnc(-c2ccc(OCc3c(C)cccc3-n3nnn(C)c3=O)c(C)c2)o1]

$^1$H-NMR (CDCl$_3$) δ: 7.91-7.84 (2H, m), 7.48-7.42 (2H, m), 7.31-7.29 (1H, m), 6.97 (1H, d, J=7.8 Hz), 5.13 (2H, s), 3.64 (3H, s), 2.68 (3H, s), 2.52 (3H, s), 2.16 (3H, s).

Production Example 13

A mixture of 0.42 g of C43A, 0.18 g of (diethylamino)sulfur trifluoride, and 5 ml of chloroform was stirred at 10° C. for 2 hours. The mixture was diluted with an aqueous ammonium chloride solution, extracted with ethyl acetate, and then concentrated under reduced pressure. The residue was subjected to silica gel chromatography to obtain 0.32 g of 1-{3-methyl-2-[[2-methyl-4-(4,4-dimethyl-2-oxazolin-2-yl)phenoxy]methyl]phenyl}-4-methyl-1,4-dihydrotetrazol-5-one (hereinafter referred to as the present compound 29).

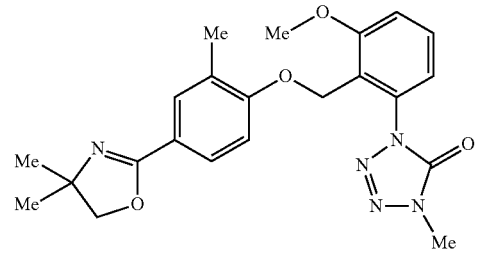 [SMILES: COc1cccc(-n2nnn(C)c2=O)c1COc1ccc(C2=NC(C)(C)CO2)cc1C]

$^1$H-NMR (CDCl$_3$) δ: 7.69-7.66 (2H, m), 7.47 (1H, t, J=8.2 Hz), 7.08 (2H, dd, J=8.2, 5.3 Hz), 6.87 (1H, d, J=9.4 Hz), 5.31 (2H, s), 4.06 (2H, s), 3.93 (3H, s), 3.58 (3H, s), 1.99 (3H, s), 1.36 (6H, s).

Production Example 14

A mixture of 0.22 g of C42A, 0.3 g of C7A, 0.18 g of potassium carbonate, and 10 ml of acetonitrile was stirred at 80° C. for 3 hours. The reaction solution was filtered and then concentrated under reduced pressure, and the residue was subjected to silica gel chromatography to obtain 0.21 g of 1-{3-methoxy-2-[[2-methyl-4-(2-methylthiazol-5-yl)phenoxy]methyl]phenyl}-4-methyl-1,4-dihydrotetrazol-5-one (hereinafter referred to as the present compound 30).

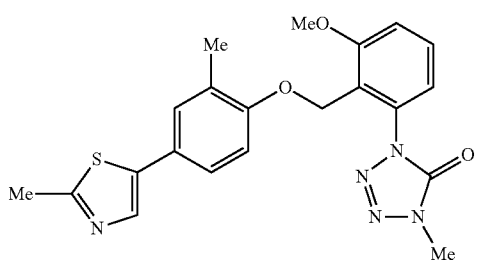 [SMILES: COc1cccc(-n2nnn(C)c2=O)c1COc1ccc(-c2cnc(C)s2)cc1C]

¹H-NMR (CDCl₃) δ: 7.64 (1H, s), 7.47 (1H, t, J=8.2 Hz), 7.26-7.22 (2H, m), 7.08 (2H, t, J=8.1 Hz), 6.87 (1H, d, J=8.2 Hz), 5.29 (2H, s), 3.93 (3H, s), 3.60 (3H, s), 2.70 (3H, s), 2.02 (3H, s).

Production Example 15

The following compound was synthesized in the same manner as in Production Example 14. A structural formula of the thus obtained present compound and ¹H-NMR data thereof are shown below.

Present Compound 31

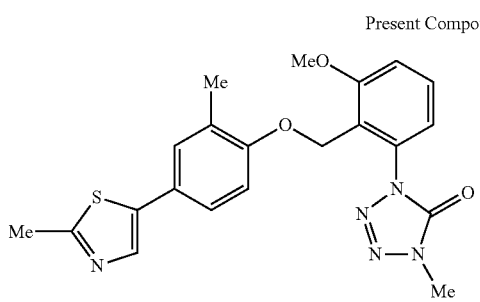

¹H-NMR (CDCl₃) δ: 7.66 (1H, s), 7.45-7.40 (2H, m), 7.29-7.27 (3H, m), 6.84 (1H, d, J=8.5 Hz), 5.06 (2H, s), 3.63 (3H, s), 2.71 (3H, s), 2.51 (3H, s), 2.12 (3H, s).

Production Example 16

A mixture of 0.21 g of C41A, 0.30 g of C16A, 0.17 g of potassium carbonate, and 10 ml of acetonitrile was stirred at 80° C. for 3 hours. The reaction solution was filtered and then concentrated under reduced pressure, and the residue was subjected to silica gel chromatography to obtain 0.33 g of 1-{3-cyclopropyl-2-[[2-methyl-4-(4-methylthiazol-2-yl)phenoxy]methyl]phenyl}-4-methyl-1,4-dihydrotetrazol-5-one (hereinafter referred to as the present compound 32).

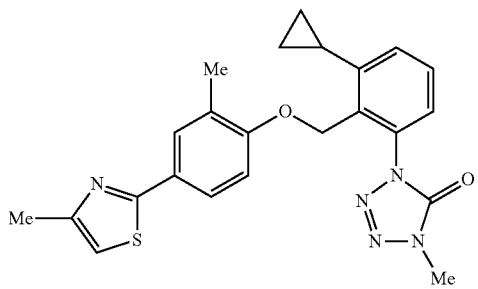 [SMILES: Cc1csc(-c2ccc(OCc3c(C4CC4)cccc3-n3nnn(C)c3=O)c(C)c2)n1]

¹H-NMR (CDCl₃) δ: 7.71-7.68 (2H, m), 7.44 (1H, t, J=7.9 Hz), 7.29-7.26 (2H, m), 6.91 (1H, d, J=9.0 Hz), 6.79 (1H, d, J=1.0 Hz), 5.31 (2H, s), 3.60 (3H, s), 2.48 (3H, d, J=1.0 Hz), 2.15-2.08 (4H, m), 1.02-0.97 (2H, m), 0.79-0.75 (2H, m).

Production Example 17

The following compounds were synthesized in the same manner as in Production Example 16. Structural formulas of the thus obtained present compounds and ¹H-NMR data thereof are shown below.

Present Compound 33

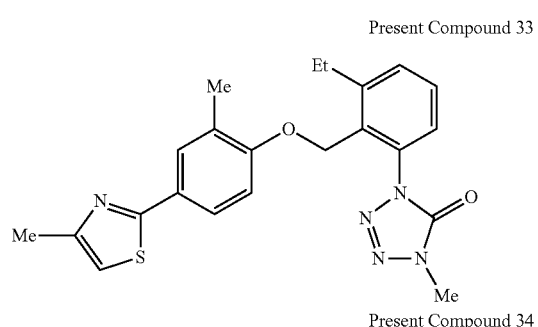

Present Compound 34

Present Compound 35

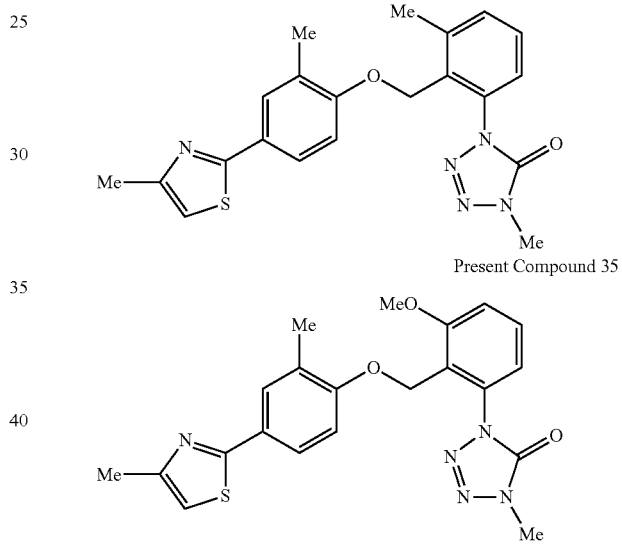

Present Compound 33

¹H-NMR (CDCl₃) δ: 7.71-7.68 (2H, m), 7.50-7.44 (2H, m), 7.29 (1H, dd, J=7.2, 1.9 Hz), 6.87 (1H, d, J=8.2 Hz), 6.79 (1H, s), 5.11 (2H, s), 3.58 (3H, s), 2.85 (2H, q, J=7.8 Hz), 2.49 (3H, s), 2.12 (3H, s), 1.28 (3H, t, J=7.8 Hz).

Present Compound 34

¹H-NMR (CDCl₃) δ: 7.71-7.68 (2H, m), 7.45-7.40 (2H, m), 7.29 (1H, dd, J=6.9, 2.3 Hz), 6.86 (1H, d, J=8.2 Hz), 6.79 (1H, d, J=1.0 Hz), 5.09 (2H, s), 3.62 (3H, s), 2.51 (3H, s), 2.49 (3H, d, J=1.0 Hz), 2.13 (3H, s).

Present Compound 35

¹H-NMR (CDCl₃) δ: 7.67-7.64 (2H, m), 7.47 (1H, t, J=8.2 Hz), 7.10-7.07 (2H, m), 6.90 (1H, d, J=9.2 Hz), 6.77 (1H, d, J=1.0 Hz), 5.32 (2H, s), 3.94 (3H, s), 3.59 (3H, s), 2.48 (3H, s), 2.03 (3H, s).

Production Example 18

A mixed solution of 0.35 g of C14A, 0.19 g of ethylene glycol, 0.21 g of trimethyl orthoformate, 0.05 g of methanesulfonic acid, and 2 ml of chloroform was stirred at room temperature for 100 hours. The reaction solution was diluted with an aqueous saturated sodium hydrogen carbonate solution and extracted with chloroform. The organic layer was washed with water and a saturated saline solution, dried over anhydrous magnesium sulfate, and then concentrated under reduced pressure, and the residue was subjected to silica gel chromatography to obtain 0.05 g of 1-{3-methyl-2-[[2-methyl-4-(2-methyldioxolan-2-yl)phenoxy]methyl]phenyl}-4-methyl-1,4-dihydrotetrazol-5-one (hereinafter referred to as the present compound 36).

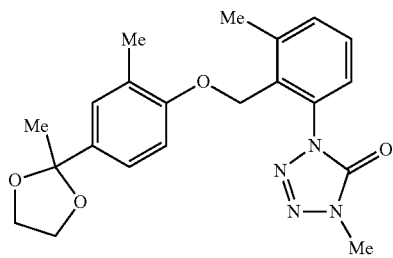 [SMILES: Cc1cc(C2(C)OCCO2)ccc1OCc1c(C)cccc1-n1nnn(C)c1=O]

$^1$H-NMR (CDCl$_3$) δ: 7.44-7.39 (2H, m), 7.27-7.21 (3H, m), 6.79 (1H, d, J=8.5 Hz), 5.02 (2H, s), 4.04-4.00 (2H, m), 3.81-3.77 (2H, m), 3.64 (3H, s), 2.50 (3H, s), 2.09 (3H, s), 1.57 (3H, s).

Production Example 19

A mixed solution of 0.5 g of C21A, 0.05 g of copper(I) iodide, 0.83 g of cesium carbonate, 0.17 g of pyrrole, and 2 ml of N,N-dimethylformamide was stirred at 120° C. for 40 hours. The reaction solution was diluted with ethyl acetate and washed with water. The organic layer was dried over anhydrous magnesium sulfate and then concentrated under reduced pressure, and the residue was subjected to silica gel chromatography to obtain 0.18 g of 1-{3-methyl-2-[[2-methyl-4-(pyrrol-1-yl)phenoxy]methyl]phenyl}-4-methyl-1,4-dihydrotetrazol-5-one (hereinafter referred to as the present compound 55).

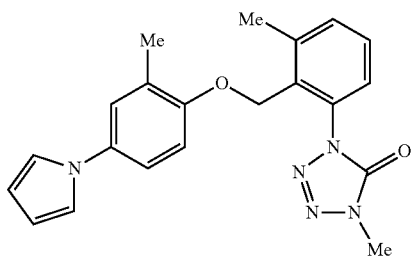 [SMILES: Cc1cc(-n2cccc2)ccc1OCc1c(C)cccc1-n1nnn(C)c1=O]

$^1$H-NMR (CDCl$_3$) δ: 7.46-7.40 (2H, m), 7.30-7.25 (1H, m), 7.14-7.13 (2H, m), 6.98 (2H, t, J=2.2 Hz), 6.86 (1H, d, J=8.6 Hz), 6.31 (2H, t, J=2.3 Hz), 5.05 (2H, s), 3.64 (3H, s), 2.52 (3H, s), 2.13 (3H, s).

Production Example 20

The following compound was synthesized in the same manner as in Production Example 19. A structural formula of the thus obtained present compound and $^1$H-NMR data thereof are shown below.

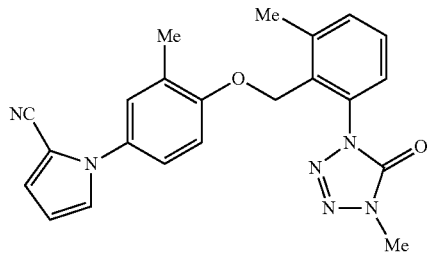 [SMILES: Cc1cc(-n2cccc2C#N)ccc1OCc1c(C)cccc1-n1nnn(C)c1=O]

$^1$H-NMR (CDCl$_3$) δ: 7.47-7.41 (2H, m), 7.29 (1H, dd, J=7.1, 2.1 Hz), 7.23-7.20 (1H, m), 7.18 (1H, dd, J=2.9, 0.6 Hz), 7.00 (1H, dd, J=2.7, 1.6 Hz), 6.95 (1H, dd, J=3.9, 1.6 Hz), 6.92 (1H, d, J=8.5 Hz), 6.30 (1H, dd, J=3.9, 2.7 Hz), 5.07 (2H, s), 3.66 (3H, s), 2.53 (3H, s), 2.15 (3H, s).

Production Example 21

A mixed solution of 0.5 g of C21A, 0.06 g of tris(dibenzylideneacetone)dipalladium, 0.11 g of xantphos, 0.83 g of cesium carbonate, 0.22 g of 2-pyrrolidone, and 5 ml of 1,4-dioxane was stirred at 100° C. for 23 hours. The reaction solution was diluted with ethyl acetate and washed with water. The organic layer was dried over anhydrous magnesium sulfate and then concentrated under reduced pressure, and the residue was subjected to silica gel chromatography to obtain 0.28 g of 1-{3-methyl-2-[[2-methyl-4-(2-pyrrolidon-1-yl)phenoxy]methyl]phenyl}-4-methyl-1,4-dihydrotetrazol-5-one (hereinafter referred to as the present compound 57).

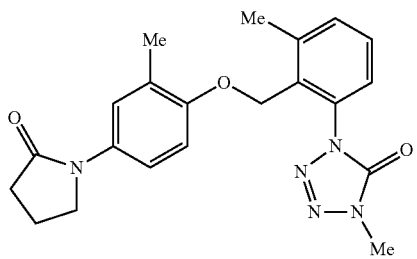 [SMILES: Cc1cc(N2CCCC2=O)ccc1OCc1c(C)cccc1-n1nnn(C)c1=O]

$^1$H-NMR (CDCl$_3$) δ: 7.42 (2H, t, J=7.2 Hz), 7.30-7.26 (3H, m), 6.82 (1H, d, J=9.2 Hz), 5.01 (2H, s), 3.80 (2H, t, J=7.1 Hz), 3.64 (3H, s), 2.58 (2H, t, J=8.1 Hz), 2.50 (3H, s), 2.18-2.09 (2H, m), 2.09 (3H, s).

Production Example 22

A mixed solution of 0.5 g of C21A, 0.03 g of copper(I) iodide, 0.03 g of L-proline, 0.35 g of potassium carbonate, 0.14 g of pyrrolidine, and 2 ml of dimethyl sulfoxide was stirred at 90° C. for 13 hours, and then the reaction solution was diluted with ethyl acetate and washed with water. The organic layer was dried over anhydrous magnesium sulfate and then concentrated under reduced pressure, the residue was subjected to silica gel chromatography to obtain 0.15 g of 1-{3-methyl-2-[[2-methyl-4-(pyrrolidin-1-yl)phenoxy]methyl]phenyl}-4-methyl-1,4-dihydrotetrazol-5-one (hereinafter referred to as the present compound 58).

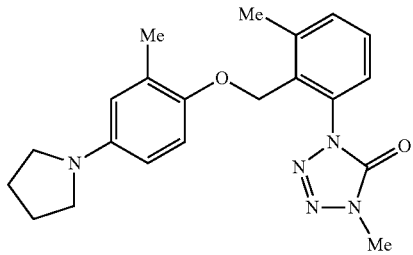 [SMILES: Cc1cc(N2CCCC2)ccc1OCc1c(C)cccc1-n1nnn(C)c1=O]

¹H-NMR (CDCl₃) δ: 7.43-7.36 (2H, m), 7.26-7.21 (1H, m), 6.76 (1H, d, J=8.7 Hz), 6.38 (1H, d, J=2.7 Hz), 6.32 (1H, dd, J=8.7, 2.7 Hz), 4.92 (2H, s), 3.64 (3H, s), 3.21 (4H, t, J=6.5 Hz), 2.51 (3H, s), 2.08 (3H, s), 1.99-1.95 (4H, m).

Production Example 23

A mixed solution of 0.35 g of C35A, 0.22 g of Lawesson's reagent, and 0.10 g of 2-amino-2-methylpropanol was reacted at 150° C. for 8 minutes under the irradiation of micro waves, and then the reaction solution was diluted with chloroform and washed with an aqueous sodium hydrogen carbonate solution. The organic layer was dried over anhydrous magnesium sulfate and then concentrated under reduced pressure, and the residue was subjected to silica gel chromatography to obtain 0.15 g of 1-{3-methyl-2-[[2-methyl-4-(4,4-dimethyl-2-thiazolin-2-yl)phenoxy]methyl]phenyl}-4-methyl-1,4-dihydrotetrazol-5-one (hereinafter referred to as the present compound 59).

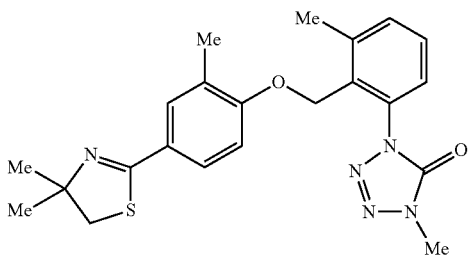 [SMILES: Cc1cc(C2=NC(C)(C)CS2)ccc1OCc1c(C)cccc1-n1nnn(C)c1=O]

¹H-NMR (CDCl₃) δ: 7.49-7.35 (4H, m), 7.31-7.28 (1H, m), 6.88 (1H, d, J=8.6 Hz), 5.09 (2H, s), 3.73 (1H, s), 3.63 (3H, s), 3.23 (1H, s), 2.49 (3H, s), 2.10 (3H, s), 1.58 (6H, s).

Production Example 24

In the same manner as in Production Example 3, 1-{3-methyl-2-[[2-methyl-4-(4-methyl-1,2,3-triazol-2-yl)phenoxy]methyl]phenyl}-4-methyl-1,4-dihydrotetrazol-5-one (hereinafter referred to as the present compound 60), and a mixture of 1-{3-methyl-2-[[2-methyl-4-(4-methyl-1,2,3-triazol-1-yl)phenoxy]methyl]phenyl}-4-methyl-1,4-dihydrotetrazol-5-one and 1-{3-methyl-2-[[2-methyl-4-(5-methyl-1,2,3-triazol-1-yl)phenoxy]methyl]phenyl}-4-methyl-1,4-dihydrotetrazol-5-one (hereinafter referred to as the present compound 61) were synthesized. Structural formulas of the thus obtained present compounds and ¹H-NMR data thereof are shown below.

Present Compound 60

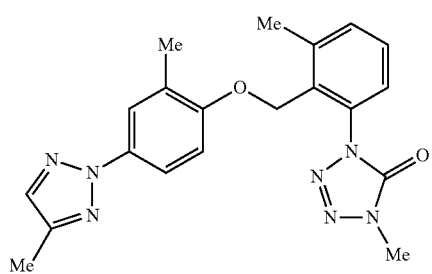

Present Compound 61

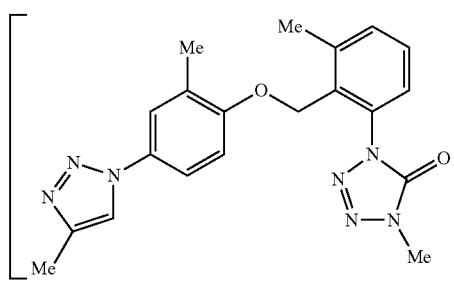

Present Compound 60

¹H-NMR (CDCl₃) δ: 7.79-7.72 (2H, m), 7.52 (1H, s), 7.48-7.39 (2H, m), 7.29 (1H, dd, J=6.9, 2.2 Hz), 6.89 (1H, d, J=8.8 Hz), 5.07 (2H, s), 3.63 (3H, s), 2.51 (3H, s), 2.40 (3H, s), 2.15 (3H, s).

Present Compound 61

¹H-NMR (CDCl₃) δ: 7.62 (0.85H, d, J=0.7 Hz), 7.56 (0.15H, d, J=0.7 Hz), 7.47-7.41 (3.7H, m), 7.30-7.28 (1H, m), 7.21-7.19 (0.30H, m), 6.95 (0.15H, d, J=9.1 Hz), 6.92 (0.85H, d, J=8.6 Hz), 5.10 (0.3H, s), 5.09 (1.7H, s), 3.66 (3H, s), 3.64 (2.55H, s), 2.53 (0.45H, s), 2.52 (2.55H, s), 2.43 (2.55H, d, J=0.7 Hz), 2.31 (0.45H, d, J=0.7 Hz), 2.18 (0.45H, s), 2.16 (2.55H, s).

Production Example 25

A mixture of 5.7 g of C45A, 1.2 ml of sulfuryl chloride, and 67 mL of chloroform was heated to 65° C. for 4 hours. After cooling to room temperature, the mixture was concentrated under reduced pressure. To the residue thus obtained, 1.2 g of thioacetamide, 1.2 g of sodium hydrogen carbonate, and 27 ml of THF were added, followed by heating to 75° C. and further stirring for 8 hours. After cooling to room temperature, water was poured into the reaction mixture and the mixture was extracted with chloroform. The organic layer was dried over anhydrous magnesium sulfate and then concentrated under reduced pressure. The residue thus obtained was subjected to silica gel column chromatography to obtain 0.9 g of ethyl 2-methyl-4-[3-methyl-4-{[2-methyl-6-(4-methyl-5-oxo-4,5-dihydrotetrazol-1-yl)phenyl]methoxy}phenyl]thiazole-5-carboxylate (hereinafter referred to as the present compound 62).

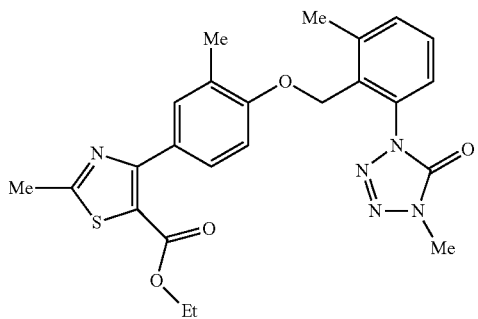 [SMILES: CCOC(=O)c1sc(C)nc1-c1ccc(OCc2c(C)cccc2-n2nnn(C)c2=O)c(C)c1]

$^1$H-NMR (CDCl$_3$) δ: 7.57 (1H, dd, J=8.4, 2.3 Hz), 7.52-7.51 (1H, m), 7.45-7.39 (2H, m), 7.29-7.27 (1H, m), 6.89 (1H, d, J=8.6 Hz), 5.07 (2H, s), 4.27 (2H, q, J=7.1 Hz), 3.65 (3H, s), 2.73 (3H, s), 2.50 (3H, s), 2.13 (3H, s), 1.30 (3H, t, J=7.1 Hz).

Production Example 26

A mixture of 0.77 g of the present compound 62, 0.18 g of potassium hydroxide, 10 mL of ethanol, and 2.5 ml of water was heated to 100° C. and stirred for 6 hours. After cooling to room temperature, the mixture was concentrated under reduced pressure. To the residue thus obtained, 20 ml of water was added and the pH was adjusted to 3 or lower using 1M hydrochloric acid. The precipitated crystal was filtered and dried to obtain a colorless crystal. To the thus obtained crystal, 8 ml of toluene, one drop pf DMF, and 0.16 ml of thionyl chloride were added, followed by heating to 70° C. and further stirring for 4 hours. The reaction solution was concentrated under reduced pressure and then added dropwise to 28% ammonia water as an ethyl acetate solution, followed by stirring at room temperature for 2 hours. The reaction solution was concentrated under reduced pressure, and then 2.5 ml of DMF and 0.55 ml of phosphorus oxychloride were added dropwise to the thus obtained crystal, followed by heating to 60° C. and further stirring for 40 minutes. The reaction solution was poured into water and extracted with chloroform, and then the organic layer was dried over anhydrous magnesium sulfate and concentrated under reduced pressure. The residue thus obtained was subjected to silica gel column chromatography to obtain 1-{3-methyl-2-[[2-methyl-4-(5-cyano-2-methylthiazol-4-yl)phenoxy]methyl]phenyl}-4-methyl-1,4-dihydrotetrazol-5-one (hereinafter referred to as the present compound 63).

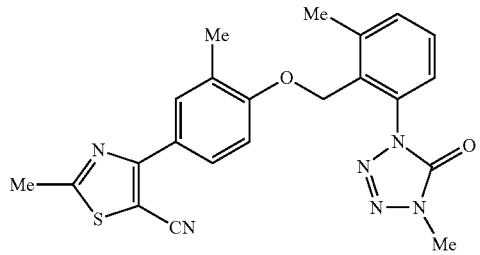 [SMILES: Cc1nc(-c2ccc(OCc3c(C)cccc3-n3nnn(C)c3=O)c(C)c2)c(C#N)s1]

$^1$H-NMR (CDCl$_3$) δ: 7.93 (1H, dd, J=8.2, 2.1 Hz), 7.87-7.86 (1H, m), 7.46-7.41 (2H, m), 7.30-7.28 (1H, m), 6.93 (1H, d, J=8.5 Hz), 5.11 (2H, s), 3.64 (3H, s), 2.78 (3H, s), 2.52 (3H, s), 2.15 (3H, s).

With respect to the production of intermediates for production of the above-mentioned present compounds, Reference Production Examples are shown below.

Reference Production Example 1

Under ice cooling, 21.9 g of anhydrous aluminum chloride was added to 250 mL of N,N-dimethylformamide, followed by stirring for 15 minutes. To this was added 10.7 g of sodium azide and, after stirring for 15 minutes, 25.0 g of 1-chloro-3-isocyanato-2-methylbenzene was added, followed by heating at 80° C. for 5 hours. After cooling, the reaction solution was added in a mixture of 35 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one (C1A).

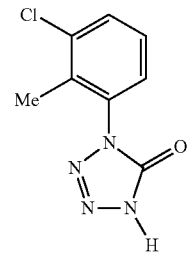

$^1$H-NMR (CDCl$_3$) δ(ppm): 2.32 (3H, s), 7.28-7.36 (2H, m), 7.57 (1H, dd, J=6.8, 2.2 Hz), 13.08 (1H, s).

Reference Production Example 2

To a mixture of 10.00 g of C1A and 100 mL of N,N-dimethylformamide, 2.30 g of 60% sodium hydride was added under ice cooling. The temperature of the mixture was raised to room temperature, followed by stirring for 1 hour. To the reaction mixture, 3.2 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 1.56 g of 1-(2-methyl-3-chlorophenyl)-4-methyl-1,4-dihydrotetrazol-5-one (CA2).

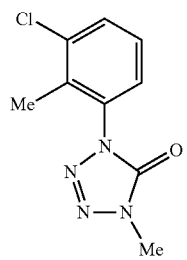

$^1$H-NMR (CDCl$_3$) δ(ppm): 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

Reference Production Example 3

A mixture of 1.56 g of C2A, 0.34 g of 1,1'-azobis(cyclohexane-1-carbonitrile), 1.42 g of N-bromosuccinimide, and 30 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.94 g of 1-(2-bromomethyl-3-chlorophenyl)-4-methyl-1,4-dihydrotetrazol-5-one (C3A).

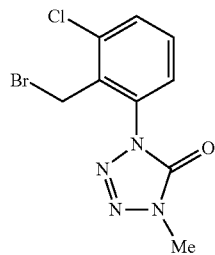

$^1$H-NMR (CDCl$_3$) δ(ppm): 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Production Example 4

A mixture of 15.0 g of 3-amino-1-methoxy-2-methylbenzene, 48.7 g of triphosgene, and 350 ml of toluene was stirred with heating under reflux for 3 hours. The reaction mixture allowed to cool was concentrated under reduced pressure to obtain 17.0 g of 1-methoxy-3-isocyanato-2-methylbenzene (C4A).

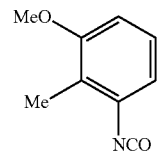

$^1$H-NMR (CDCl$_3$) δ(ppm): 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

Reference Production Example 5

Under ice cooling, 16.0 g of anhydrous aluminum chloride was added to 180 mL of N,N-dimethylformamide, followed by stirring for 15 minutes. To this was added 7.8 g of sodium azide and, after stirring for 15 minutes, 17.0 g of C4A was added, followed by heating at 80° C. for 4.5 hours. After cooling, the reaction solution was added in a mixture of 25 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one (C5A).

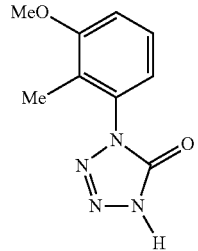

$^1$H-NMR (DMSO-D$_6$) δ(ppm): 1.99 (3H, s), 3.87 (3H, s), 7.01 (1H, d, J=8.1 Hz), 7.17 (1H, d, J=8.1 Hz). 7.36 (1H, t, J=8.3 Hz), 14.63 (1H, s).

Reference Production Example 6

To a mixture of 10.00 g of C5A and 100 mL of N,N-dimethylformamide, 2.47 g of 60% sodium hydride was added under ice cooling. The temperature of the mixture was raised to room temperature, followed by stirring for 1 hour. To the reaction mixture, 3.5 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 2.19 g of 1-(2-methyl-3-methoxyphenyl)-4-methyl-1,4-dihydrotetrazol-5-one (C6A).

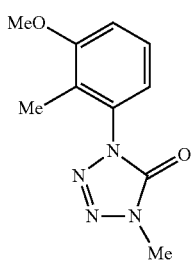

¹H-NMR (CDCl₃) δ(ppm): 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz)

Reference Production Example 7

A mixture of 2.19 g of C6A, 0.52 g of 1,1'-azobis(cyclohexane-1-carbonitrile), 2.16 g of N-bromosuccinimide, and 40 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.36 g of 1-(2-bromomethyl-3-methoxyphenyl)-4-methyl-1,4-dihydrotetrazol-5-one (C7A).

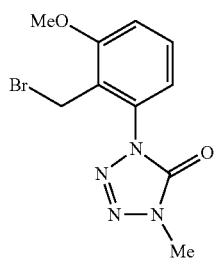 [SMILES: COc1cccc(-n2nnn(C)c2=O)c1CBr]

¹H-NMR (CDCl₃) δ(ppm): 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Production Example 8

A mixture of 25.0 g of 1-bromo-2-methyl-3-aminobenzene, 60.0 g of triphosgene, and 400 ml of toluene was stirred with heating under reflux for 3 hours. The reaction mixture allowed to cool was concentrated under reduced pressure to obtain 30.3 g of 1-bromo-3-isocyanato-2-methylbenzene (C8A).

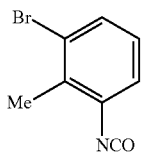

¹H-NMR (CDCl₃) δ(ppm): 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

Reference Production Example 9

Under ice cooling, 19.7 g of anhydrous aluminum chloride was added to 220 mL of N,N-dimethylformamide, followed by stirring for 15 minutes. To this was added 9.6 g of sodium azide and, after stirring for 15 minutes, 30.3 g of C8A was added, followed by heating at 80° C. for 5 hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one (C9A).

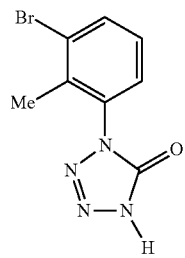

¹H-NMR (DMSO-D₆) δ(ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Production Example 10

To a mixture of 31.4 g of C9A and 250 mL of N,N-dimethylformamide, 5.90 g of 60% sodium hydride was added under ice cooling. The temperature of the mixture was raised to room temperature, followed by stirring for 1 hour. To the reaction mixture, 8.4 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one (C10A).

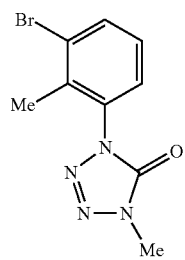

¹H-NMR (CDCl₃) δ(ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Production Example 11

A mixture of 8.47 g of C10A, 1.54 g of 1,1'-azobis(cyclohexane-1-carbonitrile), 6.44 g of N-bromosuccinimide, and 125 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.52 g of 1-(2-bromomethyl-3-bromophenyl)-4-methyl-1, 4-dihydrotetrazol-5-one (C11A).

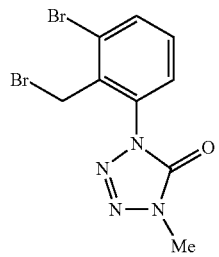 [SMILES: Cn1nnn(-c2cccc(Br)c2CBr)c1=O]

$^1$H-NMR (CDCl$_3$) δ(ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 12

A mixture of 45.0 g of C11A, 37.4 g of sodium methoxide, and 600 mL of tetrahydrofuran was stirred at room temperature for 3 hours. A saturated sodium bicarbonate solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 36.2 g of 1-(2-methoxymethyl-3-bromophenyl)-4-methyl-1,4-dihydrotetrazol-5-one (C12A).

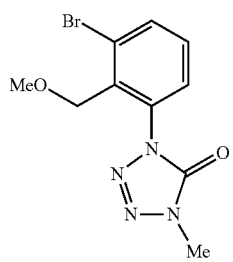

$^1$H-NMR (CDCl$_3$) δ(ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Production Example 13

A mixture of 36.2 g of C12A, 23.2 g of methylboronic acid, 66.7 g of cesium fluoride, 10.6 g of [1,1'-bis(diphenylphosphino) ferrocene]palladium (II) dichloride dichloromethane adduct, and 500 ml of dioxane was stirred at 90° C. for 5.5 hours. After cooling, the reaction mixture was filtered and the filtrate was concentrated under reduced pressure. The residue thus obtained was subjected to silica gel column chromatography to obtain 25.6 g of 1-(2-methoxymethyl-3-methylphenyl)-4-methyl-1, 4-dihydrotetrazol-5-one (C13A).

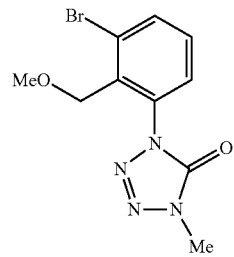 [SMILES: COCc1c(Br)cccc1-n1nnn(C)c1=O]

$^1$H-NMR (CDCl$_3$) δ(ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Reference Production Example 14

A mixture of 25.6 g of C13A, 50 mL of acetic acid, and 50 mL of a 25% hydrogen bromide-acetic acid solution was stirred at 65° C. for 1 hour. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 27.9 g of 1-(2-bromomethyl-3-methylphenyl)-4-methyl-1,4-dihydrotetrazol-5-one (C14A).

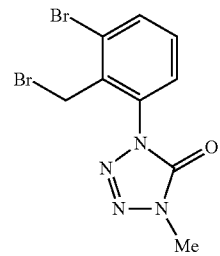

$^1$H-NMR (CDCl$_3$) δ(ppm): 2.51 (3H, s), 3.75 (3H, s), 4.51 (2H, s), 7.22-7.24 (1H, m), 7.36-7.39 (2H, m).

Reference Production Example 15

A mixture of 30.1 g of C12A, 12.9 g of cyclopropylboronic acid, 46.2 g of cesium fluoride, 8.2 g of [1,1'-bis(diphenylphosphino)ferrocene]palladium (II) dichloride dichloromethane adduct, and 680 ml of dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-(2-methoxymethyl-3-cyclopropylphenyl)-4-methyl-1,4-dihydrotetrazol-5-one (C15A).

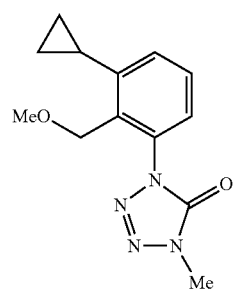 [SMILES: COCc1c(C2CC2)cccc1-n1nnn(C)c1=O]

¹H-NMR (CDCl₃) δ(ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 16

A mixture of 26.0 g of C15A, 40 mL of acetic acid, and 40 mL of a 25% hydrogen bromide-acetic acid solution was stirred at 65° C. for 2 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 30.8 g of 1-(2-bromomethyl-3-cyclopropylphenyl)-4-methyl-1,4-dihydrotetrazol-5-one (C16A).

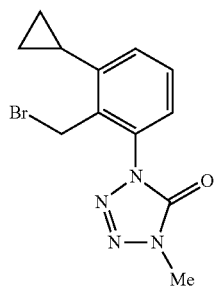 [SMILES: Cn1nnn(-c2cccc(C3CC3)c2CBr)c1=O]

¹H-NMR (CDCl₃) δ(ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 17

A mixture of 29.8 g of C12A, 35.2 g of tributylvinyltin, 11.6 g of tetrakistriphenylphosphine palladium, and 500 mL of toluene was stirred with heating under reflux for 14 hours. After cooling, an aqueous saturated ammonium chloride solution was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 19.7 g of 1-(2-methoxymethyl-3-ethenylphenyl)-4-methyl-1,4-dihydrotetrazol-5-one (C17A).

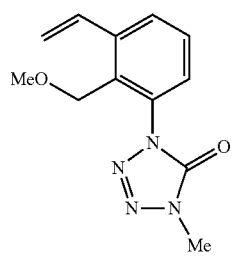 [SMILES: C=Cc1cccc(-n2nnn(C)c2=O)c1COC]

¹H-NMR (CDCl₃) δ(ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Reference Production Example 18

A mixture of 19.7 g of C17A, 3.02 g of a palladium-fibroin complex, and 1 L of methanol was stirred in a hydrogen atmosphere at room temperature for 11 hours. The reaction mixture was filtered and the filtrate was concentrated under reduced pressure. The residue thus obtained was subjected to silica gel column chromatography to obtain 19.3 g of 1-(2-methoxymethyl-3-ethylphenyl)-4-methyl-1,4-dihydrotetrazol-5-one (C18A).

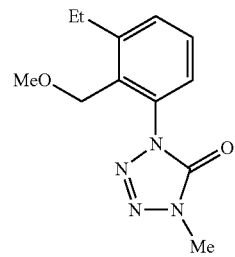 [SMILES: CCc1cccc(-n2nnn(C)c2=O)c1COC]

¹H-NMR (CDCl₃) δ(ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Reference Production Example 19

A mixture of 19.3 g of C18A, 40 mL of acetic acid, and 40 mL of a 25% hydrogen bromide-acetic acid solution was stirred at 65° C. for 1.5 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 23.3 g of 1-(2-bromomethyl-3-ethylphenyl)-4-methyl-1,4-dihydrotetrazol-5-one (C19A).

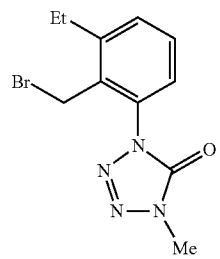 [SMILES: CCc1cccc(-n2nnn(C)c2=O)c1CBr]

¹H-NMR (CDCl₃) δ(ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Production Example 20

A mixture of 9.11 g of C3A, 5.61 g of 4-bromo-2-methylphenol, 8.29 g of potassium carbonate, and 120 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 11.8 g of 1-[2-(4-bromo-2-methylphenoxymethyl)-3-chlorophenyl]-4-methyl-1,4-dihydrotetrazol-5-one (C20A).

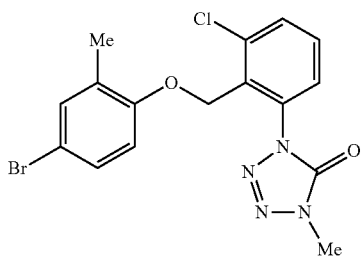 [SMILES: Cc1cc(Br)ccc1OCc1c(Cl)cccc1-n1nnn(C)c1=O]

¹H-NMR (CDCl₃) δ: 7.65 (1H, d, J=8.0 Hz), 7.51 (1H, t, J=8.0 Hz), 7.45-7.42 (1H, m), 7.30-7.24 (2H, m), 6.75 (1H, d, J=8.2 Hz), 5.31 (2H, s), 3.65 (3H, s), 2.03 (3H, s).

Reference Production Example 21

A mixture of 23.5 g of C14A, 15.5 g of 4-bromo-2-methylphenol, 22.9 g of potassium carbonate, and 330 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 30.1 g of 1-[2-(4-bromo-2-methylphenoxymethyl)-3-methylphenyl]-4-methyl-1,4-dihydrotetrazol-5-one (C21A).

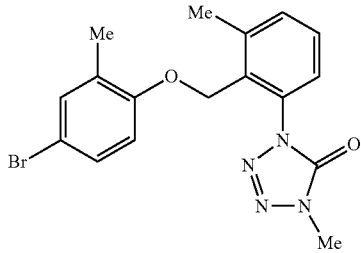 [SMILES: Cc1cc(Br)ccc1OCc1c(C)cccc1-n1nnn(C)c1=O]

¹H-NMR (CDCl₃) δ: 7.46-7.39 (2H, m), 7.29-7.26 (1H, m), 7.25-7.21 (2H, m), 6.70 (1H, d, J=9.4 Hz), 5.00 (2H, s), 3.63 (3H, s), 2.49 (3H, s), 2.06 (3H, s).

Reference Production Example 22

A mixture of 8.97 g of C7A, 5.61 g of 4-bromo-2-methylphenol, 8.29 g of potassium carbonate, and 120 mL of acetonitrile stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 12.3 g of 1-[2-(4-bromo-2-methylphenoxymethyl)-3-methoxyphenyl]-4-methyl-1,4-dihydrotetrazol-5-one (C22A).

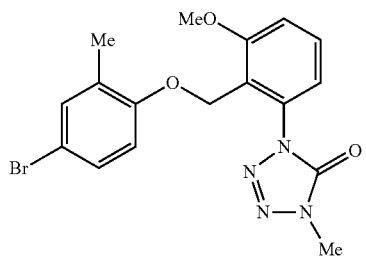 [SMILES: COc1cccc(-n2nnn(C)c2=O)c1COc1ccc(Br)cc1C]

¹H-NMR (CDCl₃) δ: 7.46 (1H, t, J=8.2 Hz), 7.20-7.15 (2H, m), 7.10-7.04 (2H, m), 6.73 (1H, d, J=8.2 Hz), 5.22 (2H, s), 3.91 (3H, s), 3.59 (3H, s), 1.96 (3H, s).

Reference Production Example 23

A mixture of 8.91 g of C19A, 5.61 g of 4-bromo-2-methylphenol, 8.29 g of potassium carbonate, and 120 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 12.2 g of 1-[2-(4-bromo-2-methylphenoxymethyl)-3-ethylphenyl]-4-methyl-1,4-dihydrotetrazol-5-one (C23A).

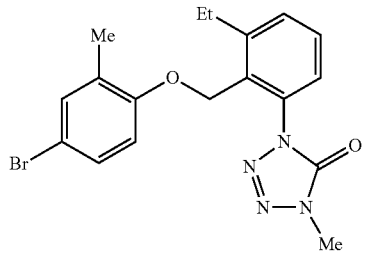

¹H-NMR (CDCl₃) δ: 7.50-7.43 (2H, m), 7.30-7.26 (1H, m), 7.25-7.21 (2H, m), 6.71 (1H, d, J=8.7 Hz), 5.02 (2H, s), 3.60 (3H, s), 2.83 (2H, q, J=7.6 Hz), 2.04 (3H, s), 1.27 (3H, t, J=7.6 Hz).

Reference Production Example 24

A mixture of 9.27 g of C16A, 5.61 g of 4-bromo-2-methylphenol, 8.29 g of potassium carbonate, and 120 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 12.8 g of 1-[2-(4-bromo-2-methylphenoxymethyl)-3-cyclopropylphenyl]-4-methyl-1,4-dihydrotetrazol-5-one (C24A).

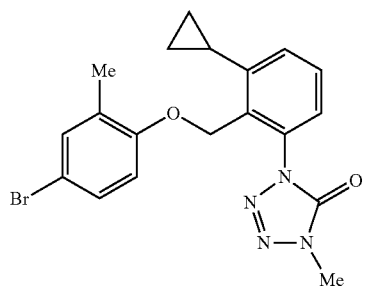 [SMILES: Cc1cc(Br)ccc1OCc1c(C2CC2)cccc1-n1nnn(C)c1=O]

$^1$H-NMR (CDCl$_3$) δ: 7.44 (1H, t, J=7.8 Hz), 7.26-7.24 (4H, m), 6.75 (1H, d, J=8.2 Hz), 5.23 (2H, s), 3.62 (3H, s), 2.12-2.07 (1H, m), 2.05 (3H, s), 1.02-0.96 (2H, m), 0.79-0.73 (2H, m).

Reference Production Example 25

A mixture of 4.25 g of C14A, 3.02 g of 4-bromo-2,5-dimethylphenol, 4.15 g of potassium carbonate, and 60 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 5.82 g of 1-[2-(4-bromo-2,5-dimethylphenoxymethyl)-3-methylphenyl]-4-methyl-1,4-dihydrotetrazol-5-one (C25A).

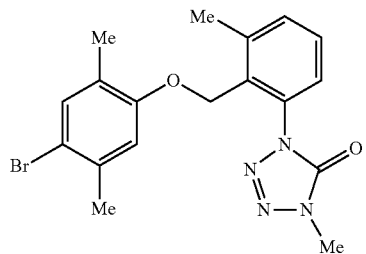 [SMILES: Cc1cc(OCc2c(C)cccc2-n2nnn(C)c2=O)c(C)cc1Br]

$^1$H-NMR (CDCl$_3$) δ: 7.45-7.37 (2H, m), 7.28-7.25 (1H, m), 7.23 (1H, s), 6.68 (1H, s), 4.99 (2H, s), 3.64 (3H, s), 2.49 (3H, s), 2.33 (3H, s), 2.01 (3H, s).

Reference Production Example 26

A mixture of 4.05 g of C21A, 2.79 g of bis(pinacolato)diboron, 0.25 g of [1,1'-bis(diphenylphosphino) ferrocene]palladium (II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 2.92 g of 1-[2-{4-(4,4,5,5-tetramethyl-[1,3,2]dioxaborolan-2-yl)-2-methylphenoxymethyl}-3-methoxyphenyl]-4-methyl-1,4-dihydrotetrazol-5-one (C26A).

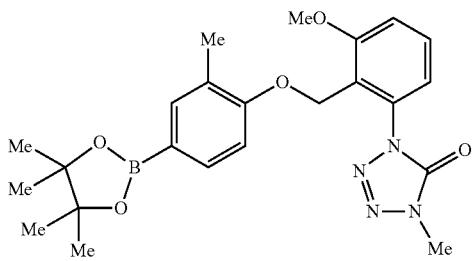 [SMILES: COc1cccc(-n2nnn(C)c2=O)c1COc1ccc(B2OC(C)(C)C(C)(C)O2)cc1C]

$^1$H-NMR (CDCl$_3$) δ: 7.58 (1H, dd, J=8.2, 1.4 Hz), 7.51 (1H, s), 7.45 (1H, t, J=8.3 Hz), 7.08-7.04 (2H, m), 6.87 (1H, d, J=8.2 Hz), 5.28 (2H, s), 3.91 (3H, s), 3.57 (3H, s), 1.97 (3H, s), 1.31 (12H, s).

Reference Production Example 27

A mixture of 3.89 g of C21A, 2.79 g of bis(pinacolato)diboron, 0.25 g of [1,1'-bis(diphenylphosphino)ferrocene]palladium (II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 3.44 g of 1-[2-{4-(4,4,5,5-tetramethyl-[1,3,2]dioxabororan-2-yl)-2-methylphenoxymethyl}-3-methylphenyl]-4-methyl-1,4-dihydrotetrazol-5-one (C27A).

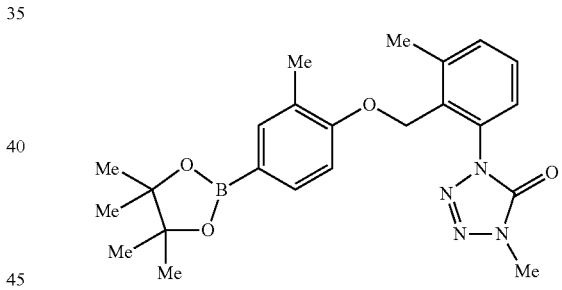

$^1$H-NMR (CDCl$_3$) δ: 7.62 (1H, dd, J=8.0, 1.4 Hz), 7.57 (1H, s), 7.44-7.38 (2H, m), 7.29-7.25 (1H, m), 6.85 (1H, d, J=8.2 Hz), 5.05 (2H, s), 3.62 (3H, s), 2.49 (3H, s), 2.08 (3H, s), 1.33 (12H, s).

Reference Production Example 28

A mixture of 2.79 g of C22A, 0.25 g of [1,1'-bis(diphenylphosphino)ferrocene]palladium (II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 3.69 g of 1-[2-{4-(4,4,5,5-tetramethyl-[1,3,2]dioxaborolan-2-yl)-2-methylphenoxymethyl}-3-chlorophenyl]-4-methyl-1,4-dihydrotetrazol-5-one (C28A).

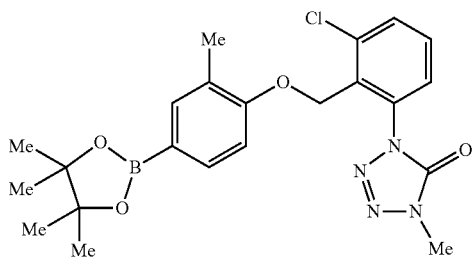

¹H-NMR (CDCl₃) δ: 7.63-7.59 (2H, m), 7.55 (1H, s), 7.46 (1H, t, J=7.9 Hz), 7.39 (1H, dd, J=8.0, 0.9 Hz), 6.85 (1H, d, J=8.2 Hz), 5.34 (2H, s), 3.59 (3H, s), 2.02 (3H, s), 1.33 (12H, s).

Reference Production Example 29

A mixture of 2.79 g of C23A, 0.25 g of [1,1'-bis(diphenylphosphino) ferrocene]palladium (II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 3.87 g of 1-[2-{4-(4,4,5,5-tetramethyl-[1,3,2]dioxaborolan-2-yl)-2-methylphenoxymethyl}-3-ethylphenyl]-4-methyl-1,4-dihydrotetrazol-5-one (C29A).

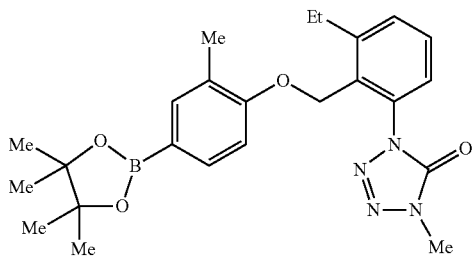 [SMILES: CCc1cccc(-n2nnn(C)c2=O)c1COc1ccc(B2OC(C)(C)C(C)(C)O2)cc1C]

¹H-NMR (CDCl₃) δ: 7.63 (1H, dd, J=8.1, 1.3 Hz), 7.56 (1H, s), 7.49-7.43 (2H, m), 7.29-7.25 (1H, m), 6.86 (1H, d, J=8.2 Hz), 5.07 (2H, s), 3.59 (3H, s), 2.83 (2H, q, J=7.6 Hz), 2.07 (3H, s), 1.33 (12H, s), 1.26 (3H, t, J=7.6 Hz).

Reference Production Example 30

A mixture of 2.79 g of C24A, 0.25 g of [1,1'-bis(diphenylphosphino) ferrocene]palladium (II) dichloride dichloromethane adduct, 2.94 g of potassium acetate, and 30 mL of dimethyl sulfoxide was stirred with heating in a nitrogen atmosphere at 80° C. for 8 hours. Water was poured into the reaction mixture allowed to cool and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 3.97 g of 1-[2-{4-(4,4,5,5-tetramethyl-[1,3,2]dioxaborolan-2-yl)-2-methylphenoxymethyl}-3-cyclopropylphenyl]-4-methyl-1,4-dihydrotetrazol-5-one (C30A).

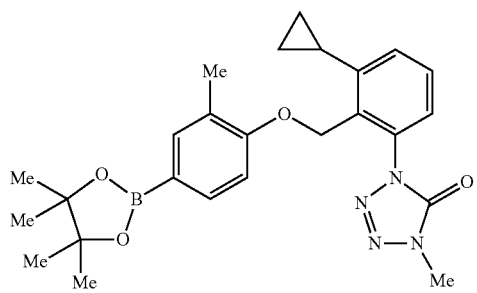 [SMILES: Cc1cc(B2OC(C)(C)C(C)(C)O2)ccc1OCc1c(C2CC2)cccc1-n1nnn(C)c1=O]

¹H-NMR (CDCl₃) δ: 7.63 (1H, d, J=8.0 Hz), 7.56 (1H, s), 7.43 (1H, t, J=7.9 Hz), 7.28-7.24 (2H, m), 6.89 (1H, d, J=8.2 Hz), 5.28 (2H, s), 3.60 (3H, s), 2.11-2.06 (4H, m), 1.33 (12H, s), 1.00-0.94 (2H, m), 0.78-0.72 (2H, m).

Reference Production Example 31

A mixture of 3.7 g of C14A, 3.0 g of 4-iodo-2-methylphenol, 3.5 g of potassium carbonate, and 50 mL of acetonitrile was stirred with heating at 80° C. for 4 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was washed with hexane and methyl tert-butyl ketone to obtain 5.0 g of 1-[2-(4-iodo-2-methylphenoxymethyl)-3-methylphenyl]-4-methyl-1,4-dihydrotetrazol-5-one (C31A).

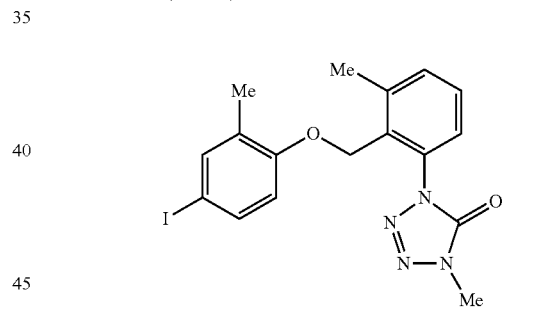

¹H-NMR (CDCl₃) δ: 7.45-7.39 (4H, m), 7.28-7.26 (1H, m), 6.60 (1H, d, J=8.6 Hz), 4.99 (2H, s), 3.63 (3H, s), 2.49 (3H, s), 2.03 (3H, s).

Reference Production Example 32

A mixture of 5.4 g of C7A, 3.0 g of methyl 4-hydroxy-3-methylbenzoic acid ester, 3.24 g of potassium carbonate, and 72 mL of acetonitrile was stirred with heating under reflux for 4 hours. After cooling, water was poured into the reaction solution and extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 6.4 g of 3-methyl-4-[2-methoxy-6-(4-methyl-5-oxo-4,5-dihydrotetrazol-1-yl)-benzyloxy]benzoic acid methyl ester (C32A).

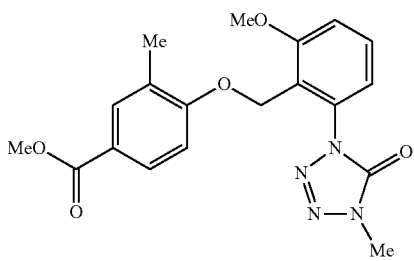 [SMILES: COC(=O)c1ccc(OCc2c(OC)cccc2-n2nnn(C)c2=O)c(C)c1]

¹H-NMR (CDCl₃) δ: 7.83 (1H, dd, J=8.6, 2.3 Hz), 7.77-7.74 (1H, m), 7.48 (1H, t, J=8.2 Hz), 7.12-7.06 (2H, m), 6.90 (1H, d, J=8.6 Hz), 5.33 (2H, s), 3.94 (3H, s), 3.86 (3H, s), 3.59 (3H, s), 2.00 (3H, s).

Reference Production Example 33

A mixture of 3.4 g of C14A, 2.1 g of 4-hydroxy-3-methylbenzoic acid methyl ester, 2.2 g of potassium carbonate, and 50 mL of acetonitrile was stirred with heating under reflux for 7 hours. After cooling, water was poured into the reaction solution and extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 3.8 g of 3-methyl-4-[2-methyl-6-(4-methyl-5-oxo-4,5-dihydrotetrazol-1-yl)-benzyloxy]benzoic acid methyl ester (C33A)

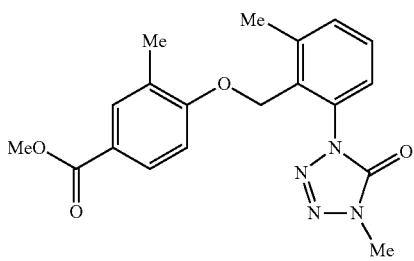 [SMILES: COC(=O)c1ccc(OCc2c(C)cccc2-n2nnn(C)c2=O)c(C)c1]

¹H-NMR (CDCl₃) δ: 7.86 (1H, dd, J=8.5, 2.4 Hz), 7.80 (1H, s), 7.46-7.40 (2H, m), 7.30-7.26 (1H, m), 6.86 (1H, d, J=8.5 Hz), 5.10 (2H, s), 3.88 (3H, s), 3.62 (3H, s), 2.50 (3H, s), 2.11 (3H, s).

Reference Production Example 34

A mixture of 1.0 g of C32A, 0.19 g of lithium hydroxide, 0.30 g of cesium fluoride, 5 mL of tetrahydrofuran, 5 mL of methanol, and 5 mL of water was stirred at room temperature for 8 hours. After concentration under reduced pressure, the pH was adjusted to lower than 7 with 12N hydrochloric acid and the precipitated solid was collected by filtration to obtain 0.64 g of 3-methyl-4-[2-methoxy-6-(4-methyl-5-oxo-4,5-dihydrotetrazol-1-yl)-benzyloxy]benzoic acid (C34A).

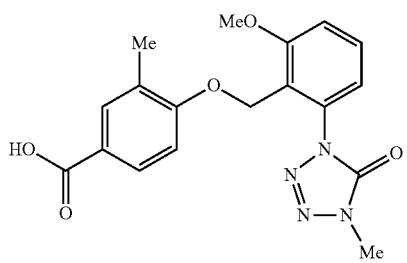

¹H-NMR (CDCl₃) δ: 7.90 (1H, dd, J=8.6, 2.3 Hz), 7.83-7.80 (1H, m), 7.48 (1H, t, J=8.2 Hz), 7.13-7.06 (2H, m), 6.92 (1H, d, J=8.6 Hz), 5.35 (2H, s), 3.94 (3H, s), 3.60 (3H, s), 2.02 (3H, s).

Reference Production Example 35

A mixture of 3.8 g of C33A, 0.74 g of lithium hydroxide, 30 mL of tetrahydrofuran, 15 mL of methanol, and 15 mL of water was stirred at room temperature for 8 hours. After concentration under reduced pressure, the pH was adjusted to lower than 7 with 12N hydrochloric acid and the precipitated solid was collected by filtration to obtain 2.0 g of 3-methyl-4-[2-methyl-6-(4-methyl-5-oxo-4,5-dihydrotetrazol-1-yl)-benzyloxy]benzoic acid (C35A).

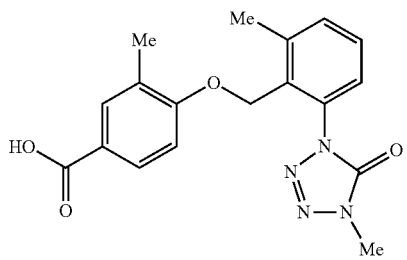 [SMILES: Cc1cc(C(=O)O)ccc1OCc1c(C)cccc1-n1nnn(C)c1=O]

¹H-NMR (DMSO-D₆) δ: 7.79-7.69 (2H, m), 7.54-7.51 (2H, m), 7.39-7.36 (1H, m), 7.06 (1H, d, J=8.7 Hz), 5.11 (2H, s), 3.53 (3H, s), 2.48 (3H, s), 2.04 (3H, s).

Reference Production Example 36

A mixture of 0.25 g of C35A, 0.20 g of 1-hydroxybenzotriazole (HOBt), 0.60 g of 1-ethyl-3-(3-dimethylaminopropyl)carbodiimide hydrochloride, 0.6 ml of diisopropylethylamine, and 3 ml of N,N-dimethylformamide was stirred at room temperature for 20 hours. Water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.25 g of N'-acetyl-3-methyl-4-{[2-methyl-6-(4-methyl-5-oxo-4,5-dihydro-1H-tetrazol-1-yl)phenyl]methoxy}benzohydrazide (C36A).

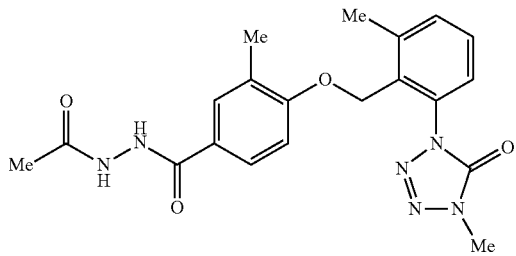 [SMILES: CC(=O)NNC(=O)c1ccc(OCc2c(C)cccc2-n2nnn(C)c2=O)c(C)c1]

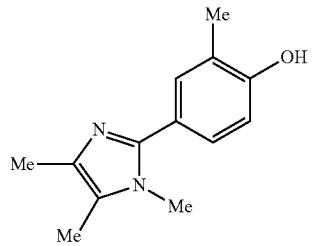

$^1$H-NMR (CDCl$_3$) δ: 8.86 (1H, s), 8.68 (1H, s), 7.64 (1H, d, J=8.7 Hz), 7.60 (1H, s), 7.43 (2H, d, J=8.0 Hz), 7.30-7.28 (1H, m), 6.86 (1H, d, J=8.5 Hz), 5.09 (2H, s), 3.63 (3H, s), 2.50 (3H, s), 2.12 (3H, s), 2.10 (3H, s).

$^1$H-NMR (CDCl$_3$) δ: 2.17 (3H, s), 2.19 (3H, s), 2.23 (3H, s), 3.49 (3H, s), 6.55 (1H, d, J=8.2 Hz), 6.97 (1H, d, J=8.2 Hz), 7.15 (1H, s).

Reference Production Example 39

Reference Production Example 37

A mixture of 4.00 g of 4-methoxy-3-methylbenzaldehyde, 2.69 g of diacetyl monoxime, an aqueous 40% methylamine solution, and 40 mL of acetic acid was stirred with heating under reflux for 4.5 hours. After allowing to stand, 6.56 g of zinc was added and the mixture was stirred with heating under reflux for 4 hours. After allowing to stand, the mixture was filtered through Cerite and the filtrate was made basic by adding ammonia water. After extraction with tert-butyl methyl ether, the organic layer was washed with water and a saturated saline solution, dried over anhydrous sodium sulfate, and then concentrated under reduced pressure. The residue thus obtained was recrystallized using chloroform and hexane to obtain 1.48 g of 2-(4-methoxy-3-methylphenyl)-1,4,5-trimethylimidazole (C37A).

A mixture of 1.86 g of 4-methoxy-3-methylphenylboronic acid, 2.00 g of 2-bromo-4-methylthiazole, 0.46 g of [1,1'-bis(diphenylphosphino) ferrocene]palladium (II) dichloride dichloromethane adduct, 4.05 g of sodium carbonate, 50 mL of dioxane, and 50 mL of water was stirred at 80° C. for 8 hours. After cooling, the reaction mixture was filtered and the filtrate was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 1.00 g of 4-methyl-2-(4-methoxy-3-methylphenyl)-thiazole (C39A).

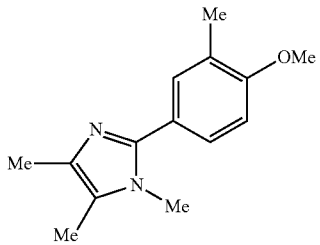 [SMILES: COc1ccc(-c2nc(C)c(C)n2C)cc1C]

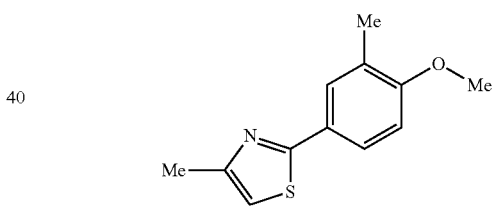

$^1$H-NMR (CDCl$_3$) δ: 2.18 (3H, s), 2.21 (3H, s), 2.25 (3H, s), 3.53 (3H, s), 3.86 (3H, s), 6.86 (1H, d, J=8.3 Hz), 7.33 (1H, dt, J=8.3, 1.1 Hz), 7.38 (1H, t, J=1.1 Hz).

$^1$H-NMR (CDCl$_3$) δ: 7.73-7.71 (2H, m), 6.84 (1H, d, J=8.8 Hz), 6.78 (1H, d, J=1.0 Hz), 3.87 (3H, s), 2.49 (3H, d, J=0.7 Hz), 2.26 (3H, s).

Reference Production Example 40

Reference Production Example 38

A mixture of 1.48 g of C37A, 15 mL of a 48% hydrobromic acid, and 15 mL of acetic acid was stirred at 110° C. for 27 hours. The reaction solution was concentrated and a saturated sodium bicarbonate solution was added, and then the mixture was extracted with a 10% methanol-chloroform solution. The organic layer was washed with a saturated saline solution, dried over anhydrous sodium sulfate, and then concentrated under reduced pressure to obtain 0.52 g of 2-(4-hydroxy-3-methylphenyl)-1,4,5-trimethylimidazole (C38A).

A mixture of 0.93 g of 4-methoxy-3-methylphenylboronic acid, 1.00 g of 5-bromo-2-methylthiazole, 0.23 g of [1,1'-bis(diphenylphosphino)ferrocene]palladium (II) dichloride dichloromethane adduct, 2.0 g of sodium carbonate, 25 mL of dioxane, and 25 mL of water was stirred at 90° C. for 6 hours. After cooling, the reaction mixture was filtered and the filtrate was extracted with ethyl acetate. The organic layer was washed with water and a saturated saline solution, dried over anhydrous sodium sulfate, and then concentrated under reduced pressure. The residue thus obtained was subjected to silica gel column chromatography to obtain 1.90 g of 2-methyl-5-(4-methoxy-3-methylphenyl)thiazole (C40A).

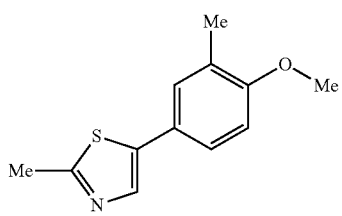 [SMILES: COc1ccc(-c2cnc(C)s2)cc1C]

¹H-NMR (CDCl₃) δ: 7.67 (1H, s), 7.32-7.30 (2H, m), 6.82 (1H, d, J=8.0 Hz), 3.85 (3H, s), 2.71 (3H, s), 2.24 (3H, s).

Reference Production Example 41

A mixture of 1.00 g of C39A, 7.1 ml of hydrobromic acid, and 7.1 ml of acetic acid was stirred at 100° C. for 13 hours. After cooling, water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.90 g of 4-methyl-2-(4-hydroxy-3-methylphenyl)thiazole (C41A).

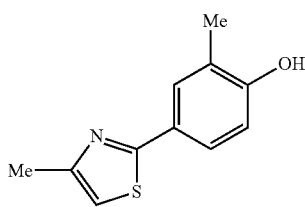 [SMILES: Cc1csc(-c2ccc(O)c(C)c2)n1]

¹H-NMR (DMSO-D₆) δ: 7.70 (1H, d, J=1.7 Hz), 7.64-7.61 (1H, m), 7.24 (1H, s), 6.90 (1H, d, J=8.3 Hz), 2.40 (3H, s), 2.18 (3H, s).

Reference Production Example 42

A mixture of 1.9 g of C40A, 13 ml of hydrobromic acid, and 13 ml of acetic acid was stirred at 100° C. for 13 hours. After cooling, water was added to the reaction mixture and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 1.8 g of 2-methyl-5-(4-hydroxy-3-methylphenyl)thiazole (C42A).

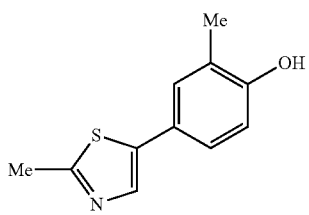 [SMILES: Cc1ncc(-c2ccc(O)c(C)c2)s1]

¹H-NMR (DMSO-D₆) δ: 7.90 (1H, s), 7.35 (1H, s), 7.25 (1H, d, J=8.2 Hz), 6.82 (1H, d, J=8.2 Hz), 2.68 (3H, s), 2.15 (3H, s).

Reference Production Example 43

A mixture of 0.90 g of C34A, 0.32 g of oxalyl chloride, 0.1 ml of N,N-dimethylformamide, and 3 ml of THF was stirred at room temperature for 5 hours. The reaction solution was concentrated under reduced pressure and 3 ml of chloroform, 0.23 g of 2-amino-2-methylpropanol, and 0.75 ml of triethylamine were added, followed by stirring at room temperature for 2 hours. The reaction solution was extracted with ethyl acetate after adjusting the pH to less than 7 with 2N hydrochloric acid. The organic layer was washed with a saturated saline solution, dried over anhydrous magnesium sulfate, and then concentrated under reduced pressure. The residue thus obtained was subjected to silica gel column chromatography to obtain 0.42 g of N-(1,1-dimethyl-2-hydroxyethyl)-3-methyl-4-{[2-methoxy-6-(4-methyl-5-oxo-4,5-dihydro-1H-tetrazol-1-yl)phenyl]methoxy}benzamide (C43A).

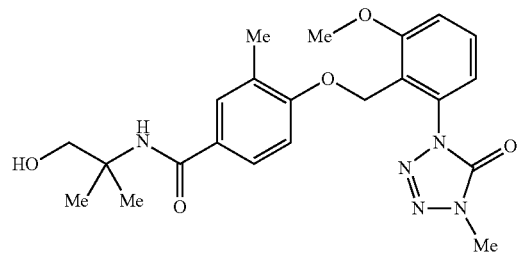 [SMILES: COc1cccc(-n2nnn(C)c2=O)c1COc1ccc(C(=O)NC(C)(C)CO)cc1C]

¹H-NMR (CDCl₃) δ: 7.53-7.44 (3H, m), 7.08 (2H, t, J=8.8 Hz), 6.88 (1H, d, J=8.5 Hz), 6.03 (1H, s), 5.32 (2H, s), 5.02 (1H, t, J=6.2 Hz), 3.94 (3H, s), 3.67 (2H, d, J=6.2 Hz), 3.60 (3H, s), 2.01 (3H, s), 1.39 (6H, s).

Reference Production Example 44

A mixture of 5.66 g of C14A, 3.00 g of 4'-hydroxy-3'-methyl-acetophenone, 5.53 g of potassium carbonate, and 40 mL of acetonitrile was stirred with heating under reflux for 4 hours. After cooling to room temperature, the reaction mixture was filtered and the filtrate was concentrated. The residue thus obtained was subjected to silica gel column chromatography to obtain 4.73 g of 1-{2-(2-methyl-4-acetyl-phenoxymethyl)-3-methylphenyl}-4-methyl-1,4-dihydrotetrazol-5-one (C44A).

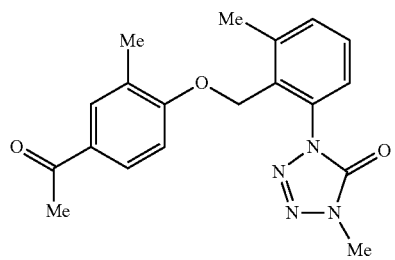 [SMILES: CC(=O)c1ccc(OCc2c(C)cccc2-n2nnn(C)c2=O)c(C)c1]

¹H-NMR (CDCl₃) δ: 7.79 (1H, dd, J=8.54, 2.24 Hz), 7.75 (1H, d, J=1.46 Hz), 7.46-7.40 (2H, m), 7.29 (1H, dd, J=7.32, 1.95 Hz), 6.86 (1H, d, J=8.54 Hz), 5.11 (2H, s), 3.62 (3H, s), 2.54 (3H, s), 2.50 (3H, s), 2.12 (3H, s).

Reference Production Example 45

At room temperature, 13.35 g of diethyl carbonate, 1.3 g of 55% sodium hydride, 0.01 g of dibenzo-18-crown-6, and 0.8 ml of ethanol were added to a mixture of 5.0 g of C44A and 47 ml of tetrahydrofuran, followed by stirring with heating under reflux for 5 hours. Water was poured into the reaction mixture, and the mixture was acidified by adding an aqueous 10% hydrochloric acid solution and then extracted with ethyl acetate. The organic layer was washed with water, dried over anhydrous magnesium sulfate, and then concentrated under reduced pressure. The residue thus obtained was subjected to silica gel column chromatography to obtain 5.7 g of ethyl 3-[3-methyl-4-{[2-methyl-6-(4-methyl-5-oxo-4,5-dihydro-1H-tetrazol-1-yl)phenyl]methoxy}phenyl]-3-oxo-propionate (C45A).

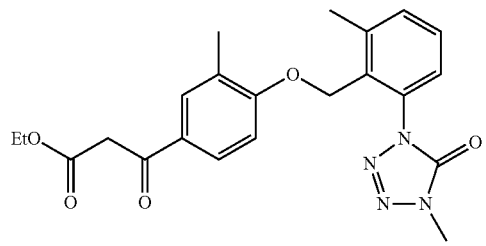 [SMILES: CCOC(=O)CC(=O)c1ccc(OCc2c(C)cccc2-n2nnn(C)c2=O)c(C)c1]

$^1$H-NMR (CDCl$_3$) δ: 7.79 (1H, d, J=8.6 Hz), 7.74 (1H, s), 7.48-7.40 (2H, m), 7.30 (1H, d, J=7.0 Hz), 6.89 (1H, dd, J=8.6, 2.5 Hz), 5.12 (2H, d, J=2.5 Hz), 4.23-4.20 (2H, m), 3.94 (2H, d, J=2.9 Hz), 3.63 (3H, d, J=2.9 Hz), 2.50 (3H, d, J=2.5 Hz), 2.12 (3H, d, J=2.5 Hz), 1.29-1.24 (3H, m).

In accordance with the above-mentioned processes, it is possible to obtain compounds HA1001-0001 to HA1513-5129.

The compounds HA1001-0001 to HA1513-5129 are tetrazolinone compounds represented by the following formulas:

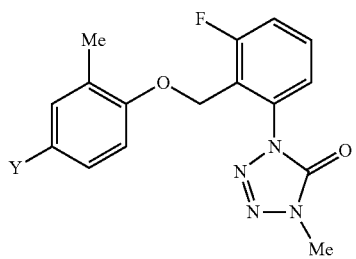
(HA1001)

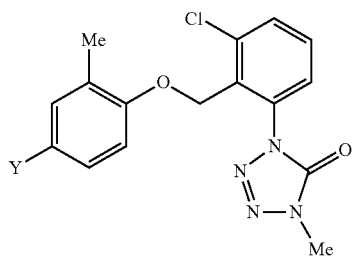
(HA1002)

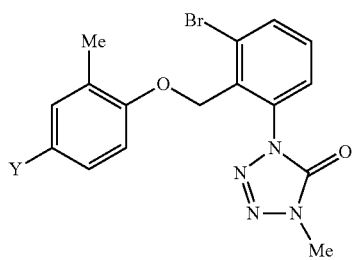
(HA1003)

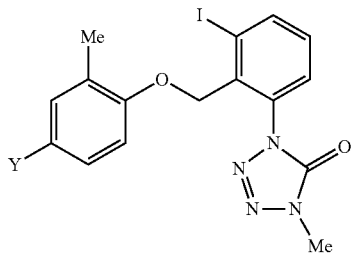
(HA1004)

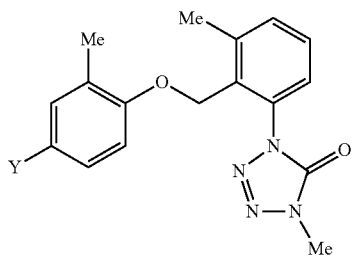
(HA1005)

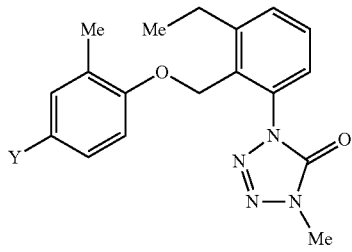
(HA1006)

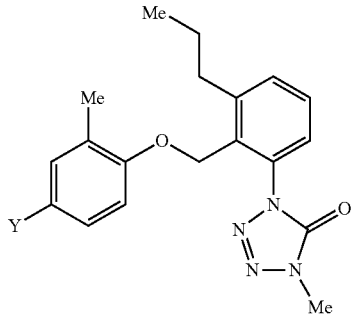
(HA1007)

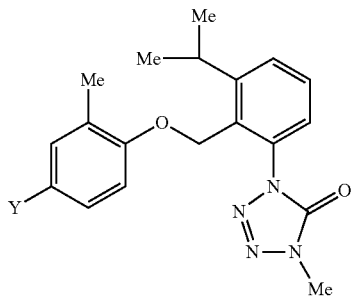
(HA1008)

-continued
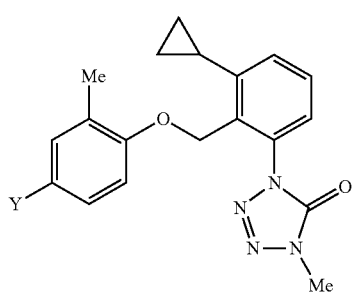
(HA1009)
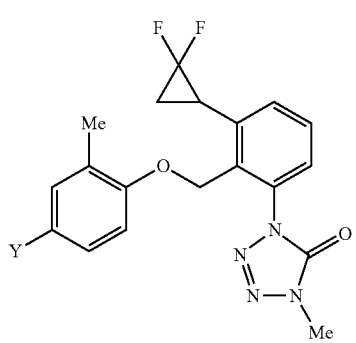
(HA1010)
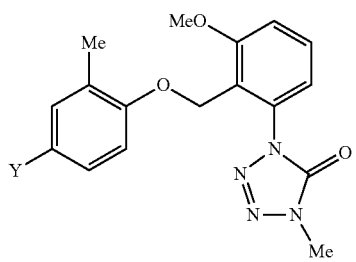
(HA1011)
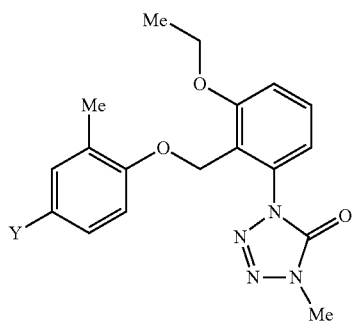
(HA1012)
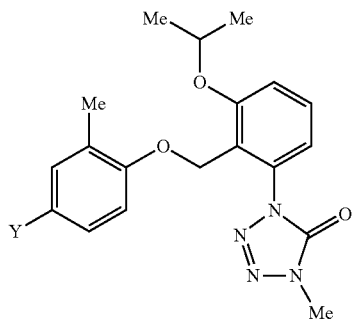
(HA1013)
-continued
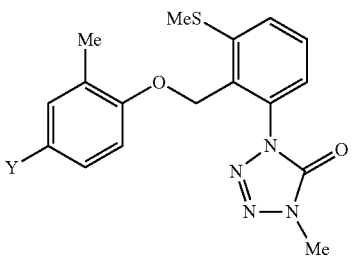
(HA1014)
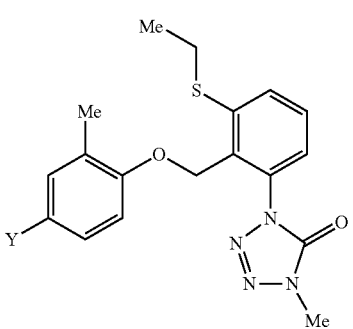
(HA1015)
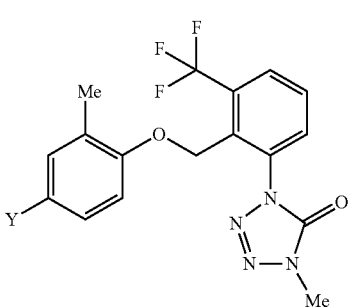
(HA1016)
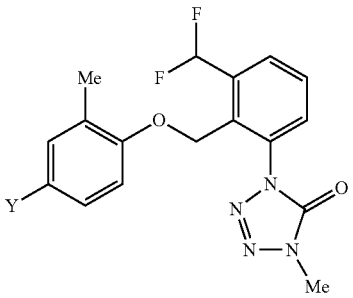
(HA1017)
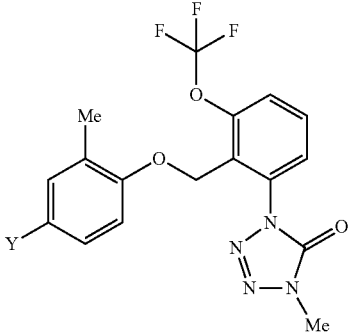
(HA1018)

(HA1019) 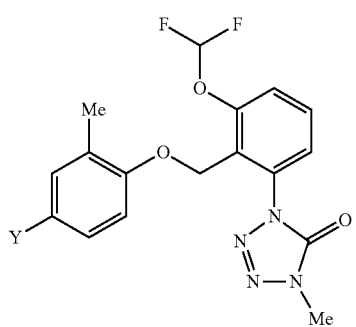
(HA1020) 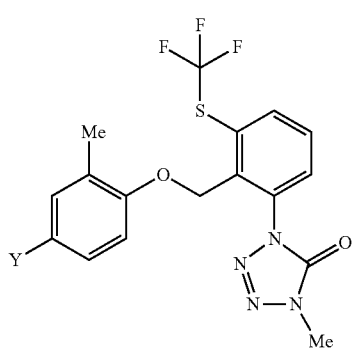
(HA1021) 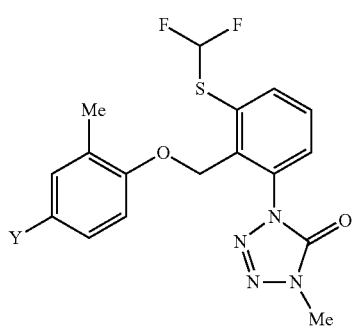
(HA1022) 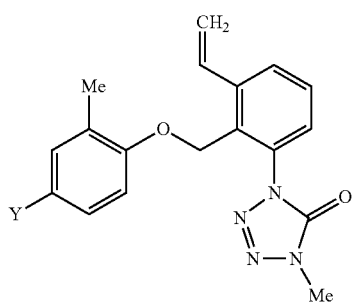
(HA1023) 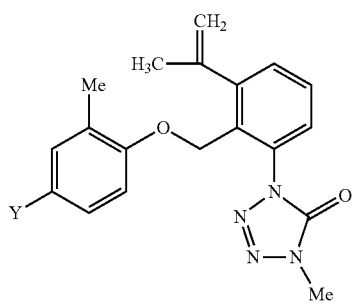
(HA1024) 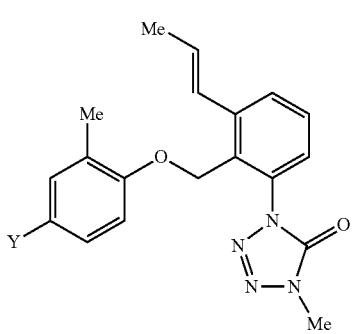
(HA1025) 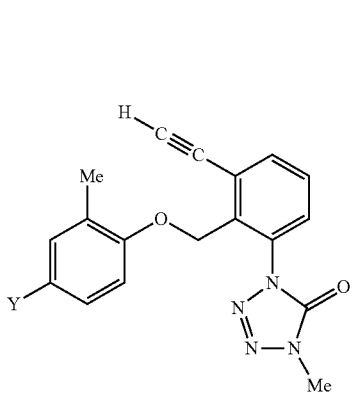
(HA1026) 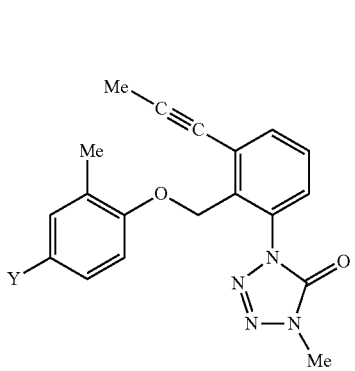
(HA1027) 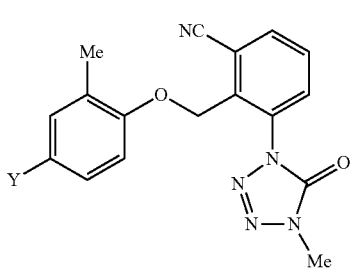
(HA1028) 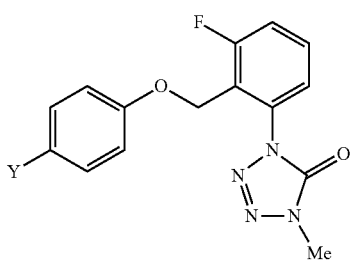

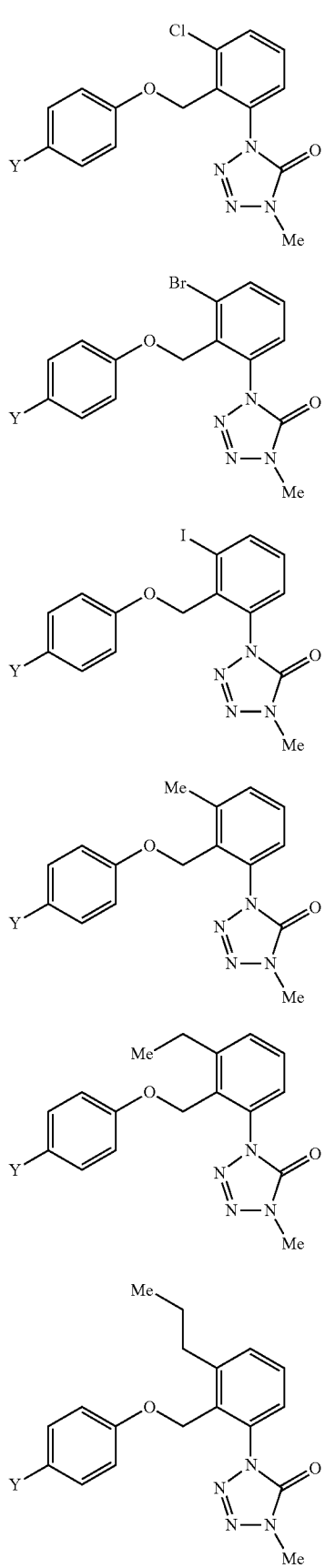
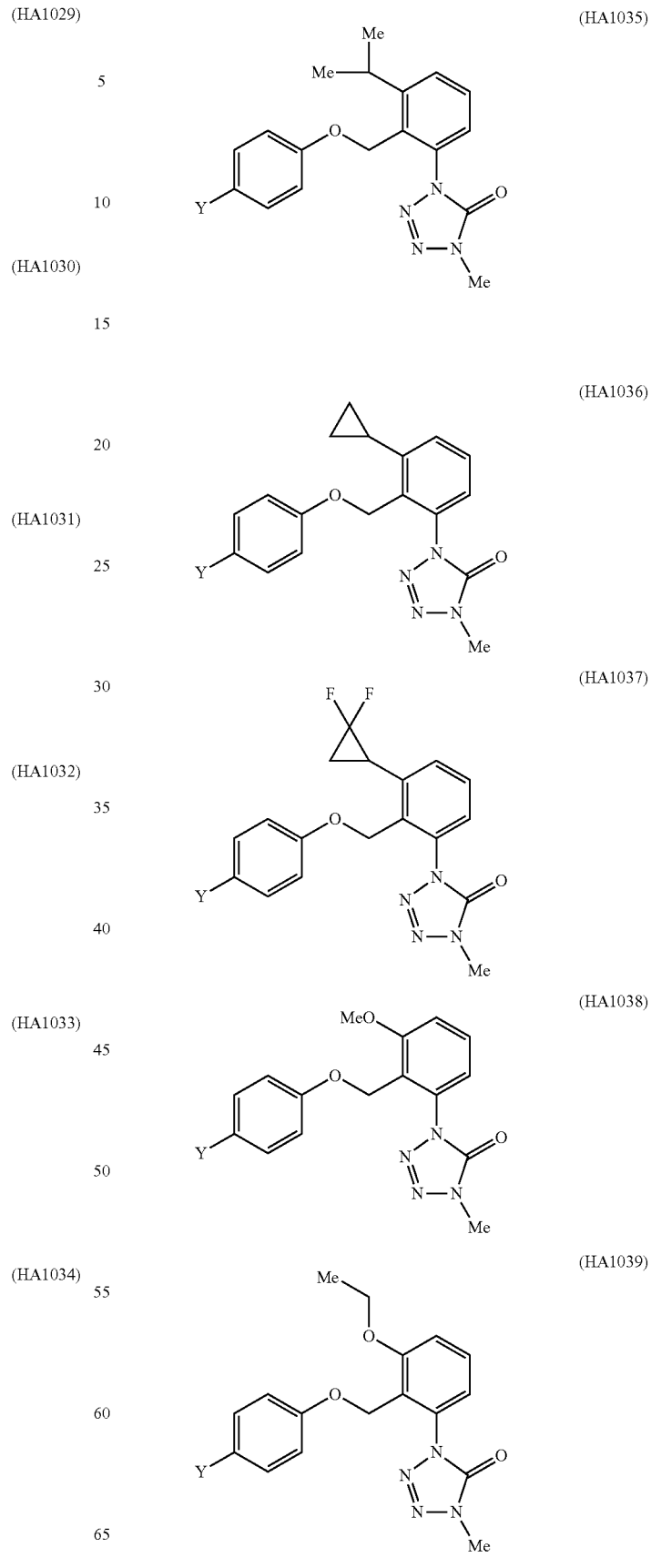

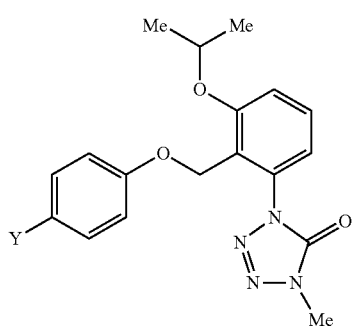
(HA1040)
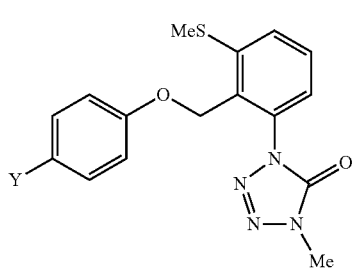
(HA10141)
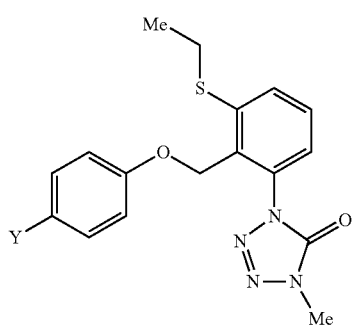
(HA1042)
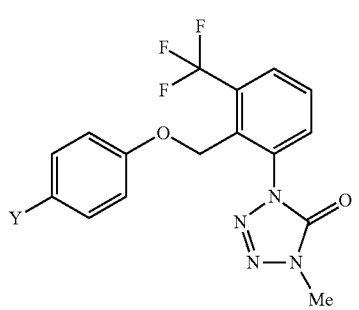
(HA1043)
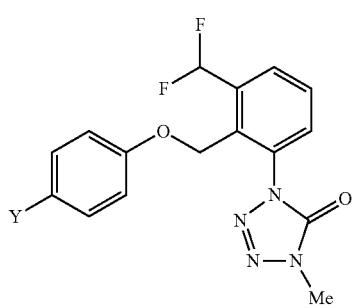
(HA1044)
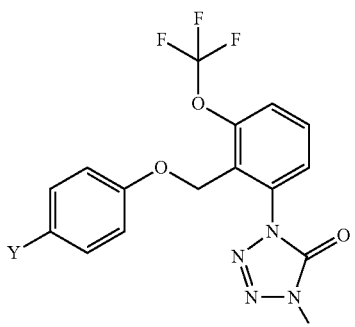
(HA1045)
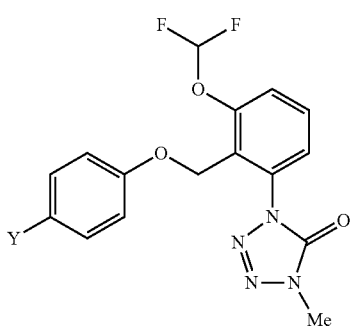
(HA1046)
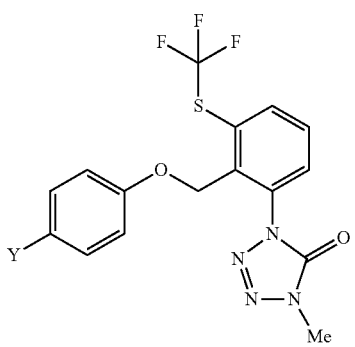
(HA1047)
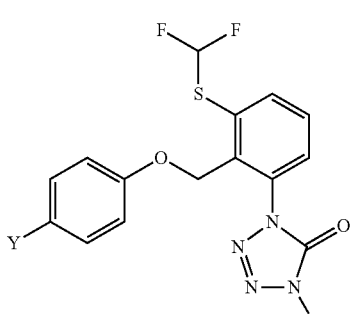
(HA1048)
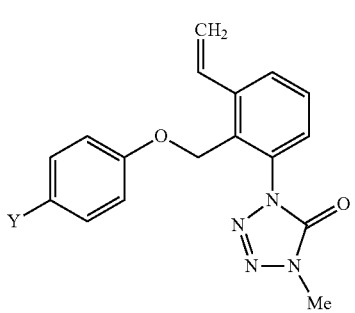
(HA1049)

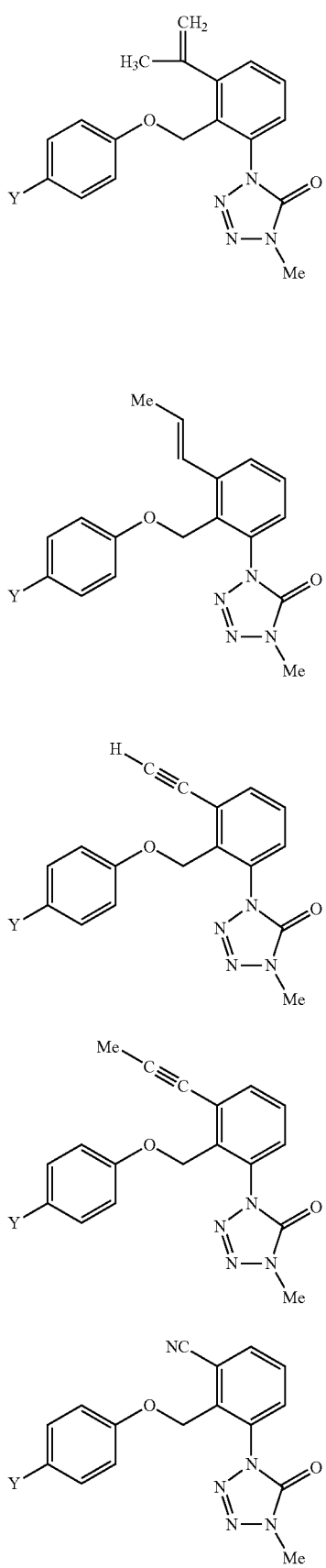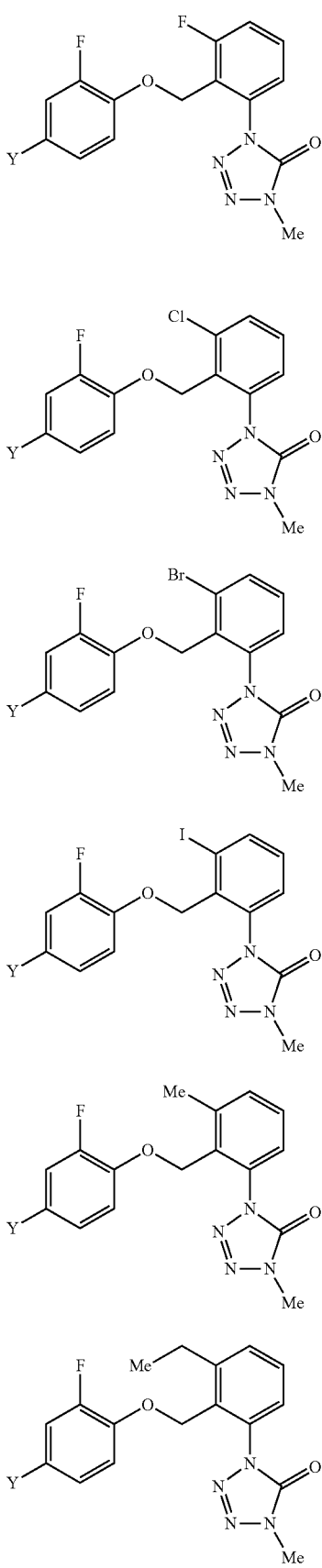

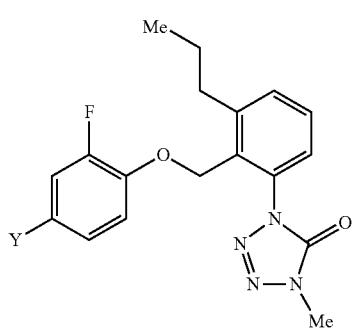
(HA1061)
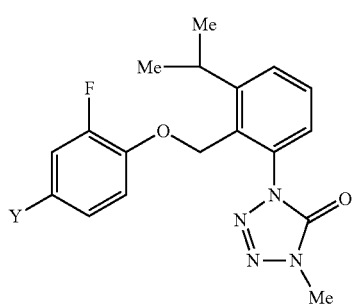
(HA1062)
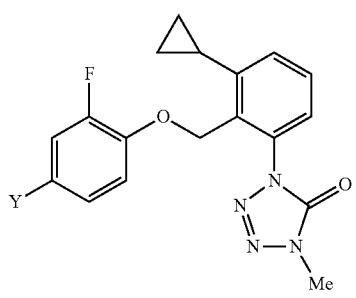
(HA1063)
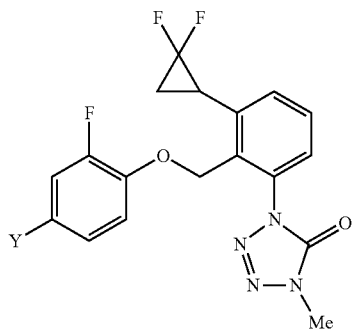
(HA1064)
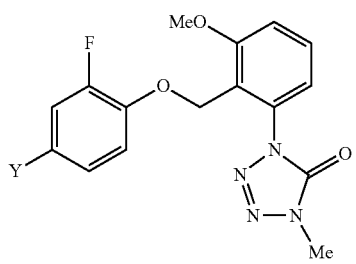
(HA1065)
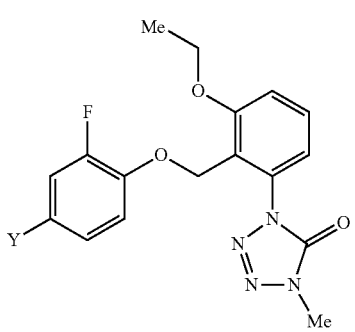
(HA1066)
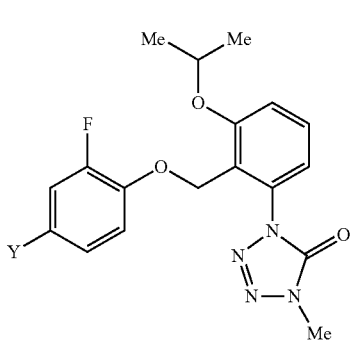
(HA1067)
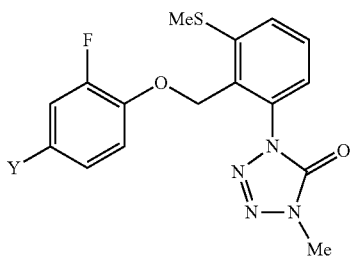
(HA1068)
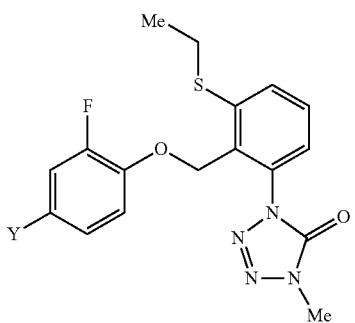
(HA1069)
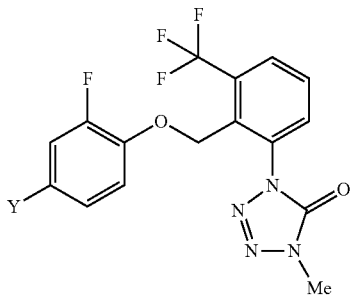
(HA1070)

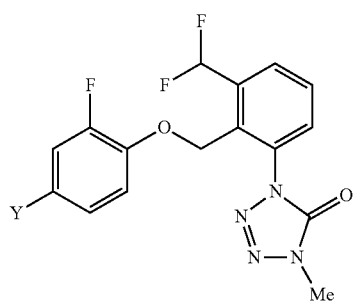
(HA1071)
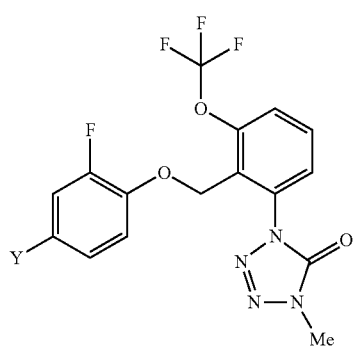
(HA1072)
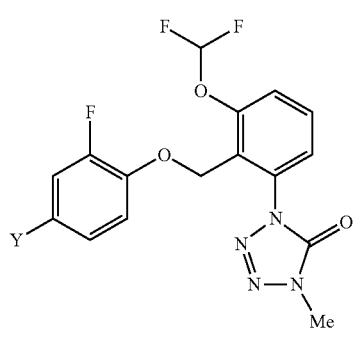
(HA1073)
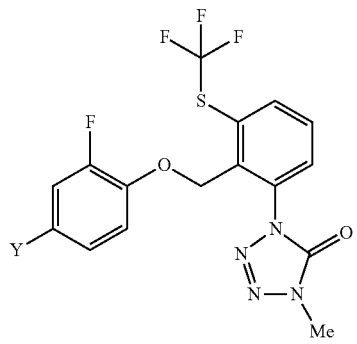
(HA1074)
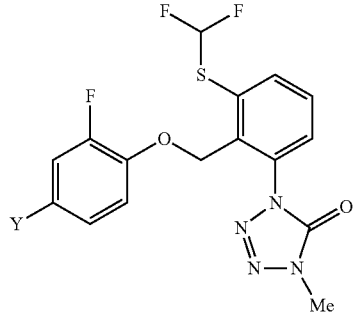
(HA1075)
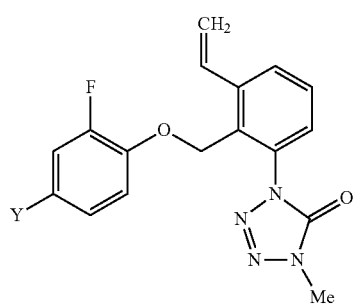
(HA1076)
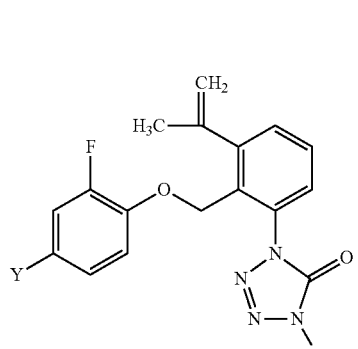
(HA1077)
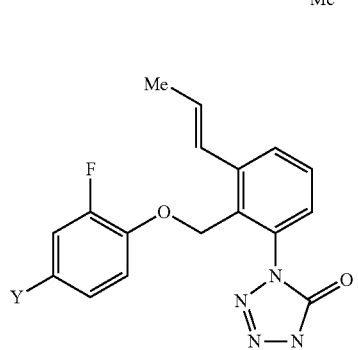
(HA1078)
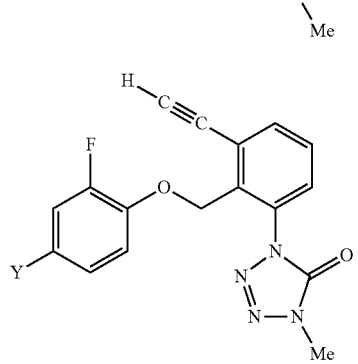
(HA1079)
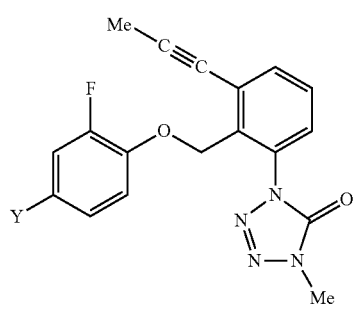
(HA1080)

-continued
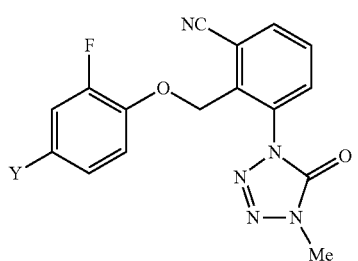
(HA1081)
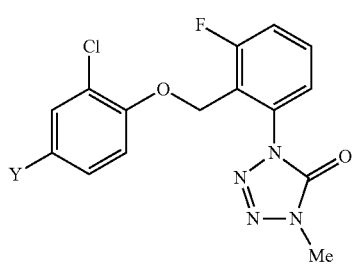
(HA1082)
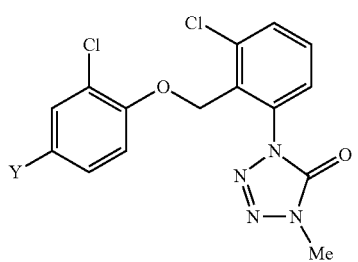
(HA1083)
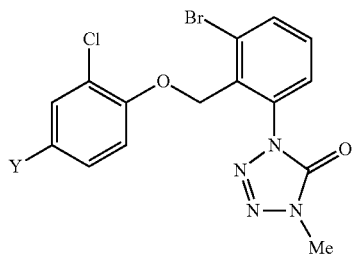
(HA1084)
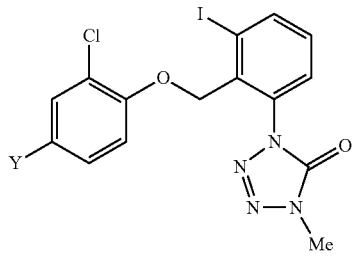
(HA1085)
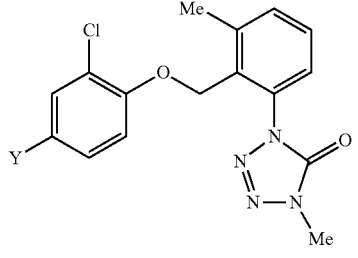
(HA1086)
-continued
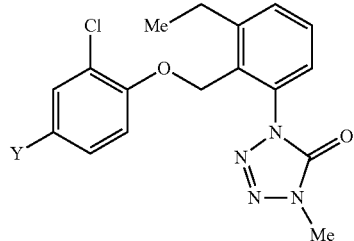
(HA1087)
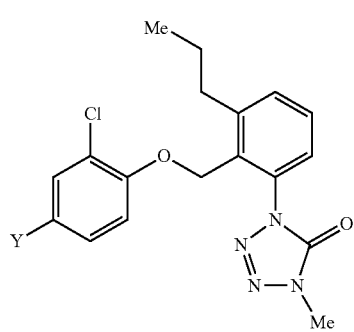
(HA1088)
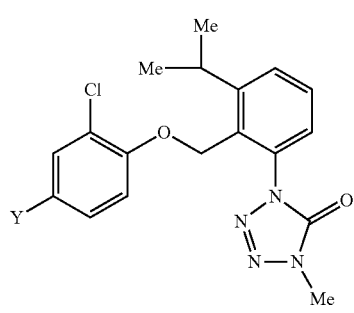
(HA1089)
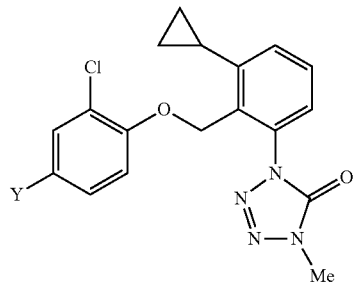
(HA1090)
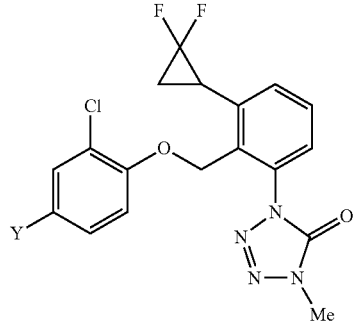
(HA1091)

(HA1092) 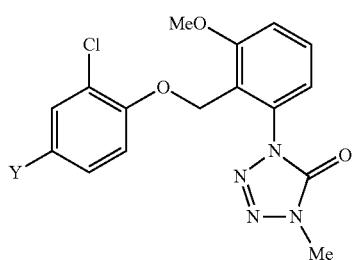
(HA1093) 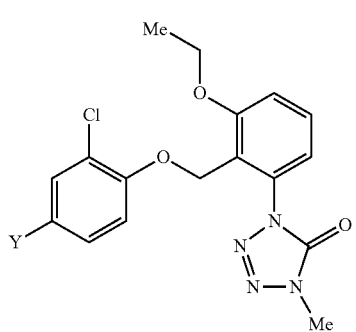
(HA1094) 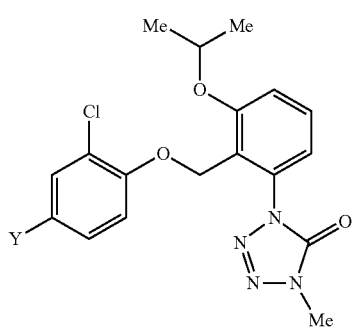
(HA1095) 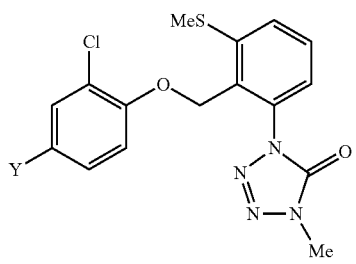
(HA1096) 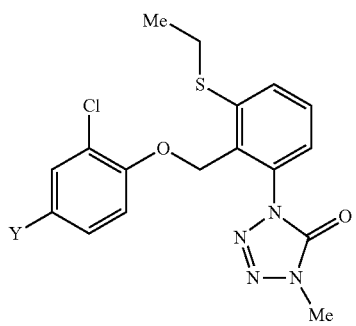
(HA1097) 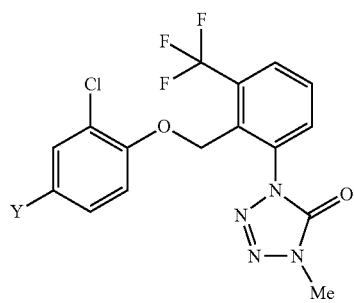
(HA1098) 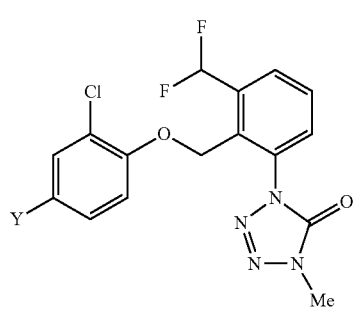
(HA1099) 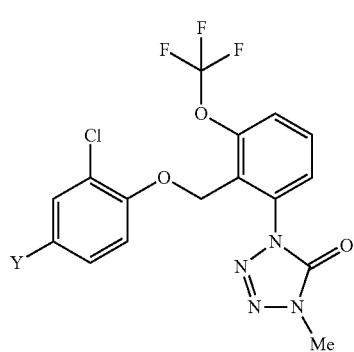
(HA1100) 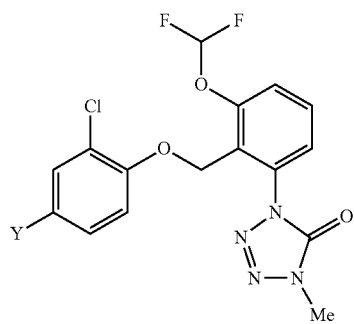
(HA1101) 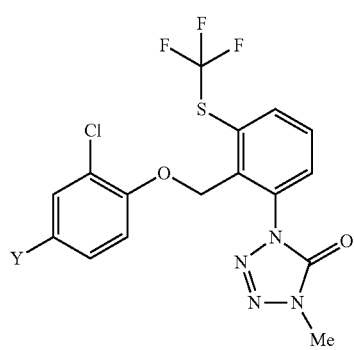

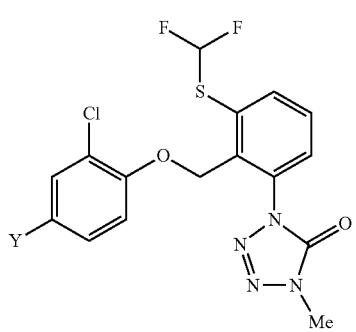
(HA1102)
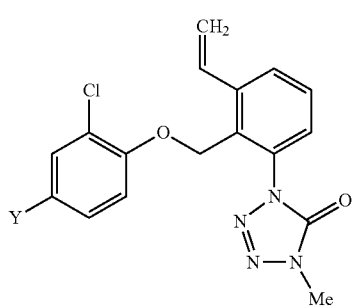
(HA1103)
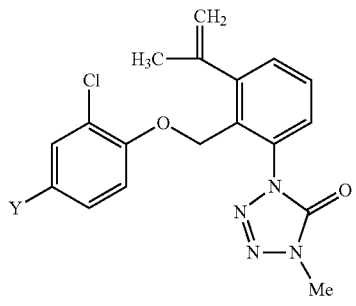
(HA1104)
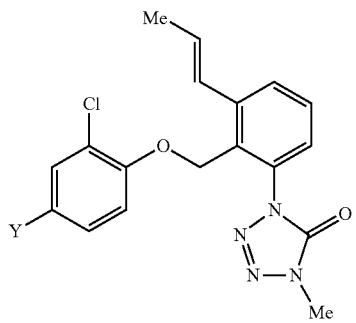
(HA1105)
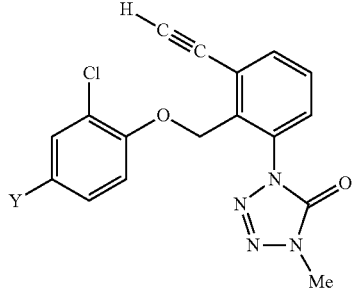
(HA1106)
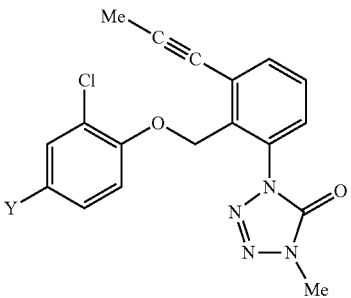
(HA1107)
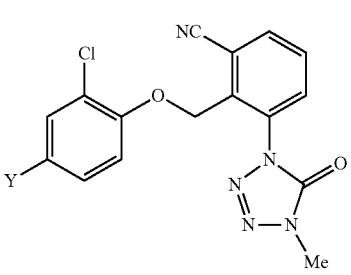
(HA1108)
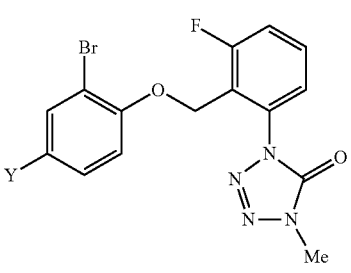
(HA1109)
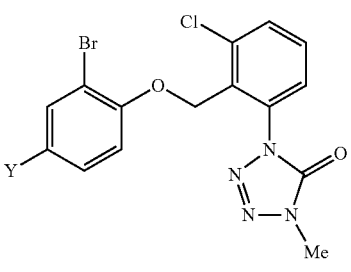
(HA1110)
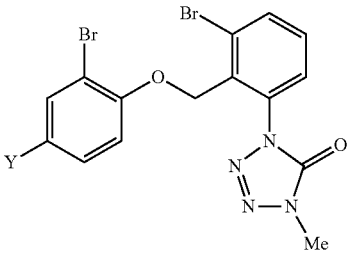
(HA1111)
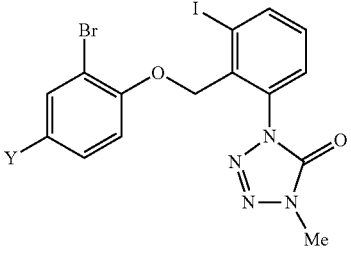
(HA1112)

163
-continued
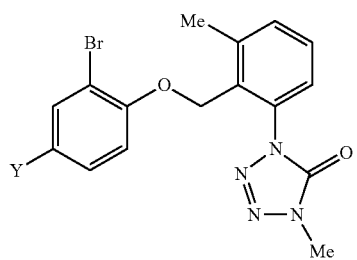 (HA1113)
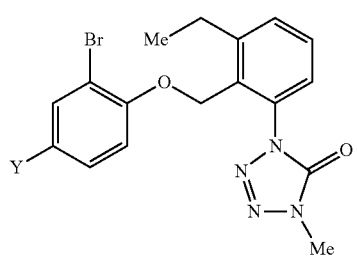 (HA1114)
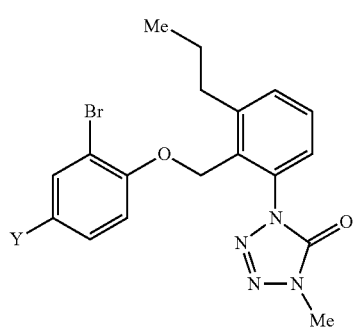 (HA1115)
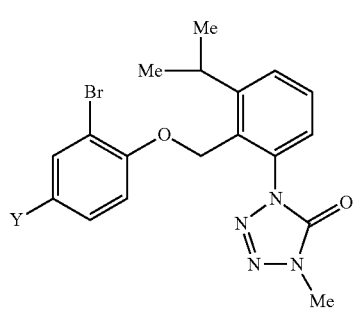 (HA1116)
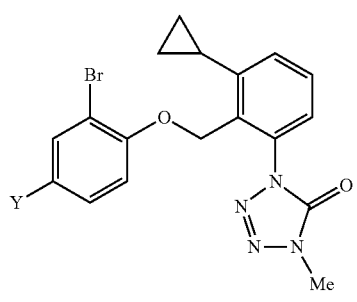 (HA1117)
164
-continued
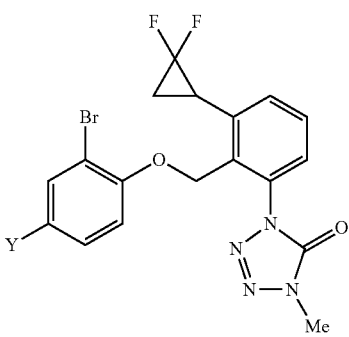 (HA1118)
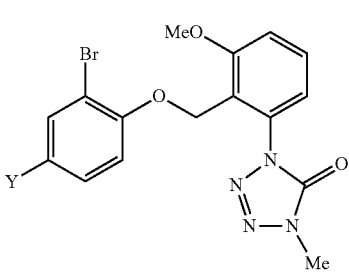 (HA1119)
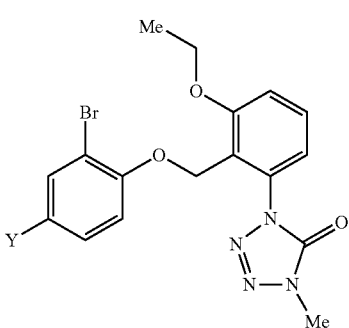 (HA1120)
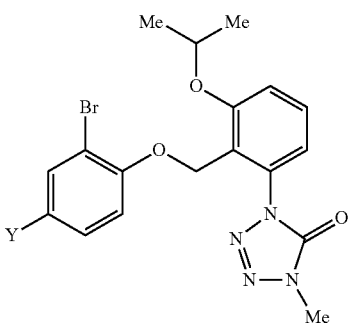 (HA1121)
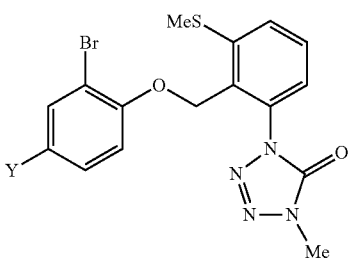 (HA1122)

(HA1123) 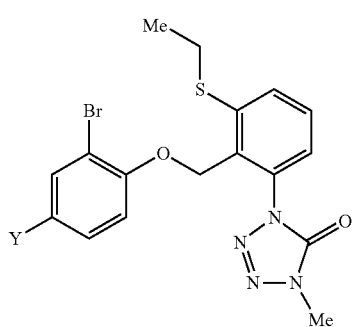
(HA1124) 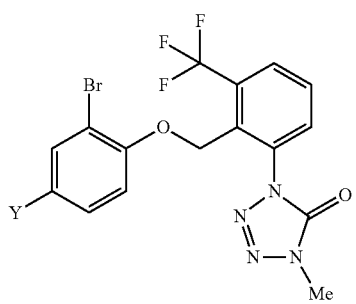
(HA1125) 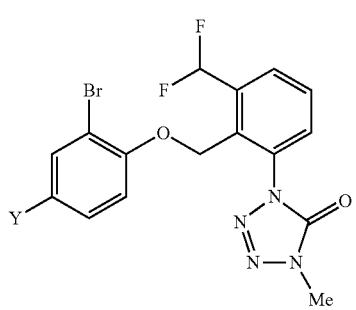
(HA1126) 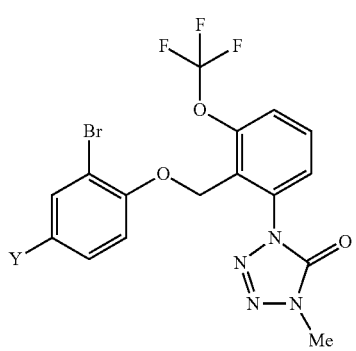
(HA1127) 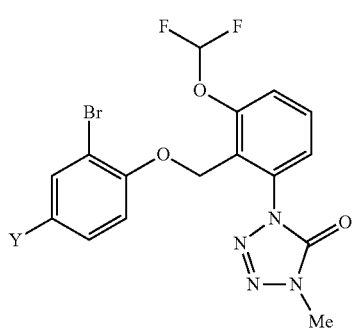
(HA1128) 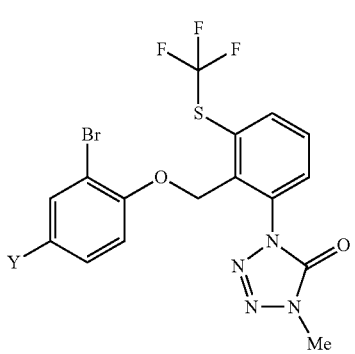
(HA1129) 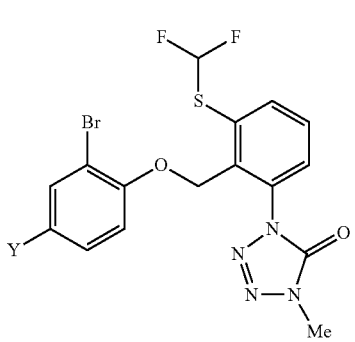
(HA1130) 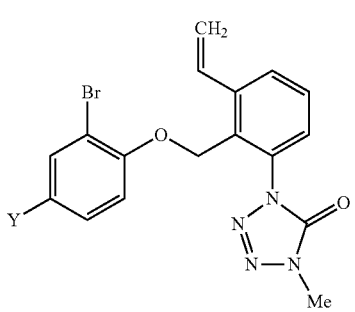
(HA1131) 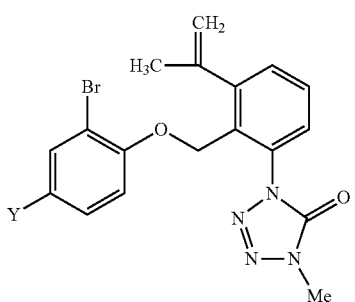
(HA1132) 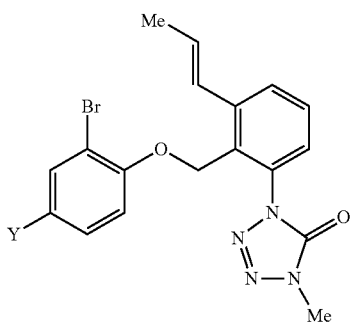

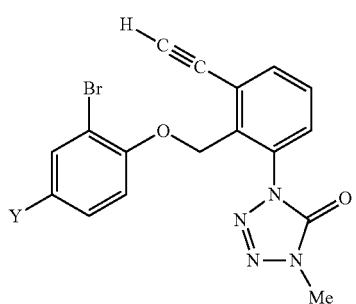 (HA1133)
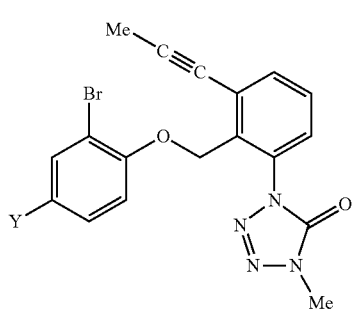 (HA1134)
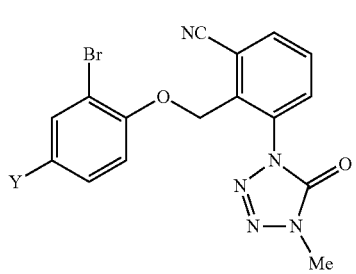 (HA1135)
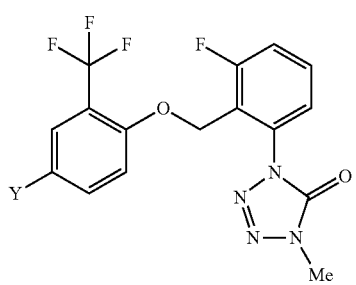 (HA1136)
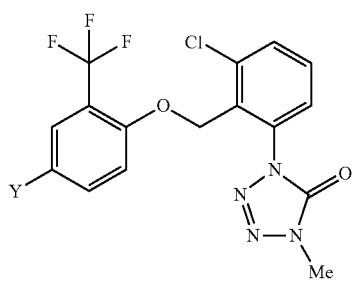 (HA1137)
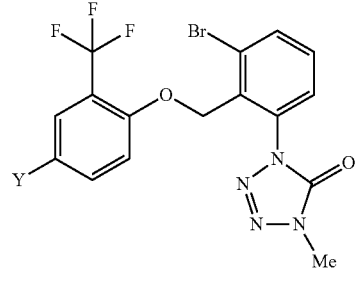 (HA1138)
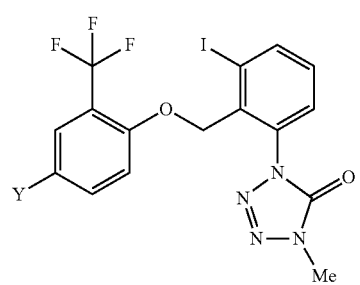 (HA1139)
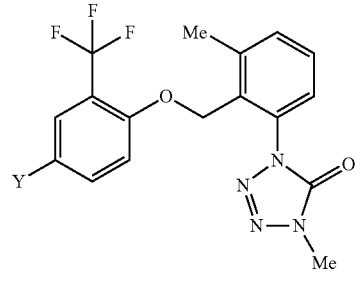 (HA1140)
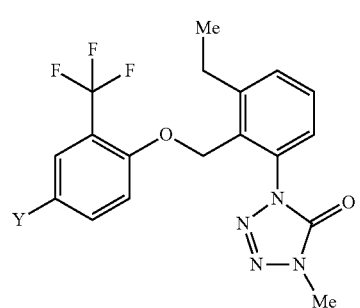 (HA1141)
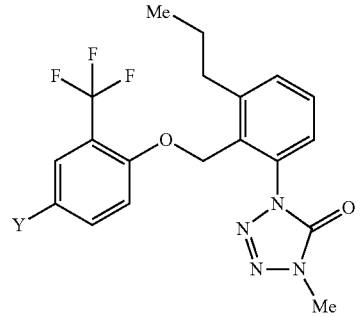 (HA1142)

(HA1143) 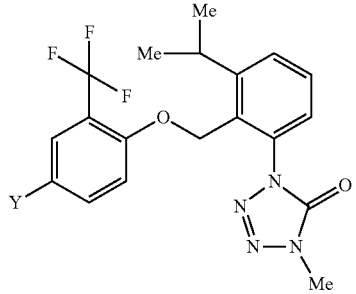
(HA1144) 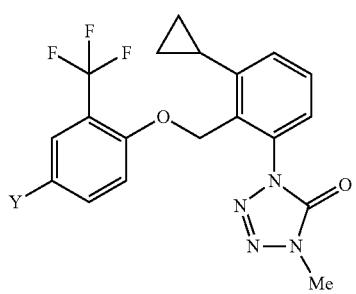
(HA1145) 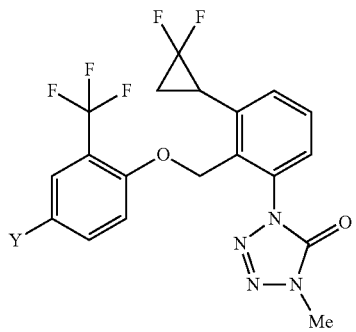
(HA1146) 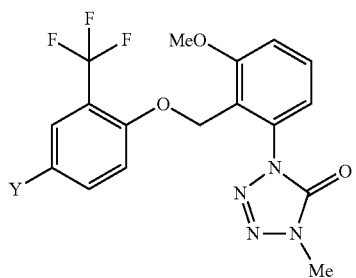
(HA1147) 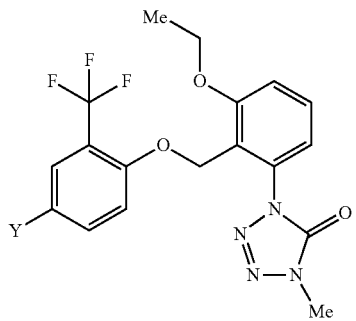
(HA1148) 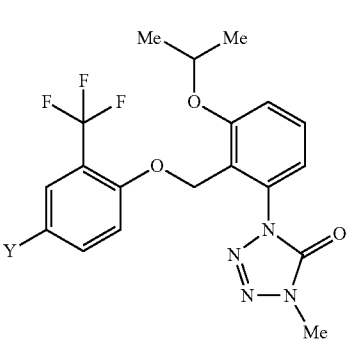
(HA1149) 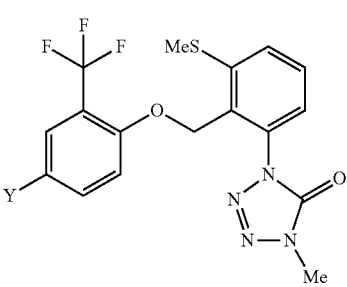
(HA1150) 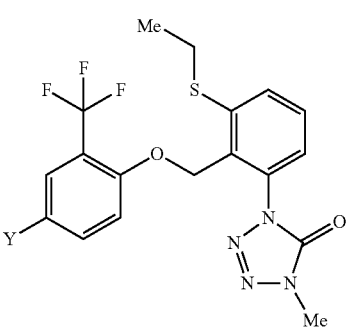
(HA1151) 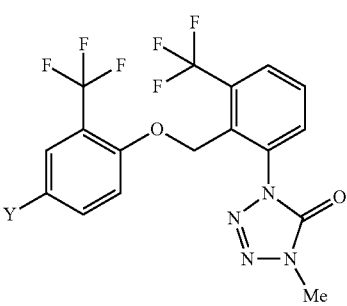
(HA1152) 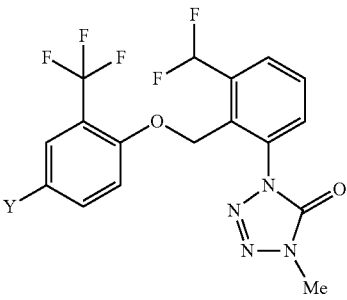

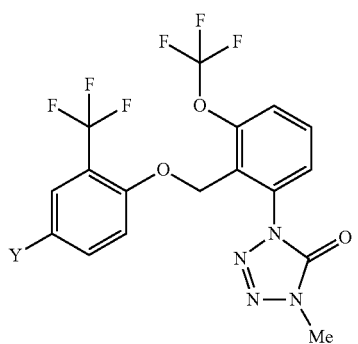 (HA1153)
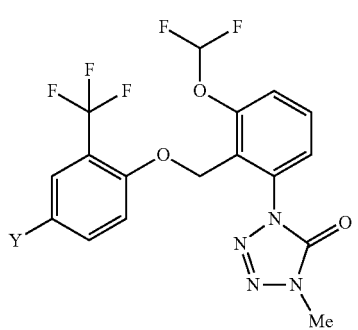 (HA1154)
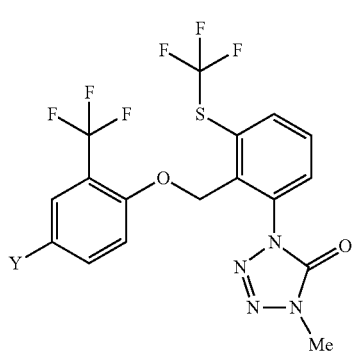 (HA1155)
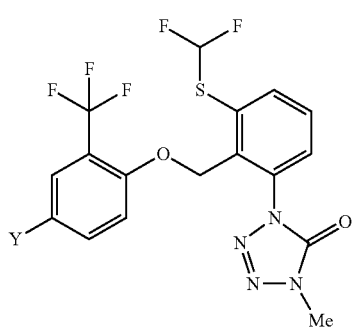 (HA1156)
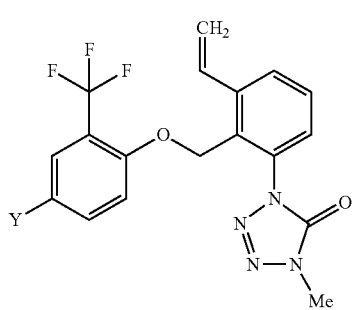 (HA1157)
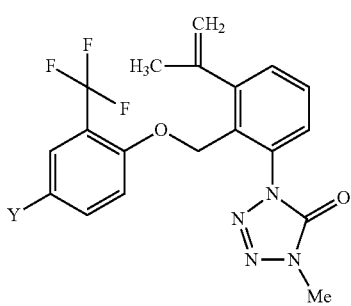 (HA1158)
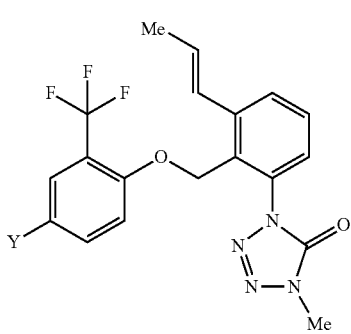 (HA1159)
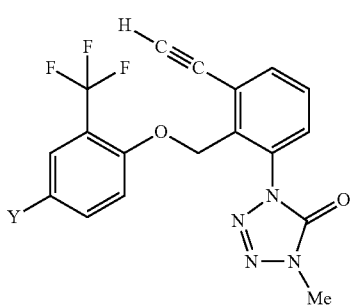 (HA1160)
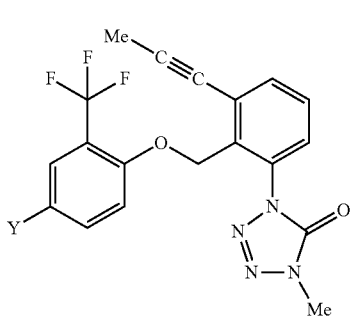 (HA1161)
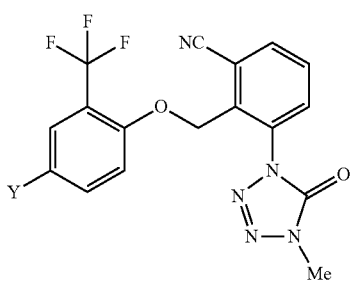 (HA1162)

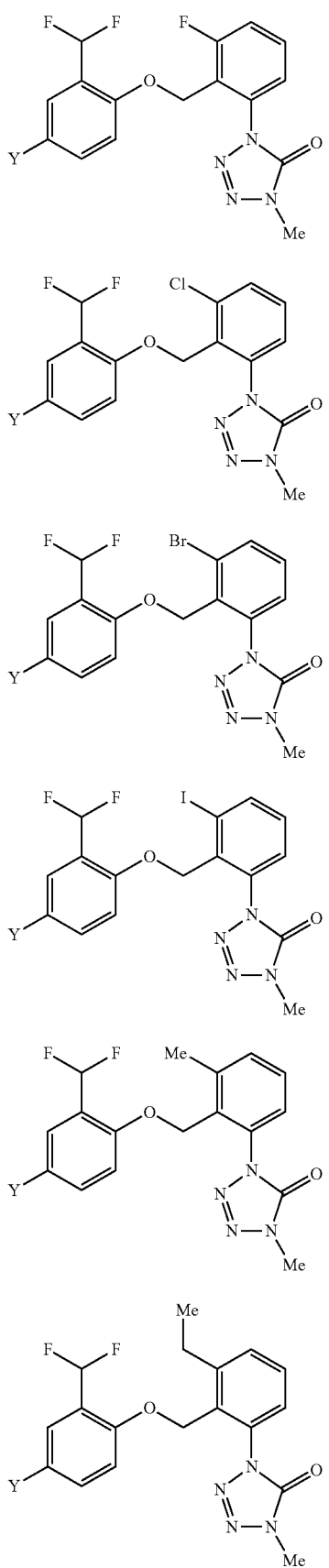
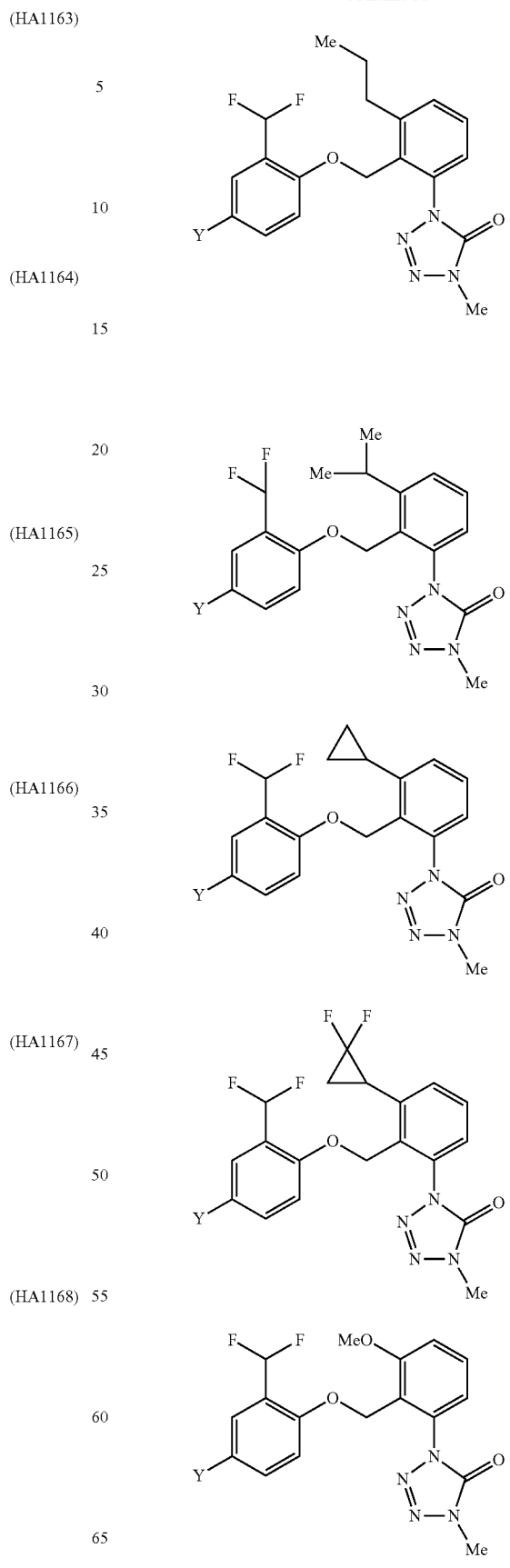

(HA1174) 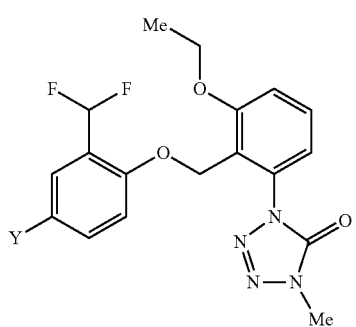
(HA1175) 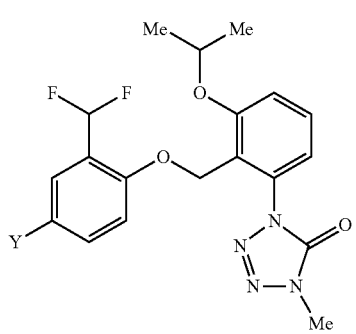
(HA1176) 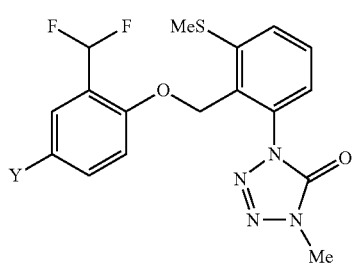
(HA1177) 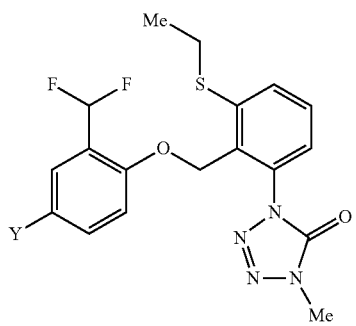
(HA1178) 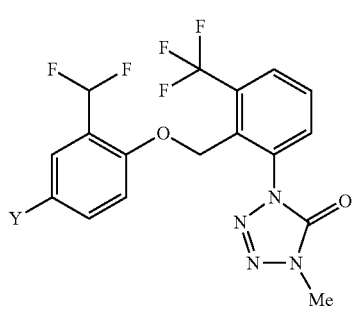
(HA1179) 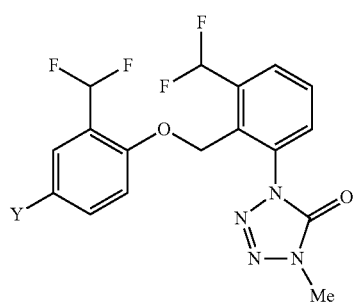
(HA1180) 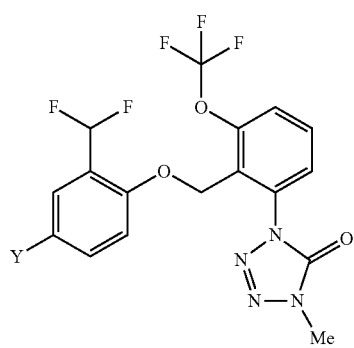
(HA1181) 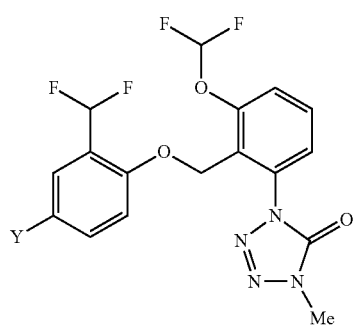
(HA1182) 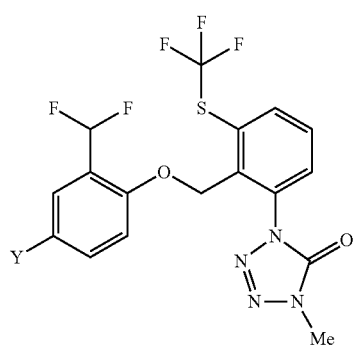
(HA1183) 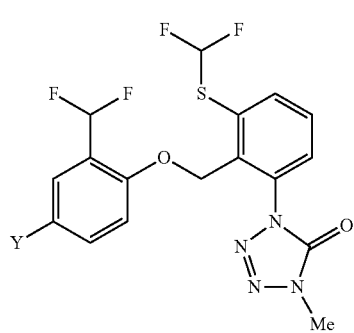

177
-continued
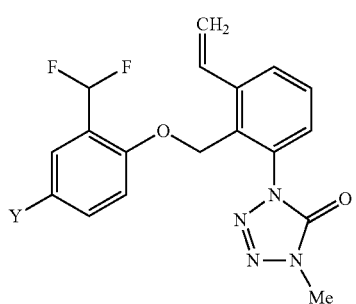
(HA1184)
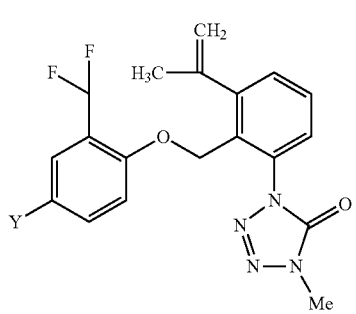
(HA1185)
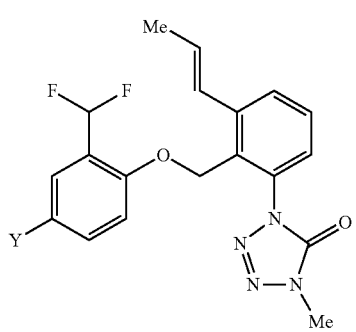
(HA1186)
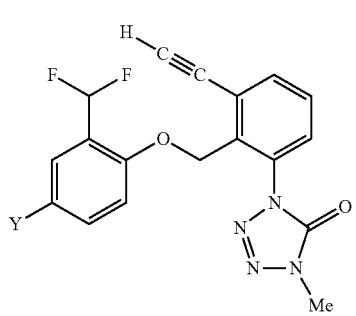
(HA1187)
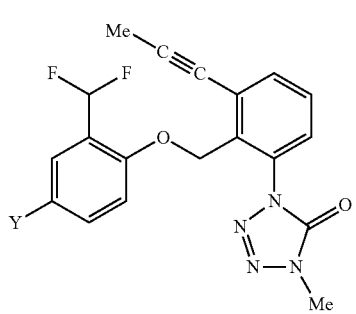
(HA1188)
178
-continued
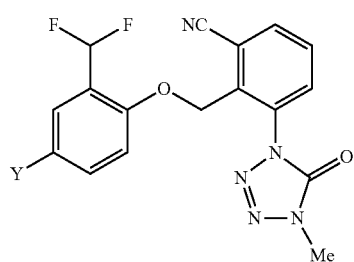
(HA1189)
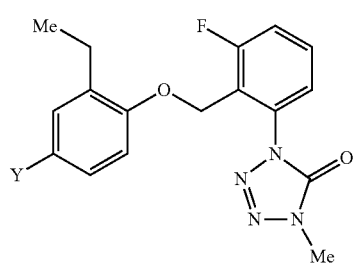
(HA1190)
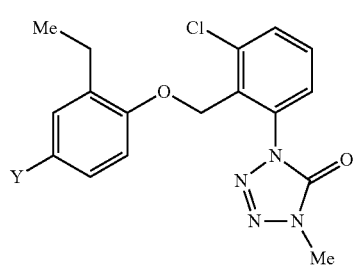
(HA1191)
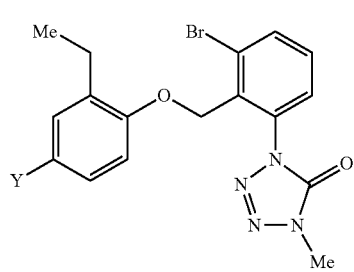
(HA1192)
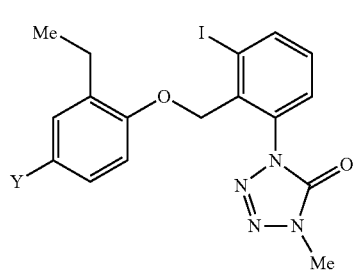
(HA1193)
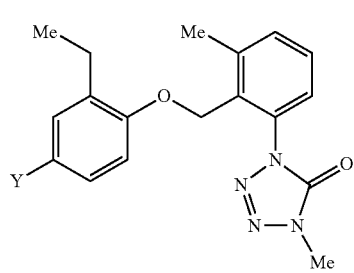
(HA1194)

(HA1195) 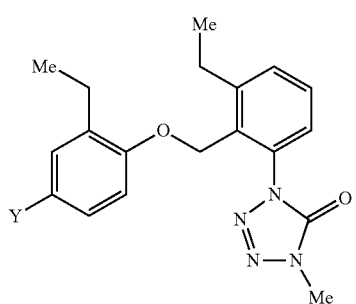
(HA1196) 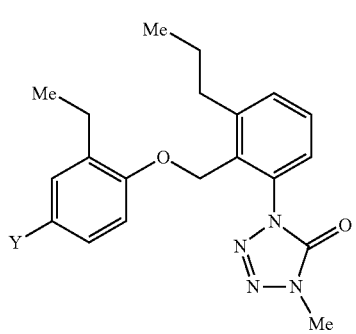
(HA1197) 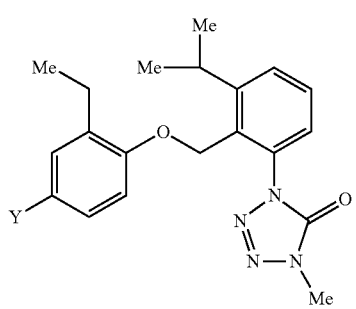
(HA1198) 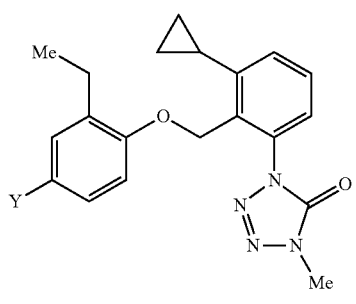
(HA1199) 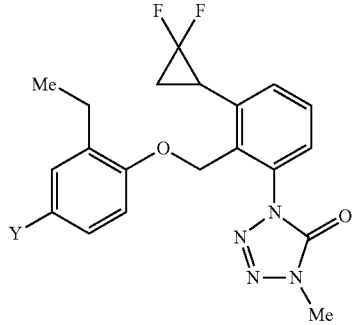
(HA1200) 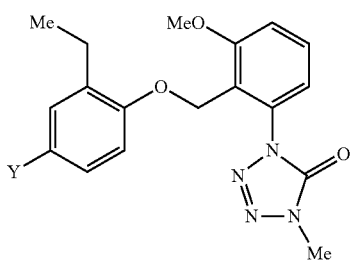
(HA1201) 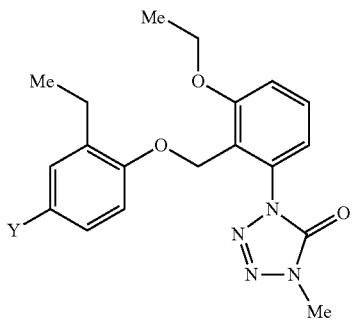
(HA1202) 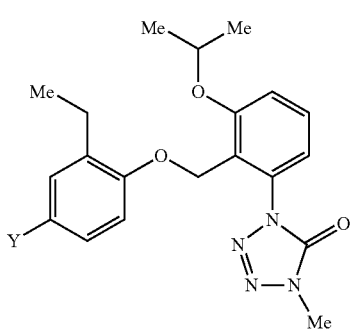
(HA1203) 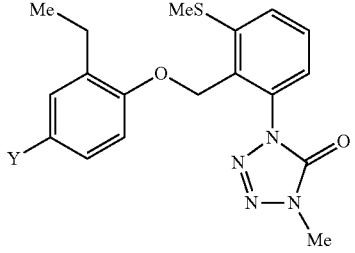
(HA1204) 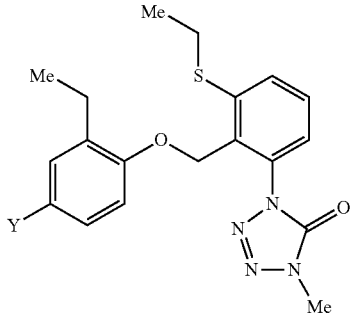

-continued
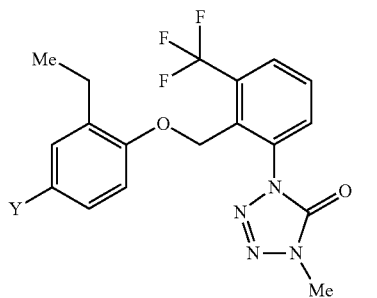 (HA1205)
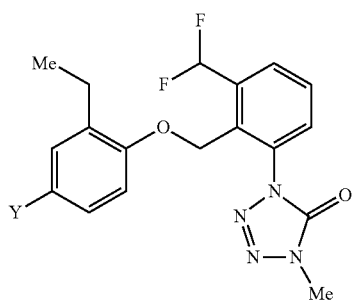 (HA1206)
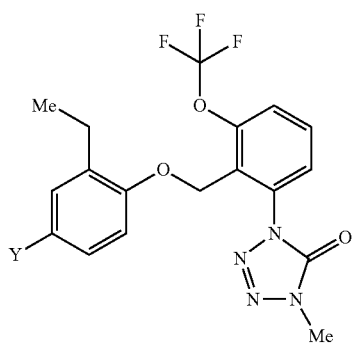 (HA1206)
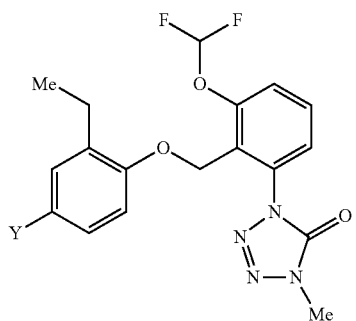 (HA1208)
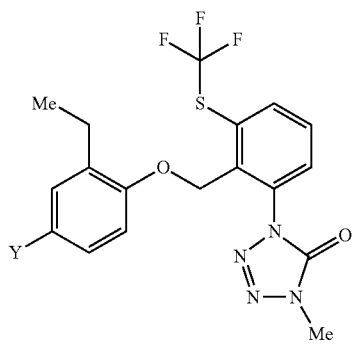 (HA1209)
-continued
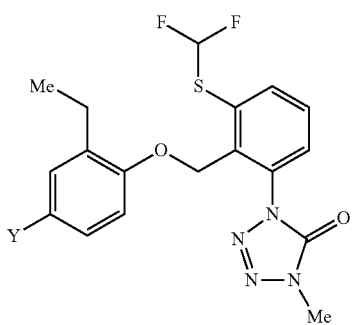 (HA1210)
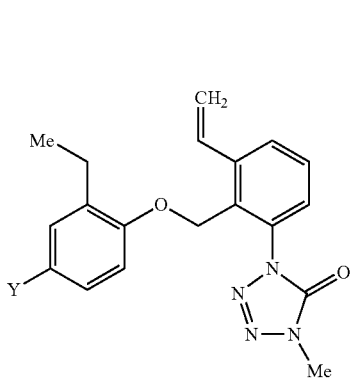 (HA1211)
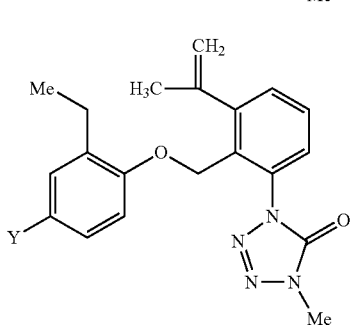 (HA1212)
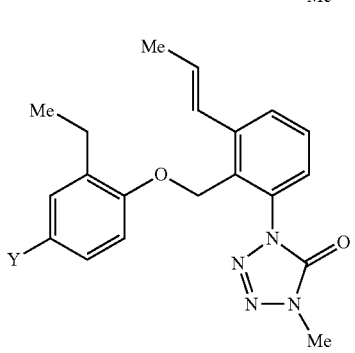 (HA1213)
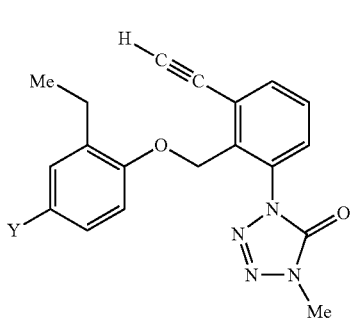 (HA1214)

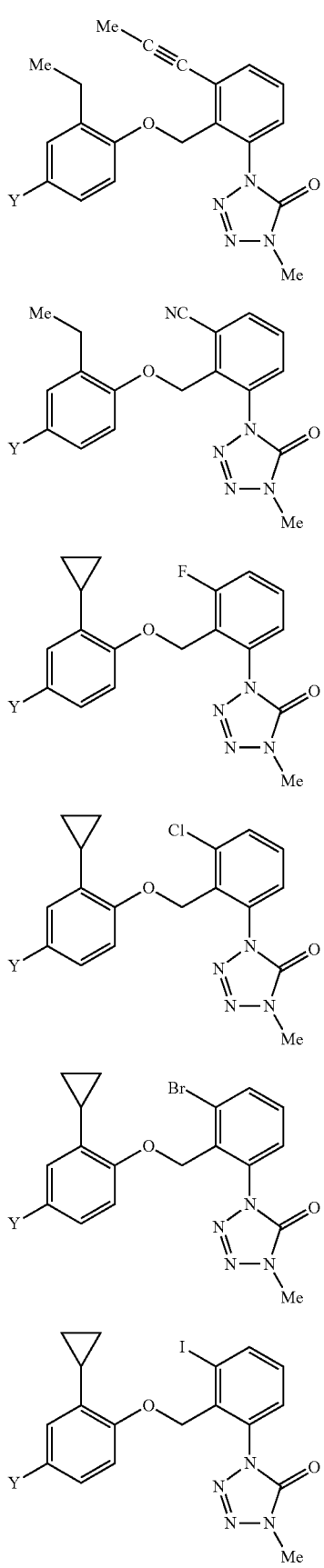
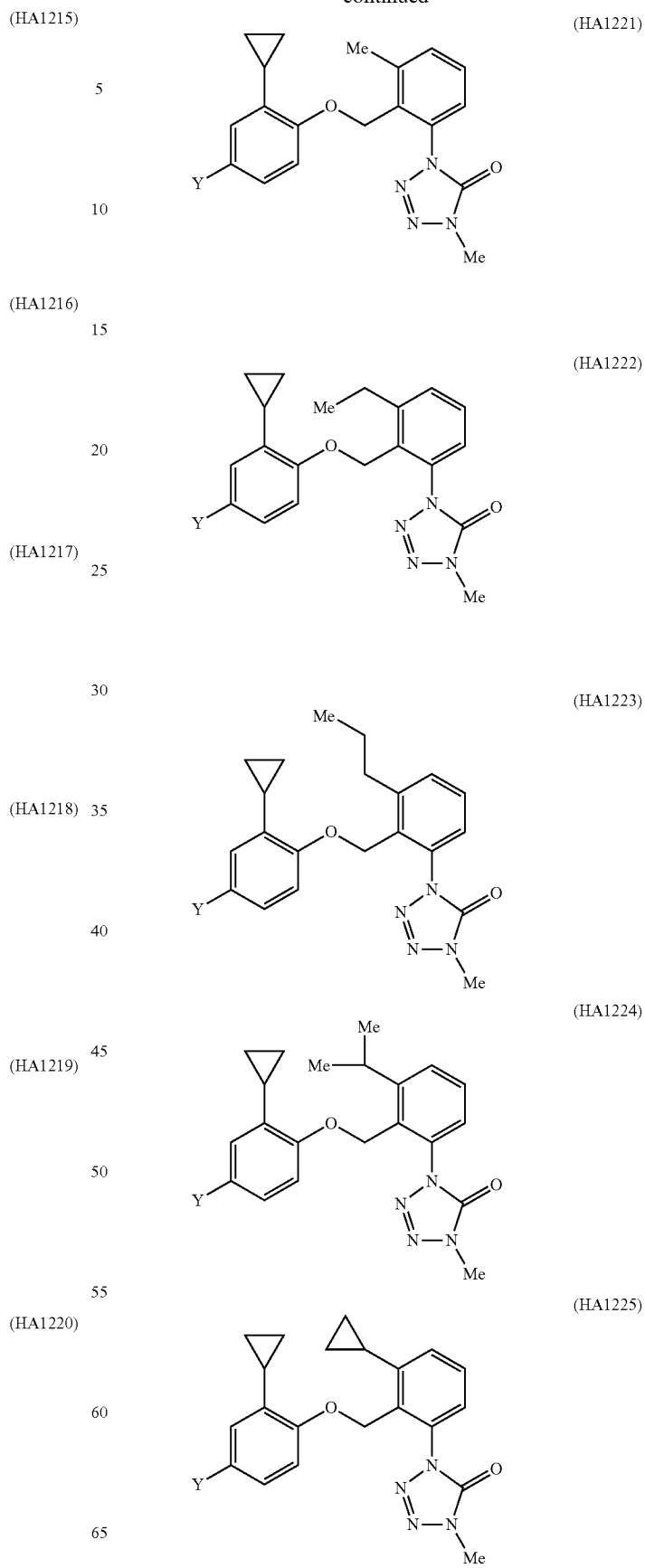

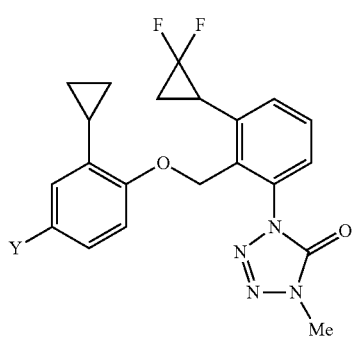
(HA1226)
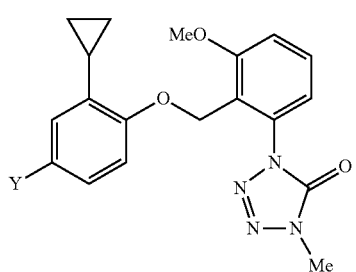
(HA1227)
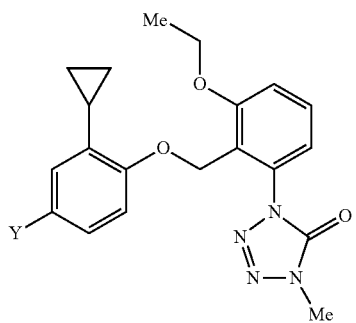
(HA1228)
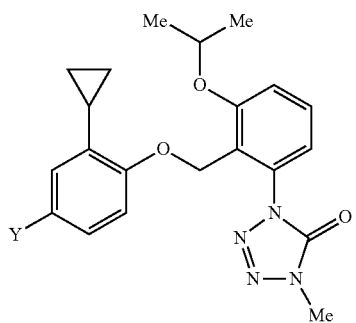
(HA1229)
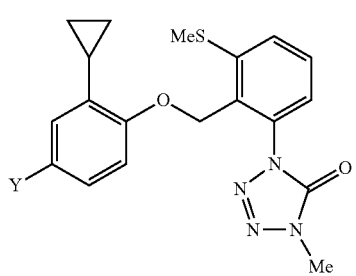
(HA1230)
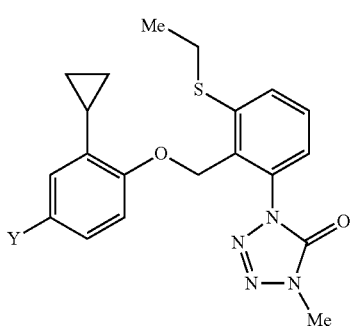
(HA1231)
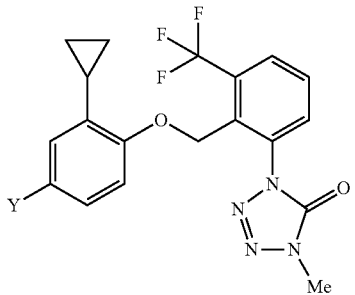
(HA1232)
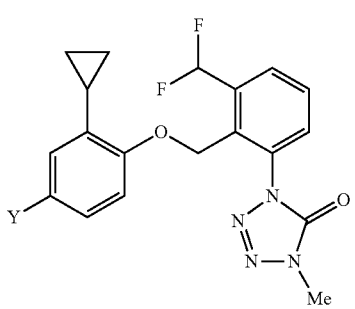
(HA1233)
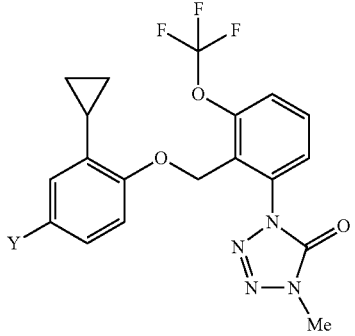
(HA1234)
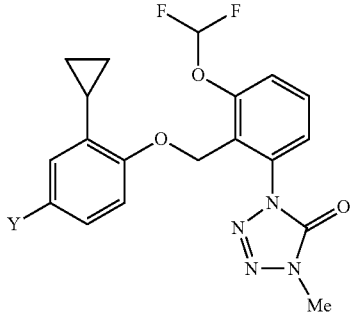
(HA1235)

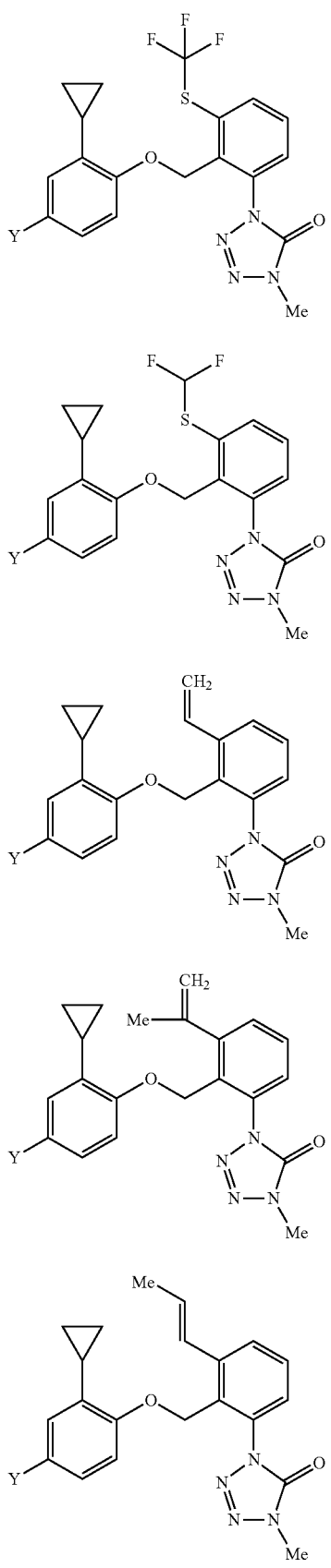
(HA1236)
(HA1237)
(HA1238)
(HA1239)
(HA1240)
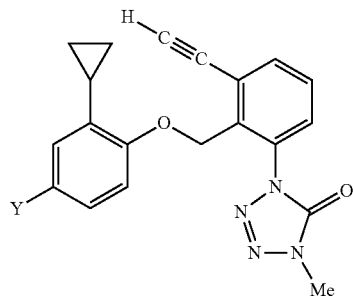
(HA1241)
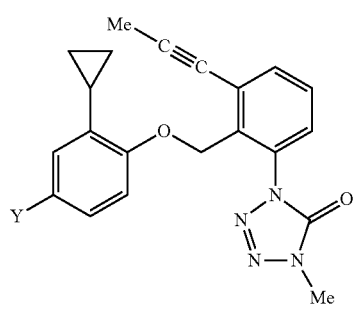
(HA1242)
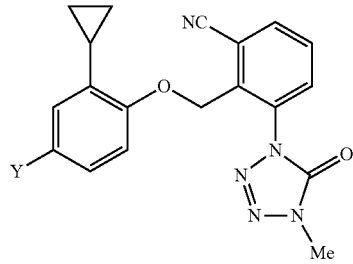
(HA1243)
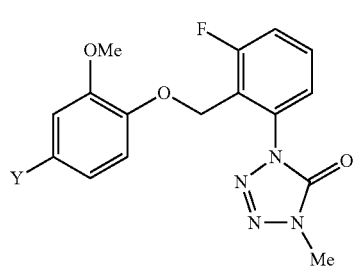
(HA1244)
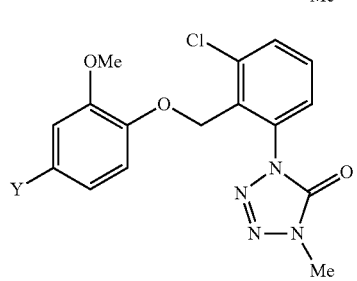
(HA1245)
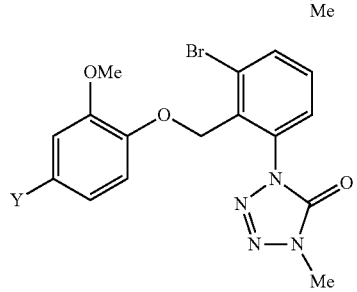
(HA1246)

-continued
(HA1247)
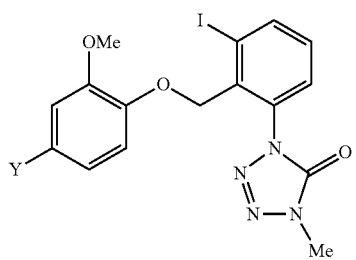
(HA1248)
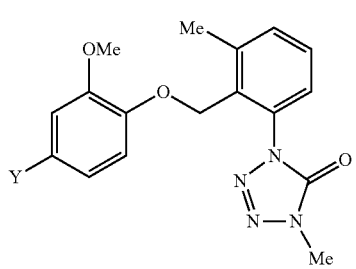
(HA1249)
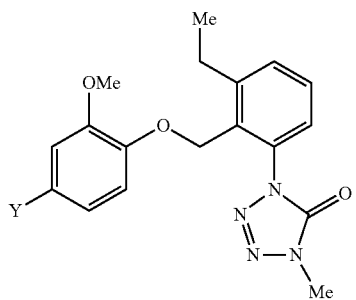
(HA1250)
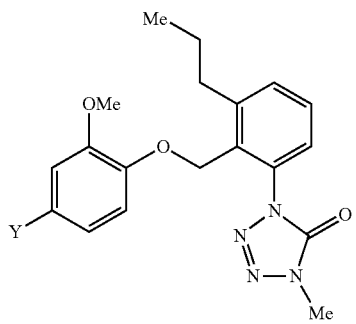
(HA1251)
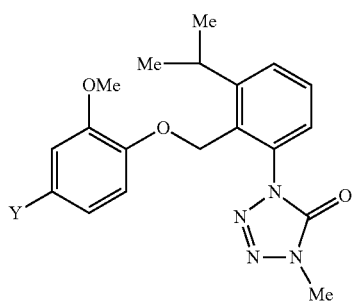
-continued
(HA1252)
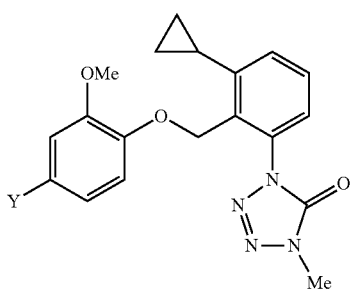
(HA1253)
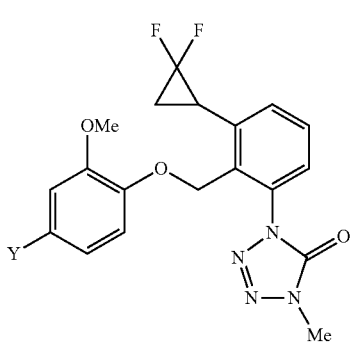
(HA1254)
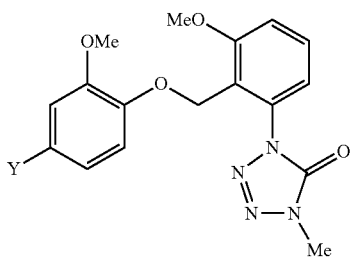
(HA1255)
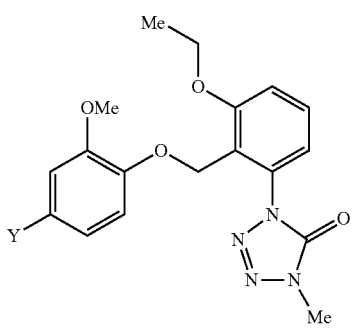
(HA1256)
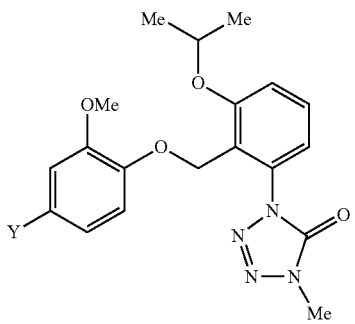

191
-continued
(HA1257)
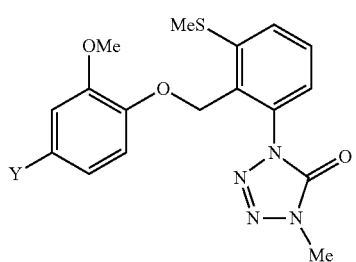
(HA1258)
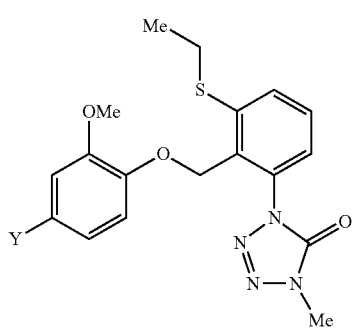
(HA1259)
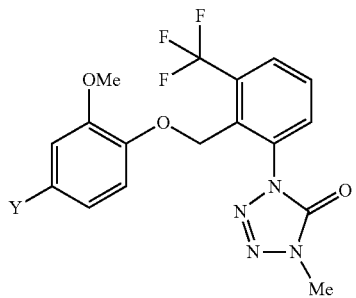
(HA1260)
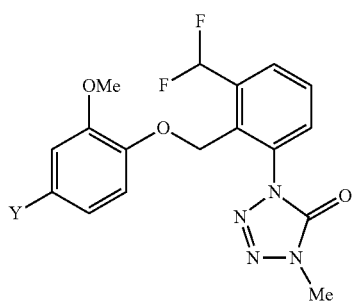
(HA1261)
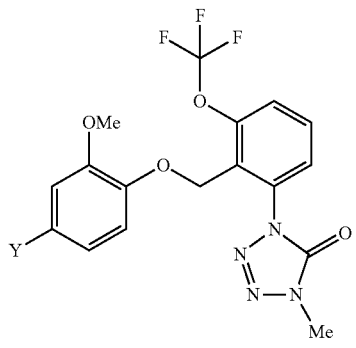
192
-continued
(HA1262)
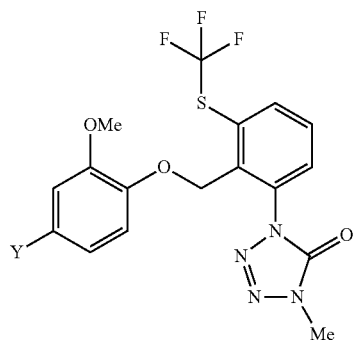
(HA1263)
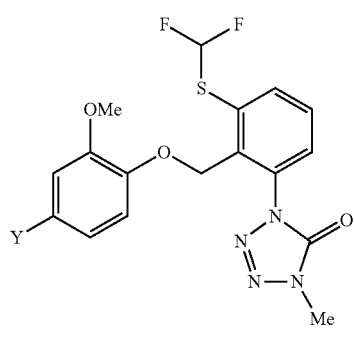
(HA1264)
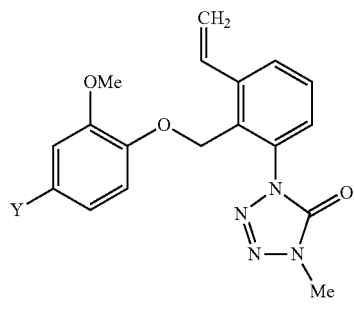
(HA1265)
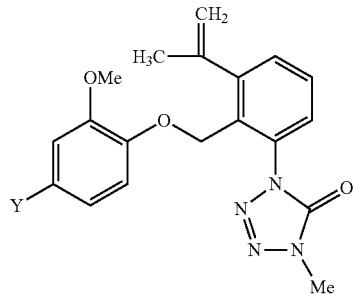
(HA1266)

| | |
|---|---|
| (HA1267) 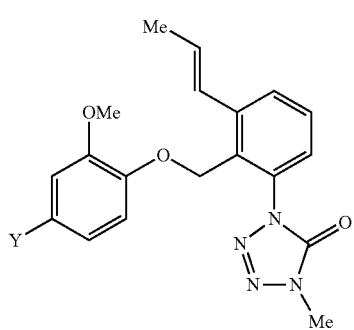 | (HA1272) 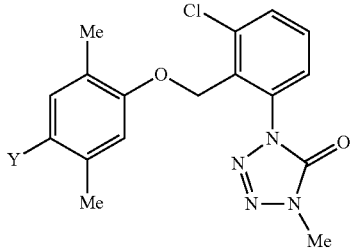 |
| (HA1268) 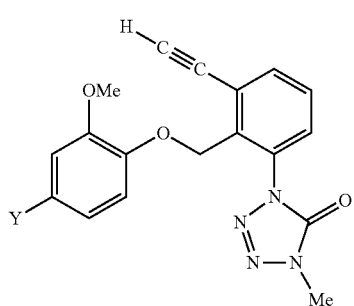 | (HA1273) 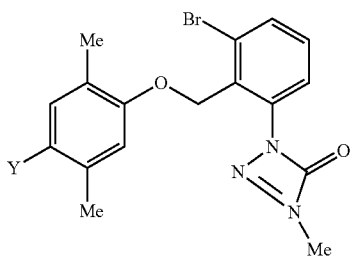 |
| | (HA1274) 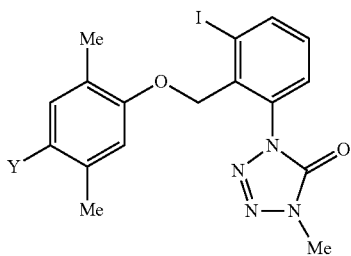 |
| (HA1269) 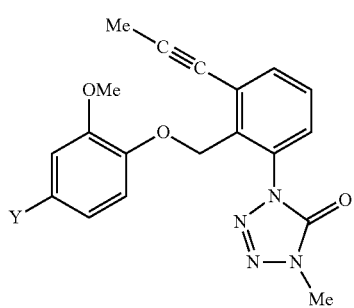 | (HA1275) 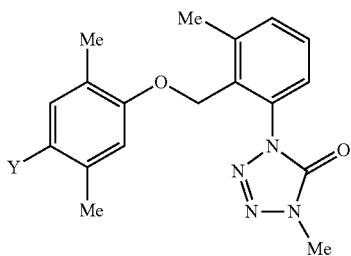 |
| (HA1270) 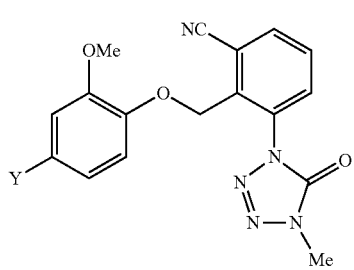 | (HA1276) 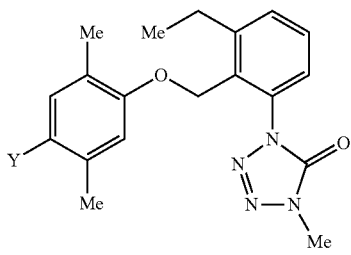 |
| (HA1271) 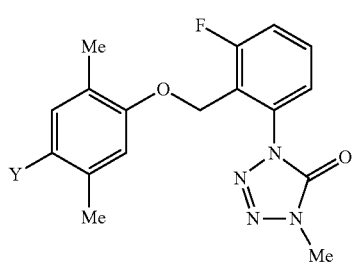 | (HA1277) |

-continued
(HA1278)
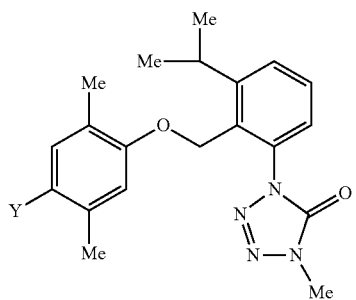
(HA1279)
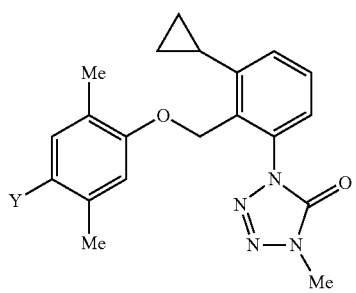
(HA1280)
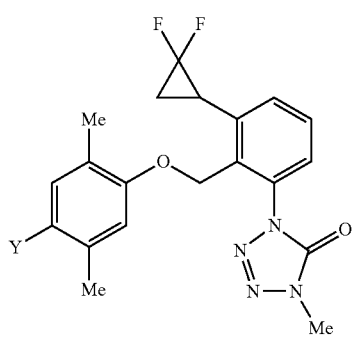
(HA1281)
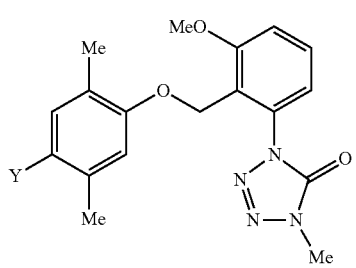
(HA1282)
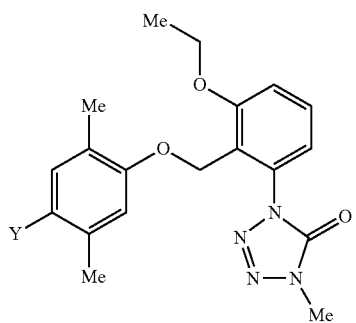
-continued
(HA1283)
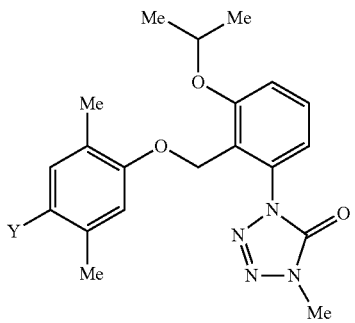
(HA1284)
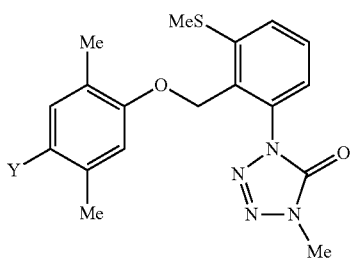
(HA1285)
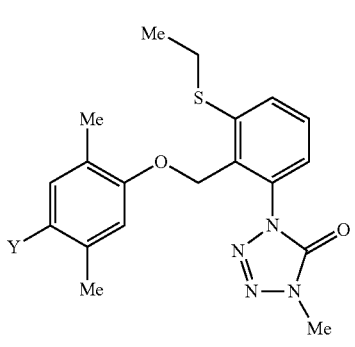
(HA1286)
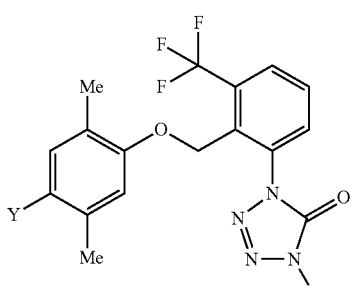
(HA1287)
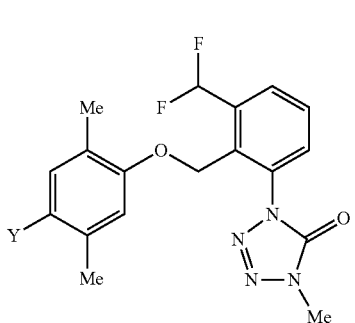

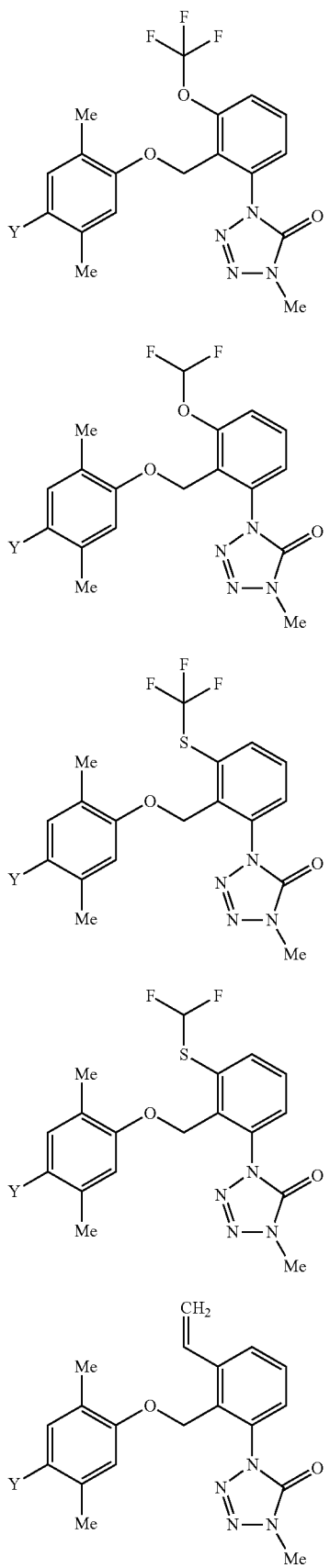
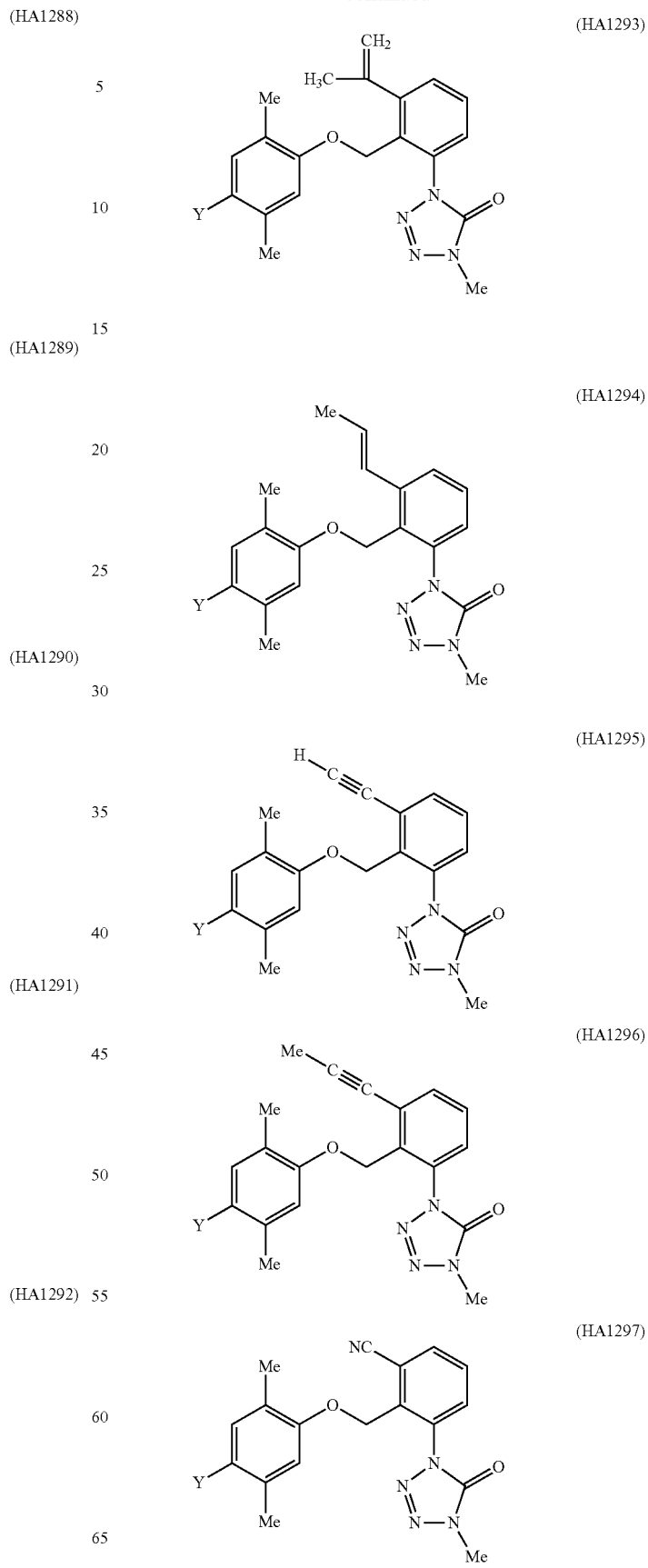

-continued
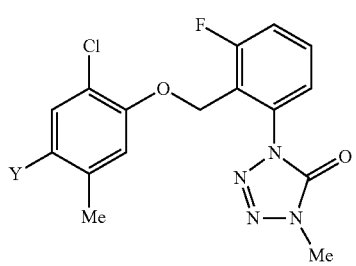
(HA1298)
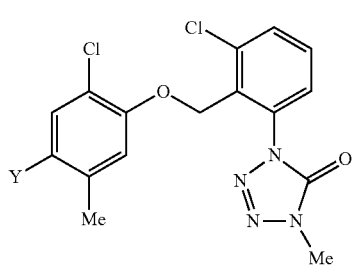
(HA1299)
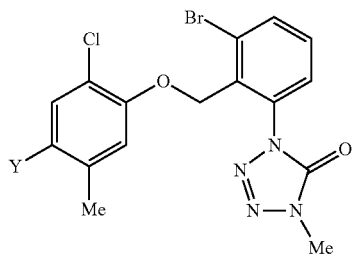
(HA1300)
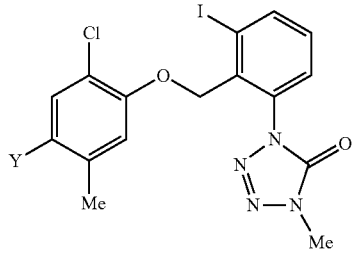
(HA1301)
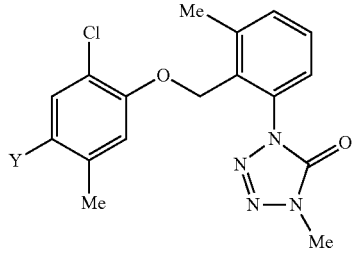
(HA1302)
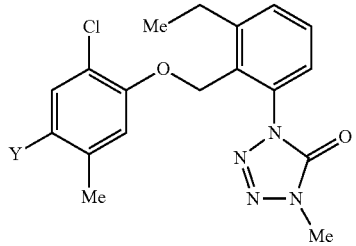
(HA1303)
-continued
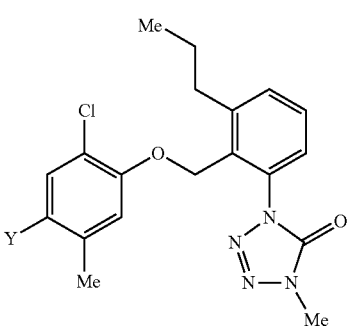
(HA1304)
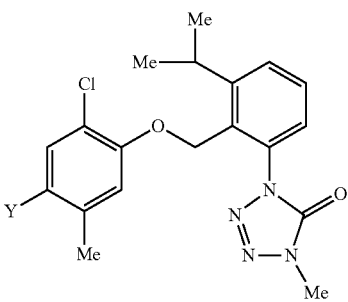
(HA1305)
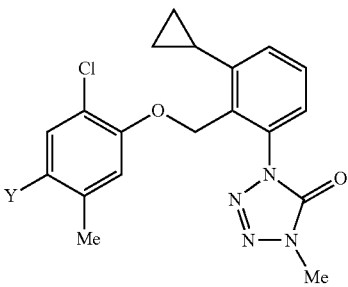
(HA1306)
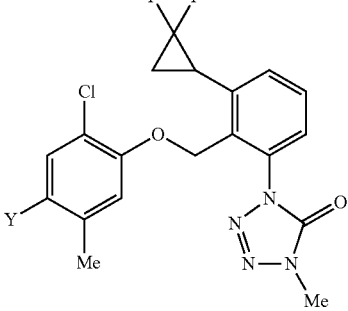
(HA1307)
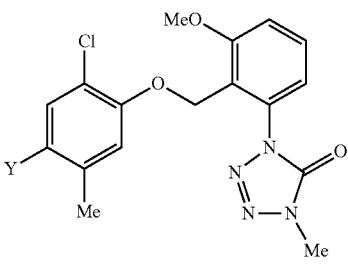
(HA1308)

-continued
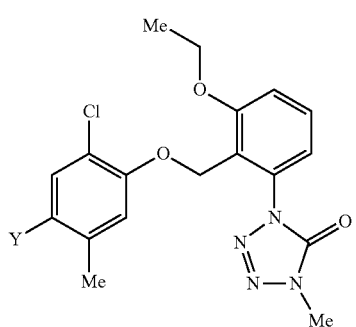
(HA1309)
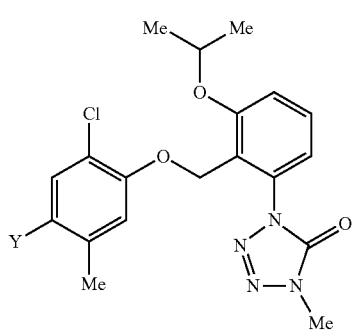
(HA1310)
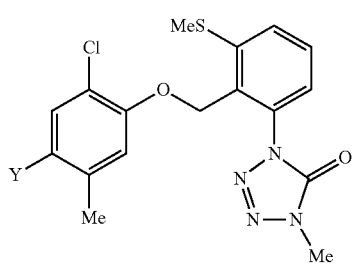
(HA1311)
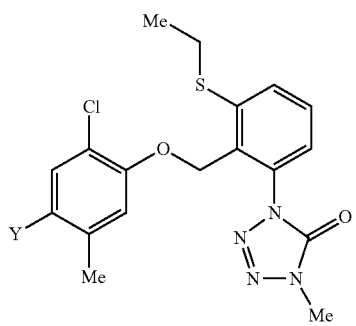
(HA1312)
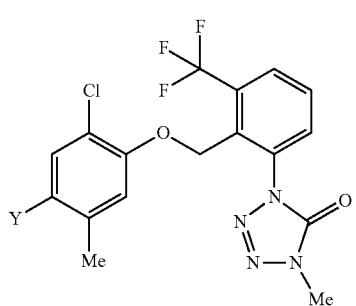
(HA1313)
-continued
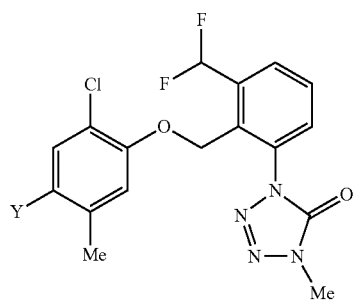
(HA1314)
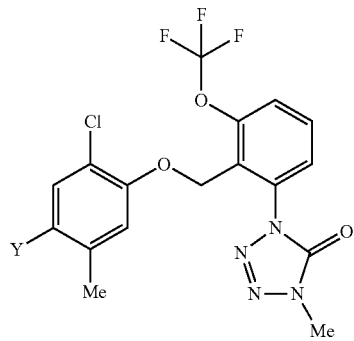
(HA1315)
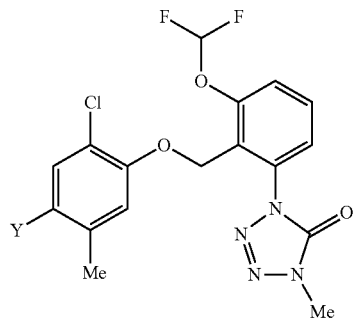
(HA1316)
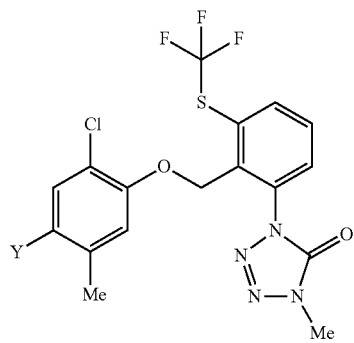
(HA1317)
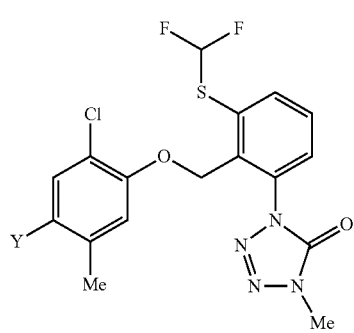
(HA1318)

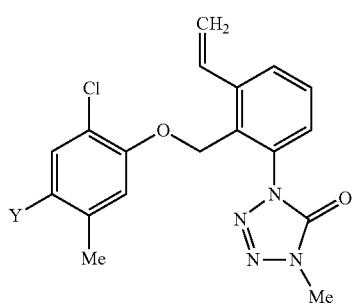
(HA1319)
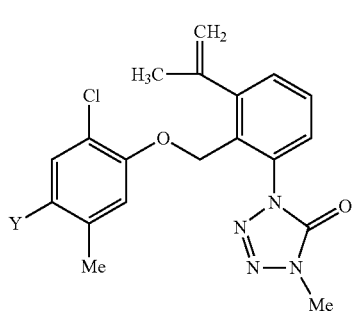
(HA1320)
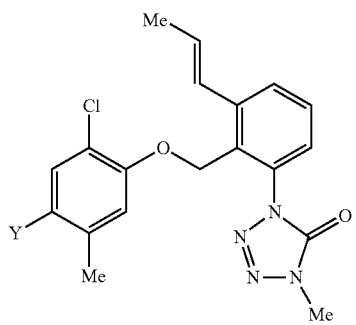
(HA1321)
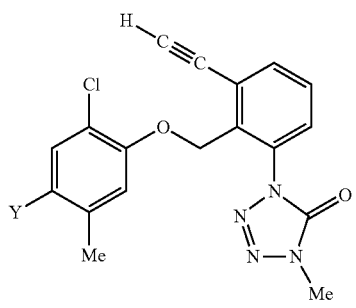
(HA1322)
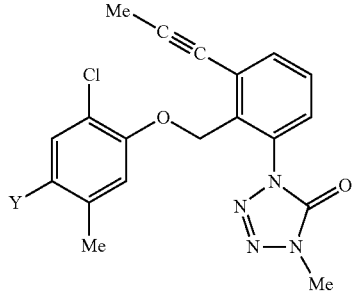
(HA1323)
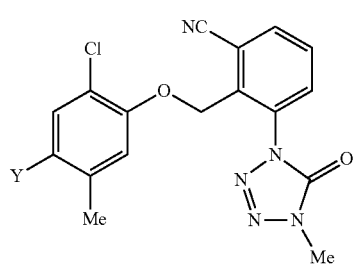
(HA1324)
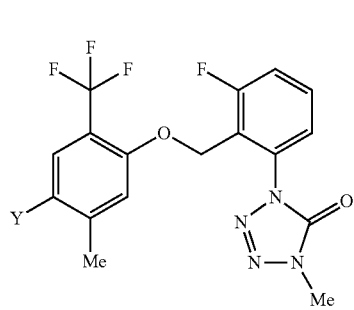
(HA1325)
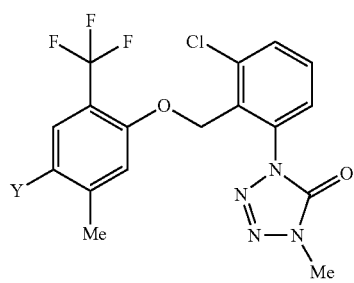
(HA1326)
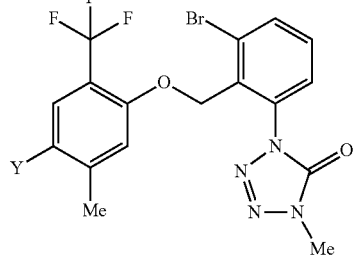
(HA1327)
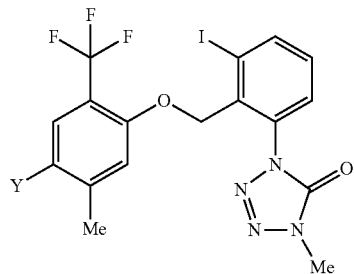
(HA1328)

(HA1329) 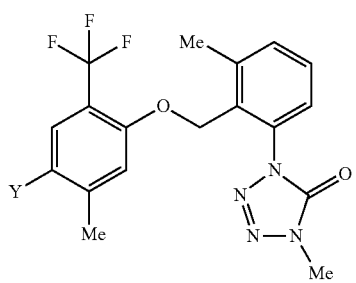
(HA1330) 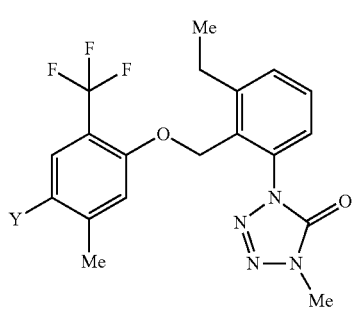
(HA1331) 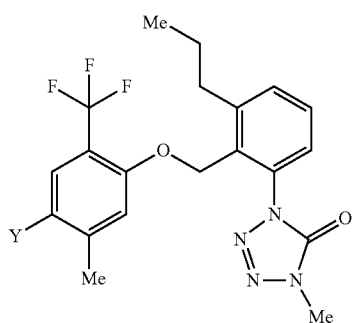
(HA1332) 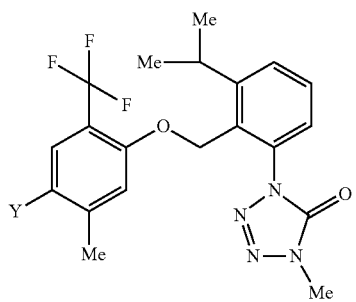
(HA1333) 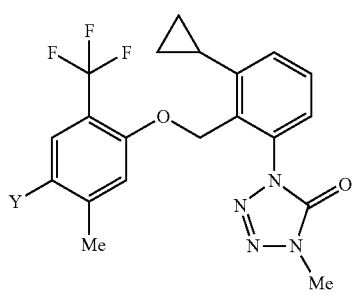
(HA1334) 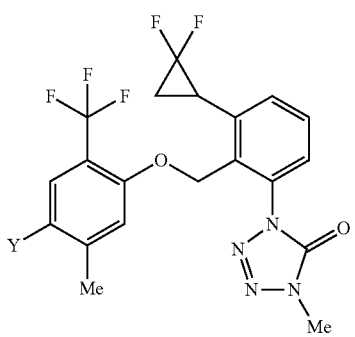
(HA1335) 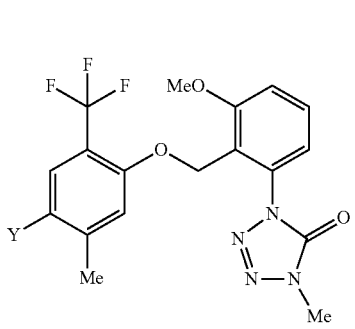
(HA1336) 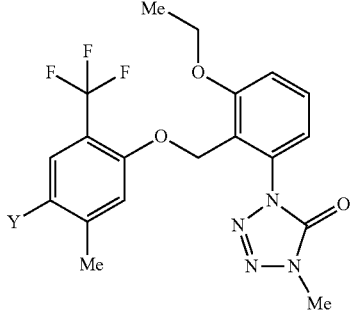
(HA1337) 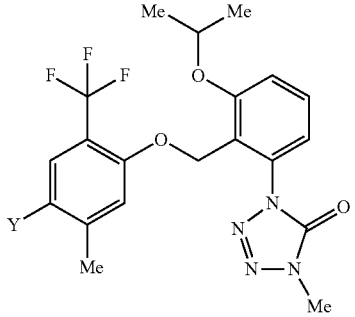
(HA1338) 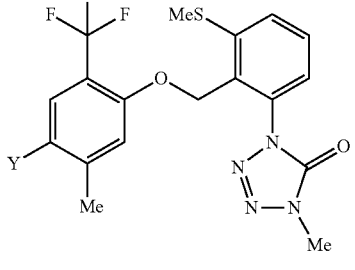

207
-continued
(HA1339)
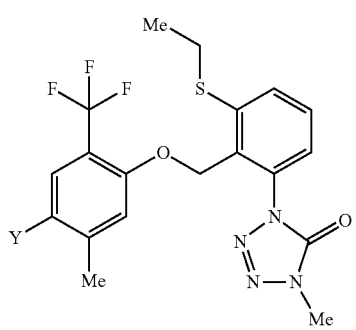
(HA1340)
(HA1341)
(HA1342)
(HA1343)
208
-continued
(HA1344)
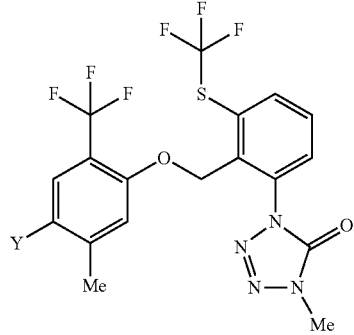
(HA1345)
(HA11346)
(HA1347)
(HA1348)

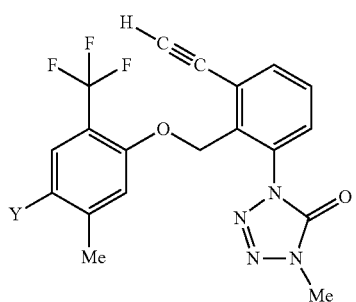
(HA1349)
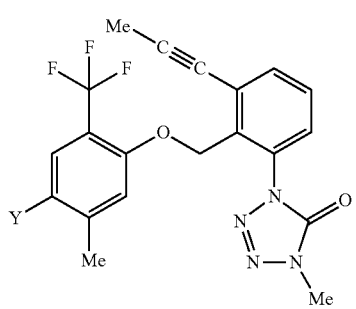
(HA1350)
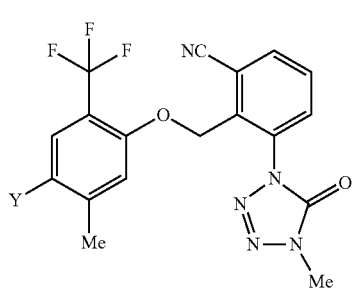
(HA1351)
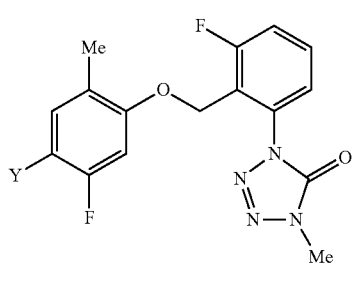
(HA1352)
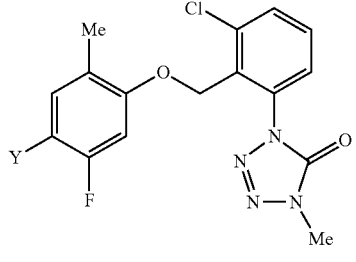
(HA1353)
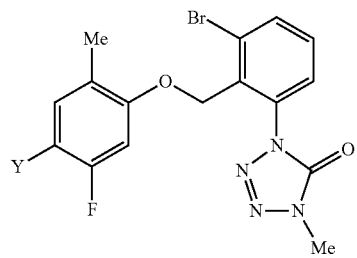
(HA13524)
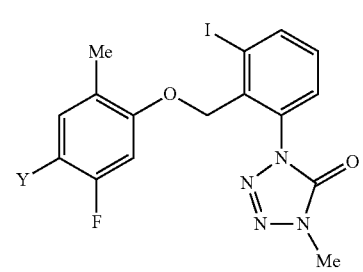
(HA1355)
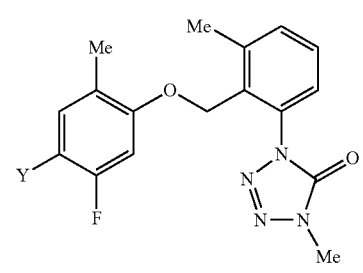
(HA1356)
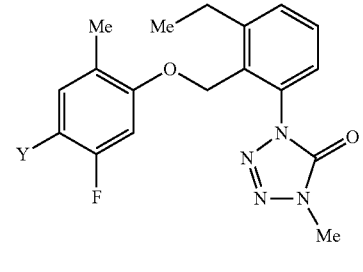
(HA1357)
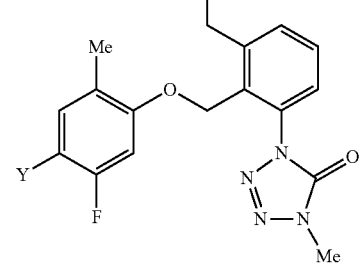
(HA1358)

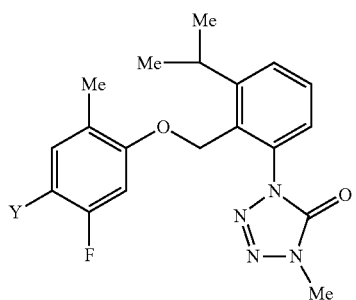
(HA1359)
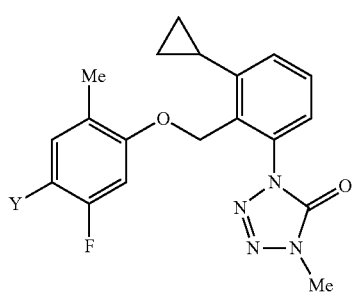
(HA1360)
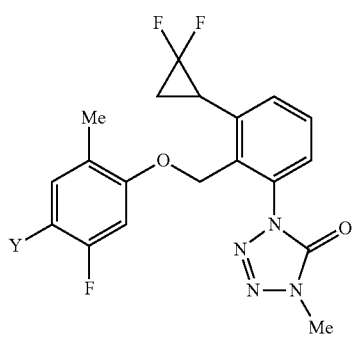
(HA1361)
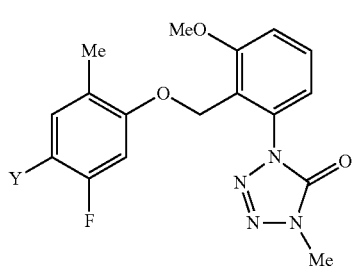
(HA1362)
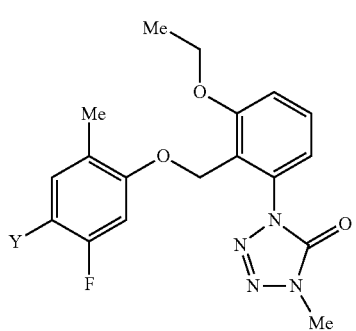
(HA1363)
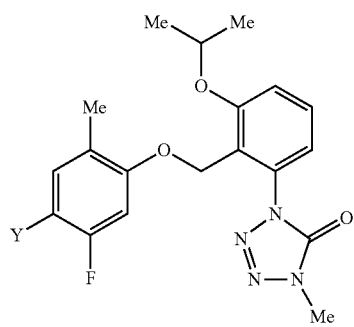
(HA1364)
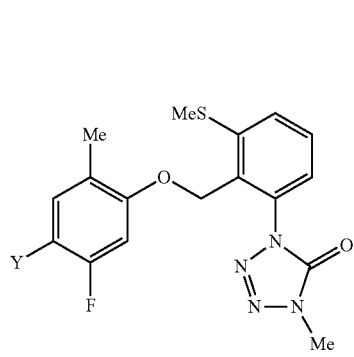
(HA1365)
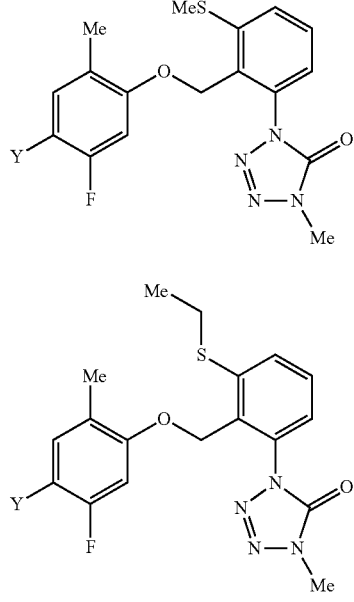
(HA1366)
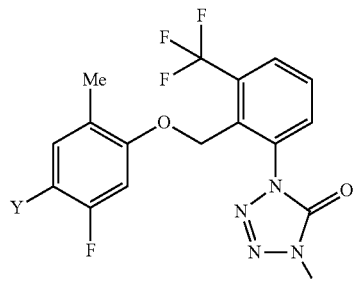
(HA1367)
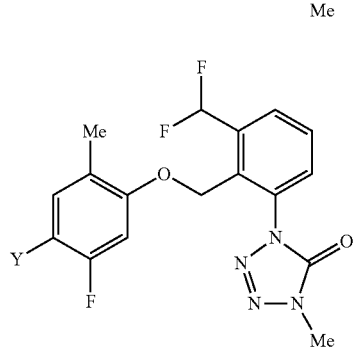
(HA1368)

(HA1369) 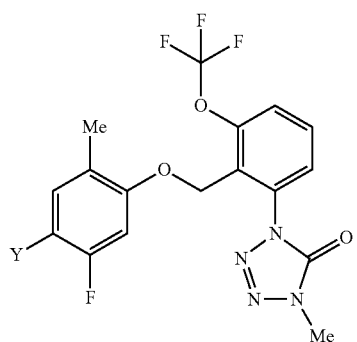
(HA1370) 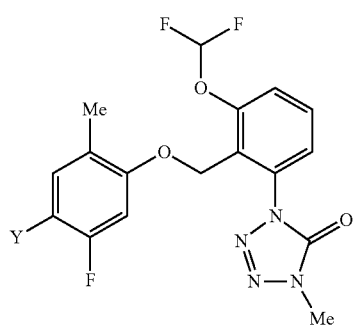
(HA1371) 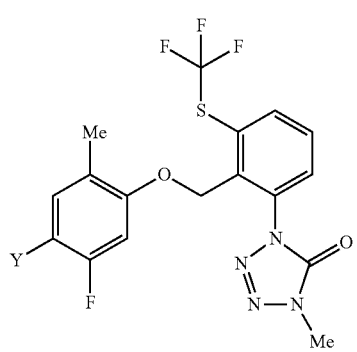
(HA1372) 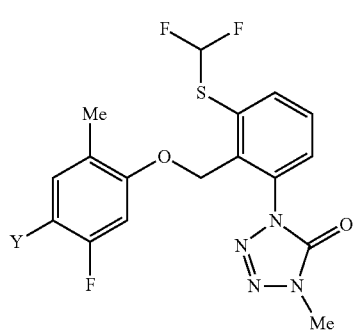
(HA1373) 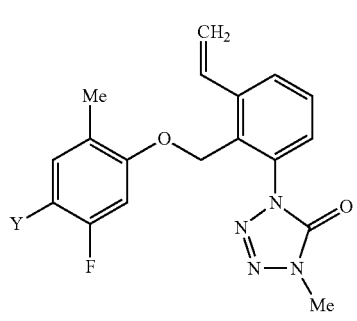
(HA1374) 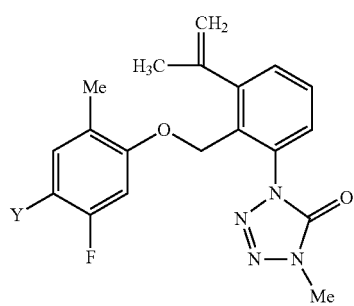
(HA1375) 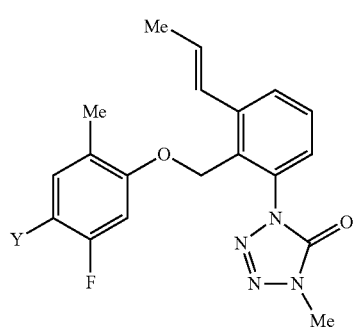
(HA1376) 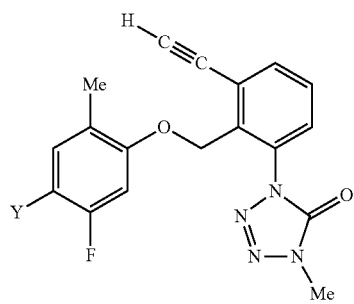
(HA1377) 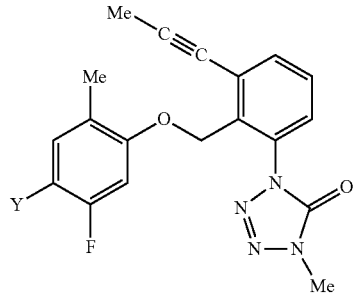
(HA1378) 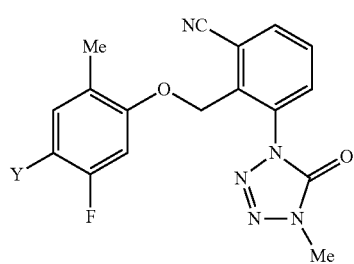

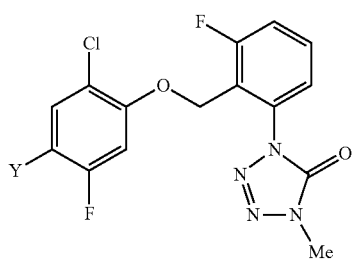
(HA1379)
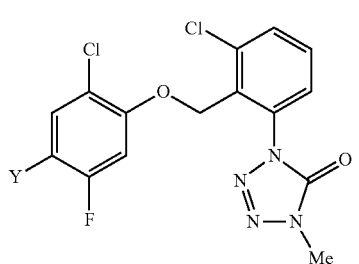
(HA1380)
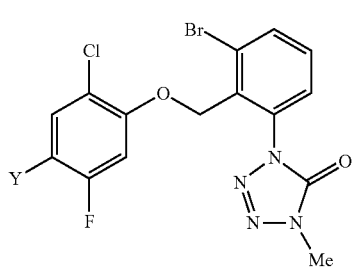
(HA1381)
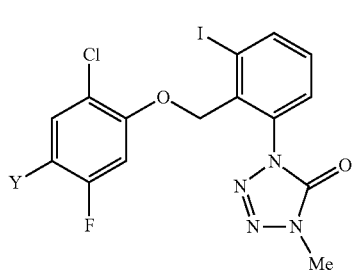
(HA1382)
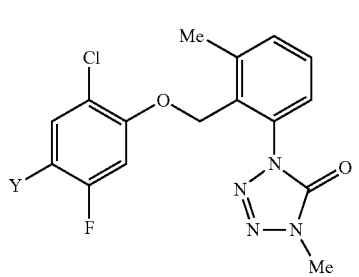
(HA1383)
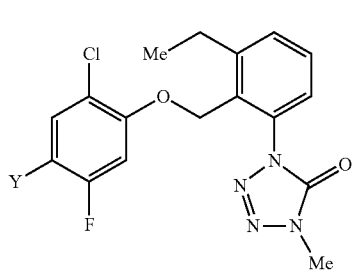
(HA1384)
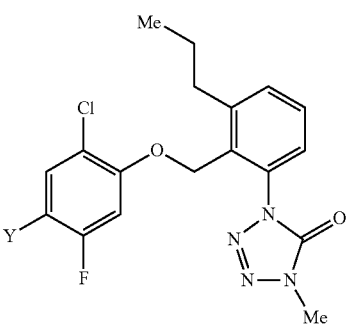
(HA1385)
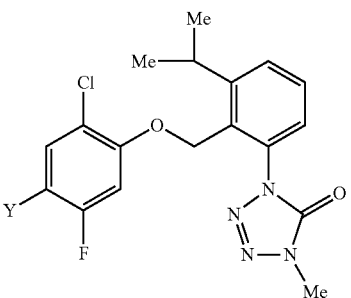
(HA1386)
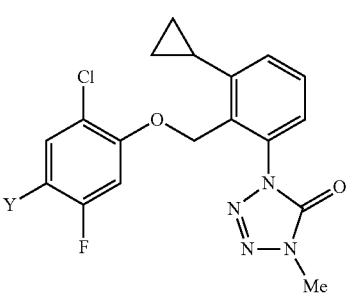
(HA1387)
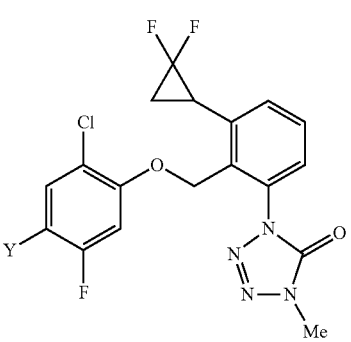
(HA1388)
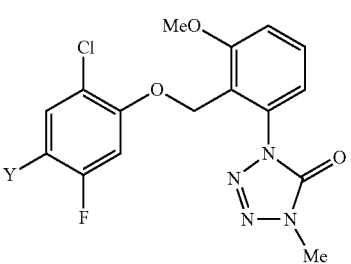
(HA1389)

-continued
(HA1390)
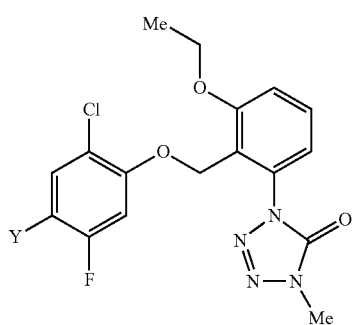
(HA1391)
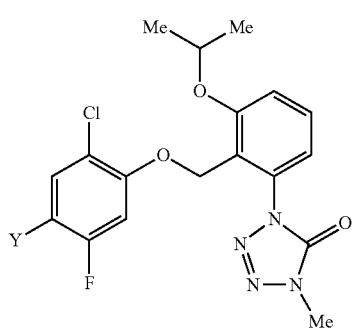
(HA1392)
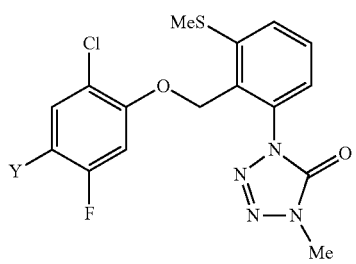
(HA1393)
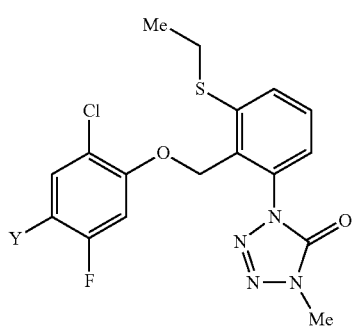
(HA1394)
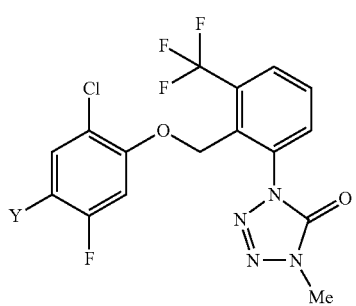
-continued
(HA1395)
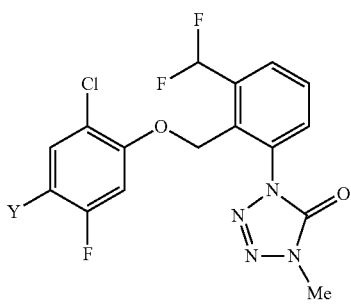
(HA1396)
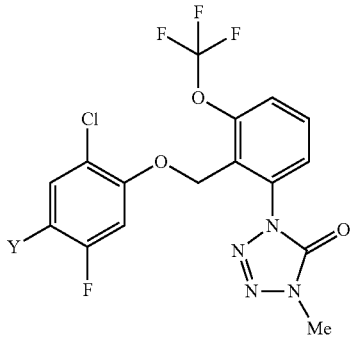
(HA1397)
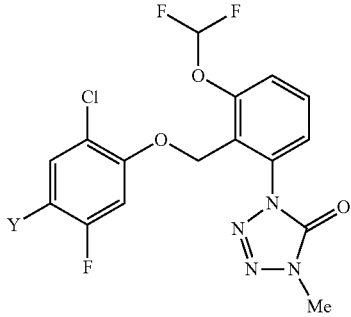
(HA1398)
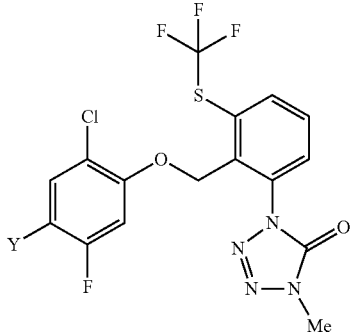
(HA1399)

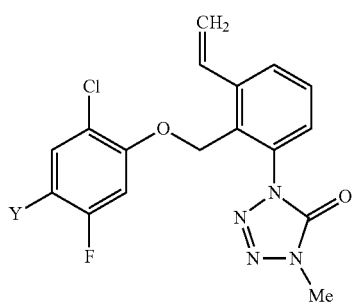
(HA1400)
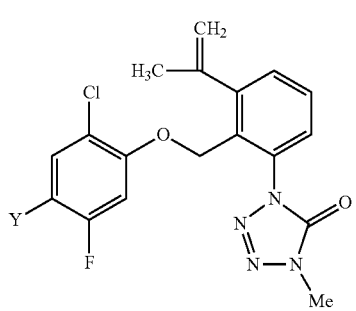
(HA1401)
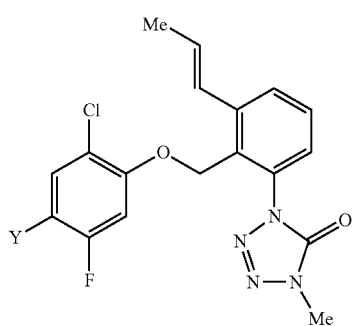
(HA1402)
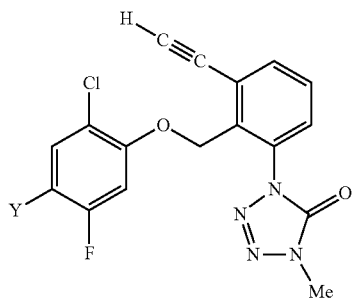
(HA1403)
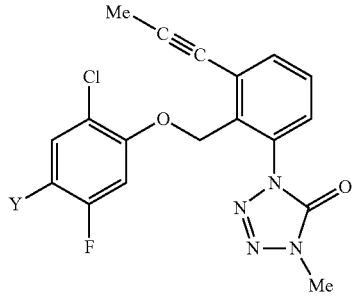
(HA1404)
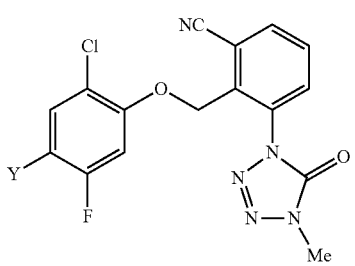
(HA1405)
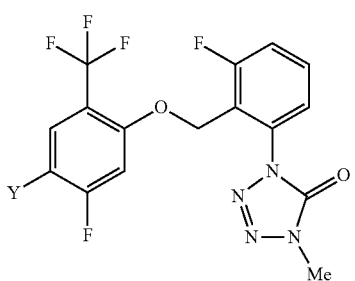
(HA1406)
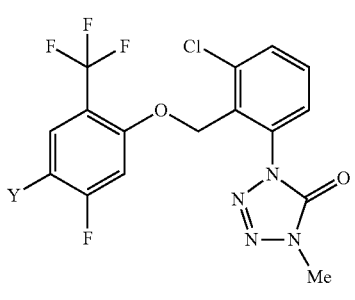
(HA1407)
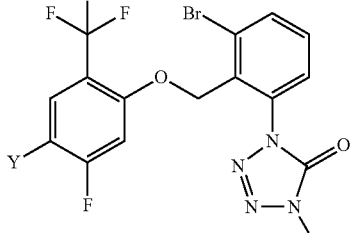
(HA1408)
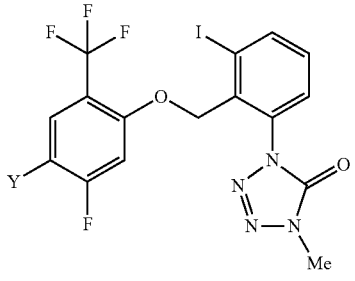
(HA1409)

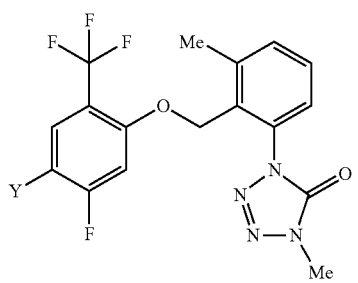
(HA1410)
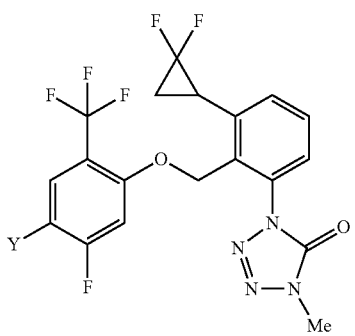
(HA1415)
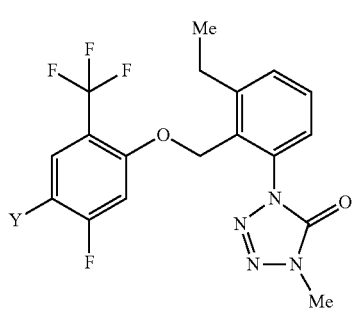
(HA1411)
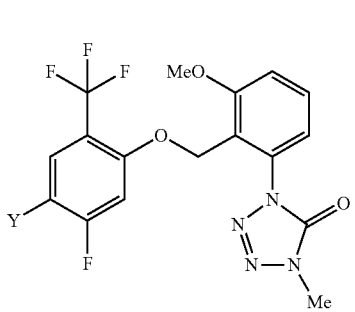
(HA1416)
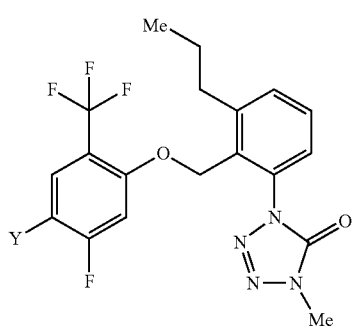
(HA1412)
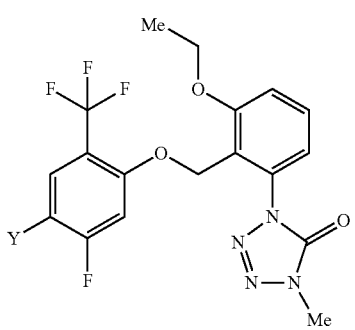
(HA1417)
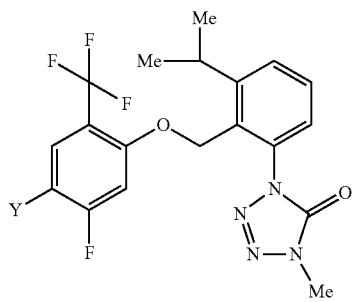
(HA1413)
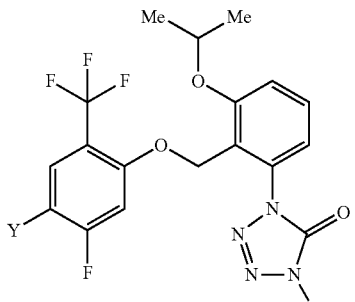
(HA1418)
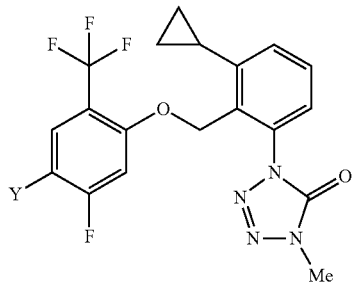
(HA1414)
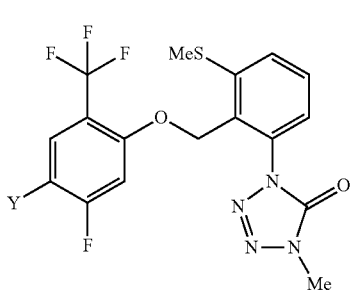
(HA1419)

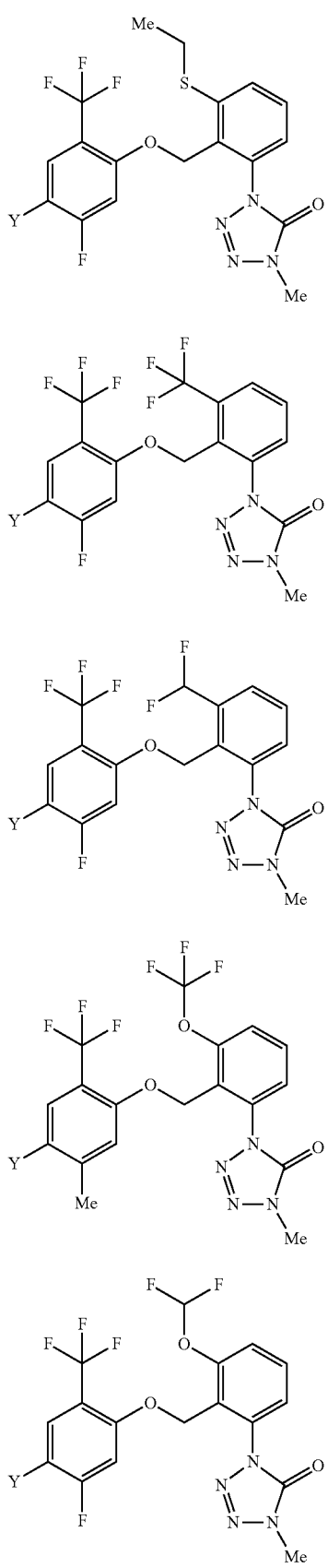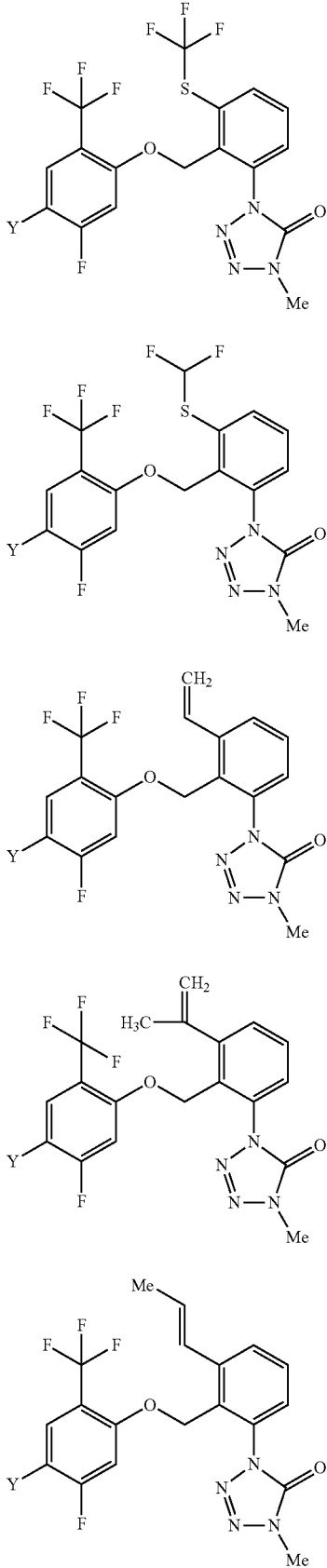

(HA1430)
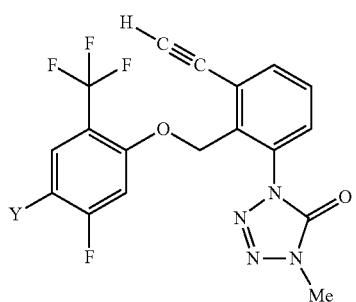
(HA1431)
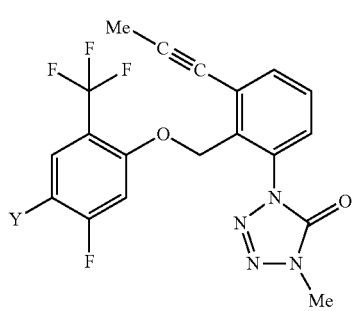
(HA1432)
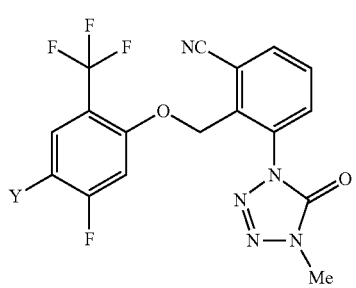
(HA1433)
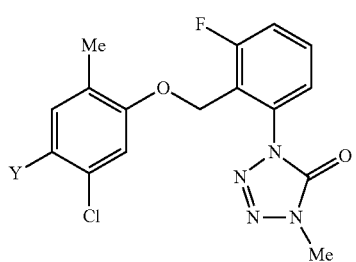
(HA1434)
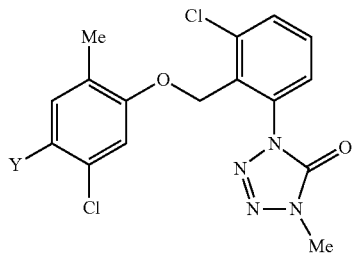
(HA1435)
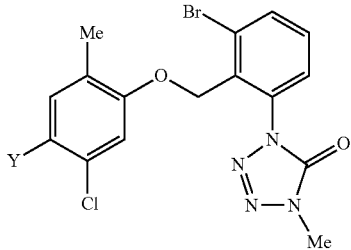
(HA1436)
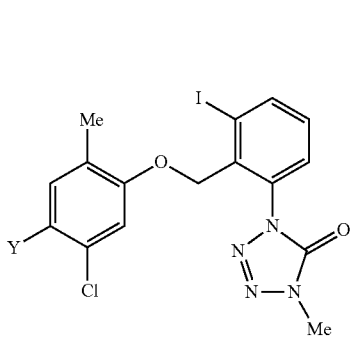
(HA1437)
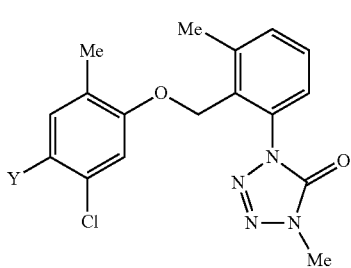
(HA1438)
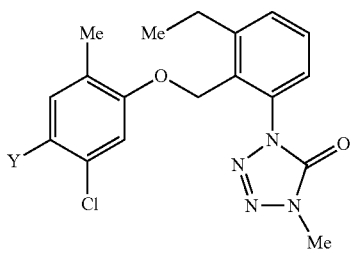
(HA1439)
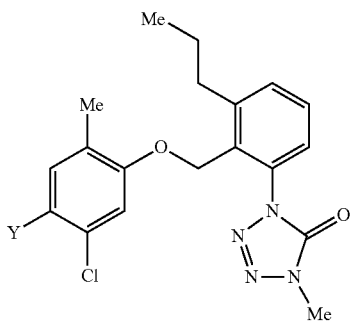

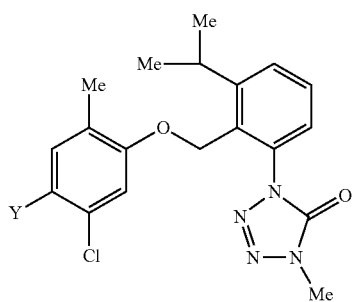 (HA1440)
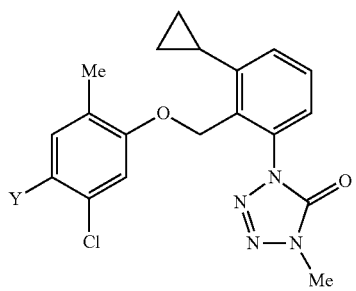 (HA1441)
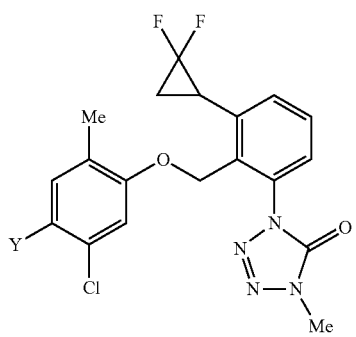 (HA1442)
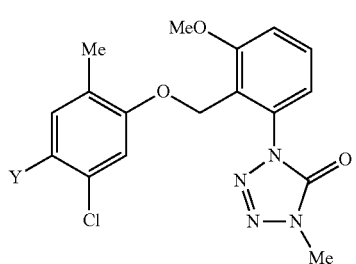 (HA1443)
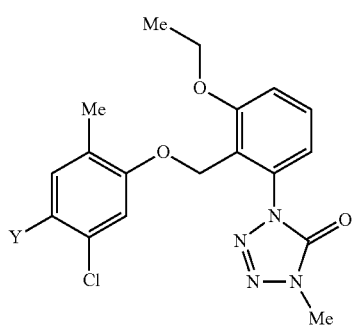 (HA1444)
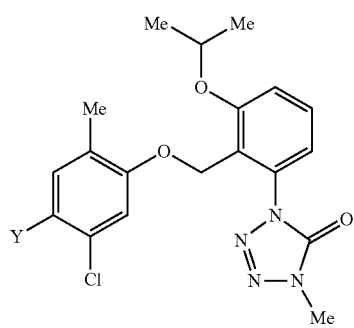 (HA1445)
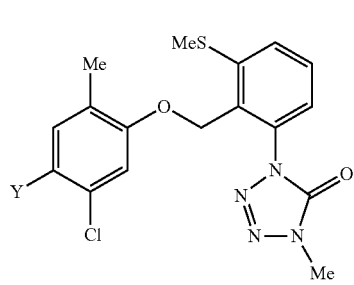 (HA1446)
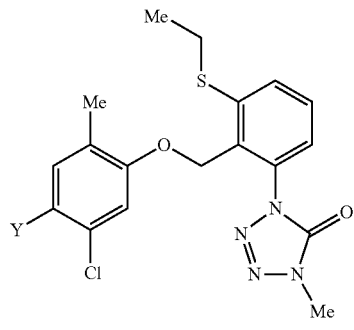 (HA1447)
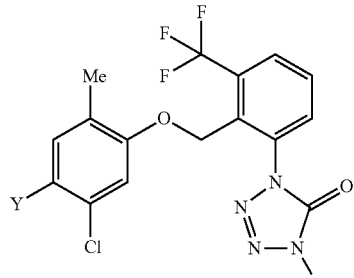 (HA1448)
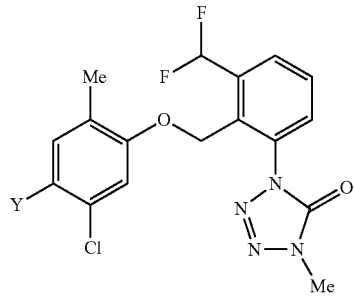 (HA1449)

(HA1450) 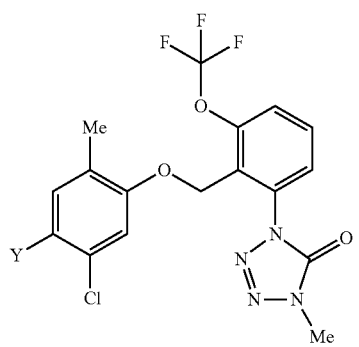
(HA1451) 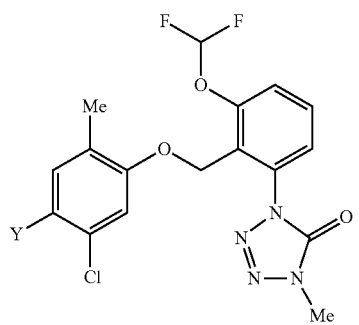
(HA1452) 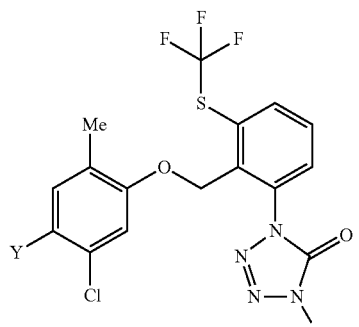
(HA1453) 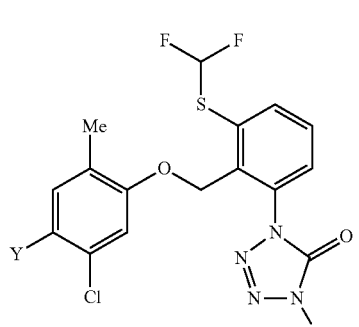
(HA1454) 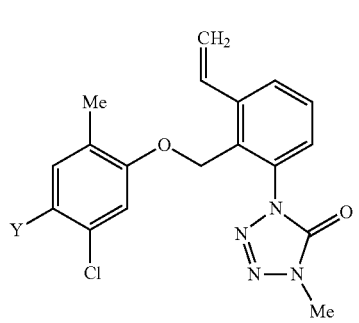
(HA1455) 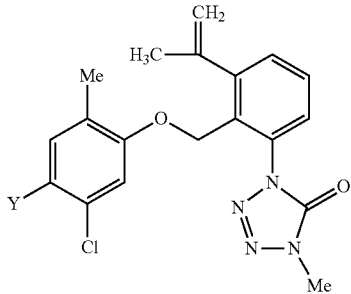
(HA1456) 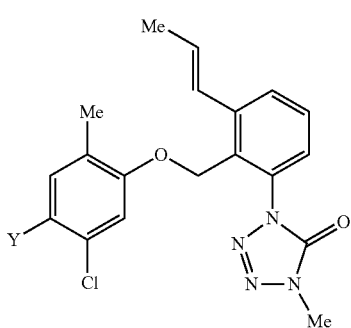
(HA1457) 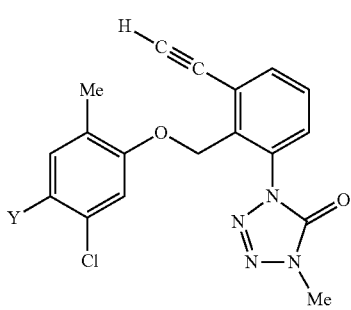
(HA1458) 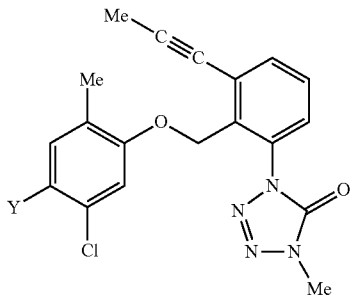
(HA1459) 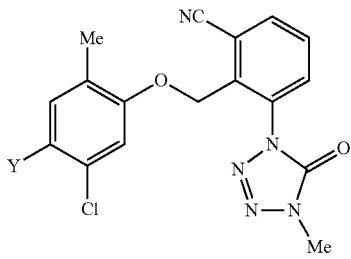

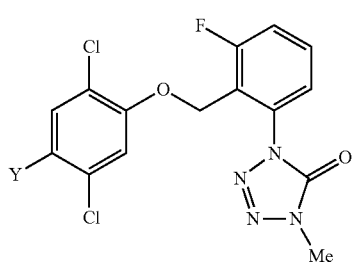
(HA1460)
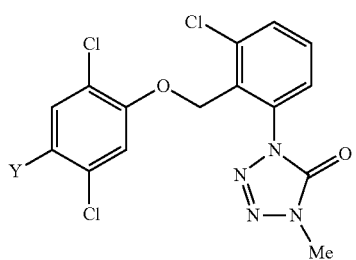
(HA1461)
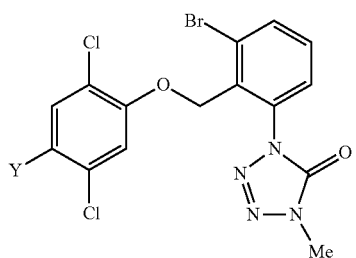
(HA1462)
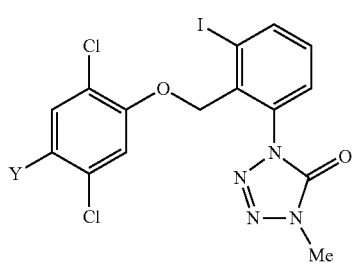
(HA1463)
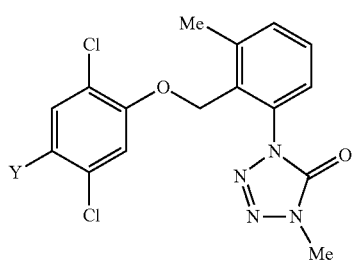
(HA1464)
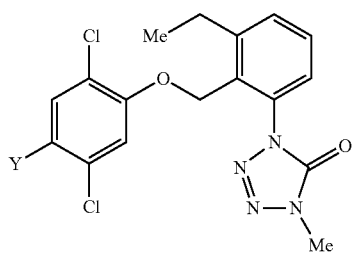
(HA1465)
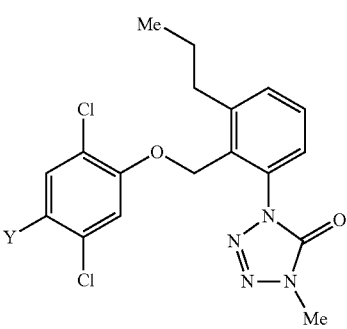
(HA1466)
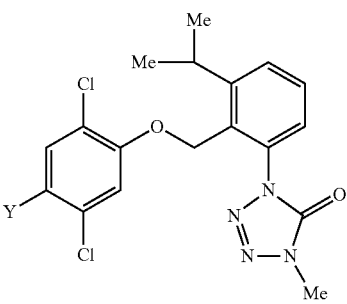
(HA1467)
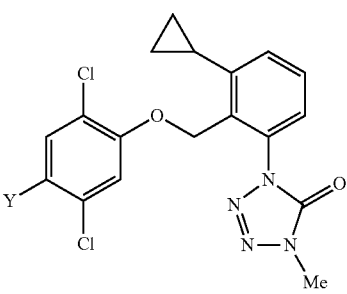
(HA1468)
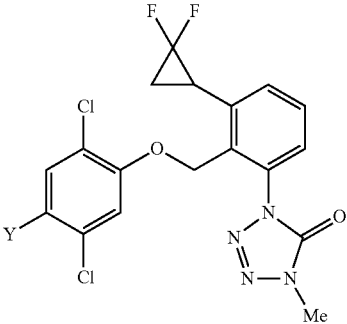
(HA1469)
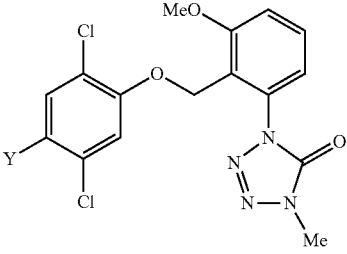
(HA1470)

-continued
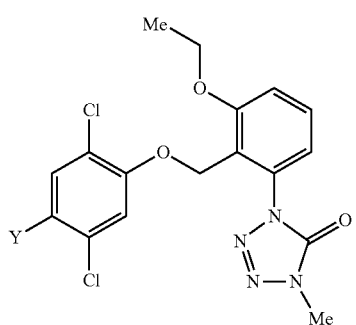 (HA1471)
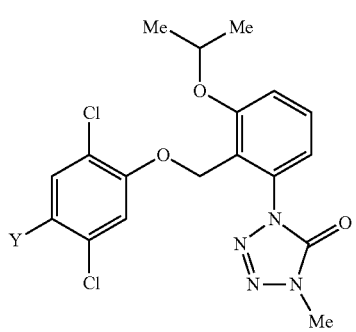 (HA1472)
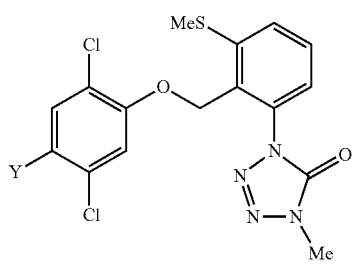 (HA1473)
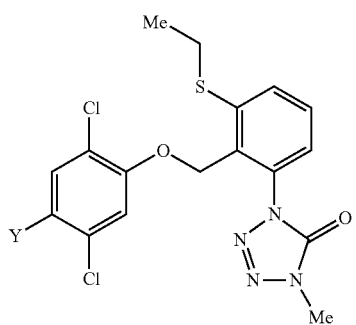 (HA1474)
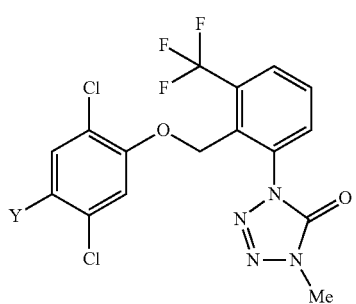 (HA1475)
-continued
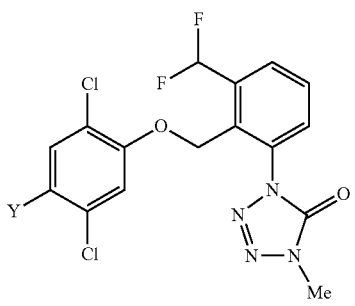 (HA1476)
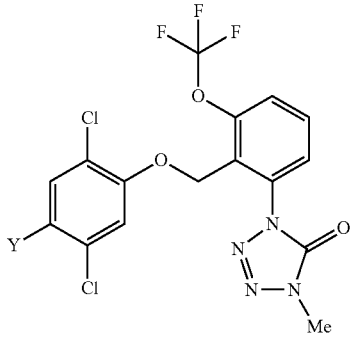 (HA1477)
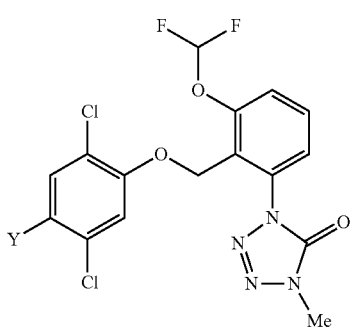 (HA1478)
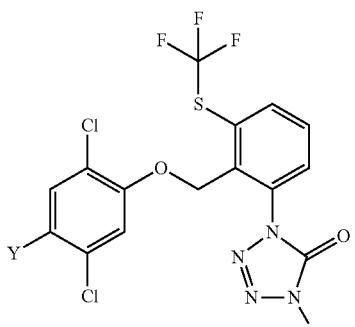 (HA1479)
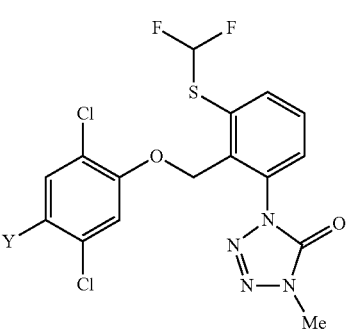 (HA14780)

(HA1481) 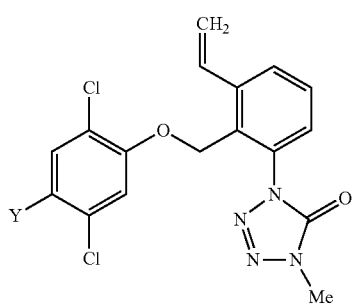
(HA1482) 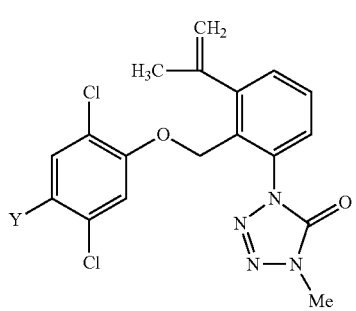
(HA1483) 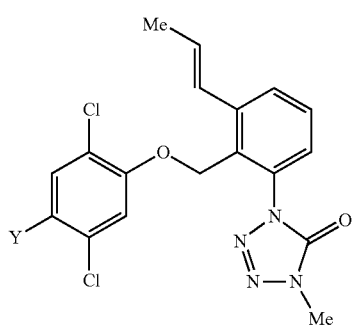
(HA1484) 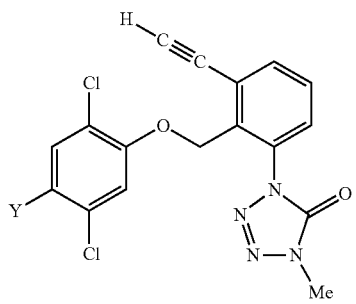
(HA1485) 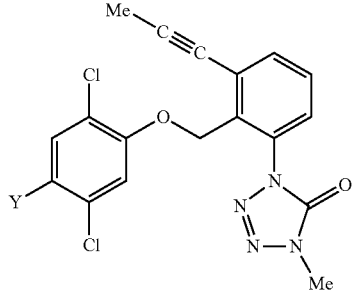
(HA1486) 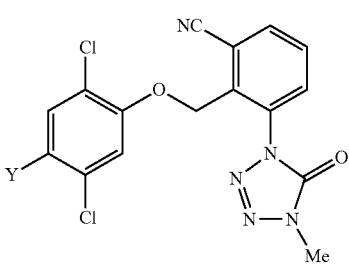
(HA1487) 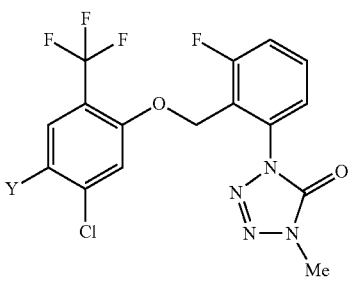
(HA1488) 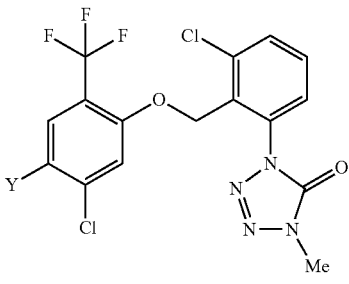
(HA1489) 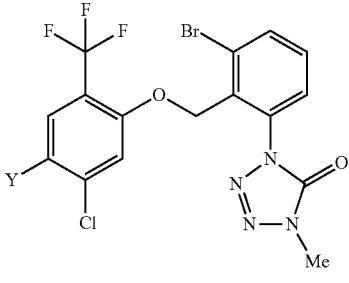
(HA1490) 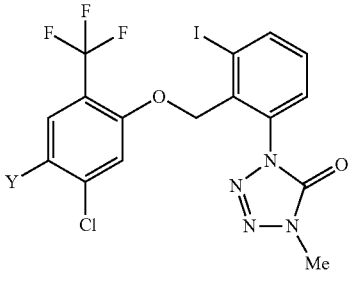

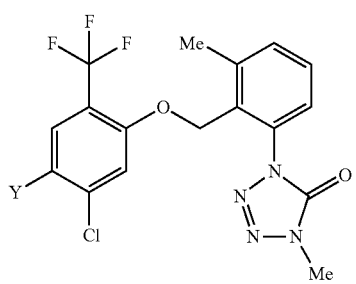 (HA1491)
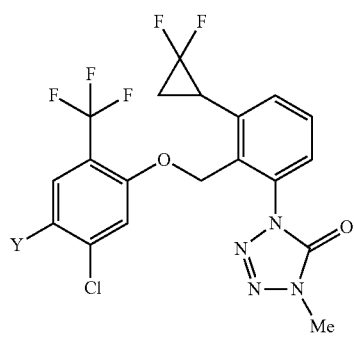 (HA1496)
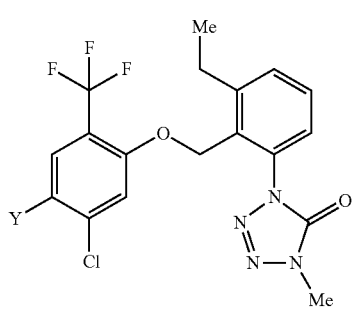 (HA1492)
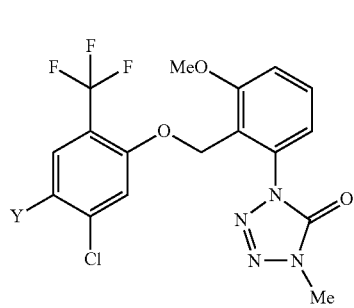 (HA1497)
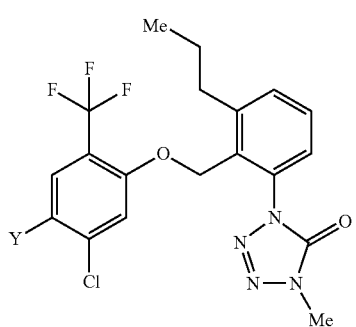 (HA1493)
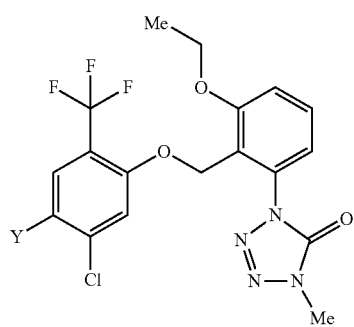 (HA1498)
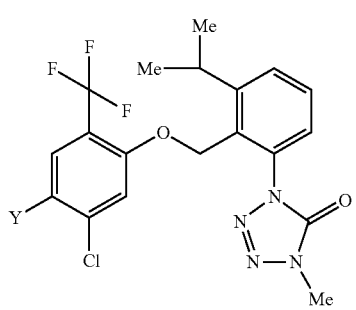 (HA1494)
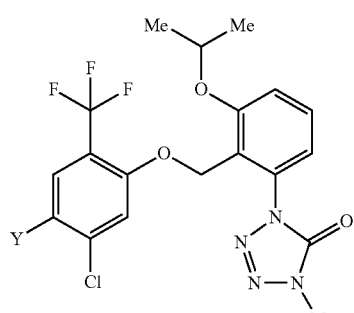 (HA1499)
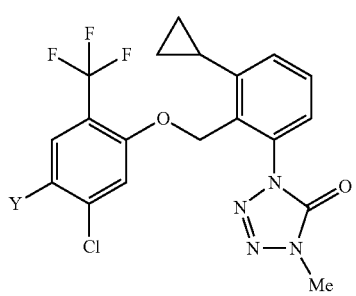 (HA1495)
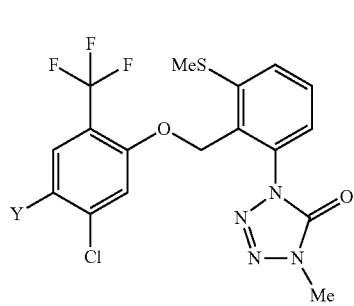 (HA1500)

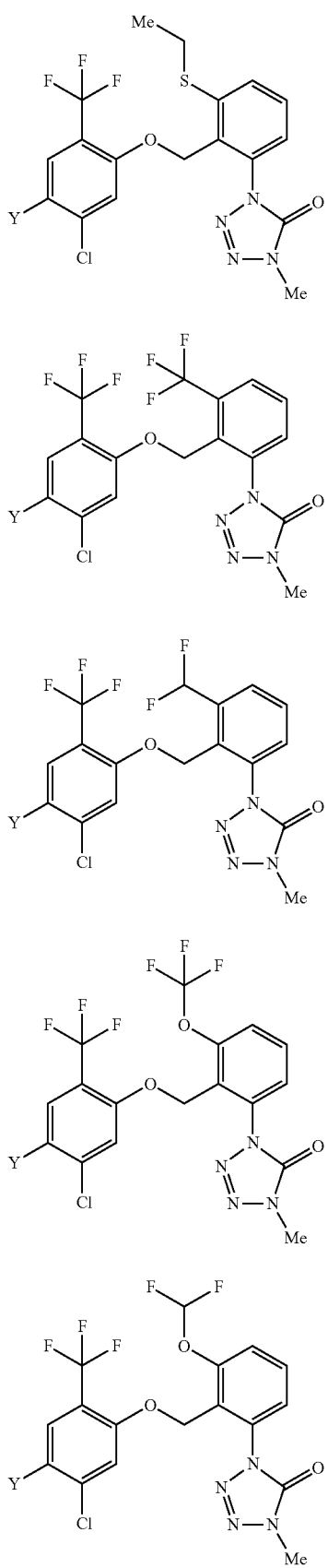
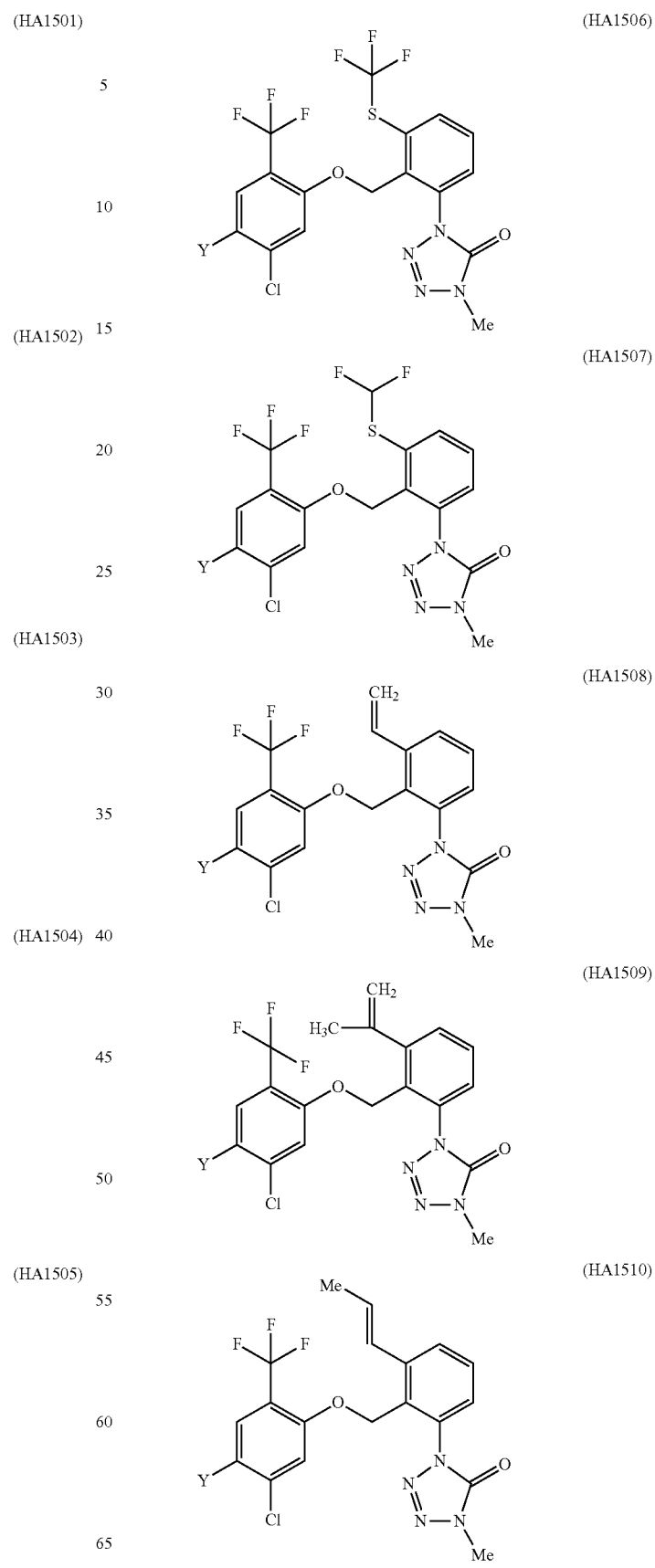

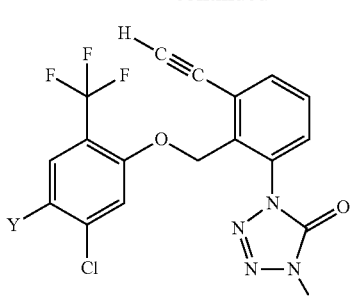
(HA1511)

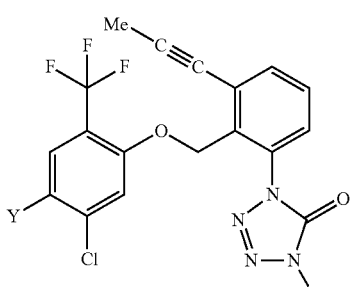
(HA1512)

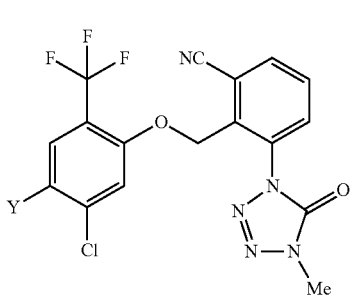
(HA1513)

wherein Y is a substituent corresponding to each of substituent numbers 1 to 5029.

For example, HA1001-0001 shows a compound represented by formula (HA1001) in which Y is substituent number 1, and is a tetrazolinone compound represented the following formula:

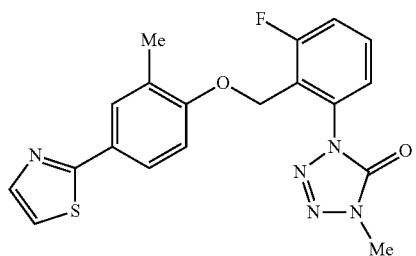
(HA1001-0001)

wherein Q is a substituent corresponding to each of substituent numbers 1 to 5029. 2-Thia mentioned in the following [substituent number; Q] represents a thiazol-2-yl group, 4-Thia represents a thiazol-4-yl group, 5-Thia represents a thiazol-5-yl group, 2-Ox represents an oxazol-2-yl group, 3-Ox represents an oxazol-3-yl group, 4-Ox represents an oxazol-4-yl group, 2-Thio represents a thiophen-2-yl group, 3-Thio represents a thiophen-3-yl group, 2-Fu represents a furan-2-yl group, 3-Fu represents a furan-3-yl group, 1-Tri represents a 1,2,3-triazol-1-yl group, 2-Tri represents a 1,2,3-triazol-2-yl group, 1-Imid represents an imidazol-1-yl group, 2-Imid represents an imidazol-2-yl group, 4-Imid represents an imidazol-4-yl group, 1-Tria represents a 1,2,4-triazol-1-yl group, 3-Tria represents a 1,2,4-triazol-3-yl group, Diox represents a 5H-1,4,2-dioxazol-3-yl group, Oxa represents a 2-oxazolidinon-3-yl group, Dihy represents a dihydrofuran-2-on-3-yl group, Imida represents a 3-methyl-imidazolidin-2-on-1-yl group, F represents fluoro, Cl represents chloro, Br represents bromo, I represents iodo, CN represents cyano, SMe represents methylthio, SEt represents ethylthio, Me represents methyl, Et represents ethyl, iPr represents isopropyl, Pr represents propyl, CF3 represents trifluoromethyl, OCF3 represents trifluoromethoxy, CHF2 represents difluoromethyl, OCHF2 represents difluoromethoxy, OMe represents methoxy, OEt represents ethoxy, cPr represents cyclopropyl, and NO2 represents a nitro group.

[1; 2-Thia], [2; 4-F-2-Thia], [3; 4-Cl-2-Thia], [4; 4-Br-2-Thia], [5; 4-I-2-Thia], [6; 4-Me-2-Thia], [7; 4-Et-2-Thia], [8; 4-Pr-2-Thia], [9; 4-iPr-2-Thia], [10; 4-CF3-2-Thia], [11; 4-CHF2-2-Thia], [12; 4-OMe-2-Thia], [13; 4-OEt-2-Thia], [14; 4-OCF3-2-Thia], [15; 4-OCHF2-2-Thia], [16; 4-CN-2-Thia], [17; 4-SMe-2-Thia], [18; 4-SEt-2-Thia], [19; 4-cPr-2-Thia], [20; 5-F-2-Thia], [21; 5-Cl-2-Thia], [22; 5-Br-2-Thia], [23; 5-I-2-Thia], [24; 5-Me-2-Thia], [25; 5-Et-2-Thia], [26; 5-Pr-2-Thia], [27; 5-iPr-2-Thia], [28; 5-CF3-2-Thia], [29; 5-CHF2-2-Thia], [30; 5-OMe-2-Thia], [31; 5-OEt-2-Thia], [32; 5-OCF3-2-Thia], [33; 5-OCHF2-2-Thia], [34; 5-CN-2-Thia], [35; 5-SMe-2-Thia], [36; 5-SEt-2-Thia], [37; 5-cPr-2-Thia], [38; 4-F-5-F-2-Thia], [39; 4-F-5-Cl-2-Thia], [40; 4-F-5-Br-2-Thia], [41; 4-F-5-I-2-Thia], [42; 4-F-5-Me-2-Thia], [43; 4-F-5-Et-2-Thia], [44; 4-F-5-Pr-2-Thia], [45; 4-F-5-iPr-2-Thia], [46; 4-F-5-CF3-2-Thia], [47; 4-F-5-CHF2-2-Thia], [48; 4-F-5-OMe-2-Thia], [49; 4-F-5-OEt-2-Thia], [50; 4-F-5-OCF3-2-Thia], [51; 4-F-5-OCHF2-2-Thia], [52; 4-F-5-CN-2-Thia], [53; 4-F-5-SMe-2-Thia], [54; 4-F-5-SEt-2-Thia], [55; 4-F-5-cPr-2-Thia], [56; 4-Cl-5-F-2-Thia], [57; 4-Cl-5-Cl-2-Thia], [58; 4-Cl-5-Br-2-Thia], [59; 4-Cl-5-I-2-Thia], [60; 4-Cl-5-Me-2-Thia], [61; 4-Cl-5-Et-2-Thia], [62; 4-Cl-5-Pr-2-Thia], [63; 4-Cl-5-iPr-2-Thia], [64; 4-Cl-5-CF3-2-Thia], [65; 4-Cl-5-CHF2-2-Thia], [66; 4-Cl-5-OMe-2-Thia], [67; 4-Cl-5-OEt-2-Thia], [68; 4-Cl-5-OCF3-2-Thia], [69; 4-Cl-5-OCHF2-2-Thia], [70; 4-Cl-5-CN-2-Thia], [71; 4-Cl-5-SMe-2-Thia], [72; 4-Cl-5-SEt-2-Thia], [73; 4-Cl-5-cPr-2-Thia], [74; 4-Me-5-F-2-Thia], [75; 4-Me-5-Cl-2-Thia], [76; 4-Me-5-Br-2-Thia], [77; 4-Me-5-I-2-Thia], [78; 4-Me-5-Me-2-Thia], [79; 4-Me-5-Et-2-Thia], [80; 4-Me-5-Pr-2-Thia], [81; 4-Me-5-iPr-2-Thia], [82; 4-Me-5-CF3-2-Thia], [83; 4-Me-5-CHF2-2-Thia], [84; 4-Me-5-OMe-2-Thia], [85; 4-Me-5-OEt-2-Thia], [86; 4-Me-5-OCF3-2-Thia], [87; 4-Me-5-OCHF2-2-Thia], [88; 4-Me-5-CN-2-Thia], [89; 4-Me-5-SMe-2-Thia], [90; 4-Me-5-SEt-2-Thia], [91; 4-Me-5-cPr-2-Thia], [92; 4-Et-5-F-2-Thia], [93; 4-Et-5-Cl-2-Thia], [94; 4-Et-5-Br-2-Thia], [95; 4-Et-5-I-2-Thia], [96; 4-Et-5-Me-2-Thia], [97; 4-Et-5-Et-2-Thia], [98; 4-Et-5-Pr-2-Thia], [99; 4-Et-5-iPr-2-Thia], [100; 4-Et-5-CF3-2-Thia],

[101; 4-Et-5-CHF2-2-Thia], [102; 4-Et-5-OMe-2-Thia], [103; 4-Et-5-OEt-2-Thia], [104; 4-Et-5-OCF3-2-Thia], [105; 4-Et-5-OCHF2-2-Thia], [106; 4-Et-5-CN-2-Thia], [107; 4-Et-5-SMe-2-Thia], [108; 4-Et-5-SEt-2-Thia], [109; 4-Et-5-cPr-2-Thia], [110; 4-CF3-5-F-2-Thia], [111; 4-CF3-5-Cl-2-Thia], [112; 4-CF3-5-Br-2-Thia], [113; 4-CF3-5-I-2-Thia], [114; 4-CF3-5-Me-2-Thia], [115; 4-CF3-5-Et-2-Thia], [116; 4-CF3-5-Pr-2-Thia], [117; 4-CF3-5-iPr-2-Thia], [118; 4-CF3-5-CF3-2-Thia], [119; 4-CF3-5-CHF2-2-Thia],

[120; 4-CF3-5-OMe-2-Thia], [121; 4-CF3-5-OEt-2-Thia], [122; 4-CF3-5-OCF3-2-Thia], [123; 4-CF3-5-OCHF2-2-Thia], [124; 4-CF3-5-CN-2-Thia], [125; 4-CF3-5-SMe-2-Thia], [126; 4-CF3-5-SEt-2-Thia], [127; 4-CF3-5-cPr-2-Thia], [128; 4-OMe-5-F-2-Thia], [129; 4-OMe-5-Cl-2-Thia], [130; 4-OMe-5-Br-2-Thia], [131; 4-OMe-5-I-2-Thia], [132; 4-OMe-5-Me-2-Thia], [133; 4-OMe-5-Et-2-Thia], [134; 4-OMe-5-Pr-2-Thia], [135; 4-OMe-5-iPr-2-Thia], [136; 4-OMe-5-CF3-2-Thia], [137; 4-OMe-5-CHF2-2-Thia], [138; 4-OMe-5-OMe-2-Thia], [139; 4-OMe-5-OEt-2-Thia], [140; 4-OMe-5-OCF3-2-Thia], [141; 4-OMe-5-OCHF2-2-Thia], [142; 4-OMe-5-CN-2-Thia], [143; 4-OMe-5-SMe-2-Thia], [144; 4-OMe-5-SEt-2-Thia], [145; 4-OMe-5-cPr-2-Thia], [146; 4-OEt-5-F-2-Thia], [147; 4-OEt-5-Cl-2-Thia], [148; 4-OEt-5-Br-2-Thia], [149; 4-OEt-5-I-2-Thia], [150; 4-OEt-5-Me-2-Thia], [151; 4-OEt-5-Et-2-Thia], [152; 4-OEt-5-Pr-2-Thia], [153; 4-OEt-5-iPr-2-Thia], [154; 4-OEt-5-CF3-2-Thia], [155; 4-OEt-5-CHF2-2-Thia], [156; 4-OEt-5-OMe-2-Thia], [157; 4-OEt-5-OEt-2-Thia], [158; 4-OEt-5-OCF3-2-Thia], [159; 4-OEt-5-OCHF2-2-Thia], [160; 4-OEt-5-CN-2-Thia], [161; 4-OEt-5-SMe-2-Thia], [162; 4-OEt-5-SEt-2-Thia], [163; 4-OEt-5-cPr-2-Thia], [164; 4-SMe-5-F-2-Thia], [165; 4-SMe-5-Cl-2-Thia], [166; 4-SMe-5-Br-2-Thia], [167; 4-SMe-5-I-2-Thia], [168; 4-SMe-5-Me-2-Thia], [169; 4-SMe-5-Et-2-Thia], [170; 4-SMe-5-Pr-2-Thia], [171; 4-SMe-5-iPr-2-Thia], [172; 4-SMe-5-CF3-2-Thia], [173; 4-SMe-5-CHF2-2-Thia], [174; 4-SMe-5-OMe-2-Thia], [175; 4-SMe-5-OEt-2-Thia], [176; 4-SMe-5-OCF3-2-Thia], [177; 4-SMe-5-OCHF2-2-Thia], [178; 4-SMe-5-CN-2-Thia], [179; 4-SMe-5-SMe-2-Thia], [180; 4-SMe-5-SEt-2-Thia], [181; 4-SMe-5-cPr-2-Thia], [182; -4-Thia], [183; 2-F-4-Thia], [184; 2-Cl-4-Thia], [185; 2-Br-4-Thia], [186; 2-I-4-Thia], [187; 2-Me-4-Thia], [188; 2-Et-4-Thia], [189; 2-Pr-4-Thia], [190; 2-iPr-4-Thia], [191; 2-CF3-4-Thia], [192; 2-CHF2-4-Thia], [193; 2-OMe-4-Thia], [194; 2-OEt-4-Thia], [195; 2-OCF3-4-Thia], [196; 2-OCHF2-4-Thia], [197; 2-CN-4-Thia], [198; 2-SMe-4-Thia], [199; 2-SEt-4-Thia], [200; 2-cPr-4-Thia],

[201; 5-F-4-Thia], [202; 5-Cl-4-Thia], [203; 5-Br-4-Thia], [204; 5-I-4-Thia], [205; 5-Me-4-Thia], [206; 5-Et-4-Thia], [207; 5-Pr-4-Thia], [208; 5-iPr-4-Thia], [209; 5-CF3-4-Thia], [210; 5-CHF2-4-Thia], [211; 5-OMe-4-Thia], [212; 5-OEt-4-Thia], [213; 5-OCF3-4-Thia], [214; 5-OCHF2-4-Thia], [215; 5-CN-4-Thia], [216; 5-SMe-4-Thia], [217; 5-SEt-4-Thia], [218; 5-cPr-4-Thia], [219; 2-F-5-F-4-Thia], [220; 2-F-5-Cl-4-Thia], [221; 2-F-5-Br-4-Thia], [222; 2-F-5-I-4-Thia], [223; 2-F-5-Me-4-Thia], [224; 2-F-5-Et-4-Thia], [225; 2-F-5-Pr-4-Thia], [226; 2-F-5-iPr-4-Thia], [227; 2-F-5-CF3-4-Thia], [228; 2-F-5-CHF2-4-Thia], [229; 2-F-5-OMe-4-Thia], [230; 2-F-5-OEt-4-Thia], [231; 2-F-5-OCF3-4-Thia], [232; 2-F-5-OCHF2-4-Thia], [233; 2-F-5-CN-4-Thia], [234; 2-F-5-SMe-4-Thia], [235; 2-F-5-SEt-4-Thia], [236; 2-F-5-cPr-4-Thia], [237; 2-Cl-5-F-4-Thia], [238; 2-Cl-5-Cl-4-Thia], [239; 2-Cl-5-Br-4-Thia], [240; 2-Cl-5-I-4-Thia], [241; 2-Cl-5-Me-4-Thia], [242; 2-Cl-5-Et-4-Thia], [243; 2-Cl-5-Pr-4-Thia], [244; 2-Cl-5-iPr-4-Thia], [245; 2-Cl-5-CF3-4-Thia], [246; 2-Cl-5-CHF2-4-Thia], [247; 2-Cl-5-OMe-4-Thia], [248; 2-Cl-5-OEt-4-Thia], [249; 2-Cl-5-OCF3-4-Thia], [250; 2-Cl-5-OCHF2-4-Thia], [251; 2-Cl-5-CN-4-Thia], [252; 2-Cl-5-SMe-4-Thia], [253; 2-Cl-5-SEt-4-Thia], [254; 2-Cl-5-cPr-4-Thia], [255; 2-Me-5-F-4-Thia], [256; 2-Me-5-Cl-4-Thia], [257; 2-Me-5-Br-4-Thia], [258; 2-Me-5-I-4-Thia], [259; 2-Me-5-Me-4-Thia], [260; 2-Me-5-Et-4-Thia], [261; 2-Me-5-Pr-4-Thia], [262; 2-Me-5-iPr-4-Thia], [263; 2-Me-5-CF3-4-Thia], [264; 2-Me-5-CHF2-4-Thia], [265; 2-Me-5-OMe-4-Thia], [266; 2-Me-5-OEt-4-Thia], [267; 2-Me-5-OCF3-4-Thia], [268; 2-Me-5-OCHF2-4-Thia], [269; 2-Me-5-CN-4-Thia], [270; 2-Me-5-SMe-4-Thia], [271; 2-Me-5-SEt-4-Thia], [272; 2-Me-5-cPr-4-Thia], [273; 2-Et-5-F-4-Thia], [274; 2-Et-5-Cl-4-Thia], [275; 2-Et-5-Br-4-Thia], [276; 2-Et-5-I-4-Thia], [277; 2-Et-5-Me-4-Thia], [278; 2-Et-5-Et-4-Thia], [279; 2-Et-5-Pr-4-Thia], [280; 2-Et-5-iPr-4-Thia], [281; 2-Et-5-CF3-4-Thia], [282; 2-Et-5-CHF2-4-Thia], [283; 2-Et-5-OMe-4-Thia], [284; 2-Et-5-OEt-4-Thia], [285; 2-Et-5-OCF3-4-Thia], [286; 2-Et-5-OCHF2-4-Thia], [287; 2-Et-5-CN-4-Thia], [288; 2-Et-5-SMe-4-Thia], [289; 2-Et-5-SEt-4-Thia], [290; 2-Et-5-cPr-4-Thia], [291; 2-CF3-5-F-4-Thia], [292; 2-CF3-5-Cl-4-Thia], [293; 2-CF3-5-Br-4-Thia], [294; 2-CF3-5-I-4-Thia], [295; 2-CF3-5-Me-4-Thia], [296; 2-CF3-5-Et-4-Thia], [297; 2-CF3-5-Pr-4-Thia], [298; 2-CF3-5-iPr-4-Thia], [299; 2-CF3-5-CF3-4-Thia], [300; 2-CF3-5-CHF2-4-Thia],

[301; 2-CF3-5-OMe-4-Thia], [302; 2-CF3-5-OEt-4-Thia], [303; 2-CF3-5-OCF3-4-Thia], [304; 2-CF3-5-OCHF2-4-Thia], [305; 2-CF3-5-CN-4-Thia], [306; 2-CF3-5-SMe-4-Thia], [307; 2-CF3-5-SEt-4-Thia], [308; 2-CF3-5-cPr-4-Thia], [309; 2-OMe-5-F-4-Thia], [310; 2-OMe-5-Cl-4-Thia], [311; 2-OMe-5-Br-4-Thia], [312; 2-OMe-5-I-4-Thia], [313; 2-OMe-5-Me-4-Thia], [314; 2-OMe-5-Et-4-Thia], [315; 2-OMe-5-Pr-4-Thia], [316; 2-OMe-5-iPr-4-Thia], [317; 2-OMe-5-CF3-4-Thia], [318; 2-OMe-5-CHF2-4-Thia], [319; 2-OMe-5-OMe-4-Thia], [320; 2-OMe-5-OEt-4-Thia], [321; 2-OMe-5-OCF3-4-Thia], [322; 2-OMe-5-OCHF2-4-Thia], [323; 2-OMe-5-CN-4-Thia], [324; 2-OMe-5-SMe-4-Thia], [325; 2-OMe-5-SEt-4-Thia], [326; 2-OMe-5-cPr-4-Thia], [327; 2-OEt-5-F-4-Thia], [328; 2-OEt-5-Cl-4-Thia], [329; 2-OEt-5-Br-4-Thia], [330; 2-OEt-5-I-4-Thia], [331; 2-OEt-5-Me-4-Thia], [332; 2-OEt-5-Et-4-Thia], [333; 2-OEt-5-Pr-4-Thia], [334; 2-OEt-5-iPr-4-Thia], [335; 2-OEt-5-CF3-4-Thia], [336; 2-OEt-5-CHF2-4-Thia], [337; 2-OEt-5-OMe-4-Thia], [338; 2-OEt-5-OEt-4-Thia], [339; 2-OEt-5-OCF3-4-Thia], [340; 2-OEt-5-OCHF2-4-Thia], [341; 2-OEt-5-CN-4-Thia], [342; 2-OEt-5-SMe-4-Thia], [343; 2-OEt-5-SEt-4-Thia], [344; 2-OEt-5-cPr-4-Thia], [345; 2-SMe-5-F-4-Thia], [346; 2-SMe-5-Cl-4-Thia], [347; 2-SMe-5-Br-4-Thia], [348; 2-SMe-5-I-4-Thia], [349; 2-SMe-5-Me-4-Thia], [350; 2-SMe-5-Et-4-Thia], [351; 2-SMe-5-Pr-4-Thia], [352; 2-SMe-5-iPr-4-Thia], [353; 2-SMe-5-CF3-4-Thia], [354; 2-SMe-5-CHF2-4-Thia], [355; 2-SMe-5-OMe-4-Thia], [356; 2-SMe-5-OEt-4-Thia], [357; 2-SMe-5-OCF3-4-Thia], [358; 2-SMe-5-OCHF2-4-Thia], [359; 2-SMe-5-CN-4-Thia], [360; 2-SMe-5-SMe-4-Thia], [361; 2-SMe-5-SEt-4-Thia], [362; 2-SMe-5-cPr-4-Thia], [363; -5-Thia], [364; 2-F-5-Thia], [365; 2-Cl-5-Thia], [366; 2-Br-5-Thia], [367; 2-I-5-Thia], [368; 2-Me-5-Thia], [369; 2-Et-5-Thia], [370; 2-Pr-5-Thia], [371; 2-iPr-5-Thia], [372; 2-CF3-5-Thia], [373; 2-CHF2-5-Thia], [374; 2-OMe-5-Thia], [375; 2-OEt-5-Thia], [376; 2-OCF3-5-Thia], [377; 2-OCHF2-5-Thia], [378; 2-CN-5-Thia], [379; 2-SMe-5-Thia], [380; 2-SEt-5-Thia], [381; 2-cPr-5-Thia], [382; 4-F-5-Thia], [383; 4-Cl-5-Thia], [384; 4-Br-5-Thia], [385; 4-I-5-Thia], [386; 4-Me-5-Thia], [387; 4-Et-5-Thia], [388; 4-Pr-5-Thia], [389; 4-iPr-5-Thia], [390; 4-CF3-5-Thia], [391; 4-CHF2-5-Thia], [392; 4-OMe-5-Thia], [393; 4-OEt-5-Thia], [394; 4-OCF3-5-Thia], [395; 4-OCHF2-5-Thia], [396; 4-CN-5-Thia], [397; 4-SMe-5-Thia], [398; 4-SEt-5-Thia], [399; 4-cPr-5-Thia], [400; 2-F-4-F-5-Thia],

[401; 2-F-4-Cl-5-Thia], [402; 2-F-4-Br-5-Thia], [403; 2-F-4-I-5-Thia], [404; 2-F-4-Me-5-Thia], [405; 2-F-4-Et-5-Thia], [406; 2-F-4-Pr-5-Thia], [407; 2-F-4-iPr-5-Thia], [408; 2-F-4-CF3-5-Thia], [409; 2-F-4-CHF2-5-Thia], [410; 2-F-4-OMe-5-Thia], [411; 2-F-4-OEt-5-Thia], [412; 2-F-4-OCF3-5-Thia], [413; 2-F-4-OCHF2-5-Thia], [414; 2-F-4-

CN-5-Thia], [415; 2-F-4-SMe-5-Thia], [416; 2-F-4-SEt-5-Thia], [417; 2-F-4-cPr-5-Thia], [418; 2-Cl-4-F-5-Thia], [419; 2-Cl-4-Cl-5-Thia], [420; 2-Cl-4-Br-5-Thia], [421; 2-Cl-4-I-5-Thia], [422; 2-Cl-4-Me-5-Thia], [423; 2-Cl-4-Et-5-Thia], [424; 2-Cl-4-Pr-5-Thia], [425; 2-Cl-4-iPr-5-Thia], [426; 2-Cl-4-CF3-5-Thia], [427; 2-Cl-4-CHF2-5-Thia], [428; 2-Cl-4-OMe-5-Thia], [429; 2-Cl-4-OEt-5-Thia], [430; 2-Cl-4-OCF3-5-Thia], [431; 2-Cl-4-OCHF2-5-Thia], [432; 2-Cl-4-CN-5-Thia], [433; 2-Cl-4-SMe-5-Thia], [434; 2-Cl-4-SEt-5-Thia], [435; 2-Cl-4-cPr-5-Thia], [436; 2-Me-4-F-5-Thia], [437; 2-Me-4-Cl-5-Thia], [438; 2-Me-4-Br-5-Thia], [439; 2-Me-4-I-5-Thia], [440; 2-Me-4-Me-5-Thia], [441; 2-Me-4-Et-5-Thia], [442; 2-Me-4-Pr-5-Thia], [443; 2-Me-4-iPr-5-Thia], [444; 2-Me-4-CF3-5-Thia], [445; 2-Me-4-CHF2-5-Thia], [446; 2-Me-4-OMe-5-Thia], [447; 2-Me-4-OEt-5-Thia], [448; 2-Me-4-OCF3-5-Thia], [449; 2-Me-4-OCHF2-5-Thia], [450; 2-Me-4-CN-5-Thia], [451; 2-Me-4-SMe-5-Thia], [452; 2-Me-4-SEt-5-Thia], [453; 2-Me-4-cPr-5-Thia], [454; 2-Et-4-F-5-Thia], [455; 2-Et-4-Cl-5-Thia], [456; 2-Et-4-Br-5-Thia], [457; 2-Et-4-I-5-Thia], [458; 2-Et-4-Me-5-Thia], [459; 2-Et-4-Et-5-Thia], [460; 2-Et-4-Pr-5-Thia], [461; 2-Et-4-iPr-5-Thia], [462; 2-Et-4-CF3-5-Thia], [463; 2-Et-4-CHF2-5-Thia], [464; 2-Et-4-OMe-5-Thia], [465; 2-Et-4-OEt-5-Thia], [466; 2-Et-4-OCF3-5-Thia], [467; 2-Et-4-OCHF2-5-Thia], [468; 2-Et-4-CN-5-Thia], [469; 2-Et-4-SMe-5-Thia], [470; 2-Et-4-SEt-5-Thia], [471; 2-Et-4-cPr-5-Thia], [472; 2-CF3-4-F-5-Thia], [473; 2-CF3-4-Cl-5-Thia], [474; 2-CF3-4-Br-5-Thia], [475; 2-CF3-4-I-5-Thia], [476; 2-CF3-4-Me-5-Thia], [477; 2-CF3-4-Et-5-Thia], [478; 2-CF3-4-Pr-5-Thia], [479; 2-CF3-4-iPr-5-Thia], [480; 2-CF3-4-CF3-5-Thia], [481; 2-CF3-4-CHF2-5-Thia], [482; 2-CF3-4-OMe-5-Thia], [483; 2-CF3-4-OEt-5-Thia], [484; 2-CF3-4-OCF3-5-Thia], [485; 2-CF3-4-OCHF2-5-Thia], [486; 2-CF3-4-OCHF2-5-Thia], [486; 2-CF3-4-CN-5-Thia], [487; 2-CF3-4-SMe-5-Thia], [488; 2-CF3-4-SEt-5-Thia], [489; 2-CF3-4-cPr-5-Thia], [490; 2-OMe-4-F-5-Thia], [491; 2-OMe-4-Cl-5-Thia], [492; 2-OMe-4-Br-5-Thia], [493; 2-OMe-4-I-5-Thia], [494; 2-OMe-4-Me-5-Thia], [495; 2-OMe-4-Et-5-Thia], [496; 2-OMe-4-Pr-5-Thia], [497; 2-OMe-4-iPr-5-Thia], [498; 2-OMe-4-CF3-5-Thia], [499; 2-OMe-4-CHF2-5-Thia], [500; 2-OMe-4-OMe-5-Thia],

[501; 2-OMe-4-OEt-5-Thia], [502; 2-OMe-4-OCF3-5-Thia], [503; 2-OMe-4-OCHF2-5-Thia], [504; 2-OMe-4-CN-5-Thia], [505; 2-OMe-4-SMe-5-Thia], [506; 2-OMe-4-SEt-5-Thia], [507; 2-OMe-4-cPr-5-Thia], [508; 2-OEt-4-F-5-Thia], [509; 2-OEt-4-Cl-5-Thia], [510; 2-OEt-4-Br-5-Thia], [511; 2-OEt-4-I-5-Thia], [512; 2-OEt-4-Me-5-Thia], [513; 2-OEt-4-Et-5-Thia], [514; 2-OEt-4-Pr-5-Thia], [515; 2-OEt-4-iPr-5-Thia], [516; 2-OEt-4-CF3-5-Thia], [517; 2-OEt-4-CHF2-5-Thia], [518; 2-OEt-4-OMe-5-Thia], [519; 2-OEt-4-OEt-5-Thia], [520; 2-OEt-4-OCF3-5-Thia], [521; 2-OEt-4-OCHF2-5-Thia], [522; 2-OEt-4-CN-5-Thia], [523; 2-OEt-4-SMe-5-Thia], [524; 2-OEt-4-SEt-5-Thia], [525; 2-OEt-4-cPr-5-Thia], [526; 2-SMe-4-F-5-Thia], [527; 2-SMe-4-Cl-5-Thia], [528; 2-SMe-4-Br-5-Thia], [529; 2-SMe-4-I-5-Thia], [530; 2-SMe-4-Me-5-Thia], [531; 2-SMe-4-Et-5-Thia], [532; 2-SMe-4-Pr-5-Thia], [533; 2-SMe-4-iPr-5-Thia], [534; 2-SMe-4-CF3-5-Thia], [535; 2-SMe-4-CHF2-5-Thia], [536; 2-SMe-4-OMe-5-Thia], [537; 2-SMe-4-OEt-5-Thia], [538; 2-SMe-4-OCF3-5-Thia], [539; 2-SMe-4-OCHF2-5-Thia], [540; 2-SMe-4-CN-5-Thia], [541; 2-SMe-4-SMe-5-Thia], [542; 2-SMe-4-SEt-5-Thia], [543; 2-SMe-4-cPr-5-Thia], [544; 2-Ox], [545; 4-F-2-Ox], [546; 4-Cl-2-Ox], [547; 4-Br-2-Ox], [548; 4-I-2-Ox], [549; 4-Me-2-Ox], [550; 4-Et-2-Ox], [551; 4-Pr-2-Ox], [552; 4-iPr-2-Ox], [553; 4-CF3-2-Ox], [554; 4-CHF2-2-Ox], [555; 4-OMe-2-Ox], [556; 4-OEt-2-Ox], [557; 4-OCF3-2-Ox], [558; 4-OCHF2-2-Ox], [559; 4-CN-2-Ox], [560; 4-SMe-2-Ox], [561; 4-SEt-2-Ox], [562; 4-cPr-2-Ox], [563; 5-F-2-Ox], [564; 5-Cl-2-Ox], [565; 5-Br-2-Ox], [566; 5-I-2-Ox], [567; 5-Me-2-Ox], [568; 5-Et-2-Ox], [569; 5-Pr-2-Ox], [570; 5-iPr-2-Ox], [571; 5-CF3-2-Ox], [572; 5-CHF2-2-Ox], [573; 5-OMe-2-Ox], [574; 5-OEt-2-Ox], [575; 5-OCF3-2-Ox], [576; 5-OCHF2-2-Ox], [577; 5-CN-2-Ox], [578; 5-SMe-2-Ox], [579; 5-SEt-2-Ox], [580; 5-cPr-2-Ox], [581; 4-F-5-F-2-Ox], [582; 4-F-5-Cl-2-Ox], [583; 4-F-5-Br-2-Ox], [584; 4-F-5-I-2-Ox], [585; 4-F-5-Me-2-Ox], [586; 4-F-5-Et-2-Ox], [587; 4-F-5-Pr-2-Ox], [588; 4-F-5-iPr-2-Ox], [589; 4-F-5-CF3-2-Ox], [590; 4-F-5-CHF2-2-Ox], [591; 4-F-5-OMe-2-Ox], [592; 4-F-5-OEt-2-Ox], [593; 4-F-5-OCF3-2-Ox], [594; 4-F-5-OCHF2-2-Ox], [595; 4-F-5-CN-2-Ox], [596; 4-F-5-SMe-2-Ox], [597; 4-F-5-SEt-2-Ox], [598; 4-F-5-cPr-2-Ox], [599; 4-Cl-5-F-2-Ox], [600; 4-Cl-5-Cl-2-Ox],

[601; 4-Cl-5-Br-2-Ox], [602; 4-Cl-5-I-2-Ox], [603; 4-Cl-5-Me-2-Ox], [604; 4-Cl-5-Et-2-Ox], [605; 4-Cl-5-Pr-2-Ox], [606; 4-Cl-5-iPr-2-Ox], [607; 4-Cl-5-CF3-2-Ox], [608; 4-Cl-5-CHF2-2-Ox], [609; 4-Cl-5-OMe-2-Ox], [610; 4-Cl-5-OEt-2-Ox], [611; 4-Cl-5-OCF3-2-Ox], [612; 4-Cl-5-OCHF2-2-Ox], [613; 4-Cl-5-CN-2-Ox], [614; 4-Cl-5-SMe-2-Ox], [615; 4-Cl-5-SEt-2-Ox], [616; 4-Cl-5-cPr-2-Ox], [617; 4-Me-5-F-2-Ox], [618; 4-Me-5-Cl-2-Ox], [619; 4-Me-5-Br-2-Ox], [620; 4-Me-5-I-2-Ox], [621; 4-Me-5-Me-2-Ox], [622; 4-Me-5-Et-2-Ox], [623; 4-Me-5-Pr-2-Ox], [624; 4-Me-5-iPr-2-Ox], [625; 4-Me-5-CF3-2-Ox], [626; 4-Me-5-CHF2-2-Ox], [627; 4-Me-5-OMe-2-Ox], [628; 4-Me-5-OEt-2-Ox], [629; 4-Me-5-OCF3-2-Ox], [630; 4-Me-5-OCHF2-2-Ox], [631; 4-Me-5-CN-2-Ox], [632; 4-Me-5-SMe-2-Ox], [633; 4-Me-5-SEt-2-Ox], [634; 4-Me-5-cPr-2-Ox], [635; 4-Et-5-F-2-Ox], [636; 4-Et-5-Cl-2-Ox], [637; 4-Et-5-Br-2-Ox], [638; 4-Et-5-I-2-Ox], [639; 4-Et-5-Me-2-Ox], [640; 4-Et-5-Et-2-Ox], [641; 4-Et-5-Pr-2-Ox], [642; 4-Et-5-iPr-2-Ox], [643; 4-Et-5-CF3-2-Ox], [644; 4-Et-5-CHF2-2-Ox], [645; 4-Et-5-OMe-2-Ox], [646; 4-Et-5-OEt-2-Ox], [647; 4-Et-5-OCF3-2-Ox], [648; 4-Et-5-OCHF2-2-Ox], [649; 4-Et-5-CN-2-Ox], [650; 4-Et-5-SMe-2-Ox], [651; 4-Et-5-SEt-2-Ox], [652; 4-Et-5-cPr-2-Ox], [653; 4-CF3-5-F-2-Ox], [654; 4-CF3-5-Cl-2-Ox], [655; 4-CF3-5-Br-2-Ox], [656; 4-CF3-5-I-2-Ox], [657; 4-CF3-5-Me-2-Ox], [658; 4-CF3-5-Et-2-Ox], [659; 4-CF3-5-Pr-2-Ox], [660; 4-CF3-5-iPr-2-Ox], [661; 4-CF3-5-CF3-2-Ox], [662; 4-CF3-5-CHF2-2-Ox], [663; 4-CF3-5-OMe-2-Ox], [664; 4-CF3-5-OEt-2-Ox], [665; 4-CF3-5-OCF3-2-Ox], [666; 4-CF3-5-OCHF2-2-Ox], [667; 4-CF3-5-CN-2-Ox], [668; 4-CF3-5-SMe-2-Ox], [669; 4-CF3-5-SEt-2-Ox], [670; 4-CF3-5-cPr-2-Ox], [671; 4-OMe-5-F-2-Ox], [672; 4-OMe-5-Cl-2-Ox], [673; 4-OMe-5-Br-2-Ox], [674; 4-OMe-5-I-2-Ox], [675; 4-OMe-5-Me-2-Ox], [676; 4-OMe-5-Et-2-Ox], [677; 4-OMe-5-Pr-2-Ox], [678; 4-OMe-5-iPr-2-Ox], [679; 4-OMe-5-CF3-2-Ox], [680; 4-OMe-5-CHF2-2-Ox], [681; 4-OMe-5-OMe-2-Ox], [682; 4-OMe-5-OEt-2-Ox], [683; 4-OMe-5-OCF3-2-Ox], [684; 4-OMe-5-OCHF2-2-Ox], [685; 4-OMe-5-CN-2-Ox], [686; 4-OMe-5-SMe-2-Ox], [687; 4-OMe-5-SEt-2-Ox], [688; 4-OMe-5-cPr-2-Ox], [689; 4-OEt-5-F-2-Ox], [690; 4-OEt-5-Cl-2-Ox], [691; 4-OEt-5-Br-2-Ox], [692; 4-OEt-5-I-2-Ox], [693; 4-OEt-5-Me-2-Ox], [694; 4-OEt-5-Et-2-Ox], [695; 4-OEt-5-Pr-2-Ox], [696; 4-OEt-5-iPr-2-Ox], [697; 4-OEt-5-CF3-2-Ox], [698; 4-OEt-5-CHF2-2-Ox], [699; 4-OEt-5-OMe-2-Ox], [700; 4-OEt-5-OEt-2-Ox],

[701; 4-OEt-5-OCF3-2-Ox], [702; 4-OEt-5-OCHF2-2-Ox], [703; 4-OEt-5-CN-2-Ox], [704; 4-OEt-5-SMe-2-Ox], [705; 4-OEt-5-SEt-2-Ox], [706; 4-OEt-5-cPr-2-Ox], [707;

4-SMe-5-F-2-Ox], [708; 4-SMe-5-Cl-2-Ox], [709; 4-SMe-5-Br-2-Ox], [710; 4-SMe-5-I-2-Ox], [711; 4-SMe-5-Me-2-Ox], [712; 4-SMe-5-Et-2-Ox], [713; 4-SMe-5-Pr-2-Ox], [714; 4-SMe-5-iPr-2-Ox], [715; 4-SMe-5-CF3-2-Ox], [716; 4-SMe-5-CHF2-2-Ox], [717; 4-SMe-5-OMe-2-Ox], [718; 4-SMe-5-OEt-2-Ox], [719; 4-SMe-5-OCF3-2-Ox], [720; 4-SMe-5-OCHF2-2-Ox], [721; 4-SMe-5-CN-2-Ox], [722; 4-SMe-5-SMe-2-Ox], [723; 4-SMe-5-SEt-2-Ox], [724; 4-SMe-5-cPr-2-Ox], [725; -4-Ox], [726; 2-F-4-Ox], [727; 2-Cl-4-Ox], [728; 2-Br-4-Ox], [729; 2-I-4-Ox], [730; 2-Me-4-Ox], [731; 2-Et-4-Ox], [732; 2-Pr-4-Ox], [733; 2-iPr-4-Ox], [734; 2-CF3-4-Ox], [735; 2-CHF2-4-Ox], [736; 2-OMe-4-Ox], [737; 2-OEt-4-Ox], [738; 2-OCF3-4-Ox], [739; 2-OCHF2-4-Ox], [740; 2-CN-4-Ox], [741; 2-SMe-4-Ox], [742; 2-SEt-4-Ox], [743; 2-cPr-4-Ox], [744; 5-F-4-Ox], [745; 5-Cl-4-Ox], [746; 5-Br-4-Ox], [747; 5-I-4-Ox], [748; 5-Me-4-Ox], [749; 5-Et-4-Ox], [750; 5-Pr-4-Ox], [751; 5-iPr-4-Ox], [752; 5-CF3-4-Ox], [753; 5-CHF2-4-Ox], [754; 5-OMe-4-Ox], [755; 5-OEt-4-Ox], [756; 5-OCF3-4-Ox], [757; 5-OCHF2-4-Ox], [758; 5-CN-4-Ox], [759; 5-SMe-4-Ox], [760; 5-SEt-4-Ox], [761; 5-cPr-4-Ox], [762; 2-F-5-F-4-Ox], [763; 2-F-5-Cl-4-Ox], [764; 2-F-5-Br-4-Ox], [765; 2-F-5-I-4-Ox], [766; 2-F-5-Me-4-Ox], [767; 2-F-5-Et-4-Ox], [768; 2-F-5-Pr-4-Ox], [769; 2-F-5-iPr-4-Ox], [770; 2-F-5-CF3-4-Ox], [771; 2-F-5-CHF2-4-Ox], [772; 2-F-5-OMe-4-Ox], [773; 2-F-5-OEt-4-Ox], [774; 2-F-5-OCF3-4-Ox], [775; 2-F-5-OCHF2-4-Ox], [776; 2-F-5-CN-4-Ox], [777; 2-F-5-SMe-4-Ox], [778; 2-F-5-SEt-4-Ox], [779; 2-F-5-cPr-4-Ox], [780; 2-Cl-5-F-4-Ox], [781; 2-Cl-5-Cl-4-Ox], [782; 2-Cl-5-Br-4-Ox], [783; 2-Cl-5-I-4-Ox], [784; 2-Cl-5-Me-4-Ox], [785; 2-Cl-5-Et-4-Ox], [786; 2-Cl-5-Pr-4-Ox], [787; 2-Cl-5-iPr-4-Ox], [788; 2-Cl-5-CF3-4-Ox], [789; 2-Cl-5-CHF2-4-Ox], [790; 2-Cl-5-OMe-4-Ox], [791; 2-Cl-5-OEt-4-Ox], [792; 2-Cl-5-OCF3-4-Ox], [793; 2-Cl-5-OCHF2-4-Ox], [794; 2-Cl-5-CN-4-Ox], [795; 2-Cl-5-SMe-4-Ox], [796; 2-Cl-5-SEt-4-Ox], [797; 2-Cl-5-cPr-4-Ox], [798; 2-Me-5-F-4-Ox], [799; 2-Me-5-Cl-4-Ox], [800; 2-Me-5-Br-4-Ox],

[801; 2-Me-5-I-4-Ox], [802; 2-Me-5-Me-4-Ox], [803; 2-Me-5-Et-4-Ox], [804; 2-Me-5-Pr-4-Ox], [805; 2-Me-5-iPr-4-Ox], [806; 2-Me-5-CF3-4-Ox], [807; 2-Me-5-CHF2-4-Ox], [808; 2-Me-5-OMe-4-Ox], [809; 2-Me-5-OEt-4-Ox], [810; 2-Me-5-OCF3-4-Ox], [811; 2-Me-5-OCHF2-4-Ox], [812; 2-Me-5-CN-4-Ox], [813; 2-Me-5-SMe-4-Ox], [814; 2-Me-5-SEt-4-Ox], [815; 2-Me-5-cPr-4-Ox], [816; 2-Et-5-F-4-Ox], [817; 2-Et-5-Cl-4-Ox], [818; 2-Et-5-Br-4-Ox], [819; 2-Et-5-I-4-Ox], [820; 2-Et-5-Me-4-Ox], [821; 2-Et-5-Et-4-Ox], [822; 2-Et-5-Pr-4-Ox], [823; 2-Et-5-iPr-4-Ox], [824; 2-Et-5-CF3-4-Ox], [825; 2-Et-5-CHF2-4-Ox], [826; 2-Et-5-OMe-4-Ox], [827; 2-Et-5-OEt-4-Ox], [828; 2-Et-5-OCF3-4-Ox], [829; 2-Et-5-OCHF2-4-Ox], [830; 2-Et-5-CN-4-Ox], [831; 2-Et-5-SMe-4-Ox], [832; 2-Et-5-SEt-4-Ox], [833; 2-Et-5-cPr-4-Ox], [834; 2-CF3-5-F-4-Ox], [835; 2-CF3-5-Cl-4-Ox], [836; 2-CF3-5-Br-4-Ox], [837; 2-CF3-5-I-4-Ox], [838; 2-CF3-5-Me-4-Ox], [839; 2-CF3-5-Et-4-Ox], [840; 2-CF3-5-Pr-4-Ox], [841; 2-CF3-5-iPr-4-Ox], [842; 2-CF3-5-CF3-4-Ox], [843; 2-CF3-5-CHF2-4-Ox], [844; 2-CF3-5-OMe-4-Ox], [845; 2-CF3-5-OEt-4-Ox], [846; 2-CF3-5-OCF3-4-Ox], [847; 2-CF3-5-OCHF2-4-Ox], [848; 2-CF3-5-CN-4-Ox], [849; 2-CF3-5-SMe-4-Ox], [850; 2-CF3-5-SEt-4-Ox], [851; 2-CF3-5-cPr-4-Ox], [852; 2-OMe-5-F-4-Ox], [853; 2-OMe-5-Cl-4-Ox], [854; 2-OMe-5-Br-4-Ox], [855; 2-OMe-5-I-4-Ox], [856; 2-OMe-5-Me-4-Ox], [857; 2-OMe-5-Et-4-Ox], [858; 2-OMe-5-Pr-4-Ox], [859; 2-OMe-5-iPr-4-Ox], [860; 2-OMe-5-CF3-4-Ox], [861; 2-OMe-5-CHF2-4-Ox], [862; 2-OMe-5-OMe-4-Ox], [863; 2-OMe-5-OEt-4-Ox], [864; 2-OMe-5-OCF3-4-Ox], [865; 2-OMe-5-OCHF2-4-Ox], [866; 2-OMe-5-CN-4-Ox], [867; 2-OMe-5-SMe-4-Ox], [868; 2-OMe-5-SEt-4-Ox], [869; 2-OMe-5-cPr-4-Ox], [870; 2-OEt-5-F-4-Ox], [871; 2-OEt-5-Cl-4-Ox], [872; 2-OEt-5-Br-4-Ox], [873; 2-OEt-5-I-4-Ox], [874; 2-OEt-5-Me-4-Ox], [875; 2-OEt-5-Et-4-Ox], [876; 2-OEt-5-Pr-4-Ox], [877; 2-OEt-5-iPr-4-Ox], [878; 2-OEt-5-CF3-4-Ox], [879; 2-OEt-5-CHF2-4-Ox], [880; 2-OEt-5-OMe-4-Ox], [881; 2-OEt-5-OEt-4-Ox], [882; 2-OEt-5-OCF3-4-Ox], [883; 2-OEt-5-OCHF2-4-Ox], [884; 2-OEt-5-CN-4-Ox], [885; 2-OEt-5-SMe-4-Ox], [886; 2-OEt-5-SEt-4-Ox], [887; 2-OEt-5-cPr-4-Ox], [888; 2-SMe-5-F-4-Ox], [889; 2-SMe-5-Cl-4-Ox], [890; 2-SMe-5-Br-4-Ox], [891; 2-SMe-5-I-4-Ox], [892; 2-SMe-5-Me-4-Ox], [893; 2-SMe-5-Et-4-Ox], [894; 2-SMe-5-Pr-4-Ox], [895; 2-SMe-5-iPr-4-Ox], [896; 2-SMe-5-CF3-4-Ox], [897; 2-SMe-5-CHF2-4-Ox], [898; 2-SMe-5-OMe-4-Ox], [899; 2-SMe-5-OEt-4-Ox], [900; 2-SMe-5-OCF3-4-Ox],

[901; 2-SMe-5-OCHF2-4-Ox], [902; 2-SMe-5-CN-4-Ox], [903; 2-SMe-5-SMe-4-Ox], [904; 2-SMe-5-SEt-4-Ox], [905; 2-SMe-5-cPr-4-Ox], [906; -5-Ox], [907; 2-F-5-Ox], [908; 2-Cl-5-Ox], [909; 2-Br-5-Ox], [910; 2-I-5-Ox], [911; 2-Me-5-Ox], [912; 2-Et-5-Ox], [913; 2-Pr-5-Ox], [914; 2-iPr-5-Ox], [915; 2-CF3-5-Ox], [916; 2-CHF2-5-Ox], [917; 2-OMe-5-Ox], [918; 2-OEt-5-Ox], [919; 2-OCF3-5-Ox], [920; 2-OCHF2-5-Ox], [921; 2-CN-5-Ox], [922; 2-SMe-5-Ox], [923; 2-SEt-5-Ox], [924; 2-cPr-5-Ox], [925; 4-F-5-Ox], [926; 4-Cl-5-Ox], [927; 4-Br-5-Ox], [928; 4-I-5-Ox], [929; 4-Me-5-Ox], [930; 4-Et-5-Ox], [931; 4-Pr-5-Ox], [932; 4-iPr-5-Ox], [933; 4-CF3-5-Ox], [934; 4-CHF2-5-Ox], [935; 4-OMe-5-Ox], [936; 4-OEt-5-Ox], [937; 4-OCF3-5-Ox], [938; 4-OCHF2-5-Ox], [939; 4-CN-5-Ox], [940; 4-SMe-5-Ox], [941; 4-SEt-5-Ox], [942; 4-cPr-5-Ox], [943; 2-F-4-F-5-Ox], [944; 2-F-4-Cl-5-Ox], [945; 2-F-4-Br-5-Ox], [946; 2-F-4-I-5-Ox], [947; 2-F-4-Me-5-Ox], [948; 2-F-4-Et-5-Ox], [949; 2-F-4-Pr-5-Ox], [950; 2-F-4-iPr-5-Ox], [951; 2-F-4-CF3-5-Ox], [952; 2-F-4-CHF2-5-Ox], [953; 2-F-4-OMe-5-Ox], [954; 2-F-4-OEt-5-Ox], [955; 2-F-4-OCF3-5-Ox], [956; 2-F-4-OCHF2-5-Ox], [957; 2-F-4-CN-5-Ox], [958; 2-F-4-SMe-5-Ox], [959; 2-F-4-SEt-5-Ox], [960; 2-F-4-cPr-5-Ox], [961; 2-Cl-4-F-5-Ox], [962; 2-Cl-4-Cl-5-Ox], [963; 2-Cl-4-Br-5-Ox], [964; 2-Cl-4-I-5-Ox], [965; 2-Cl-4-Me-5-Ox], [966; 2-Cl-4-Et-5-Ox], [967; 2-Cl-4-Pr-5-Ox], [968; 2-Cl-4-iPr-5-Ox], [969; 2-Cl-4-CF3-5-Ox], [970; 2-Cl-4-CHF2-5-Ox], [971; 2-Cl-4-OMe-5-Ox], [972; 2-Cl-4-OEt-5-Ox], [973; 2-Cl-4-OCF3-5-Ox], [974; 2-Cl-4-OCHF2-5-Ox], [975; 2-Cl-4-CN-5-Ox], [976; 2-Cl-4-SMe-5-Ox], [977; 2-Cl-4-SEt-5-Ox], [978; 2-Cl-4-cPr-5-Ox], [979; 2-Me-4-F-5-Ox], [980; 2-Me-4-Cl-5-Ox], [981; 2-Me-4-Br-5-Ox], [982; 2-Me-4-I-5-Ox], [983; 2-Me-4-Me-5-Ox], [984; 2-Me-4-Et-5-Ox], [985; 2-Me-4-Pr-5-Ox], [986; 2-Me-4-iPr-5-Ox], [987; 2-Me-4-CF3-5-Ox], [988; 2-Me-4-CHF2-5-Ox], [989; 2-Me-4-OMe-5-Ox], [990; 2-Me-4-OEt-5-Ox], [991; 2-Me-4-OCF3-5-Ox], [992; 2-Me-4-OCHF2-5-Ox], [993; 2-Me-4-CN-5-Ox], [994; 2-Me-4-SMe-5-Ox], [995; 2-Me-4-SEt-5-Ox], [996; 2-Me-4-cPr-5-Ox], [997; 2-Et-4-F-5-Ox], [998; 2-Et-4-Cl-5-Ox], [999; 2-Et-4-Br-5-Ox], [1000; 2-Et-4-I-5-Ox],

[1001; 2-Et-4-Me-5-Ox], [1002; 2-Et-4-Et-5-Ox], [1003; 2-Et-4-Pr-5-Ox], [1004; 2-Et-4-iPr-5-Ox], [1005; 2-Et-4-CF3-5-Ox], [1006; 2-Et-4-CHF2-5-Ox], [1007; 2-Et-4-OMe-5-Ox], [1008; 2-Et-4-OEt-5-Ox], [1009; 2-Et-4-OCF3-5-Ox], [1010; 2-Et-4-OCHF2-5-Ox], [1011; 2-Et-4-CN-5-Ox], [1012; 2-Et-4-SMe-5-Ox], [1013; 2-Et-4-SEt-5-Ox], [1014; 2-Et-4-cPr-5-Ox], [1015; 2-CF3-4-F-5-Ox], [1016; 2-CF3-4-Cl-5-Ox], [1017; 2-CF3-4-Br-5-Ox], [1018; 2-CF3-4-I-5-Ox], [1019; 2-CF3-4-Me-5-Ox], [1020; 2-CF3-4-Et-5-Ox], [1021; 2-CF3-4-Pr-5-Ox], [1022; 2-CF3-4-iPr-

5-Ox], [1023; 2-CF3-4-CF3-5-Ox], [1024; 2-CF3-4-CHF2-5-Ox], [1025; 2-CF3-4-OMe-5-Ox], [1026; 2-CF3-4-OEt-5-Ox], [1027; 2-CF3-4-OCF3-5-Ox], [1028; 2-CF3-4-OCHF2-5-Ox], [1029; 2-CF3-4-CN-5-Ox], [1030; 2-CF3-4-SMe-5-Ox], [1031; 2-CF3-4-SEt-5-Ox], [1032; 2-CF3-4-cPr-5-Ox], [1033; 2-OMe-4-F-5-Ox], [1034; 2-OMe-4-Cl-5-Ox], [1035; 2-OMe-4-Br-5-Ox], [1036; 2-OMe-4-I-5-Ox], [1037; 2-OMe-4-Me-5-Ox], [1038; 2-OMe-4-Et-5-Ox], [1039; 2-OMe-4-Pr-5-Ox], [1040; 2-OMe-4-iPr-5-Ox], [1041; 2-OMe-4-CF3-5-Ox], [1042; 2-OMe-4-CHF2-5-Ox], [1043; 2-OMe-4-OMe-5-Ox], [1044; 2-OMe-4-OEt-5-Ox], [1045; 2-OMe-4-OCF3-5-Ox], [1046; 2-OMe-4-OCHF2-5-Ox], [1047; 2-OMe-4-CN-5-Ox], [1048; 2-OMe-4-SMe-5-Ox], [1049; 2-OMe-4-SEt-5-Ox], [1050; 2-OMe-4-cPr-5-Ox], [1051; 2-OEt-4-F-5-Ox], [1052; 2-OEt-4-Cl-5-Ox], [1053; 2-OEt-4-Br-5-Ox], [1054; 2-OEt-4-I-5-Ox], [1055; 2-OEt-4-Me-5-Ox], [1056; 2-OEt-4-Et-5-Ox], [1057; 2-OEt-4-Pr-5-Ox], [1058; 2-OEt-4-iPr-5-Ox], [1059; 2-OEt-4-CF3-5-Ox], [1060; 2-OEt-4-CHF2-5-Ox], [1061; 2-OEt-4-OMe-5-Ox], [1062; 2-OEt-4-OEt-5-Ox], [1063; 2-OEt-4-OCF3-5-Ox], [1064; 2-OEt-4-OCHF2-5-Ox], [1065; 2-OEt-4-CN-5-Ox], [1066; 2-OEt-4-SMe-5-Ox], [1067; 2-OEt-4-SEt-5-Ox], [1068; 2-OEt-4-cPr-5-Ox], [1069; 2-SMe-4-F-5-Ox], [1070; 2-SMe-4-Cl-5-Ox], [1071; 2-SMe-4-Br-5-Ox], [1072; 2-SMe-4-I-5-Ox], [1073; 2-SMe-4-Me-5-Ox], [1074; 2-SMe-4-Et-5-Ox], [1075; 2-SMe-4-Pr-5-Ox], [1076; 2-SMe-4-iPr-5-Ox], [1077; 2-SMe-4-CF3-5-Ox], [1078; 2-SMe-4-CHF2-5-Ox], [1079; 2-SMe-4-OMe-5-Ox], [1080; 2-SMe-4-OEt-5-Ox], [1081; 2-SMe-4-OCF3-5-Ox], [1082; 2-SMe-4-OCHF2-5-Ox], [1083; 2-SMe-4-CN-5-Ox], [1084; 2-SMe-4-SMe-5-Ox], [1085; 2-SMe-4-SEt-5-Ox], [1086; 2-SMe-4-cPr-5-Ox], [1197; -2-Fu], [1198; 4-F-2-Fu], [1199; 4-Cl-2-Fu], [1200; 4-Br-2-Fu],

[1201; 4-I-2-Fu], [1202; 4-Me-2-Fu], [1203; 4-Et-2-Fu], [1204; 4-Pr-2-Fu], [1205; 4-iPr-2-Fu], [1206; 4-CF3-2-Fu], [1207; 4-CHF2-2-Fu], [1208; 4-OMe-2-Fu], [1209; 4-OEt-2-Fu], [1210; 4-OCF3-2-Fu], [1211; 4-OCHF2-2-Fu], [1212; 4-CN-2-Fu], [1213; 4-SMe-2-Fu], [1214; 4-SEt-2-Fu], [1215; 4-cPr-2-Fu], [1216; 5-F-2-Fu], [1217; 5-Cl-2-Fu], [1218; 5-Br-2-Fu], [1219; 5-I-2-Fu], [1220; 5-Me-2-Fu], [1221; 5-Et-2-Fu], [1222; 5-Pr-2-Fu], [1223; 5-iPr-2-Fu], [1224; 5-CF3-2-Fu], [1225; 5-CHF2-2-Fu], [1226; 5-OMe-2-Fu], [1227; 5-OEt-2-Fu], [1228; 5-OCF3-2-Fu], [1229; 5-OCHF2-2-Fu], [1230; 5-CN-2-Fu], [1231; 5-SMe-2-Fu], [1232; 5-SEt-2-Fu], [1233; 5-cPr-2-Fu], [1234; 4-F-5-F-2-Fu], [1235; 4-F-5-Cl-2-Fu], [1236; 4-F-5-Br-2-Fu], [1237; 4-F-5-I-2-Fu], [1238; 4-F-5-Me-2-Fu], [1239; 4-F-5-Et-2-Fu], [1240; 4-F-5-Pr-2-Fu], [1241; 4-F-5-iPr-2-Fu], [1242; 4-F-5-CF3-2-Fu], [1243; 4-F-5-CHF2-2-Fu], [1244; 4-F-5-OMe-2-Fu], [1245; 4-F-5-OEt-2-Fu], [1246; 4-F-5-OCF3-2-Fu], [1247; 4-F-5-OCHF2-2-Fu], [1248; 4-F-5-CN-2-Fu], [1249; 4-F-5-SMe-2-Fu], [1250; 4-F-5-SEt-2-Fu], [1251; 4-F-5-cPr-2-Fu], [1252; 4-Cl-5-F-2-Fu], [1253; 4-Cl-5-Cl-2-Fu], [1254; 4-Cl-5-Br-2-Fu], [1255; 4-Cl-5-I-2-Fu], [1256; 4-Cl-5-Me-2-Fu], [1257; 4-Cl-5-Et-2-Fu], [1258; 4-Cl-5-Pr-2-Fu], [1259; 4-Cl-5-iPr-2-Fu], [1260; 4-Cl-5-CF3-2-Fu], [1261; 4-Cl-5-CHF2-2-Fu], [1262; 4-Cl-5-OMe-2-Fu], [1263; 4-Cl-5-OEt-2-Fu], [1264; 4-Cl-5-OCF3-2-Fu], [1265; 4-Cl-5-OCHF2-2-Fu], [1266; 4-Cl-5-CN-2-Fu], [1267; 4-Cl-5-SMe-2-Fu], [1268; 4-Cl-5-SEt-2-Fu], [1269; 4-Cl-5-cPr-2-Fu], [1270; 4-Me-5-F-2-Fu], [1271; 4-Me-5-Cl-2-Fu], [1272; 4-Me-5-Br-2-Fu], [1273; 4-Me-5-I-2-Fu], [1274; 4-Me-5-Me-2-Fu], [1275; 4-Me-5-Et-2-Fu], [1276; 4-Me-5-Pr-2-Fu], [1277; 4-Me-5-iPr-2-Fu], [1278; 4-Me-5-CF3-2-Fu], [1279; 4-Me-5-CHF2-2-Fu], [1280; 4-Me-5-OMe-2-Fu], [1281; 4-Me-5-OEt-2-Fu], [1282; 4-Me-5-OCF3-2-Fu], [1283; 4-Me-5-OCHF2-2-Fu], [1284; 4-Me-5-CN-2-Fu], [1285; 4-Me-5-SMe-2-Fu], [1286; 4-Me-5-SEt-2-Fu], [1287; 4-Me-5-cPr-2-Fu], [1288; 4-Et-5-F-2-Fu], [1289; 4-Et-5-Cl-2-Fu], [1290; 4-Et-5-Br-2-Fu], [1291; 4-Et-5-I-2-Fu], [1292; 4-Et-5-Me-2-Fu], [1293; 4-Et-5-Et-2-Fu], [1294; 4-Et-5-Pr-2-Fu], [1295; 4-Et-5-iPr-2-Fu], [1296; 4-Et-5-CF3-2-Fu], [1297; 4-Et-5-CHF2-2-Fu], [1298; 4-Et-5-OMe-2-Fu], [1299; 4-Et-5-OEt-2-Fu], [1300; 4-Et-5-OCF3-2-Fu],

[1301; 4-Et-5-OCHF2-2-Fu], [1302; 4-Et-5-CN-2-Fu], [1303; 4-Et-5-SMe-2-Fu], [1304; 4-Et-5-SEt-2-Fu], [1305; 4-Et-5-cPr-2-Fu], [1306; 4-CF3-5-F-2-Fu], [1307; 4-CF3-5-Cl-2-Fu], [1308; 4-CF3-5-Br-2-Fu], [1309; 4-CF3-5-I-2-Fu], [1310; 4-CF3-5-Me-2-Fu], [1311; 4-CF3-5-Et-2-Fu], [1312; 4-CF3-5-Pr-2-Fu], [1313; 4-CF3-5-iPr-2-Fu], [1314; 4-CF3-5-CF3-2-Fu], [1315; 4-CF3-5-CHF2-2-Fu], [1316; 4-CF3-5-OMe-2-Fu], [1317; 4-CF3-5-OEt-2-Fu], [1318; 4-CF3-5-OCF3-2-Fu], [1319; 4-CF3-5-OCHF2-2-Fu], [1320; 4-CF3-5-CN-2-Fu], [1321; 4-CF3-5-SMe-2-Fu], [1322; 4-CF3-5-SEt-2-Fu], [1323; 4-CF3-5-cPr-2-Fu], [1324; 4-OMe-5-F-2-Fu], [1325; 4-OMe-5-Cl-2-Fu], [1326; 4-OMe-5-Br-2-Fu], [1327; 4-OMe-5-I-2-Fu], [1328; 4-OMe-5-Me-2-Fu], [1329; 4-OMe-5-Et-2-Fu], [1330; 4-OMe-5-Pr-2-Fu], [1331; 4-OMe-5-iPr-2-Fu], [1332; 4-OMe-5-CF3-2-Fu], [1333; 4-OMe-5-CHF2-2-Fu], [1334; 4-OMe-5-OMe-2-Fu], [1335; 4-OMe-5-OEt-2-Fu], [1336; 4-OMe-5-OCF3-2-Fu], [1337; 4-OMe-5-OCHF2-2-Fu], [1338; 4-OMe-5-CN-2-Fu], [1339; 4-OMe-5-SMe-2-Fu], [1340; 4-OMe-5-SEt-2-Fu], [1341; 4-OMe-5-cPr-2-Fu], [1342; 4-OEt-5-F-2-Fu], [1343; 4-OEt-5-Cl-2-Fu], [1344; 4-OEt-5-Br-2-Fu], [1345; 4-OEt-5-I-2-Fu], [1346; 4-OEt-5-Me-2-Fu], [1347; 4-OEt-5-Et-2-Fu], [1348; 4-OEt-5-Pr-2-Fu], [1349; 4-OEt-5-iPr-2-Fu], [1350; 4-OEt-5-CF3-2-Fu], [1351; 4-OEt-5-CHF2-2-Fu], [1352; 4-OEt-5-OMe-2-Fu], [1353; 4-OEt-5-OEt-2-Fu], [1354; 4-OEt-5-OCF3-2-Fu], [1355; 4-OEt-5-OCHF2-2-Fu], [1356; 4-OEt-5-CN-2-Fu], [1357; 4-OEt-5-SMe-2-Fu], [1358; 4-OEt-5-SEt-2-Fu], [1359; 4-OEt-5-cPr-2-Fu], [1360; 4-SMe-5-F-2-Fu], [1361; 4-SMe-5-Cl-2-Fu], [1362; 4-SMe-5-Br-2-Fu], [1363; 4-SMe-5-I-2-Fu], [1364; 4-SMe-5-Me-2-Fu], [1365; 4-SMe-5-Et-2-Fu], [1366; 4-SMe-5-Pr-2-Fu], [1367; 4-SMe-5-iPr-2-Fu], [1368; 4-SMe-5-CF3-2-Fu], [1369; 4-SMe-5-CHF2-2-Fu], [1370; 4-SMe-5-OMe-2-Fu], [1371; 4-SMe-5-OEt-2-Fu], [1372; 4-SMe-5-OCF3-2-Fu], [1373; 4-SMe-5-OCHF2-2-Fu], [1374; 4-SMe-5-CN-2-Fu], [1375; 4-SMe-5-SMe-2-Fu], [1376; 4-SMe-5-SEt-2-Fu], [1377; 4-SMe-5-cPr-2-Fu], [1378; 3-F-2-Fu], [1379; 3-Cl-2-Fu], [1380; 3-Br-2-Fu], [1381; 3-I-2-Fu], [1382; 3-Me-2-Fu], [1383; 3-Et-2-Fu], [1384; 3-Pr-2-Fu], [1385; 3-iPr-2-Fu], [1386; 3-CF3-2-Fu], [1387; 3-CHF2-2-Fu], [1388; 3-OMe-2-Fu], [1389; 3-OEt-2-Fu], [1390; 3-OCF3-2-Fu], [1391; 3-OCHF2-2-Fu], [1392; 3-F-4-F-2-Fu], [1393; 3-F-4-Cl-2-Fu], [1394; 3-F-4-Br-2-Fu], [1395; 3-F-4-I-2-Fu], [1396; 3-F-4-Me-2-Fu], [1397; 3-F-4-Et-2-Fu], [1398; 3-F-4-Pr-2-Fu], [1399; 3-F-4-iPr-2-Fu], [1400; 3-F-4-CF3-2-Fu],

[1401; 3-F-4-CHF2-2-Fu], [1402; 3-F-4-OMe-2-Fu], [1403; 3-F-4-OEt-2-Fu], [1404; 3-F-4-OCF3-2-Fu], [1405; 3-F-4-OCHF2-2-Fu], [1406; 3-F-4-CN-2-Fu], [1407; 3-F-4-SMe-2-Fu], [1408; 3-F-4-SEt-2-Fu], [1409; 3-F-4-cPr-2-Fu], [1410; 3-Cl-4-F-2-Fu], [1411; 3-Cl-4-Cl-2-Fu], [1412; 3-Cl-4-Br-2-Fu], [1413; 3-Cl-4-I-2-Fu], [1414; 3-Cl-4-Me-2-Fu], [1415; 3-Cl-4-Et-2-Fu], [1416; 3-Cl-4-Pr-2-Fu], [1417; 3-Cl-4-iPr-2-Fu], [1418; 3-Cl-4-CF3-2-Fu], [1419; 3-Cl-4-CHF2-2-Fu], [1420; 3-Cl-4-OMe-2-Fu], [1421; 3-Cl-4-OEt-2-Fu], [1422; 3-Cl-4-OCF3-2-Fu], [1423; 3-Cl-4-OCHF2-2-Fu], [1424; 3-Cl-4-CN-2-Fu], [1425; 3-Cl-4-SMe-2-Fu], [1426; 3-Cl-4-SEt-2-Fu], [1427; 3-Cl-4-cPr-2-

Fu], [1428; 3-Me-4-F-2-Fu], [1429; 3-Me-4-Cl-2-Fu], [1430; 3-Me-4-Br-2-Fu], [1431; 3-Me-4-I-2-Fu], [1432; 3-Me-4-Me-2-Fu], [1433; 3-Me-4-Et-2-Fu], [1434; 3-Me-4-Pr-2-Fu], [1435; 3-Me-4-iPr-2-Fu], [1436; 3-Me-4-CF3-2-Fu], [1437; 3-Me-4-CHF2-2-Fu], [1438; 3-Me-4-OMe-2-Fu], [1439; 3-Me-4-OEt-2-Fu], [1440; 3-Me-4-OCF3-2-Fu], [1441; 3-Me-4-OCHF2-2-Fu], [1442; 3-Me-4-CN-2-Fu], [1443; 3-Me-4-SMe-2-Fu], [1444; 3-Me-4-SEt-2-Fu], [1445; 3-Me-4-cPr-2-Fu], [1446; 3-Et-4-F-2-Fu], [1447; 3-Et-4-Cl-2-Fu], [1448; 3-Et-4-Br-2-Fu], [1449; 3-Et-4-I-2-Fu], [1450; 3-Et-4-Me-2-Fu], [1451; 3-Et-4-Et-2-Fu], [1452; 3-Et-4-Pr-2-Fu], [1453; 3-Et-4-iPr-2-Fu], [1454; 3-Et-4-CF3-2-Fu], [1455; 3-Et-4-CHF2-2-Fu], [1456; 3-Et-4-OMe-2-Fu], [1457; 3-Et-4-OEt-2-Fu], [1458; 3-Et-4-OCF3-2-Fu], [1459; 3-Et-4-OCHF2-2-Fu], [1460; 3-Et-4-CN-2-Fu], [1461; 3-Et-4-SMe-2-Fu], [1462; 3-Et-4-SEt-2-Fu], [1463; 3-Et-4-cPr-2-Fu], [1464; 3-CF3-4-F-2-Fu], [1465; 3-CF3-4-Cl-2-Fu], [1466; 3-CF3-4-Br-2-Fu], [1467; 3-CF3-4-I-2-Fu], [1468; 3-CF3-4-Me-2-Fu], [1469; 3-CF3-4-Et-2-Fu], [1470; 3-CF3-4-Pr-2-Fu], [1471; 3-CF3-4-iPr-2-Fu], [1472; 3-CF3-4-CF3-2-Fu], [1473; 3-CF3-4-CHF2-2-Fu], [1474; 3-CF3-4-OMe-2-Fu], [1475; 3-CF3-4-OEt-2-Fu], [1476; 3-CF3-4-OCF3-2-Fu], [1477; 3-CF3-4-OCHF2-2-Fu], [1478; 3-CF3-4-CN-2-Fu], [1479; 3-CF3-4-SMe-2-Fu], [1480; 3-CF3-4-SEt-2-Fu], [1481; 3-CF3-4-cPr-2-Fu], [1482; 3-OMe-4-F-2-Fu], [1483; 3-OMe-4-Cl-2-Fu], [1484; 3-OMe-4-Br-2-Fu], [1485; 3-OMe-4-I-2-Fu], [1486; 3-OMe-4-Me-2-Fu], [1487; 3-OMe-4-Et-2-Fu], [1488; 3-OMe-4-Pr-2-Fu], [1489; 3-OMe-4-iPr-2-Fu], [1490; 3-OMe-4-CF3-2-Fu], [1491; 3-OMe-4-CHF2-2-Fu], [1492; 3-OMe-4-OMe-2-Fu], [1493; 3-OMe-4-OEt-2-Fu], [1494; 3-OMe-4-OCF3-2-Fu], [1495; 3-OMe-4-OCHF2-2-Fu], [1496; 3-OMe-4-CN-2-Fu], [1497; 3-OMe-4-SMe-2-Fu], [1498; 3-OMe-4-SEt-2-Fu], [1499; 3-OMe-4-cPr-2-Fu], [1500; 3-OEt-4-F-2-Fu],

[1501; 3-OEt-4-Cl-2-Fu], [1502; 3-OEt-4-Br-2-Fu], [1503; 3-OEt-4-I-2-Fu], [1504; 3-OEt-4-Me-2-Fu], [1505; 3-OEt-4-Et-2-Fu], [1506; 3-OEt-4-Pr-2-Fu], [1507; 3-OEt-4-iPr-2-Fu], [1508; 3-OEt-4-CF3-2-Fu], [1509; 3-OEt-4-CHF2-2-Fu], [1510; 3-OEt-4-OMe-2-Fu], [1511; 3-OEt-4-OEt-2-Fu], [1512; 3-OEt-4-OCF3-2-Fu], [1513; 3-OEt-4-OCHF2-2-Fu], [1514; 3-OEt-4-CN-2-Fu], [1515; 3-OEt-4-SMe-2-Fu], [1516; 3-OEt-4-SEt-2-Fu], [1517; 3-OEt-4-cPr-2-Fu], [1518; 3-SMe-4-F-2-Fu], [1519; 3-SMe-4-Cl-2-Fu], [1520; 3-SMe-4-Br-2-Fu], [1521; 3-SMe-4-I-2-Fu], [1522; 3-SMe-4-Me-2-Fu], [1523; 3-SMe-4-Et-2-Fu], [1524; 3-SMe-4-Pr-2-Fu], [1525; 3-SMe-4-iPr-2-Fu], [1526; 3-SMe-4-CF3-2-Fu], [1527; 3-SMe-4-CHF2-2-Fu], [1528; 3-SMe-4-OMe-2-Fu], [1529; 3-SMe-4-OEt-2-Fu], [1530; 3-SMe-4-OCF3-2-Fu], [1531; 3-SMe-4-OCHF2-2-Fu], [1532; 3-SMe-4-CN-2-Fu], [1533; 3-SMe-4-SMe-2-Fu], [1534; 3-SMe-4-SEt-2-Fu], [1535; 3-SMe-4-cPr-2-Fu], [1536; 3-F-5-F-2-Fu], [1537; 3-F-5-Cl-2-Fu], [1538; 3-F-5-Br-2-Fu], [1539; 3-F-5-I-2-Fu], [1540; 3-F-5-Me-2-Fu], [1541; 3-F-5-Et-2-Fu], [1542; 3-F-5-Pr-2-Fu], [1543; 3-F-5-iPr-2-Fu], [1544; 3-F-5-CF3-2-Fu], [1545; 3-F-5-CHF2-2-Fu], [1546; 3-F-5-OMe-2-Fu], [1547; 3-F-5-OEt-2-Fu], [1548; 3-F-5-OCF3-2-Fu], [1549; 3-F-5-OCHF2-2-Fu], [1550; 3-F-5-CN-2-Fu], [1551; 3-F-5-SMe-2-Fu], [1552; 3-F-5-SEt-2-Fu], [1553; 3-F-5-cPr-2-Fu], [1554; 3-Cl-5-F-2-Fu], [1555; 3-Cl-5-Cl-2-Fu], [1556; 3-Cl-5-Br-2-Fu], [1557; 3-Cl-5-I-2-Fu], [1558; 3-Cl-5-Me-2-Fu], [1559; 3-Cl-5-Et-2-Fu], [1560; 3-Cl-5-Pr-2-Fu], [1561; 3-Cl-5-iPr-2-Fu], [1562; 3-Cl-5-CF3-2-Fu], [1563; 3-Cl-5-CHF2-2-Fu], [1564; 3-Cl-5-OMe-2-Fu], [1565; 3-Cl-5-OEt-2-Fu], [1566; 3-Cl-5-OCF3-2-Fu], [1567; 3-Cl-5-OCHF2-2-Fu], [1568; 3-Cl-5-CN-2-Fu], [1569; 3-Cl-5-SMe-2-Fu], [1570; 3-Cl-5-SEt-2-Fu], [1571; 3-Cl-5-cPr-2-Fu], [1572; 3-Me-5-F-2-Fu], [1573; 3-Me-5-Cl-2-Fu], [1574; 3-Me-5-Br-2-Fu], [1575; 3-Me-5-I-2-Fu], [1576; 3-Me-5-Me-2-Fu], [1577; 3-Me-5-Et-2-Fu], [1578; 3-Me-5-Pr-2-Fu], [1579; 3-Me-5-iPr-2-Fu], [1580; 3-Me-5-CF3-2-Fu], [1581; 3-Me-5-CHF2-2-Fu], [1582; 3-Me-5-OMe-2-Fu], [1583; 3-Me-5-OEt-2-Fu], [1584; 3-Me-5-OCF3-2-Fu], [1585; 3-Me-5-OCHF2-2-Fu], [1586; 3-Me-5-CN-2-Fu], [1587; 3-Me-5-SMe-2-Fu], [1588; 3-Me-5-SEt-2-Fu], [1589; 3-Me-5-cPr-2-Fu], [1590; 3-Et-5-F-2-Fu], [1591; 3-Et-5-Cl-2-Fu], [1592; 3-Et-5-Br-2-Fu], [1593; 3-Et-5-I-2-Fu], [1594; 3-Et-5-Me-2-Fu], [1595; 3-Et-5-Et-2-Fu], [1596; 3-Et-5-Pr-2-Fu], [1597; 3-Et-5-iPr-2-Fu], [1598; 3-Et-5-CF3-2-Fu], [1599; 3-Et-5-CHF2-2-Fu], [1600; 3-Et-5-OMe-2-Fu],

[1601; 3-Et-5-OEt-2-Fu], [1602; 3-Et-5-OCF3-2-Fu], [1603; 3-Et-5-OCHF2-2-Fu], [1604; 3-Et-5-CN-2-Fu], [1605; 3-Et-5-SMe-2-Fu], [1606; 3-Et-5-SEt-2-Fu], [1607; 3-Et-5-cPr-2-Fu], [1608; 3-CF3-5-F-2-Fu], [1609; 3-CF3-5-Cl-2-Fu], [1610; 3-CF3-5-Br-2-Fu], [1611; 3-CF3-5-I-2-Fu], [1612; 3-CF3-5-Me-2-Fu], [1613; 3-CF3-5-Et-2-Fu], [1614; 3-CF3-5-Pr-2-Fu], [1615; 3-CF3-5-iPr-2-Fu], [1616; 3-CF3-5-CF3-2-Fu], [1617; 3-CF3-5-CHF2-2-Fu], [1618; 3-CF3-5-OMe-2-Fu], [1619; 3-CF3-5-OEt-2-Fu], [1620; 3-CF3-5-OCF3-2-Fu], [1621; 3-CF3-5-OCHF2-2-Fu], [1622; 3-CF3-5-CN-2-Fu], [1623; 3-CF3-5-SMe-2-Fu], [1624; 3-CF3-5-SEt-2-Fu], [1625; 3-CF3-5-cPr-2-Fu], [1626; 3-OMe-5-F-2-Fu], [1627; 3-OMe-5-Cl-2-Fu], [1628; 3-OMe-5-Br-2-Fu], [1629; 3-OMe-5-I-2-Fu], [1630; 3-OMe-5-Me-2-Fu], [1631; 3-OMe-5-Et-2-Fu], [1632; 3-OMe-5-Pr-2-Fu], [1633; 3-OMe-5-iPr-2-Fu], [1634; 3-OMe-5-CF3-2-Fu], [1635; 3-OMe-5-CHF2-2-Fu], [1636; 3-OMe-5-OMe-2-Fu], [1637; 3-OMe-5-OEt-2-Fu], [1638; 3-OMe-5-OCF3-2-Fu], [1639; 3-OMe-5-OCHF2-2-Fu], [1640; 3-OMe-5-CN-2-Fu], [1641; 3-OMe-5-SMe-2-Fu], [1642; 3-OMe-5-SEt-2-Fu], [1643; 3-OMe-5-cPr-2-Fu], [1644; 3-OEt-5-F-2-Fu], [1645; 3-OEt-5-Cl-2-Fu], [1646; 3-OEt-5-Br-2-Fu], [1647; 3-OEt-5-I-2-Fu], [1648; 3-OEt-5-Me-2-Fu], [1649; 3-OEt-5-Et-2-Fu], [1650; 3-OEt-5-Pr-2-Fu], [1651; 3-OEt-5-iPr-2-Fu], [1652; 3-OEt-5-CF3-2-Fu], [1653; 3-OEt-5-CHF2-2-Fu], [1654; 3-OEt-5-OMe-2-Fu], [1655; 3-OEt-5-OEt-2-Fu], [1656; 3-OEt-5-OCF3-2-Fu], [1657; 3-OEt-5-OCHF2-2-Fu], [1658; 3-OEt-5-CN-2-Fu], [1659; 3-OEt-5-SMe-2-Fu], [1660; 3-OEt-5-SEt-2-Fu], [1661; 3-OEt-5-cPr-2-Fu], [1662; 3-SMe-5-F-2-Fu], [1663; 3-SMe-5-Cl-2-Fu], [1664; 3-SMe-5-Br-2-Fu], [1665; 3-SMe-5-I-2-Fu], [1666; 3-SMe-5-Me-2-Fu], [1667; 3-SMe-5-Et-2-Fu], [1668; 3-SMe-5-Pr-2-Fu], [1669; 3-SMe-5-iPr-2-Fu], [1670; 3-SMe-5-CF3-2-Fu], [1671; 3-SMe-5-CHF2-2-Fu], [1672; 3-SMe-5-OMe-2-Fu], [1673; 3-SMe-5-OEt-2-Fu], [1674; 3-SMe-5-OCF3-2-Fu], [1675; 3-SMe-5-OCHF2-2-Fu], [1676; 3-SMe-5-CN-2-Fu], [1677; 3-SMe-5-SMe-2-Fu], [1678; 3-SMe-5-SEt-2-Fu], [1679; 3-SMe-5-cPr-2-Fu], [1680; 3-Me-4-Me-5-F-2-Fu], [1681; 3-Me-4-Me-5-Cl-2-Fu], [1682; 3-Me-4-Me-5-Br-2-Fu], [1683; 3-Me-4-Me-5-I-2-Fu], [1684; 3-Me-4-Me-5-Me-2-Fu], [1685; 3-Me-4-Me-5-Et-2-Fu], [1686; 3-Me-4-Me-5-Pr-2-Fu], [1687; 3-Me-4-Me-5-iPr-2-Fu], [1688; 3-Me-4-Me-5-CF3-2-Fu], [1689; 3-Me-4-Me-5-CHF2-2-Fu], [1690; 3-Me-4-Me-5-OMe-2-Fu], [1691; 3-Me-4-Me-5-OEt-2-Fu], [1692; 3-Me-4-Me-5-OCF3-2-Fu], [1693; 3-Me-4-Me-5-OCHF2-2-Fu], [1694; 3-Me-4-Me-5-CN-2-Fu], [1695; 3-Me-4-Me-5-SMe-2-Fu], [1696; 3-Me-4-Me-5-SEt-2-Fu], [1697; 3-Me-4-Me-5-cPr-2-Fu], [1698; 3-Me-4-F-5-Me-2-Fu], [1699; 3-Me-4-Cl-5-Me-2-Fu], [1700; 3-Me-4-Br-5-Me-2-Fu],

[1701; 3-Me-4-I-5-Me-2-Fu], [1702; 3-Me-4-Et-5-Me-2-Fu], [1703; 3-Me-4-Pr-5-Me-2-Fu], [1704; 3-Me-4-iPr-5-

Me-2-Fu], [1705; 3-Me-4-CF3-5-Me-2-Fu], [1706; 3-Me-4-CHF2-5-Me-2-Fu], [1707; 3-Me-4-OMe-5-Me-2-Fu], [1708; 3-Me-4-OEt-5-Me-2-Fu], [1709; 3-Me-4-OCF3-5-Me-2-Fu], [1710; 3-Me-4-OCHF2-5-Me-2-Fu], [1711; 3-Me-4-CN-5-Me-2-Fu], [1712; 3-Me-4-SMe-5-Me-2-Fu], [1713; 3-Me-4-SEt-5-Me-2-Fu], [1714; 3-Me-4-cPr-5-Me-2-Fu], [1715; 2-Thio], [1716; 4-F-2-Thio], [1717; 4-Cl-2-Thio], [1718; 4-Br-2-Thio], [1719; 4-I-2-Thio], [1720; 4-Me-2-Thio], [1721; 4-Et-2-Thio], [1722; 4-Pr-2-Thio], [1723; 4-iPr-2-Thio], [1724; 4-CF3-2-Thio], [1725; 4-CHF2-2-Thio], [1726; 4-OMe-2-Thio], [1727; 4-OEt-2-Thio], [1728; 4-OCF3-2-Thio], [1729; 4-OCHF2-2-Thio], [1730; 4-CN-2-Thio], [1731; 4-SMe-2-Thio], [1732; 4-SEt-2-Thio], [1733; 4-cPr-2-Thio], [1734; 5-F-2-Thio], [1735; 5-Cl-2-Thio], [1736; 5-Br-2-Thio], [1737; 5-I-2-Thio], [1738; 5-Me-2-Thio], [1739; 5-Et-2-Thio], [1740; 5-Pr-2-Thio], [1741; 5-iPr-2-Thio], [1742; 5-CF3-2-Thio], [1743; 5-CHF2-2-Thio], [1744; 5-OMe-2-Thio], [1745; 5-OEt-2-Thio], [1746; 5-OCF3-2-Thio], [1747; 5-OCHF2-2-Thio], [1748; 5-CN-2-Thio], [1749; 5-SMe-2-Thio], [1750; 5-SEt-2-Thio], [1751; 5-cPr-2-Thio], [1752; 4-F-5-F-2-Thio], [1753; 4-F-5-Cl-2-Thio], [1754; 4-F-5-Br-2-Thio], [1755; 4-F-5-I-2-Thio], [1756; 4-F-5-Me-2-Thio], [1757; 4-F-5-Et-2-Thio], [1758; 4-F-5-Pr-2-Thio], [1759; 4-F-5-iPr-2-Thio], [1760; 4-F-5-CF3-2-Thio], [1761; 4-F-5-CHF2-2-Thio], [1762; 4-F-5-OMe-2-Thio], [1763; 4-F-5-OEt-2-Thio], [1764; 4-F-5-OCF3-2-Thio], [1765; 4-F-5-OCHF2-2-Thio], [1766; 4-F-5-CN-2-Thio], [1767; 4-F-5-SMe-2-Thio], [1768; 4-F-5-SEt-2-Thio], [1769; 4-F-5-cPr-2-Thio], [1770; 4-Cl-5-F-2-Thio], [1771; 4-Cl-5-Cl-2-Thio], [1772; 4-Cl-5-Br-2-Thio], [1773; 4-Cl-5-I-2-Thio], [1774; 4-Cl-5-Me-2-Thio], [1775; 4-Cl-5-Et-2-Thio], [1776; 4-Cl-5-Pr-2-Thio], [1777; 4-Cl-5-iPr-2-Thio], [1778; 4-Cl-5-CF3-2-Thio], [1779; 4-Cl-5-CHF2-2-Thio], [1780; 4-Cl-5-OMe-2-Thio], [1781; 4-Cl-5-OEt-2-Thio], [1782; 4-Cl-5-OCF3-2-Thio], [1783; 4-Cl-5-OCHF2-2-Thio], [1784; 4-Cl-5-CN-2-Thio], [1785; 4-Cl-5-SMe-2-Thio], [1786; 4-Cl-5-SEt-2-Thio], [1787; 4-Cl-5-cPr-2-Thio], [1788; 4-Me-5-F-2-Thio], [1789; 4-Me-5-Cl-2-Thio], [1790; 4-Me-5-Br-2-Thio], [1791; 4-Me-5-I-2-Thio], [1792; 4-Me-5-Me-2-Thio], [1793; 4-Me-5-Et-2-Thio], [1794; 4-Me-5-Pr-2-Thio], [1795; 4-Me-5-iPr-2-Thio], [1796; 4-Me-5-CF3-2-Thio], [1797; 4-Me-5-CHF2-2-Thio], [1798; 4-Me-5-OMe-2-Thio], [1799; 4-Me-5-OEt-2-Thio], [1800; 4-Me-5-OCF3-2-Thio],

[1801; 4-Me-5-OCHF2-2-Thio], [1802; 4-Me-5-CN-2-Thio], [1803; 4-Me-5-SMe-2-Thio], [1804; 4-Me-5-SEt-2-Thio], [1805; 4-Me-5-cPr-2-Thio], [1806; 4-Et-5-F-2-Thio], [1807; 4-Et-5-Cl-2-Thio], [1808; 4-Et-5-Br-2-Thio], [1809; 4-Et-5-I-2-Thio], [1810; 4-Et-5-Me-2-Thio], [1811; 4-Et-5-Et-2-Thio], [1812; 4-Et-5-Pr-2-Thio], [1813; 4-Et-5-iPr-2-Thio], [1814; 4-Et-5-CF3-2-Thio], [1815; 4-Et-5-CHF2-2-Thio], [1816; 4-Et-5-OMe-2-Thio], [1817; 4-Et-5-OEt-2-Thio], [1818; 4-Et-5-OCF3-2-Thio], [1819; 4-Et-5-OCHF2-2-Thio], [1820; 4-Et-5-CN-2-Thio], [1821; 4-Et-5-SMe-2-Thio], [1822; 4-Et-5-SEt-2-Thio], [1823; 4-Et-5-cPr-2-Thio], [1824; 4-CF3-5-F-2-Thio], [1825; 4-CF3-5-Cl-2-Thio], [1826; 4-CF3-5-Br-2-Thio], [1827; 4-CF3-5-I-2-Thio], [1828; 4-CF3-5-Me-2-Thio], [1829; 4-CF3-5-Et-2-Thio], [1830; 4-CF3-5-Pr-2-Thio], [1831; 4-CF3-5-iPr-2-Thio], [1832; 4-CF3-5-CF3-2-Thio], [1833; 4-CF3-5-CHF2-2-Thio], [1834; 4-CF3-5-OMe-2-Thio], [1835; 4-CF3-5-OEt-2-Thio], [1836; 4-CF3-5-OCF3-2-Thio], [1837; 4-CF3-5-OCHF2-2-Thio], [1838; 4-CF3-5-CN-2-Thio], [1839; 4-CF3-5-SMe-2-Thio], [1840; 4-CF3-5-SEt-2-Thio], [1841; 4-CF3-5-cPr-2-Thio], [1842; 4-OMe-5-F-2-Thio], [1843; 4-OMe-5-Cl-2-Thio], [1844; 4-OMe-5-Br-2-Thio], [1845; 4-OMe-5-I-2-Thio], [1846; 4-OMe-5-Me-2-Thio], [1847; 4-OMe-5-Et-2-Thio], [1848; 4-OMe-5-Pr-2-Thio], [1849; 4-OMe-5-iPr-2-Thio], [1850; 4-OMe-5-CF3-2-Thio], [1851; 4-OMe-5-CHF2-2-Thio], [1852; 4-OMe-5-OMe-2-Thio], [1853; 4-OMe-5-OEt-2-Thio], [1854; 4-OMe-5-OCF3-2-Thio], [1855; 4-OMe-5-OCHF2-2-Thio], [1856; 4-OMe-5-CN-2-Thio], [1857; 4-OMe-5-SMe-2-Thio], [1858; 4-OMe-5-SEt-2-Thio], [1859; 4-OMe-5-cPr-2-Thio], [1860; 4-OEt-5-F-2-Thio], [1861; 4-OEt-5-Cl-2-Thio], [1862; 4-OEt-5-Br-2-Thio], [1863; 4-OEt-5-I-2-Thio], [1864; 4-OEt-5-Me-2-Thio], [1865; 4-OEt-5-Et-2-Thio], [1866; 4-OEt-5-Pr-2-Thio], [1867; 4-OEt-5-iPr-2-Thio], [1868; 4-OEt-5-CF3-2-Thio], [1869; 4-OEt-5-CHF2-2-Thio], [1870; 4-OEt-5-OMe-2-Thio], [1871; 4-OEt-5-OEt-2-Thio], [1872; 4-OEt-5-OCF3-2-Thio], [1873; 4-OEt-5-OCHF2-2-Thio], [1874; 4-OEt-5-CN-2-Thio], [1875; 4-OEt-5-SMe-2-Thio], [1876; 4-OEt-5-SEt-2-Thio], [1877; 4-OEt-5-cPr-2-Thio], [1878; 4-SMe-5-F-2-Thio], [1879; 4-SMe-5-Cl-2-Thio], [1880; 4-SMe-5-Br-2-Thio], [1881; 4-SMe-5-I-2-Thio], [1882; 4-SMe-5-Me-2-Thio], [1883; 4-SMe-5-Et-2-Thio], [1884; 4-SMe-5-Pr-2-Thio], [1885; 4-SMe-5-iPr-2-Thio], [1886; 4-SMe-5-CF3-2-Thio], [1887; 4-SMe-5-CHF2-2-Thio], [1888; 4-SMe-5-OMe-2-Thio], [1889; 4-SMe-5-OEt-2-Thio], [1890; 4-SMe-5-OCF3-2-Thio], [1891; 4-SMe-5-OCHF2-2-Thio], [1892; 4-SMe-5-CN-2-Thio], [1893; 4-SMe-5-SMe-2-Thio], [1894; 4-SMe-5-SEt-2-Thio], [1895; 4-SMe-5-cPr-2-Thio], [1896; 3-F-2-Thio], [1897; 3-Cl-2-Thio], [1898; 3-Br-2-Thio], [1899; 3-I-2-Thio], [1900; 3-Me-2-Thio],

[1901; 3-Et-2-Thio], [1902; 3-Pr-2-Thio], [1903; 3-iPr-2-Thio], [1904; 3-CF3-2-Thio], [1905; 3-CHF2-2-Thio], [1906; 3-OMe-2-Thio], [1907; 3-OEt-2-Thio], [1908; 3-OCF3-2-Thio], [1909; 3-OCHF2-2-Thio], [1910; 3-F-4-F-2-Thio], [1911; 3-F-4-Cl-2-Thio], [1912; 3-F-4-Br-2-Thio], [1913; 3-F-4-I-2-Thio], [1914; 3-F-4-Me-2-Thio], [1915; 3-F-4-Et-2-Thio], [1916; 3-F-4-Pr-2-Thio], [1917; 3-F-4-iPr-2-Thio], [1918; 3-F-4-CF3-2-Thio], [1919; 3-F-4-CHF2-2-Thio], [1920; 3-F-4-OMe-2-Thio], [1921; 3-F-4-OEt-2-Thio], [1922; 3-F-4-OCF3-2-Thio], [1923; 3-F-4-OCHF2-2-Thio], [1924; 3-F-4-CN-2-Thio], [1925; 3-F-4-SMe-2-Thio], [1926; 3-F-4-SEt-2-Thio], [1927; 3-F-4-cPr-2-Thio], [1928; 3-Cl-4-F-2-Thio], [1929; 3-Cl-4-Cl-2-Thio], [1930; 3-Cl-4-Br-2-Thio], [1931; 3-Cl-4-I-2-Thio], [1932; 3-Cl-4-Me-2-Thio], [1933; 3-Cl-4-Et-2-Thio], [1934; 3-Cl-4-Pr-2-Thio], [1935; 3-Cl-4-iPr-2-Thio], [1936; 3-Cl-4-CF3-2-Thio], [1937; 3-Cl-4-CHF2-2-Thio], [1938; 3-Cl-4-OMe-2-Thio], [1939; 3-Cl-4-OEt-2-Thio], [1940; 3-Cl-4-OCF3-2-Thio], [1941; 3-Cl-4-OCHF2-2-Thio], [1942; 3-Cl-4-CN-2-Thio], [1943; 3-Cl-4-SMe-2-Thio], [1944; 3-Cl-4-SEt-2-Thio], [1945; 3-Cl-4-cPr-2-Thio], [1946; 3-Me-4-F-2-Thio], [1947; 3-Me-4-Cl-2-Thio], [1948; 3-Me-4-Br-2-Thio], [1949; 3-Me-4-I-2-Thio], [1950; 3-Me-4-Me-2-Thio], [1951; 3-Me-4-Et-2-Thio], [1952; 3-Me-4-Pr-2-Thio], [1953; 3-Me-4-iPr-2-Thio], [1954; 3-Me-4-CF3-2-Thio], [1955; 3-Me-4-CHF2-2-Thio], [1956; 3-Me-4-OMe-2-Thio], [1957; 3-Me-4-OEt-2-Thio], [1958; 3-Me-4-OCF3-2-Thio], [1959; 3-Me-4-OCHF2-2-Thio], [1960; 3-Me-4-CN-2-Thio], [1961; 3-Me-4-SMe-2-Thio], [1962; 3-Me-4-SEt-2-Thio], [1963; 3-Me-4-cPr-2-Thio], [1964; 3-Et-4-F-2-Thio], [1965; 3-Et-4-Cl-2-Thio], [1966; 3-Et-4-Br-2-Thio], [1967; 3-Et-4-I-2-Thio], [1968; 3-Et-4-Me-2-Thio], [1969; 3-Et-4-Et-2-Thio], [1970; 3-Et-4-Pr-2-Thio], [1971; 3-Et-4-iPr-2-Thio], [1972; 3-Et-4-CF3-2-Thio], [1973; 3-Et-4-CHF2-2-Thio], [1974; 3-Et-4-OMe-2-Thio], [1975; 3-Et-4-OEt-2-Thio], [1976; 3-Et-4-OCF3-2-Thio], [1977; 3-Et-4-OCHF2-2-Thio], [1978; 3-Et-4-CN-2-Thio], [1979; 3-Et-4-SMe-2-Thio], [1980; 3-Et-4-SEt-2-Thio],

[1981; 3-Et-4-cPr-2-Thio], [1982; 3-CF3-4-F-2-Thio], [1983; 3-CF3-4-Cl-2-Thio], [1984; 3-CF3-4-Br-2-Thio], [1985; 3-CF3-4-I-2-Thio], [1986; 3-CF3-4-Me-2-Thio], [1987; 3-CF3-4-Et-2-Thio], [1988; 3-CF3-4-Pr-2-Thio], [1989; 3-CF3-4-iPr-2-Thio], [1990; 3-CF3-4-CF3-2-Thio], [1991; 3-CF3-4-CHF2-2-Thio], [1992; 3-CF3-4-OMe-2-Thio], [1993; 3-CF3-4-OEt-2-Thio], [1994; 3-CF3-4-OCF3-2-Thio], [1995; 3-CF3-4-OCHF2-2-Thio], [1996; 3-CF3-4-CN-2-Thio], [1997; 3-CF3-4-SMe-2-Thio], [1998; 3-CF3-4-SEt-2-Thio], [1999; 3-CF3-4-cPr-2-Thio], [2000; 3-OMe-4-F-2-Thio],

[2001; 3-OMe-4-Cl-2-Thio], [2002; 3-OMe-4-Br-2-Thio], [2003; 3-OMe-4-I-2-Thio], [2004; 3-OMe-4-Me-2-Thio], [2005; 3-OMe-4-Et-2-Thio], [2006; 3-OMe-4-Pr-2-Thio], [2007; 3-OMe-4-iPr-2-Thio], [2008; 3-OMe-4-CF3-2-Thio], [2009; 3-OMe-4-CHF2-2-Thio], [2010; 3-OMe-4-OMe-2-Thio], [2011; 3-OMe-4-OEt-2-Thio], [2012; 3-OMe-4-OCF3-2-Thio], [2013; 3-OMe-4-OCHF2-2-Thio], [2014; 3-OMe-4-CN-2-Thio], [2015; 3-OMe-4-SMe-2-Thio], [2016; 3-OMe-4-SEt-2-Thio], [2017; 3-OMe-4-cPr-2-Thio], [2018; 3-OEt-4-F-2-Thio], [2019; 3-OEt-4-Cl-2-Thio], [2020; 3-OEt-4-Br-2-Thio], [2021; 3-OEt-4-I-2-Thio], [2022; 3-OEt-4-Me-2-Thio], [2023; 3-OEt-4-Et-2-Thio], [2024; 3-OEt-4-Pr-2-Thio], [2025; 3-OEt-4-iPr-2-Thio], [2026; 3-OEt-4-CF3-2-Thio], [2027; 3-OEt-4-CHF2-2-Thio], [2028; 3-OEt-4-OMe-2-Thio], [2029; 3-OEt-4-OEt-2-Thio], [2030; 3-OEt-4-OCF3-2-Thio], [2031; 3-OEt-4-OCHF2-2-Thio], [2032; 3-OEt-4-CN-2-Thio], [2033; 3-OEt-4-SMe-2-Thio], [2034; 3-OEt-4-SEt-2-Thio], [2035; 3-OEt-4-cPr-2-Thio], [2036; 3-SMe-4-F-2-Thio], [2037; 3-SMe-4-Cl-2-Thio], [2038; 3-SMe-4-Br-2-Thio], [2039; 3-SMe-4-I-2-Thio], [2040; 3-SMe-4-Me-2-Thio], [2041; 3-SMe-4-Et-2-Thio], [2042; 3-SMe-4-Pr-2-Thio], [2043; 3-SMe-4-iPr-2-Thio], [2044; 3-SMe-4-CF3-2-Thio], [2045; 3-SMe-4-CHF2-2-Thio], [2046; 3-SMe-4-OMe-2-Thio], [2047; 3-SMe-4-OEt-2-Thio], [2048; 3-SMe-4-OCF3-2-Thio], [2049; 3-SMe-4-OCHF2-2-Thio], [2050; 3-SMe-4-CN-2-Thio], [2051; 3-SMe-4-SMe-2-Thio], [2052; 3-SMe-4-SEt-2-Thio], [2053; 3-SMe-4-cPr-2-Thio], [2054; 3-F-5-F-2-Thio], [2055; 3-F-5-Cl-2-Thio], [2056; 3-F-5-Br-2-Thio], [2057; 3-F-5-I-2-Thio], [2058; 3-F-5-Me-2-Thio], [2059; 3-F-5-Et-2-Thio], [2060; 3-F-5-Pr-2-Thio], [2061; 3-F-5-iPr-2-Thio], [2062; 3-F-5-CF3-2-Thio], [2063; 3-F-5-CHF2-2-Thio], [2064; 3-F-5-OMe-2-Thio], [2065; 3-F-5-OEt-2-Thio], [2066; 3-F-5-OCF3-2-Thio], [2067; 3-F-5-OCHF2-2-Thio], [2068; 3-F-5-CN-2-Thio], [2069; 3-F-5-SMe-2-Thio], [2070; 3-F-5-SEt-2-Thio], [2071; 3-F-5-cPr-2-Thio], [2072; 3-Cl-5-F-2-Thio], [2073; 3-Cl-5-Cl-2-Thio], [2074; 3-Cl-5-Br-2-Thio], [2075; 3-Cl-5-I-2-Thio], [2076; 3-Cl-5-Me-2-Thio], [2077; 3-Cl-5-Et-2-Thio], [2078; 3-Cl-5-Pr-2-Thio], [2079; 3-Cl-5-iPr-2-Thio], [2080; 3-Cl-5-CF3-2-Thio], [2081; 3-Cl-5-CHF2-2-Thio], [2082; 3-Cl-5-OMe-2-Thio], [2083; 3-Cl-5-OEt-2-Thio], [2084; 3-Cl-5-OCF3-2-Thio], [2085; 3-Cl-5-OCHF2-2-Thio], [2086; 3-Cl-5-CN-2-Thio], [2087; 3-Cl-5-SMe-2-Thio], [2088; 3-Cl-5-SEt-2-Thio], [2089; 3-Cl-5-cPr-2-Thio], [2090; 3-Me-5-F-2-Thio], [2091; 3-Me-5-Cl-2-Thio], [2092; 3-Me-5-Br-2-Thio], [2093; 3-Me-5-I-2-Thio], [2094; 3-Me-5-Me-2-Thio], [2095; 3-Me-5-Et-2-Thio], [2096; 3-Me-5-Pr-2-Thio], [2097; 3-Me-5-iPr-2-Thio], [2098; 3-Me-5-CF3-2-Thio], [2099; 3-Me-5-CHF2-2-Thio], [2100; 3-Me-5-OMe-2-Thio],

[2101; 3-Me-5-OEt-2-Thio], [2102; 3-Me-5-OCF3-2-Thio], [2103; 3-Me-5-OCHF2-2-Thio], [2104; 3-Me-5-CN-2-Thio], [2105; 3-Me-5-SMe-2-Thio], [2106; 3-Me-5-SEt-2-Thio], [2107; 3-Me-5-cPr-2-Thio], [2108; 3-Et-5-F-2-Thio], [2109; 3-Et-5-Cl-2-Thio], [2110; 3-Et-5-Br-2-Thio], [2111; 3-Et-5-I-2-Thio], [2112; 3-Et-5-Me-2-Thio], [2113; 3-Et-5-Et-2-Thio], [2114; 3-Et-5-Pr-2-Thio], [2115; 3-Et-5-iPr-2-Thio], [2116; 3-Et-5-CF3-2-Thio], [2117; 3-Et-5-CHF2-2-Thio], [2118; 3-Et-5-OMe-2-Thio], [2119; 3-Et-5-OEt-2-Thio], [2120; 3-Et-5-OCF3-2-Thio], [2121; 3-Et-5-OCHF2-2-Thio], [2122; 3-Et-5-CN-2-Thio], [2123; 3-Et-5-SMe-2-Thio], [2124; 3-Et-5-SEt-2-Thio], [2125; 3-Et-5-cPr-2-Thio], [2126; 3-CF3-5-F-2-Thio], [2127; 3-CF3-5-Cl-2-Thio], [2128; 3-CF3-5-Br-2-Thio], [2129; 3-CF3-5-I-2-Thio], [2130; 3-CF3-5-Me-2-Thio], [2131; 3-CF3-5-Et-2-Thio], [2132; 3-CF3-5-Pr-2-Thio], [2133; 3-CF3-5-iPr-2-Thio], [2134; 3-CF3-5-CF3-2-Thio], [2135; 3-CF3-5-CHF2-2-Thio], [2136; 3-CF3-5-OMe-2-Thio], [2137; 3-CF3-5-OEt-2-Thio], [2138; 3-CF3-5-OCF3-2-Thio], [2139; 3-CF3-5-OCHF2-2-Thio], [2140; 3-CF3-5-CN-2-Thio], [2141; 3-CF3-5-SMe-2-Thio], [2142; 3-CF3-5-SEt-2-Thio], [2143; 3-CF3-5-cPr-2-Thio], [2144; 3-OMe-5-F-2-Thio], [2145; 3-OMe-5-Cl-2-Thio], [2146; 3-OMe-5-Br-2-Thio], [2147; 3-OMe-5-I-2-Thio], [2148; 3-OMe-5-Me-2-Thio], [2149; 3-OMe-5-Et-2-Thio], [2150; 3-OMe-5-Pr-2-Thio], [2151; 3-OMe-5-iPr-2-Thio], [2152; 3-OMe-5-CF3-2-Thio], [2153; 3-OMe-5-CHF2-2-Thio], [2154; 3-OMe-5-OMe-2-Thio], [2155; 3-OMe-5-OEt-2-Thio], [2156; 3-OMe-5-OCF3-2-Thio], [2157; 3-OMe-5-OCHF2-2-Thio], [2158; 3-OMe-5-CN-2-Thio], [2159; 3-OMe-5-SMe-2-Thio], [2160; 3-OMe-5-SEt-2-Thio], [2161; 3-OMe-5-cPr-2-Thio], [2162; 3-OEt-5-F-2-Thio], [2163; 3-OEt-5-Cl-2-Thio], [2164; 3-OEt-5-Br-2-Thio], [2165; 3-OEt-5-I-2-Thio], [2166; 3-OEt-5-Me-2-Thio], [2167; 3-OEt-5-Et-2-Thio], [2168; 3-OEt-5-Pr-2-Thio], [2169; 3-OEt-5-iPr-2-Thio], [2170; 3-OEt-5-CF3-2-Thio], [2171; 3-OEt-5-CHF2-2-Thio], [2172; 3-OEt-5-OMe-2-Thio], [2173; 3-OEt-5-OEt-2-Thio], [2174; 3-OEt-5-OCF3-2-Thio], [2175; 3-OEt-5-OCHF2-2-Thio], [2176; 3-OEt-5-CN-2-Thio], [2177; 3-OEt-5-SMe-2-Thio], [2178; 3-OEt-5-SEt-2-Thio], [2179; 3-OEt-5-cPr-2-Thio], [2180; 3-SMe-5-F-2-Thio], [2181; 3-SMe-5-Cl-2-Thio], [2182; 3-SMe-5-Br-2-Thio], [2183; 3-SMe-5-I-2-Thio], [2184; 3-SMe-5-Me-2-Thio], [2185; 3-SMe-5-Et-2-Thio], [2186; 3-SMe-5-Pr-2-Thio], [2187; 3-SMe-5-iPr-2-Thio], [2188; 3-SMe-5-CF3-2-Thio], [2189; 3-SMe-5-CHF2-2-Thio], [2190; 3-SMe-5-OMe-2-Thio], [2191; 3-SMe-5-OEt-2-Thio], [2192; 3-SMe-5-OCF3-2-Thio], [2193; 3-SMe-5-OCHF2-2-Thio], [2194; 3-SMe-5-CN-2-Thio], [2195; 3-SMe-5-SMe-2-Thio], [2196; 3-SMe-5-SEt-2-Thio], [2197; 3-SMe-5-cPr-2-Thio], [2198; 3-Me-4-Me-5-F-2-Thio], [2199; 3-Me-4-Me-5-Cl-2-Thio], [2200; 3-Me-4-Me-5-Br-2-Thio],

[2201; 3-Me-4-Me-5-I-2-Thio], [2202; 3-Me-4-Me-5-Me-2-Thio], [2203; 3-Me-4-Me-5-Et-2-Thio], [2204; 3-Me-4-Me-5-Pr-2-Thio], [2205; 3-Me-4-Me-5-iPr-2-Thio], [2206; 3-Me-4-Me-5-CF3-2-Thio], [2207; 3-Me-4-Me-5-CHF2-2-Thio], [2208; 3-Me-4-Me-5-OMe-2-Thio], [2209; 3-Me-4-Me-5-OEt-2-Thio], [2210; 3-Me-4-Me-5-OCF3-2-Thio], [2211; 3-Me-4-Me-5-OCHF2-2-Thio], [2212; 3-Me-4-Me-5-CN-2-Thio], [2213; 3-Me-4-Me-5-SMe-2-Thio], [2214; 3-Me-4-Me-5-SEt-2-Thio], [2215; 3-Me-4-Me-5-cPr-2-Thio], [2216; 3-Me-4-F-5-Me-2-Thio], [2217; 3-Me-4-Cl-5-Me-2-Thio], [2218; 3-Me-4-Br-5-Me-2-Thio], [2219; 3-Me-4-I-5-Me-2-Thio], [2220; 3-Me-4-Et-5-Me-2-Thio], [2221; 3-Me-4-Pr-5-Me-2-Thio], [2222; 3-Me-4-iPr-5-Me-2-Thio], [2223; 3-Me-4-CF3-5-Me-2-Thio], [2224; 3-Me-4-CHF2-5-Me-2-Thio], [2225; 3-Me-4-OMe-5-Me-2-Thio], [2226; 3-Me-4-OEt-5-Me-2-Thio], [2227; 3-Me-4-OCF3-5-Me-2-Thio], [2228; 3-Me-4-OCHF2-5-Me-2-Thio], [2229; 3-Me-4-CN-5-Me-2-Thio], [2230; 3-Me-4-SMe-5-Me-2-Thio], [2231; 3-Me-4-SEt-5-Me-2-Thio], [2232; 3-Me-4-cPr-5-Me-2-Thio], [2233; -3-Fu], [2234;

F-3-Fu], [2235; Cl-3-Fu], [2236; Br-3-Fu], [2237; I-3-Fu], [2238; Me-3-Fu], [2239; Et-3-Fu], [2240; Pr-3-Fu], [2241; iPr-3-Fu], [2242; CF3-3-Fu], [2243; CHF2-3-Fu], [2244; OMe-3-Fu], [2245; OEt-3-Fu], [2246; OCF3-3-Fu], [2247; OCHF2-3-Fu], [2248; CN-3-Fu], [2249; SMe-3-Fu], [2250; SEt-3-Fu], [2251; cPr-3-Fu], [2252; 5-F-3-Fu], [2253; 5-Cl-3-Fu], [2254; 5-Br-3-Fu], [2255; 5-I-3-Fu], [2256; 5-Me-3-Fu], [2257; 5-Et-3-Fu], [2258; 5-Pr-3-Fu], [2259; 5-iPr-3-Fu], [2260; 5-CF3-3-Fu], [2261; 5-CHF2-3-Fu], [2262; 5-OMe-3-Fu], [2263; 5-OEt-3-Fu], [2264; 5-OCF3-3-Fu], [2265; 5-OCHF2-3-Fu], [2266; 5-CN-3-Fu], [2267; 5-SMe-3-Fu], [2268; 5-SEt-3-Fu], [2269; 5-cPr-3-Fu], [2270; 2-F-5-F-3-Fu], [2271; 2-F-5-Cl-3-Fu], [2272; 2-F-5-Br-3-Fu], [2273; 2-F-5-I-3-Fu], [2274; 2-F-5-Me-3-Fu], [2275; 2-F-5-Et-3-Fu], [2276; 2-F-5-Pr-3-Fu], [2277; 2-F-5-iPr-3-Fu], [2278; 2-F-5-CF3-3-Fu], [2279; 2-F-5-CHF2-3-Fu], [2280; 2-F-5-OMe-3-Fu], [2281; 2-F-5-OEt-3-Fu], [2282; 2-F-5-OCF3-3-Fu], [2283; 2-F-5-OCHF2-3-Fu], [2284; 2-F-5-CN-3-Fu], [2285; 2-F-5-SMe-3-Fu], [2286; 2-F-5-SEt-3-Fu], [2287; 2-F-5-cPr-3-Fu], [2288; 2-Cl-5-F-3-Fu], [2289; 2-Cl-5-Cl-3-Fu], [2290; 2-Cl-5-Br-3-Fu], [2291; 2-Cl-5-I-3-Fu], [2292; 2-Cl-5-Me-3-Fu], [2293; 2-Cl-5-Et-3-Fu], [2294; 2-Cl-5-Pr-3-Fu], [2295; 2-Cl-5-iPr-3-Fu], [2296; 2-Cl-5-CF3-3-Fu], [2297; 2-Cl-5-CHF2-3-Fu], [2298; 2-Cl-5-OMe-3-Fu], [2299; 2-Cl-5-OEt-3-Fu], [2300; 2-Cl-5-OCF3-3-Fu],

[2301; 2-Cl-5-OCHF2-3-Fu], [2302; 2-Cl-5-CN-3-Fu], [2303; 2-Cl-5-SMe-3-Fu], [2304; 2-Cl-5-SEt-3-Fu], [2305; 2-Cl-5-cPr-3-Fu], [2306; 2-Me-5-F-3-Fu], [2307; 2-Me-5-Cl-3-Fu], [2308; 2-Me-5-Br-3-Fu], [2309; 2-Me-5-I-3-Fu], [2310; 2-Me-5-Me-3-Fu], [2311; 2-Me-5-Et-3-Fu], [2312; 2-Me-5-Pr-3-Fu], [2313; 2-Me-5-iPr-3-Fu], [2314; 2-Me-5-CF3-3-Fu], [2315; 2-Me-5-CHF2-3-Fu], [2316; 2-Me-5-OMe-3-Fu], [2317; 2-Me-5-OEt-3-Fu], [2318; 2-Me-5-OCF3-3-Fu], [2319; 2-Me-5-OCHF2-3-Fu], [2320; 2-Me-5-CN-3-Fu], [2321; 2-Me-5-SMe-3-Fu], [2322; 2-Me-5-SEt-3-Fu], [2323; 2-Me-5-cPr-3-Fu], [2324; 2-Et-5-F-3-Fu], [2325; 2-Et-5-Cl-3-Fu], [2326; 2-Et-5-Br-3-Fu], [2327; 2-Et-5-I-3-Fu], [2328; 2-Et-5-Me-3-Fu], [2329; 2-Et-5-Et-3-Fu], [2330; 2-Et-5-Pr-3-Fu], [2331; 2-Et-5-iPr-3-Fu], [2332; 2-Et-5-CF3-3-Fu], [2333; 2-Et-5-CHF2-3-Fu], [2334; 2-Et-5-OMe-3-Fu], [2335; 2-Et-5-OEt-3-Fu], [2336; 2-Et-5-OCF3-3-Fu], [2337; 2-Et-5-OCHF2-3-Fu], [2338; 2-Et-5-CN-3-Fu], [2339; 2-Et-5-SMe-3-Fu], [2340; 2-Et-5-SEt-3-Fu], [2341; 2-Et-5-cPr-3-Fu], [2342; 2-CF3-5-F-3-Fu], [2343; 2-CF3-5-Cl-3-Fu], [2344; 2-CF3-5-Br-3-Fu], [2345; 2-CF3-5-I-3-Fu], [2346; 2-CF3-5-Me-3-Fu], [2347; 2-CF3-5-Et-3-Fu], [2348; 2-CF3-5-Pr-3-Fu], [2349; 2-CF3-5-iPr-3-Fu], [2350; 2-CF3-5-CF3-3-Fu], [2351; 2-CF3-5-CHF2-3-Fu], [2352; 2-CF3-5-OMe-3-Fu], [2353; 2-CF3-5-OEt-3-Fu], [2354; 2-CF3-5-OCF3-3-Fu], [2355; 2-CF3-5-OCHF2-3-Fu], [2356; 2-CF3-5-CN-3-Fu], [2357; 2-CF3-5-SMe-3-Fu], [2358; 2-CF3-5-SEt-3-Fu], [2359; 2-CF3-5-cPr-3-Fu], [2360; 2-OMe-5-F-3-Fu], [2361; 2-OMe-5-Cl-3-Fu], [2362; 2-OMe-5-Br-3-Fu], [2363; 2-OMe-5-I-3-Fu], [2364; 2-OMe-5-Me-3-Fu], [2365; 2-OMe-5-Et-3-Fu], [2366; 2-OMe-5-Pr-3-Fu], [2367; 2-OMe-5-iPr-3-Fu], [2368; 2-OMe-5-CF3-3-Fu], [2369; 2-OMe-5-CHF2-3-Fu], [2370; 2-OMe-5-OMe-3-Fu], [2371; 2-OMe-5-OEt-3-Fu], [2372; 2-OMe-5-OCF3-3-Fu], [2373; 2-OMe-5-OCHF2-3-Fu], [2374; 2-OMe-5-CN-3-Fu], [2375; 2-OMe-5-SMe-3-Fu], [2376; 2-OMe-5-SEt-3-Fu], [2377; 2-OMe-5-cPr-3-Fu], [2378; 2-OEt-5-F-3-Fu], [2379; 2-OEt-5-Cl-3-Fu], [2380; 2-OEt-5-Br-3-Fu], [2381; 2-OEt-5-I-3-Fu], [2382; 2-OEt-5-Me-3-Fu], [2383; 2-OEt-5-Et-3-Fu], [2384; 2-OEt-5-Pr-3-Fu], [2385; 2-OEt-5-iPr-3-Fu], [2386; 2-OEt-5-CF3-3-Fu], [2387; 2-OEt-5-CHF2-3-Fu], [2388; 2-OEt-5-OMe-3-Fu], [2389; 2-OEt-5-OEt-3-Fu], [2390; 2-OEt-5-OCF3-3-Fu], [2391; 2-OEt-5-OCHF2-3-Fu], [2392; 2-OEt-5-CN-3-Fu], [2393; 2-OEt-5-SMe-3-Fu], [2394; 2-OEt-5-SEt-3-Fu], [2395; 2-OEt-5-cPr-3-Fu], [2396; 2-SMe-5-F-3-Fu], [2397; 2-SMe-5-Cl-3-Fu], [2398; 2-SMe-5-Br-3-Fu], [2399; 2-SMe-5-I-3-Fu], [2400; 2-SMe-5-Me-3-Fu],

[2401; 2-SMe-5-Et-3-Fu], [2402; 2-SMe-5-Pr-3-Fu], [2403; 2-SMe-5-iPr-3-Fu], [2404; 2-SMe-5-CF3-3-Fu], [2405; 2-SMe-5-CHF2-3-Fu], [2406; 2-SMe-5-OMe-3-Fu], [2407; 2-SMe-5-OEt-3-Fu], [2408; 2-SMe-5-OCF3-3-Fu], [2409; 2-SMe-5-OCHF2-3-Fu], [2410; 2-SMe-5-CN-3-Fu], [2411; 2-SMe-5-SMe-3-Fu], [2412; 2-SMe-5-SEt-3-Fu], [2413; 2-SMe-5-cPr-3-Fu], [2414; 4-F-3-Fu], [2415; 4-Cl-3-Fu], [2416; 4-Br-3-Fu], [2417; 4-I-3-Fu], [2418; 4-Me-3-Fu], [2419; 4-Et-3-Fu], [2420; 4-Pr-3-Fu], [2421; 4-iPr-3-Fu], [2422; 4-CF3-3-Fu], [2423; 4-CHF2-3-Fu], [2424; 4-OMe-3-Fu], [2425; 4-OEt-3-Fu], [2426; 4-OCF3-3-Fu], [2427; 4-OCHF2-3-Fu], [2428; 2-F-4-F-3-Fu], [2429; 2-Cl-4-F-3-Fu], [2430; 2-Br-4-F-3-Fu], [2431; 2-I-4-F-3-Fu], [2432; 2-Me-4-F-3-Fu], [2433; 2-Et-4-F-3-Fu], [2434; 2-Pr-4-F-3-Fu], [2435; 2-iPr-4-F-3-Fu], [2436; 2-CF3-4-F-3-Fu], [2437; 2-CHF2-4-F-3-Fu], [2438; 2-OMe-4-F-3-Fu], [2439; 2-OEt-4-F-3-Fu], [2440; 2-OCF3-4-F-3-Fu], [2441; 2-OCHF2-4-F-3-Fu], [2442; 2-CN-4-F-3-Fu], [2443; 2-SMe-4-F-3-Fu], [2444; 2-SEt-4-F-3-Fu], [2445; 2-cPr-4-F-3-Fu], [2446; 2-F-4-Cl-3-Fu], [2447; 2-Cl-4-Cl-3-Fu], [2448; 2-Br-4-Cl-3-Fu], [2449; 2-I-4-Cl-3-Fu], [2450; 2-Me-4-Cl-3-Fu], [2451; 2-Et-4-Cl-3-Fu], [2452; 2-Pr-4-Cl-3-Fu], [2453; 2-iPr-4-Cl-3-Fu], [2454; 2-CF3-4-Cl-3-Fu], [2455; 2-CHF2-4-Cl-3-Fu], [2456; 2-OMe-4-Cl-3-Fu], [2457; 2-OEt-4-Cl-3-Fu], [2458; 2-OCF3-4-Cl-3-Fu], [2459; 2-OCHF2-4-Cl-3-Fu], [2460; 2-CN-4-Cl-3-Fu], [2461; 2-SMe-4-Cl-3-Fu], [2462; 2-SEt-4-Cl-3-Fu], [2463; 2-cPr-4-Cl-3-Fu], [2464; 2-F-4-Me-3-Fu], [2465; 2-Cl-4-Me-3-Fu], [2466; 2-Br-4-Me-3-Fu], [2467; 2-I-4-Me-3-Fu], [2468; 2-Me-4-Me-3-Fu], [2469; 2-Et-4-Me-3-Fu], [2470; 2-Pr-4-Me-3-Fu], [2471; 2-iPr-4-Me-3-Fu], [2472; 2-CF3-4-Me-3-Fu], [2473; 2-CHF2-4-Me-3-Fu], [2474; 2-OMe-4-Me-3-Fu], [2475; 2-OEt-4-Me-3-Fu], [2476; 2-OCF3-4-Me-3-Fu], [2477; 2-OCHF2-4-Me-3-Fu], [2478; 2-CN-4-Me-3-Fu], [2479; 2-SMe-4-Me-3-Fu], [2480; 2-SEt-4-Me-3-Fu], [2481; 2-cPr-4-Me-3-Fu], [2482; 2-F-4-Et-3-Fu], [2483; 2-Cl-4-Et-3-Fu], [2484; 2-Br-4-Et-3-Fu], [2485; 2-I-4-Et-3-Fu], [2486; 2-Me-4-Et-3-Fu], [2487; 2-Et-4-Et-3-Fu], [2488; 2-Pr-4-Et-3-Fu], [2489; 2-iPr-4-Et-3-Fu], [2490; 2-CF3-4-Et-3-Fu], [2491; 2-CHF2-4-Et-3-Fu], [2492; 2-OMe-4-Et-3-Fu], [2493; 2-OEt-4-Et-3-Fu], [2494; 2-OCF3-4-Et-3-Fu], [2495; 2-OCHF2-4-Et-3-Fu], [2496; 2-CN-4-Et-3-Fu], [2497; 2-SMe-4-Et-3-Fu], [2498; 2-SEt-4-Et-3-Fu], [2499; 2-cPr-4-Et-3-Fu], [2500; 2-F-4-CF3-3-Fu],

[2501; 2-Cl-4-CF3-3-Fu], [2502; 2-Br-4-CF3-3-Fu], [2503; 2-I-4-CF3-3-Fu], [2504; 2-Me-4-CF3-3-Fu], [2505; 2-Et-4-CF3-3-Fu], [2506; 2-Pr-4-CF3-3-Fu], [2507; 2-iPr-4-CF3-3-Fu], [2508; 2-CF3-4-CF3-3-Fu], [2509; 2-CHF2-4-CF3-3-Fu], [2510; 2-OMe-4-CF3-3-Fu], [2511; 2-OEt-4-CF3-3-Fu], [2512; 2-OCF3-4-CF3-3-Fu], [2513; 2-OCHF2-4-CF3-3-Fu], [2514; 2-CN-4-CF3-3-Fu], [2515; 2-SMe-4-CF3-3-Fu], [2516; 2-SEt-4-CF3-3-Fu], [2517; 2-cPr-4-CF3-3-Fu], [2518; 2-F-4-OMe-3-Fu], [2519; 2-Cl-4-OMe-3-Fu], [2520; 2-Br-4-OMe-3-Fu], [2521; 2-I-4-OMe-3-Fu], [2522; 2-Me-4-OMe-3-Fu], [2523; 2-Et-4-OMe-3-Fu], [2524; 2-Pr-4-OMe-3-Fu], [2525; 2-iPr-4-OMe-3-Fu], [2526; 2-CF3-4-OMe-3-Fu], [2527; 2-CHF2-4-OMe-3-Fu], [2528; 2-OMe-4-OMe-3-Fu], [2529; 2-OEt-4-OMe-3-Fu], [2530; 2-OCF3-4-OMe-3-Fu], [2531; 2-OCHF2-4-OMe-3-Fu], [2532; 2-CN-4-OMe-3-Fu], [2533; 2-SMe-4-OMe-3-Fu], [2534;

2-SEt-4-OMe-3-Fu], [2535; 2-cPr-4-OMe-3-Fu], [2536; 2-F-4-OEt-3-Fu], [2537; 2-Cl-4-OEt-3-Fu], [2538; 2-Br-4-OEt-3-Fu], [2539; 2-I-4-OEt-3-Fu], [2540; 2-Me-4-OEt-3-Fu], [2541; 2-Et-4-OEt-3-Fu], [2542; 2-Pr-4-OEt-3-Fu], [2543; 2-iPr-4-OEt-3-Fu], [2544; 2-CF3-4-OEt-3-Fu], [2545; 2-CHF2-4-OEt-3-Fu], [2546; 2-OMe-4-OEt-3-Fu], [2547; 2-OEt-4-OEt-3-Fu], [2548; 2-OCF3-4-OEt-3-Fu], [2549; 2-OCHF2-4-OEt-3-Fu], [2550; 2-CN-4-OEt-3-Fu], [2551; 2-SMe-4-OEt-3-Fu], [2552; 2-SEt-4-OEt-3-Fu], [2553; 2-cPr-4-OEt-3-Fu], [2554; 2-F-4-SMe-3-Fu], [2555; 2-Cl-4-SMe-3-Fu], [2556; 2-Br-4-SMe-3-Fu], [2557; 2-I-4-SMe-3-Fu], [2558; 2-Me-4-SMe-3-Fu], [2559; 2-Et-4-SMe-3-Fu], [2560; 2-Pr-4-SMe-3-Fu], [2561; 2-iPr-4-SMe-3-Fu], [2562; 2-CF3-4-SMe-3-Fu], [2563; 2-CHF2-4-SMe-3-Fu], [2564; 2-OMe-4-SMe-3-Fu], [2565; 2-OEt-4-SMe-3-Fu], [2566; 2-OCF3-4-SMe-3-Fu], [2567; 2-OCHF2-4-SMe-3-Fu], [2568; 2-CN-4-SMe-3-Fu], [2569; 2-SMe-4-SMe-3-Fu], [2570; 2-SEt-4-SMe-3-Fu], [2571; 2-cPr-4-SMe-3-Fu], [2572; 4-F-5-F-3-Fu], [2573; 4-F-5-Cl-3-Fu], [2574; 4-F-5-Br-3-Fu], [2575; 4-F-5-I-3-Fu], [2576; 4-F-5-Me-3-Fu], [2577; 4-F-5-Et-3-Fu], [2578; 4-F-5-Pr-3-Fu], [2579; 4-F-5-iPr-3-Fu], [2580; 4-F-5-CF3-3-Fu], [2581; 4-F-5-CHF2-3-Fu], [2582; 4-F-5-OMe-3-Fu], [2583; 4-F-5-OEt-3-Fu], [2584; 4-F-5-OCF3-3-Fu], [2585; 4-F-5-OCHF2-3-Fu], [2586; 4-F-5-CN-3-Fu], [2587; 4-F-5-SMe-3-Fu], [2588; 4-F-5-SEt-3-Fu], [2589; 4-F-5-cPr-3-Fu], [2590; 4-Cl-5-F-3-Fu], [2591; 4-Cl-5-Cl-3-Fu], [2592; 4-Cl-5-Br-3-Fu], [2593; 4-Cl-5-I-3-Fu], [2594; 4-Cl-5-Me-3-Fu], [2595; 4-Cl-5-Et-3-Fu], [2596; 4-Cl-5-Pr-3-Fu], [2597; 4-Cl-5-iPr-3-Fu], [2598; 4-Cl-5-CF3-3-Fu], [2599; 4-Cl-5-CHF2-3-Fu], [2600; 4-Cl-5-OMe-3-Fu],

[2601; 4-Cl-5-OEt-3-Fu], [2602; 4-Cl-5-OCF3-3-Fu], [2603; 4-Cl-5-OCHF2-3-Fu], [2604; 4-Cl-5-CN-3-Fu], [2605; 4-Cl-5-SMe-3-Fu], [2606; 4-Cl-5-SEt-3-Fu], [2607; 4-Cl-5-cPr-3-Fu], [2608; 4-Me-5-F-3-Fu], [2609; 4-Me-5-Cl-3-Fu], [2610; 4-Me-5-Br-3-Fu], [2611; 4-Me-5-I-3-Fu], [2612; 4-Me-5-Me-3-Fu], [2613; 4-Me-5-Et-3-Fu], [2614; 4-Me-5-Pr-3-Fu], [2615; 4-Me-5-iPr-3-Fu], [2616; 4-Me-5-CF3-3-Fu], [2617; 4-Me-5-CHF2-3-Fu], [2618; 4-Me-5-OMe-3-Fu], [2619; 4-Me-5-OEt-3-Fu], [2620; 4-Me-5-OCF3-3-Fu], [2621; 4-Me-5-OCHF2-3-Fu], [2622; 4-Me-5-CN-3-Fu], [2623; 4-Me-5-SMe-3-Fu], [2624; 4-Me-5-SEt-3-Fu], [2625; 4-Me-5-cPr-3-Fu], [2626; 4-Et-5-F-3-Fu], [2627; 4-Et-5-Cl-3-Fu], [2628; 4-Et-5-Br-3-Fu], [2629; 4-Et-5-I-3-Fu], [2630; 4-Et-5-Me-3-Fu], [2631; 4-Et-5-Et-3-Fu], [2632; 4-Et-5-Pr-3-Fu], [2633; 4-Et-5-iPr-3-Fu], [2634; 4-Et-5-CF3-3-Fu], [2635; 4-Et-5-CHF2-3-Fu], [2636; 4-Et-5-OMe-3-Fu], [2637; 4-Et-5-OEt-3-Fu], [2638; 4-Et-5-OCF3-3-Fu], [2639; 4-Et-5-OCHF2-3-Fu], [2640; 4-Et-5-CN-3-Fu], [2641; 4-Et-5-SMe-3-Fu], [2642; 4-Et-5-SEt-3-Fu], [2643; 4-Et-5-cPr-3-Fu], [2644; 4-CF3-5-F-3-Fu], [2645; 4-CF3-5-Cl-3-Fu], [2646; 4-CF3-5-Br-3-Fu], [2647; 4-CF3-5-I-3-Fu], [2648; 4-CF3-5-Me-3-Fu], [2649; 4-CF3-5-Et-3-Fu], [2650; 4-CF3-5-Pr-3-Fu], [2651; 4-CF3-5-iPr-3-Fu], [2652; 4-CF3-5-CF3-3-Fu], [2653; 4-CF3-5-CHF2-3-Fu], [2654; 4-CF3-5-OMe-3-Fu], [2655; 4-CF3-5-OEt-3-Fu], [2656; 4-CF3-5-OCF3-3-Fu], [2657; 4-CF3-5-OCHF2-3-Fu], [2658; 4-CF3-5-CN-3-Fu], [2659; 4-CF3-5-SMe-3-Fu], [2660; 4-CF3-5-SEt-3-Fu], [2661; 4-CF3-5-cPr-3-Fu], [2662; 4-OMe-5-F-3-Fu], [2663; 4-OMe-5-Cl-3-Fu], [2664; 4-OMe-5-Br-3-Fu], [2665; 4-OMe-5-I-3-Fu], [2666; 4-OMe-5-Me-3-Fu], [2667; 4-OMe-5-Et-3-Fu], [2668; 4-OMe-5-Pr-3-Fu], [2669; 4-OMe-5-iPr-3-Fu], [2670; 4-OMe-5-CF3-3-Fu], [2671; 4-OMe-5-CHF2-3-Fu], [2672; 4-OMe-5-OMe-3-Fu], [2673; 4-OMe-5-OEt-3-Fu], [2674; 4-OMe-5-OCF3-3-Fu], [2675; 4-OMe-5-OCHF2-3-Fu], [2676; 4-OMe-5-CN-3-Fu], [2677; 4-OMe-5-SMe-3-Fu], [2678; 4-OMe-5-SEt-3-Fu], [2679; 4-OMe-5-cPr-3-Fu], [2680; 4-OEt-5-F-3-Fu], [2681; 4-OEt-5-Cl-3-Fu], [2682; 4-OEt-5-Br-3-Fu], [2683; 4-OEt-5-I-3-Fu], [2684; 4-OEt-5-Me-3-Fu], [2685; 4-OEt-5-Et-3-Fu], [2686; 4-OEt-5-Pr-3-Fu], [2687; 4-OEt-5-iPr-3-Fu], [2688; 4-OEt-5-CF3-3-Fu], [2689; 4-OEt-5-CHF2-3-Fu], [2690; 4-OEt-5-OMe-3-Fu], [2691; 4-OEt-5-OEt-3-Fu], [2692; 4-OEt-5-OCF3-3-Fu], [2693; 4-OEt-5-OCHF2-3-Fu], [2694; 4-OEt-5-CN-3-Fu], [2695; 4-OEt-5-SMe-3-Fu], [2696; 4-OEt-5-SEt-3-Fu], [2697; 4-OEt-5-cPr-3-Fu], [2698; 4-SMe-5-F-3-Fu], [2699; 4-SMe-5-Cl-3-Fu], [2700; 4-SMe-5-Br-3-Fu],

[2701; 4-SMe-5-I-3-Fu], [2702; 4-SMe-5-Me-3-Fu], [2703; 4-SMe-5-Et-3-Fu], [2704; 4-SMe-5-Pr-3-Fu], [2705; 4-SMe-5-iPr-3-Fu], [2706; 4-SMe-5-CF3-3-Fu], [2707; 4-SMe-5-CHF2-3-Fu], [2708; 4-SMe-5-OMe-3-Fu], [2709; 4-SMe-5-OEt-3-Fu], [2710; 4-SMe-5-OCF3-3-Fu], [2711; 4-SMe-5-OCHF2-3-Fu], [2712; 4-SMe-5-CN-3-Fu], [2713; 4-SMe-5-SMe-3-Fu], [2714; 4-SMe-5-SEt-3-Fu], [2715; 4-SMe-5-cPr-3-Fu], [2716; 2-Me-4-Me-5-F-3-Fu], [2717; 2-Me-4-Me-5-Cl-3-Fu], [2718; 2-Me-4-Me-5-Br-3-Fu], [2719; 2-Me-4-Me-5-I-3-Fu], [2720; 2-Me-4-Me-5-Me-3-Fu], [2721; 2-Me-4-Me-5-Et-3-Fu], [2722; 2-Me-4-Me-5-Pr-3-Fu], [2723; 2-Me-4-Me-5-iPr-3-Fu], [2724; 2-Me-4-Me-5-CF3-3-Fu], [2725; 2-Me-4-Me-5-CHF2-3-Fu], [2726; 2-Me-4-Me-5-OMe-3-Fu], [2727; 2-Me-4-Me-5-OEt-3-Fu], [2728; 2-Me-4-Me-5-OCF3-3-Fu], [2729; 2-Me-4-Me-5-OCHF2-3-Fu], [2730; 2-Me-4-Me-5-CN-3-Fu], [2731; 2-Me-4-Me-5-SMe-3-Fu], [2732; 2-Me-4-Me-5-SEt-3-Fu], [2733; 2-Me-4-Me-5-cPr-3-Fu], [2734; 2-F-4-Me-5-Me-3-Fu], [2735; 2-Cl-4-Me-5-Me-3-Fu], [2736; 2-Br-4-Me-5-Me-3-Fu], [2737; 2-I-4-Me-5-Me-3-Fu], [2738; 2-Et-4-Me-5-Me-3-Fu], [2739; 2-Pr-4-Me-5-Me-3-Fu], [2740; 2-iPr-4-Me-5-Me-3-Fu], [2741; 2-CF3-4-Me-5-Me-3-Fu], [2742; 2-CHF2-4-Me-5-Me-3-Fu], [2743; 2-OMe-4-Me-5-Me-3-Fu], [2744; 2-OEt-4-Me-5-Me-3-Fu], [2745; 2-OCF3-4-Me-5-Me-3-Fu], [2746; 2-OCHF2-4-Me-5-Me-3-Fu], [2747; 2-CN-4-Me-5-Me-3-Fu], [2748; 2-SMe-4-Me-5-Me-3-Fu], [2749; 2-SEt-4-Me-5-Me-3-Fu], [2750; 2-cPr-4-Me-5-Me-3-Fu], [2751; 3-Thio], [2752; 2-F-3-Thio], [2753; 2-Cl-3-Thio], [2754; 2-Br-3-Thio], [2755; 2-I-3-Thio], [2756; 2-Me-3-Thio], [2757; 2-Et-3-Thio], [2758; 2-Pr-3-Thio], [2759; 2-iPr-3-Thio], [2760; 2-CF3-3-Thio], [2761; 2-CHF2-3-Thio], [2762; 2-OMe-3-Thio], [2763; 2-OEt-3-Thio], [2764; 2-OCF3-3-Thio], [2765; 2-OCHF2-3-Thio], [2766; 2-CN-3-Thio], [2767; 2-SMe-3-Thio], [2768; 2-SEt-3-Thio], [2769; 2-cPr-3-Thio], [2770; 5-F-3-Thio], [2771; 5-Cl-3-Thio], [2772; 5-Br-3-Thio], [2773; 5-I-3-Thio], [2774; 5-Me-3-Thio], [2775; 5-Et-3-Thio], [2776; 5-Pr-3-Thio], [2777; 5-iPr-3-Thio], [2778; 5-CF3-3-Thio], [2779; 5-CHF2-3-Thio], [2780; 5-OMe-3-Thio], [2781; 5-OEt-3-Thio], [2782; 5-OCF3-3-Thio], [2783; 5-OCHF2-3-Thio], [2784; 5-CN-3-Thio], [2785; 5-SMe-3-Thio], [2786; 5-SEt-3-Thio], [2787; 5-cPr-3-Thio], [2788; 2-F-5-F-3-Thio], [2789; 2-F-5-Cl-3-Thio], [2790; 2-F-5-Br-3-Thio], [2791; 2-F-5-I-3-Thio], [2792; 2-F-5-Me-3-Thio], [2793; 2-F-5-Et-3-Thio], [2794; 2-F-5-Pr-3-Thio], [2795; 2-F-5-iPr-3-Thio], [2796; 2-F-5-CF3-3-Thio], [2797; 2-F-5-CHF2-3-Thio], [2798; 2-F-5-OMe-3-Thio], [2799; 2-F-5-OEt-3-Thio], [2800; 2-F-5-OCF3-3-Thio],

[2801; 2-F-5-OCHF2-3-Thio], [2802; 2-F-5-CN-3-Thio], [2803; 2-F-5-SMe-3-Thio], [2804; 2-F-5-SEt-3-Thio], [2805; 2-F-5-cPr-3-Thio], [2806; 2-Cl-5-F-3-Thio], [2807; 2-Cl-5-Cl-3-Thio], [2808; 2-Cl-5-Br-3-Thio], [2809; 2-Cl-5-I-3-Thio], [2810; 2-Cl-5-Me-3-Thio], [2811; 2-Cl-5-Et-3-Thio], [2812; 2-Cl-5-Pr-3-Thio], [2813; 2-Cl-5-iPr-3-Thio], [2814; 2-Cl-5-CF3-3-Thio], [2815; 2-Cl-5-CHF2-3-Thio], [2816; 2-Cl-5-OMe-3-Thio], [2817; 2-Cl-5-OEt-3-Thio],

[2818; 2-Cl-5-OCF3-3-Thio], [2819; 2-Cl-5-OCHF2-3-Thio], [2820; 2-Cl-5-CN-3-Thio], [2821; 2-Cl-5-SMe-3-Thio], [2822; 2-Cl-5-SEt-3-Thio], [2823; 2-Cl-5-cPr-3-Thio], [2824; 2-Me-5-F-3-Thio], [2825; 2-Me-5-Cl-3-Thio], [2826; 2-Me-5-Br-3-Thio], [2827; 2-Me-5-I-3-Thio], [2828; 2-Me-5-Me-3-Thio], [2829; 2-Me-5-Et-3-Thio], [2830; 2-Me-5-Pr-3-Thio], [2831; 2-Me-5-iPr-3-Thio], [2832; 2-Me-5-CF3-3-Thio], [2833; 2-Me-5-CHF2-3-Thio], [2834; 2-Me-5-OMe-3-Thio], [2835; 2-Me-5-OEt-3-Thio], [2836; 2-Me-5-OCF3-3-Thio], [2837; 2-Me-5-OCHF2-3-Thio], [2838; 2-Me-5-CN-3-Thio], [2839; 2-Me-5-SMe-3-Thio], [2840; 2-Me-5-SEt-3-Thio], [2841; 2-Me-5-cPr-3-Thio], [2842; 2-Et-5-F-3-Thio], [2843; 2-Et-5-Cl-3-Thio], [2844; 2-Et-5-Br-3-Thio], [2845; 2-Et-5-I-3-Thio], [2846; 2-Et-5-Me-3-Thio], [2847; 2-Et-5-Et-3-Thio], [2848; 2-Et-5-Pr-3-Thio], [2849; 2-Et-5-iPr-3-Thio], [2850; 2-Et-5-CF3-3-Thio], [2851; 2-Et-5-CHF2-3-Thio], [2852; 2-Et-5-OMe-3-Thio], [2853; 2-Et-5-OEt-3-Thio], [2854; 2-Et-5-OCF3-3-Thio], [2855; 2-Et-5-OCHF2-3-Thio], [2856; 2-Et-5-CN-3-Thio], [2857; 2-Et-5-SMe-3-Thio], [2858; 2-Et-5-SEt-3-Thio], [2859; 2-Et-5-cPr-3-Thio], [2860; 2-CF3-5-F-3-Thio], [2861; 2-CF3-5-Cl-3-Thio], [2862; 2-CF3-5-Br-3-Thio], [2863; 2-CF3-5-I-3-Thio], [2864; 2-CF3-5-Me-3-Thio], [2865; 2-CF3-5-Et-3-Thio], [2866; 2-CF3-5-Pr-3-Thio], [2867; 2-CF3-5-iPr-3-Thio], [2868; 2-CF3-5-CF3-3-Thio], [2869; 2-CF3-5-CHF2-3-Thio], [2870; 2-CF3-5-OMe-3-Thio], [2871; 2-CF3-5-OEt-3-Thio], [2872; 2-CF3-5-OCF3-3-Thio], [2873; 2-CF3-5-OCHF2-3-Thio], [2874; 2-CF3-5-CN-3-Thio], [2875; 2-CF3-5-SMe-3-Thio], [2876; 2-CF3-5-SEt-3-Thio], [2877; 2-CF3-5-cPr-3-Thio], [2878; 2-OMe-5-F-3-Thio], [2879; 2-OMe-5-Cl-3-Thio], [2880; 2-OMe-5-Br-3-Thio], [2881; 2-OMe-5-I-3-Thio], [2882; 2-OMe-5-Me-3-Thio], [2883; 2-OMe-5-Et-3-Thio], [2884; 2-OMe-5-Pr-3-Thio], [2885; 2-OMe-5-iPr-3-Thio], [2886; 2-OMe-5-CF3-3-Thio], [2887; 2-OMe-5-CHF2-3-Thio], [2888; 2-OMe-5-OMe-3-Thio], [2889; 2-OMe-5-OEt-3-Thio], [2890; 2-OMe-5-OCF3-3-Thio], [2891; 2-OMe-5-OCHF2-3-Thio], [2892; 2-OMe-5-CN-3-Thio], [2893; 2-OMe-5-SMe-3-Thio], [2894; 2-OMe-5-SEt-3-Thio], [2895; 2-OMe-5-cPr-3-Thio], [2896; 2-OEt-5-F-3-Thio], [2897; 2-OEt-5-Cl-3-Thio], [2898; 2-OEt-5-Br-3-Thio], [2899; 2-OEt-5-I-3-Thio], [2900; 2-OEt-5-Me-3-Thio],

[2901; 2-OEt-5-Et-3-Thio], [2902; 2-OEt-5-Pr-3-Thio], [2903; 2-OEt-5-iPr-3-Thio], [2904; 2-OEt-5-CF3-3-Thio], [2905; 2-OEt-5-CHF2-3-Thio], [2906; 2-OEt-5-OMe-3-Thio], [2907; 2-OEt-5-OEt-3-Thio], [2908; 2-OEt-5-OCF3-3-Thio], [2909; 2-OEt-5-OCHF2-3-Thio], [2910; 2-OEt-5-CN-3-Thio], [2911; 2-OEt-5-SMe-3-Thio], [2912; 2-OEt-5-SEt-3-Thio], [2913; 2-OEt-5-cPr-3-Thio], [2914; 2-SMe-5-F-3-Thio], [2915; 2-SMe-5-Cl-3-Thio], [2916; 2-SMe-5-Br-3-Thio], [2917; 2-SMe-5-I-3-Thio], [2918; 2-SMe-5-Me-3-Thio], [2919; 2-SMe-5-Et-3-Thio], [2920; 2-SMe-5-Pr-3-Thio], [2921; 2-SMe-5-iPr-3-Thio], [2922; 2-SMe-5-CF3-3-Thio], [2923; 2-SMe-5-CHF2-3-Thio], [2924; 2-SMe-5-OMe-3-Thio], [2925; 2-SMe-5-OEt-3-Thio], [2926; 2-SMe-5-OCF3-3-Thio], [2927; 2-SMe-5-OCHF2-3-Thio], [2928; 2-SMe-5-CN-3-Thio], [2929; 2-SMe-5-SMe-3-Thio], [2930; 2-SMe-5-SEt-3-Thio], [2931; 2-SMe-5-cPr-3-Thio], [2932; 4-F-3-Thio], [2933; 4-Cl-3-Thio], [2934; 4-Br-3-Thio], [2935; 4-I-3-Thio], [2936; 4-Me-3-Thio], [2937; 4-Et-3-Thio], [2938; 4-Pr-3-Thio], [2939; 4-iPr-3-Thio], [2940; 4-CF3-3-Thio], [2941; 4-CHF2-3-Thio], [2942; 4-OMe-3-Thio], [2943; 4-OEt-3-Thio], [2944; 4-OCF3-3-Thio], [2945; 4-OCHF2-3-Thio], [2946; 2-F-4-F-3-Thio], [2947; 2-Cl-4-F-3-Thio], [2948; 2-Br-4-F-3-Thio], [2949; 2-I-4-F-3-Thio], [2950; 2-Me-4-F-3-Thio], [2951; 2-Et-4-F-3-Thio], [2952; 2-Pr-4-F-3-Thio], [2953; 2-iPr-4-F-3-Thio], [2954; 2-CF3-4-F-3-Thio], [2955; 2-CHF2-4-F-3-Thio], [2956; 2-OMe-4-F-3-Thio], [2957; 2-OEt-4-F-3-Thio], [2958; 2-OCF3-4-F-3-Thio], [2959; 2-OCHF2-4-F-3-Thio], [2960; 2-CN-4-F-3-Thio], [2961; 2-SMe-4-F-3-Thio], [2962; 2-SEt-4-F-3-Thio], [2963; 2-cPr-4-F-3-Thio], [2964; 2-F-4-Cl-3-Thio], [2965; 2-Cl-4-Cl-3-Thio], [2966; 2-Br-4-Cl-3-Thio], [2967; 2-I-4-Cl-3-Thio], [2968; 2-Me-4-Cl-3-Thio], [2969; 2-Et-4-Cl-3-Thio], [2970; 2-Pr-4-Cl-3-Thio], [2971; 2-iPr-4-Cl-3-Thio], [2972; 2-CF3-4-Cl-3-Thio], [2973; 2-CHF2-4-Cl-3-Thio], [2974; 2-OMe-4-Cl-3-Thio], [2975; 2-OEt-4-Cl-3-Thio], [2976; 2-OCF3-4-Cl-3-Thio], [2977; 2-OCHF2-4-Cl-3-Thio], [2978; 2-CN-4-Cl-3-Thio], [2979; 2-SMe-4-Cl-3-Thio], [2980; 2-SEt-4-Cl-3-Thio], [2981; 2-cPr-4-Cl-3-Thio], [2982; 2-F-4-Me-3-Thio], [2983; 2-Cl-4-Me-3-Thio], [2984; 2-Br-4-Me-3-Thio], [2985; 2-I-4-Me-3-Thio], [2986; 2-Me-4-Me-3-Thio], [2987; 2-Et-4-Me-3-Thio], [2988; 2-Pr-4-Me-3-Thio], [2989; 2-iPr-4-Me-3-Thio], [2990; 2-CF3-4-Me-3-Thio], [2991; 2-CHF2-4-Me-3-Thio], [2992; 2-OMe-4-Me-3-Thio], [2993; 2-OEt-4-Me-3-Thio], [2994; 2-OCF3-4-Me-3-Thio], [2995; 2-OCHF2-4-Me-3-Thio], [2996; 2-CN-4-Me-3-Thio], [2997; 2-SMe-4-Me-3-Thio], [2998; 2-SEt-4-Me-3-Thio], [2999; 2-cPr-4-Me-3-Thio], [3000; 2-F-4-Et-3-Thio],

[3001; 2-Cl-4-Et-3-Thio], [3002; 2-Br-4-Et-3-Thio], [3003; 2-I-4-Et-3-Thio], [3004; 2-Me-4-Et-3-Thio], [3005; 2-Et-4-Et-3-Thio], [3006; 2-Pr-4-Et-3-Thio], [3007; 2-iPr-4-Et-3-Thio], [3008; 2-CF3-4-Et-3-Thio], [3009; 2-CHF2-4-Et-3-Thio], [3010; 2-OMe-4-Et-3-Thio], [3011; 2-OEt-4-Et-3-Thio], [3012; 2-OCF3-4-Et-3-Thio], [3013; 2-OCHF2-4-Et-3-Thio], [3014; 2-CN-4-Et-3-Thio], [3015; 2-SMe-4-Et-3-Thio], [3016; 2-SEt-4-Et-3-Thio], [3017; 2-cPr-4-Et-3-Thio], [3018; 2-F-4-CF3-3-Thio], [3019; 2-Cl-4-CF3-3-Thio], [3020; 2-Br-4-CF3-3-Thio], [3021; 2-I-4-CF3-3-Thio], [3022; 2-Me-4-CF3-3-Thio], [3023; 2-Et-4-CF3-3-Thio], [3024; 2-Pr-4-CF3-3-Thio], [3025; 2-iPr-4-CF3-3-Thio], [3026; 2-CF3-4-CF3-3-Thio], [3027; 2-CHF2-4-CF3-3-Thio], [3028; 2-OMe-4-CF3-3-Thio], [3029; 2-OEt-4-CF3-3-Thio], [3030; 2-OCF3-4-CF3-3-Thio], [3031; 2-OCHF2-4-CF3-3-Thio], [3032; 2-CN-4-CF3-3-Thio], [3033; 2-SMe-4-CF3-3-Thio], [3034; 2-SEt-4-CF3-3-Thio], [3035; 2-cPr-4-CF3-3-Thio], [3036; 2-F-4-OMe-3-Thio], [3037; 2-Cl-4-OMe-3-Thio], [3038; 2-Br-4-OMe-3-Thio], [3039; 2-I-4-OMe-3-Thio], [3040; 2-Me-4-OMe-3-Thio], [3041; 2-Et-4-OMe-3-Thio], [3042; 2-Pr-4-OMe-3-Thio], [3043; 2-iPr-4-OMe-3-Thio], [3044; 2-CF3-4-OMe-3-Thio], [3045; 2-CHF2-4-OMe-3-Thio], [3046; 2-OMe-4-OMe-3-Thio], [3047; 2-OEt-4-OMe-3-Thio], [3048; 2-OCF3-4-OMe-3-Thio], [3049; 2-OCHF2-4-OMe-3-Thio], [3050; 2-CN-4-OMe-3-Thio], [3051; 2-SMe-4-OMe-3-Thio], [3052; 2-SEt-4-OMe-3-Thio], [3053; 2-cPr-4-OMe-3-Thio], [3054; 2-F-4-OEt-3-Thio], [3055; 2-Cl-4-OEt-3-Thio], [3056; 2-Br-4-OEt-3-Thio], [3057; 2-I-4-OEt-3-Thio], [3058; 2-Me-4-OEt-3-Thio], [3059; 2-Et-4-OEt-3-Thio], [3060; 2-Pr-4-OEt-3-Thio], [3061; 2-iPr-4-OEt-3-Thio], [3062; 2-CF3-4-OEt-3-Thio], [3063; 2-CHF2-4-OEt-3-Thio], [3064; 2-OMe-4-OEt-3-Thio], [3065; 2-OEt-4-OEt-3-Thio], [3066; 2-OCF3-4-OEt-3-Thio], [3067; 2-OCHF2-4-OEt-3-Thio], [3068; 2-CN-4-OEt-3-Thio], [3069; 2-SMe-4-OEt-3-Thio], [3070; 2-SEt-4-OEt-3-Thio], [3071; 2-cPr-4-OEt-3-Thio], [3072; 2-F-4-SMe-3-Thio], [3073; 2-Cl-4-SMe-3-Thio], [3074; 2-Br-4-SMe-3-Thio], [3075; 2-I-4-SMe-3-Thio], [3076; 2-Me-4-SMe-3-Thio], [3077; 2-Et-4-SMe-3-Thio], [3078; 2-Pr-4-SMe-3-Thio], [3079; 2-iPr-4-SMe-3-Thio], [3080; 2-CF3-4-SMe-3-Thio], [3081; 2-CHF2-4-SMe-3-Thio], [3082; 2-OMe-4-SMe-3-Thio], [3083; 2-OEt-4-SMe-3-Thio], [3084; 2-OCF3-4-

SMe-3-Thio], [3085; 2-OCHF2-4-SMe-3-Thio], [3086; 2-CN-4-SMe-3-Thio], [3087; 2-SMe-4-SMe-3-Thio], [3088; 2-SEt-4-SMe-3-Thio], [3089; 2-cPr-4-SMe-3-Thio], [3090; 4-F-5-F-3-Thio], [3091; 4-F-5-Cl-3-Thio], [3092; 4-F-5-Br-3-Thio], [3093; 4-F-5-I-3-Thio], [3094; 4-F-5-Me-3-Thio], [3095; 4-F-5-Et-3-Thio], [3096; 4-F-5-Pr-3-Thio], [3097; 4-F-5-iPr-3-Thio], [3098; 4-F-5-CF3-3-Thio], [3099; 4-F-5-CHF2-3-Thio], [3100; 4-F-5-OMe-3-Thio],

[3101; 4-F-5-OEt-3-Thio], [3102; 4-F-5-OCF3-3-Thio], [3103; 4-F-5-OCHF2-3-Thio], [3104; 4-F-5-CN-3-Thio], [3105; 4-F-5-SMe-3-Thio], [3106; 4-F-5-SEt-3-Thio], [3107; 4-F-5-cPr-3-Thio], [3108; 4-Cl-5-F-3-Thio], [3109; 4-Cl-5-Cl-3-Thio], [3110; 4-Cl-5-Br-3-Thio], [3111; 4-Cl-5-I-3-Thio], [3112; 4-Cl-5-Me-3-Thio], [3113; 4-Cl-5-Et-3-Thio], [3114; 4-Cl-5-Pr-3-Thio], [3115; 4-Cl-5-iPr-3-Thio], [3116; 4-Cl-5-CF3-3-Thio], [3117; 4-Cl-5-CHF2-3-Thio], [3118; 4-Cl-5-OMe-3-Thio], [3119; 4-Cl-5-OEt-3-Thio], [3120; 4-Cl-5-OCF3-3-Thio], [3121; 4-Cl-5-OCHF2-3-Thio], [3122; 4-Cl-5-CN-3-Thio], [3123; 4-Cl-5-SMe-3-Thio], [3124; 4-Cl-5-SEt-3-Thio], [3125; 4-Cl-5-cPr-3-Thio], [3126; 4-Me-5-F-3-Thio], [3127; 4-Me-5-Cl-3-Thio], [3128; 4-Me-5-Br-3-Thio], [3129; 4-Me-5-I-3-Thio], [3130; 4-Me-5-Me-3-Thio], [3131; 4-Me-5-Et-3-Thio], [3132; 4-Me-5-Pr-3-Thio], [3133; 4-Me-5-iPr-3-Thio], [3134; 4-Me-5-CF3-3-Thio], [3135; 4-Me-5-CHF2-3-Thio], [3136; 4-Me-5-OMe-3-Thio], [3137; 4-Me-5-OEt-3-Thio], [3138; 4-Me-5-OCF3-3-Thio], [3139; 4-Me-5-OCHF2-3-Thio], [3140; 4-Me-5-CN-3-Thio], [3141; 4-Me-5-SMe-3-Thio], [3142; 4-Me-5-SEt-3-Thio], [3143; 4-Me-5-cPr-3-Thio], [3144; 4-Et-5-F-3-Thio], [3145; 4-Et-5-Cl-3-Thio], [3146; 4-Et-5-Br-3-Thio], [3147; 4-Et-5-I-3-Thio], [3148; 4-Et-5-Me-3-Thio], [3149; 4-Et-5-Et-3-Thio], [3150; 4-Et-5-Pr-3-Thio], [3151; 4-Et-5-iPr-3-Thio], [3152; 4-Et-5-CF3-3-Thio], [3153; 4-Et-5-CHF2-3-Thio], [3154; 4-Et-5-OMe-3-Thio], [3155; 4-Et-5-OEt-3-Thio], [3156; 4-Et-5-OCF3-3-Thio], [3157; 4-Et-5-OCHF2-3-Thio], [3158; 4-Et-5-CN-3-Thio], [3159; 4-Et-5-SMe-3-Thio], [3160; 4-Et-5-SEt-3-Thio], [3161; 4-Et-5-cPr-3-Thio], [3162; 4-CF3-5-F-3-Thio], [3163; 4-CF3-5-Cl-3-Thio], [3164; 4-CF3-5-Br-3-Thio], [3165; 4-CF3-5-I-3-Thio], [3166; 4-CF3-5-Me-3-Thio], [3167; 4-CF3-5-Et-3-Thio], [3168; 4-CF3-5-Pr-3-Thio], [3169; 4-CF3-5-iPr-3-Thio], [3170; 4-CF3-5-CF3-3-Thio], [3171; 4-CF3-5-CHF2-3-Thio], [3172; 4-CF3-5-OMe-3-Thio], [3173; 4-CF3-5-OEt-3-Thio], [3174; 4-CF3-5-OCF3-3-Thio], [3175; 4-CF3-5-OCHF2-3-Thio], [3176; 4-CF3-5-CN-3-Thio], [3177; 4-CF3-5-SMe-3-Thio], [3178; 4-CF3-5-SEt-3-Thio], [3179; 4-CF3-5-cPr-3-Thio], [3180; 4-OMe-5-F-3-Thio], [3181; 4-OMe-5-Cl-3-Thio], [3182; 4-OMe-5-Br-3-Thio], [3183; 4-OMe-5-I-3-Thio], [3184; 4-OMe-5-Me-3-Thio], [3185; 4-OMe-5-Et-3-Thio], [3186; 4-OMe-5-Pr-3-Thio], [3187; 4-OMe-5-iPr-3-Thio], [3188; 4-OMe-5-CF3-3-Thio], [3189; 4-OMe-5-CHF2-3-Thio], [3190; 4-OMe-5-OMe-3-Thio], [3191; 4-OMe-5-OEt-3-Thio], [3192; 4-OMe-5-OCF3-3-Thio], [3193; 4-OMe-5-OCHF2-3-Thio], [3194; 4-OMe-5-CN-3-Thio], [3195; 4-OMe-5-SMe-3-Thio], [3196; 4-OMe-5-SEt-3-Thio], [3197; 4-OMe-5-cPr-3-Thio], [3198; 4-OEt-5-F-3-Thio], [3199; 4-OEt-5-Cl-3-Thio], [3200; 4-OEt-5-Br-3-Thio],

[3201; 4-OEt-5-I-3-Thio], [3202; 4-OEt-5-Me-3-Thio], [3203; 4-OEt-5-Et-3-Thio], [3204; 4-OEt-5-Pr-3-Thio], [3205; 4-OEt-5-iPr-3-Thio], [3206; 4-OEt-5-CF3-3-Thio], [3207; 4-OEt-5-CHF2-3-Thio], [3208; 4-OEt-5-OMe-3-Thio], [3209; 4-OEt-5-OEt-3-Thio], [3210; 4-OEt-5-OCF3-3-Thio], [3211; 4-OEt-5-OCHF2-3-Thio], [3212; 4-OEt-5-CN-3-Thio], [3213; 4-OEt-5-SMe-3-Thio], [3214; 4-OEt-5-SEt-3-Thio], [3215; 4-OEt-5-cPr-3-Thio], [3216; 4-SMe-5-F-3-Thio], [3217; 4-SMe-5-Cl-3-Thio], [3218; 4-SMe-5-Br-3-Thio], [3219; 4-SMe-5-I-3-Thio], [3220; 4-SMe-5-Me-3-Thio], [3221; 4-SMe-5-Et-3-Thio], [3222; 4-SMe-5-Pr-3-Thio], [3223; 4-SMe-5-iPr-3-Thio], [3224; 4-SMe-5-CF3-3-Thio], [3225; 4-SMe-5-CHF2-3-Thio], [3226; 4-SMe-5-OMe-3-Thio], [3227; 4-SMe-5-OEt-3-Thio], [3228; 4-SMe-5-OCF3-3-Thio], [3229; 4-SMe-5-OCHF2-3-Thio], [3230; 4-SMe-5-CN-3-Thio], [3231; 4-SMe-5-SMe-3-Thio], [3232; 4-SMe-5-SEt-3-Thio], [3233; 4-SMe-5-cPr-3-Thio], [3234; 2-Me-4-Me-5-F-3-Thio], [3235; 2-Me-4-Me-5-Cl-3-Thio], [3236; 2-Me-4-Me-5-Br-3-Thio], [3237; 2-Me-4-Me-5-I-3-Thio], [3238; 2-Me-4-Me-5-Me-3-Thio], [3239; 2-Me-4-Me-5-Et-3-Thio], [3240; 2-Me-4-Me-5-Pr-3-Thio], [3241; 2-Me-4-Me-5-iPr-3-Thio], [3242; 2-Me-4-Me-5-CF3-3-Thio], [3243; 2-Me-4-Me-5-CHF2-3-Thio], [3244; 2-Me-4-Me-5-OMe-3-Thio], [3245; 2-Me-4-Me-5-OEt-3-Thio], [3246; 2-Me-4-Me-5-OCF3-3-Thio], [3247; 2-Me-4-Me-5-OCHF2-3-Thio], [3248; 2-Me-4-Me-5-CN-3-Thio], [3249; 2-Me-4-Me-5-SMe-3-Thio], [3250; 2-Me-4-Me-5-SEt-3-Thio], [3251; 2-Me-4-Me-5-cPr-3-Thio], [3252; 2-F-4-Me-5-Me-3-Thio], [3253; 2-Cl-4-Me-5-Me-3-Thio], [3254; 2-Br-4-Me-5-Me-3-Thio], [3255; 2-I-4-Me-5-Me-3-Thio], [3256; 2-Et-4-Me-5-Me-3-Thio], [3257; 2-Pr-4-Me-5-Me-3-Thio], [3258; 2-iPr-4-Me-5-Me-3-Thio], [3259; 2-CF3-4-Me-5-Me-3-Thio], [3260; 2-CHF2-4-Me-5-Me-3-Thio], [3261; 2-OMe-4-Me-5-Me-3-Thio], [3262; 2-OEt-4-Me-5-Me-3-Thio], [3263; 2-OCF3-4-Me-5-Me-3-Thio], [3264; 2-OCHF2-4-Me-5-Me-3-Thio], [3265; 2-CN-4-Me-5-Me-3-Thio], [3266; 2-SMe-4-Me-5-Me-3-Thio], [3267; 2-SEt-4-Me-5-Me-3-Thio], [3268; 2-cPr-4-Me-5-Me-3-Thio],

[3383; 2-Tri], [3384; 4-F-2-Tri], [3385; 4-Cl-2-Tri], [3386; 4-Br-2-Tri], [3387; 4-Me-2-Tri], [3388; 4-Et-2-Tri], [3389; 4-OMe-2-Tri], [3390; 4-SMe-2-Tri], [3391; 4-CF3-2-Tri], [3392; 4-F-5-F-2-Tri], [3393; 4-F-5-Cl-2-Tri], [3394; 4-F-5-Br-2-Tri], [3395; 4-F-5-Me-2-Tri], [3396; 4-F-5-Et-2-Tri], [3397; 4-F-5-OMe-2-Tri], [3398; 4-F-5-SMe-2-Tri], [3399; 4-F-5-CF3-2-Tri], [3400; 4-Me-5-F-2-Tri],

[3401; 4-Me-5-Cl-2-Tri], [3402; 4-Me-5-Br-2-Tri], [3403; 4-Me-5-Me-2-Tri], [3404; 4-Me-5-Et-2-Tri], [3405; 4-Me-5-OMe-2-Tri], [3406; 4-Me-5-SMe-2-Tri], [3407; 4-Me-5-CF3-2-Tri], [3408; 4-OMe-5-F-2-Tri], [3409; 4-OMe-5-Cl-2-Tri], [3410; 4-OMe-5-Br-2-Tri], [3411; 4-OMe-5-Me-2-Tri], [3412; 4-OMe-5-Et-2-Tri], [3413; 4-OMe-5-OMe-2-Tri], [3414; 4-OMe-5-SMe-2-Tri], [3415; 4-OMe-5-CF3-2-Tri], [3416; 1-Tri], [3417; 4-F-1-Tri], [3418; 4-Cl-1-Tri], [3419; 4-Br-1-Tri], [3420; 4-Me-1-Tri], [3421; 4-Et-1-Tri], [3422; 4-OMe-1-Tri], [3423; 4-SMe-1-Tri], [3424; 4-CF3-1-Tri], [3425; 5-F-1-Tri], [3426; 5-Cl-1-Tri], [3427; 5-Br-1-Tri], [3428; 5-Me-1-Tri], [3429; 5-Et-1-Tri], [3430; 5-OMe-1-Tri], [3431; 5-SMe-1-Tri], [3432; 5-CF3-1-Tri], [3433; 4-F-5-F-1-Tri], [3434; 4-F-5-Cl-1-Tri], [3435; 4-F-5-Br-1-Tri], [3436; 4-F-5-Me-1-Tri], [3437; 4-F-5-Et-1-Tri], [3438; 4-F-5-OMe-1-Tri], [3439; 4-F-5-SMe-1-Tri], [3440; 4-F-5-CF3-1-Tri], [3441; 4-Me-5-F-1-Tri], [3442; 4-Me-5-Cl-1-Tri], [3443; 4-Me-5-Br-1-Tri], [3444; 4-Me-5-Me-1-Tri], [3445; 4-Me-5-Et-1-Tri], [3446; 4-Me-5-OMe-1-Tri], [3447; 4-Me-5-SMe-1-Tri], [3448; 4-Me-5-CF3-1-Tri], [3449; 4-OMe-5-F-1-Tri], [3450; 4-OMe-5-Cl-1-Tri], [3451; 4-OMe-5-Br-1-Tri], [3452; 4-OMe-5-Me-1-Tri], [3453; 4-OMe-5-Et-1-Tri], [3454; 4-OMe-5-OMe-1-Tri], [3455; 4-OMe-5-SMe-1-Tri], [3456; 4-OMe-5-CF3-1-Tri],

[3854; 2-oxazolin-4-yl], [3855; 2-Me-2-oxazolin-4-yl], [3856; 4-Me-2-oxazolin-4-yl], [3857; 5-Me-2-oxazolin-4-yl], [3858; 2-Me-4-Me-2-oxazolin-4-yl], [3859; 2-Me-5-Me-2-oxazolin-4-yl], [3860; 4-Me-5-Me-2-oxazolin-4-yl], [3861; 5,5-diMe-2-oxazolin-4-yl], [3862; 2-Me-4-Me-5-

Me-2-oxazolin-5-yl], [3863; 2-oxazolin-5-yl], [3864; 2-Me-2-oxazolin-5-yl], [3865; 5-Me-2-oxazolin-5-yl], [3866; 4-Me-2-oxazolin-5-yl], [3867; 2-Me-5-Me-2-oxazolin-5-yl], [3868; 2-Me-4-Me-2-oxazolin-5-yl], [3869; 5-Me-4-Me-2-oxazolin-5-yl], [3870; 4,4-diMe-2-oxazolin-5-yl], [3871; 2-Me-5-Me-4-Me-2-oxazolin-5-yl], [3872; 3-oxazolin-2-yl], [3873; 2-Me-3-oxazolin-2-yl], [3874; 4-Me-3-oxazolin-2-yl], [3875; 5-Me-3-oxazolin-2-yl], [3876; 2-Me-4-Me-3-oxazolin-2-yl], [3877; 2-Me-5-Me-3-oxazolin-2-yl], [3878; 4-Me-5-Me-3-oxazolin-2-yl], [3879; 5,5-diMe-3-oxazolin-2-yl], [3880; 2-Me-4-Me-5-Me-3-oxazolin-2-yl], [3881; 3-oxazolin-4-yl], [3882; 2-Me-3-oxazolin-4-yl], [3883; 5-Me-3-oxazolin-4-yl], [3884; 2,2-diMe-3-oxazolin-4-yl], [3885; 5,5-diMe-3-oxazolin-4-yl], [3886; 2-Me-5-Me-3-oxazolin-4-yl], [3887; 3-oxazolin-5-yl], [3888; 2-Me-3-oxazolin-5-yl], [3889; 4-Me-3-oxazolin-5-yl], [3890; 5-Me-3-oxazolin-5-yl], [3891; 2-Me-2-Me-3-oxazolin-5-yl], [3892; 2-Me-4-Me-3-oxazolin-5-yl], [3893; 2-Me-5-Me-3-oxazolin-5-yl], [3894; 4-Me-5-Me-3-oxazolin-5-yl], [3895; 2-Me-4-Me-5-Me-3-oxazolin-5-yl], [3896; N-Me-4-oxazolin-2-yl], [3897; 2-Me-N-Me-4-oxazolin-2-yl], [3898; 4-Me-N-Me-4-oxazolin-2-yl], [3899; 5-Me-N-Me-4-oxazolin-2-yl], [3900; 2-Me-5-Me-N-Me-4-oxazolin-2-yl],

[3901; 4-Me-5-Me-N-Me-4-oxazolin-2-yl], [3902; 2-Me-4-Me-5-Me-N-Me-4-oxazolin-2-yl], [3903; 2-Me-4-Me-N-Me-4-oxazolin-2-yl], [3904; N-Me-4-oxazolin-4-yl], [3905; 2-Me-N-Me-4-oxazolin-4-yl], [3906; 5-Me-N-Me-4-oxazolin-4-yl], [3907; 2-Me-5-Me-N-Me-4-oxazolin-4-yl], [3908; 2,2,5,N-tetraMe-4-oxazolin-4-yl], [3909; N-Me-4-oxazolin-5-yl], [3910; 2-Me-N-Me-4-oxazolin-5-yl], [3911; 5-Me-N-Me-4-oxazolin-5-yl], [3912; 2-Me-5-Me-N-Me-4-oxazolin-5-yl], [3913; 2,2,5,N-tetraMe-4-oxazolin-5-yl], [3914; oxazolidin-2-on-4-yl], [3915; 4-Me-oxazolidin-2-on-4-yl], [3916; 5-Me-oxazolidin-2-on-4-yl], [3917; 4-Me-5-Me-oxazolidin-2-on-4-yl], [3918; 5-Me-5-Me-oxazolidin-2-on-4-yl], [3919; -oxazolidin-2-on-5-yl], [3920; 4-Me-oxazolidin-2-on-5-yl], [3921; 5-Me-oxazolidin-2-on-5-yl], [3922; 4-Me-5-Me-oxazolidin-2-on-5-yl], [3923; 4,4-diMe-oxazolidin-2-on-5-yl], [3924; N-Me-oxazolidin-4-on-2-yl], [3925; 2-Me-N-Me-oxazolidin-4-on-2-yl], [3926; 5-Me-N-Me-oxazolidin-4-on-2-yl], [3927; 2-Me-5-Me-N-Me-oxazolidin-4-on-2-yl], [3928; 2,5,5,N-tetraMe-oxazolidin-4-on-2-yl], [3929; N-Me-oxazolidin-4-on-5-yl], [3930; 2-Me-N-Me-oxazolidin-4-on-5-yl], [3931; 5-Me-N-Me-oxazolidin-4-on-5-yl], [3932; 2-Me-5-Me-N-Me-oxazolidin-4-on-5-yl], [3933; 2,5,5,N-tetraMe-oxazolidin-4-on-5-yl], [3934; N-Me-oxazolidin-5-on-2-yl], [3935; 2-Me-N-Me-oxazolidin-5-on-2-yl], [3936; 4-Me-N-Me-oxazolidin-5-on-2-yl], [3937; 2-Me-4-Me-N-Me-oxazolidin-5-on-2-yl], [3938; 2,4,4,N-tetraMe-oxazolidin-5-on-2-yl], [3939; N-Me-oxazolidin-5-on-4-yl], [3940; 2-Me-N-Me-oxazolidin-5-on-4-yl], [3941; 4-Me-N-Me-oxazolidin-5-on-4-yl], [3942; 2-Me-4-Me-N-Me-oxazolidin-5-on-4-yl], [3943; 2,4,4,N-tetraMe-oxazolidin-5-on-4-yl], [3944; 2-thiazolin-4-yl], [3945; 2-Me-2-thiazolin-4-yl], [3946; 4-Me-2-thiazolin-4-yl], [3947; 5-Me-2-thiazolin-4-yl], [3948; 2-Me-4-Me-2-thiazolin-4-yl], [3949; 2-Me-5-Me-2-thiazolin-4-yl], [3950; 4-Me-5-Me-2-thiazolin-4-yl], [3951; 5-Me-5-Me-2-thiazolin-4-yl], [3952; 2-Me-4-Me-5-Me-2-thiazolin-5-yl], [3953; 2-thiazolin-5-yl], [3954; 2-Me-2-thiazolin-5-yl], [3955; 5-Me-2-thiazolin-5-yl], [3956; 4-Me-2-thiazolin-5-yl], [3957; 2-Me-5-Me-2-thiazolin-5-yl], [3958; 2-Me-4-Me-2-thiazolin-5-yl], [3959; 5-Me-4-Me-2-thiazolin-5-yl], [3960; 4,4-diMe-2-thiazolin-5-yl], [3961; 2-Me-5-Me-4-Me-2-thiazolin-5-yl], [3962; 3-thiazolin-2-yl], [3963; 2-Me-3-thiazolin-2-yl], [3964; 4-Me-3-thiazolin-2-yl], [3965; 5-Me-3-thiazolin-2-yl], [3966; 2-Me-4-Me-3-thiazolin-2-yl], [3967; 2-Me-5-Me-3-thiazolin-2-yl], [3968; 4-Me-5-Me-3-thiazolin-2-yl], [3969; 5,5-diMe-3-thiazolin-2-yl], [3970; 2-Me-4-Me-5-Me-3-thiazolin-2-yl], [3971; 3-thiazolin-4-yl], [3972; 2-Me-3-thiazolin-4-yl], [3973; 5-Me-3-thiazolin-4-yl], [3974; 2,2-diMe-3-thiazolin-4-yl], [3975; 5,5-diMe-3-thiazolin-4-yl], [3976; 2-Me-5-Me-3-thiazolin-4-yl], [3977; 3-thiazolin-5-yl], [3978; 2-Me-3-thiazolin-5-yl], [3979; 4-Me-3-thiazolin-5-yl], [3980; 5-Me-3-thiazolin-5-yl], [3981; 2,2-diMe-3-thiazolin-5-yl], [3982; 2-Me-4-Me-3-thiazolin-5-yl], [3983; 2-Me-5-Me-3-thiazolin-5-yl], [3984; 4-Me-5-Me-3-thiazolin-5-yl], [3985; 2-Me-4-Me-5-Me3-thiazolin-5-yl], [3986; N-Me-4-thiazolin-2-yl], [3987; 2-Me-N-Me-4-thiazolin-2-yl], [3988; 4-Me-N-Me-4-thiazolin-2-yl], [3989; 5-Me-N-Me-4-thiazolin-2-yl], [3990; 2-Me-5-Me-N-Me-4-thiazolin-2-yl], [3991; 4-Me-5-Me-N-Me-4-thiazolin-2-yl], [3992; 1-Imid], [3993; 2-F-1-Imid], [3994; 2-Cl-1-Imid], [3995; 2-Br-1-Imid], [3996; 2-I-1-Imid], [3997; 2-Me-1-Imid], [3998; 2-Et-1-Imid], [3999; 2-Pr-1-Imid], [4000; 2-iPr-1-Imid],

[4001; 2-CF3-1-Imid], [4002; 2-NO2-1-Imid], [4003; 2-CHF2-1-Imid], [4004; 2-OMe-1-Imid], [4005; 2-OEt-1-Imid], [4006; 2-OCF3-1-Imid], [4007; 2-OCHF2-1-Imid], [4008; 2-CN-1-Imid], [4009; 2-SMe-1-Imid], [4010; 2-SEt-1-Imid], [4011; 2-cPr-1-Imid], [4012; 5-F-1-Imid], [4013; 5-Cl-1-Imid], [4014; 5-Br-1-Imid], [4015; 5-I-1-Imid], [4016; 5-Me-1-Imid], [4017; 5-Et-1-Imid], [4018; 5-Pr-1-Imid], [4019; 5-iPr-1-Imid], [4020; 5-CF3-1-Imid], [4021; 5-NO2-1-Imid], [4022; 5-CHF2-1-Imid], [4023; 5-OMe-1-Imid], [4024; 5-OEt-1-Imid], [4025; 5-OCF3-1-Imid], [4026; 5-OCHF2-1-Imid], [4027; 5-CN-1-Imid], [4028; 5-SMe-1-Imid], [4029; 5-SEt-1-Imid], [4030; 5-cPr-1-Imid], [4031; 2-F-5-F-1-Imid], [4032; 2-F-5-Cl-1-Imid], [4033; 2-F-5-Br-1-Imid], [4034; 2-F-5-I-1-Imid], [4035; 2-F-5-Me-1-Imid], [4036; 2-F-5-Et-1-Imid], [4037; 2-F-5-Pr-1-Imid], [4038; 2-F-5-iPr-1-Imid], [4039; 2-F-5-CF3-1-Imid], [4040; 2-F-5-NO2-1-Imid], [4041; 2-F-5-CHF2-1-Imid], [4042; 2-F-5-OMe-1-Imid], [4043; 2-F-5-OEt-1-Imid], [4044; 2-F-5-OCF3-1-Imid], [4045; 2-F-5-OCHF2-1-Imid], [4046; 2-F-5-CN-1-Imid], [4047; 2-F-5-SMe-1-Imid], [4048; 2-F-5-SEt-1-Imid], [4049; 2-F-5-cPr-1-Imid], [4050; 2-Cl-5-F-1-Imid], [4051; 2-Cl-5-Cl-1-Imid], [4052; 2-Cl-5-Br-1-Imid], [4053; 2-Cl-5-I-1-Imid], [4054; 2-Cl-5-Me-1-Imid], [4055; 2-Cl-5-Et-1-Imid], [4056; 2-Cl-5-Pr-1-Imid], [4057; 2-Cl-5-iPr-1-Imid], [4058; 2-Cl-5-CF3-1-Imid], [4059; 2-Cl-5-NO2-1-Imid], [4060; 2-Cl-5-CHF2-1-Imid], [4061; 2-Cl-5-OMe-1-Imid], [4062; 2-Cl-5-OEt-1-Imid], [4063; 2-Cl-5-OCF3-1-Imid], [4064; 2-Cl-5-OCHF2-1-Imid], [4065; 2-Cl-5-CN-1-Imid], [4066; 2-Cl-5-SMe-1-Imid], [4067; 2-Cl-5-SEt-1-Imid], [4068; 2-Cl-5-cPr-1-Imid], [4069; 2-Me-5-F-1-Imid], [4070; 2-Me-5-Cl-1-Imid], [4071; 2-Me-5-Br-1-Imid], [4072; 2-Me-5-I-1-Imid], [4073; 2-Me-5-Me-1-Imid], [4074; 2-Me-5-Et-1-Imid], [4075; 2-Me-5-Pr-1-Imid], [4076; 2-Me-5-iPr-1-Imid], [4078; 2-Me-5-CF3-1-Imid], [4079; 2-Me-5-NO2-1-Imid], [4080; 2-Me-5-CHF2-1-Imid], [4081; 2-Me-5-OMe-1-Imid], [4082; 2-Me-5-OEt-1-Imid], [4083; 2-Me-5-OCF3-1-Imid], [4084; 2-Me-5-OCHF2-1-Imid], [4085; 2-Me-5-CN-1-Imid], [4086; 2-Me-5-SMe-1-Imid], [4087; 2-Me-5-SEt-1-Imid], [4088; 2-Me-5-cPr-1-Imid], [4089; 2-Et-5-F-1-Imid], [4090; 2-Et-5-Cl-1-Imid], [4091; 2-Et-5-Br-1-Imid], [4092; 2-Et-5-I-1-Imid], [4093; 2-Et-5-Me-1-Imid], [4094; 2-Et-5-Et-1-Imid], [4095; 2-Et-5-Pr-1-Imid], [4096; 2-Et-5-iPr-1-Imid], [4097; 2-Et-5-CF3-1-Imid], [4098; 2-Et-5-NO2-1-Imid], [4099; 2-Et-5-CHF2-1-Imid], [4100; 2-Et-5-OMe-1-Imid],

[4101; 2-Et-5-OEt-1-Imid], [4102; 2-Et-5-OCF3-1-Imid], [4103; 2-Et-5-OCHF2-1-Imid], [4104; 2-Et-5-CN-1-Imid],

[4105; 2-Et-5-SMe-1-Imid], [4106; 2-Et-5-SEt-1-Imid], [4107; 2-Et-5-cPr-1-Imid], [4108; 2-CF3-5-F-1-Imid], [4109; 2-CF3-5-Cl-1-Imid], [4110; 2-CF3-5-Br-1-Imid], [4111; 2-CF3-5-I-1-Imid], [4112; 2-CF3-5-Me-1-Imid], [4113; 2-CF3-5-Et-1-Imid], [4114; 2-CF3-5-Pr-1-Imid], [4115; 2-CF3-5-iPr-1-Imid], [4116; 2-CF3-5-CF3-1-Imid], [4117; 2-CF3-5-CHF2-1-Imid], [4118; 2-CF3-5-OMe-1-Imid], [4119; 2-CF3-5-OEt-1-Imid], [4120; 2-CF3-5-OCF3-1-Imid], [4121; 2-CF3-5-OCHF2-1-Imid], [4122; 2-CF3-5-CN-1-Imid], [4123; 2-CF3-5-SMe-1-Imid], [4124; 2-CF3-5-SEt-1-Imid], [4125; 2-CF3-5-cPr-1-Imid], [4126; 2-NO2-5-F-1-Imid], [4127; 2-NO2-5-Cl-1-Imid], [4128; 2-NO2-5-Br-1-Imid], [4129; 2-NO2-5-I-1-Imid], [4130; 2-NO2-5-Me-1-Imid], [4131; 2-NO2-5-Et-1-Imid], [4132; 2-NO2-5-Pr-1-Imid], [4133; 2-NO2-5-iPr-1-Imid], [4134; 2-NO2-5-NO2-1-Imid], [4135; 2-NO2-5-CHF2-1-Imid], [4136; 2-NO2-5-OMe-1-Imid], [4137; 2-NO2-5-OEt-1-Imid], [4138; 2-NO2-5-OCF3-1-Imid], [4139; 2-NO2-5-OCHF2-1-Imid], [4140; 2-NO2-5-CN-1-Imid], [4141; 2-NO2-5-SMe-1-Imid], [4142; 2-NO2-5-SEt-1-Imid], [4143; 2-NO2-5-cPr-1-Imid], [4144; 2-OMe-5-F-1-Imid], [4145; 2-OMe-5-Cl-1-Imid], [4146; 2-OMe-5-Br-1-Imid], [4147; 2-OMe-5-I-1-Imid], [4148; 2-OMe-5-Me-1-Imid], [4149; 2-OMe-5-Et-1-Imid], [4150; 2-OMe-5-Pr-1-Imid], [4151; 2-OMe-5-iPr-1-Imid], [4152; 2-OMe-5-CF3-1-Imid], [4153; 2-OMe-5-NO2-1-Imid], [4154; 2-OMe-5-CHF2-1-Imid], [4155; 2-OMe-5-OMe-1-Imid], [4156; 2-OMe-5-OEt-1-Imid], [4157; 2-OMe-5-OCF3-1-Imid], [4158; 2-OMe-5-OCHF2-1-Imid], [4159; 2-OMe-5-CN-1-Imid], [4160; 2-OMe-5-SMe-1-Imid], [4161; 2-OMe-5-SEt-1-Imid], [4162; 2-OMe-5-cPr-1-Imid], [4163; 2-OEt-5-F-1-Imid], [4164; 2-OEt-5-Cl-1-Imid], [4165; 2-OEt-5-Br-1-Imid], [4166; 2-OEt-5-I-1-Imid], [4167; 2-OEt-5-Me-1-Imid], [4168; 2-OEt-5-Et-1-Imid], [4169; 2-OEt-5-Pr-1-Imid], [4170; 2-OEt-5-iPr-1-Imid], [4171; 2-OEt-5-CF3-1-Imid], [4172; 2-OEt-5-NO2-1-Imid], [4173; 2-OEt-5-CHF2-1-Imid], [4174; 2-OEt-5-OMe-1-Imid], [4175; 2-OEt-5-OEt-1-Imid], [4176; 2-OEt-5-OCF3-1-Imid], [4177; 2-OEt-5-OCHF2-1-Imid], [4178; 2-OEt-5-CN-1-Imid], [4179; 2-OEt-5-SMe-1-Imid], [4180; 2-OEt-5-SEt-1-Imid], [4181; 2-OEt-5-cPr-1-Imid], [4182; 2-SMe-5-F-1-Imid], [4183; 2-SMe-5-Cl-1-Imid], [4184; 2-SMe-5-Br-1-Imid], [4185; 2-SMe-5-I-1-Imid], [4186; 2-SMe-5-Me-1-Imid], [4187; 2-SMe-5-Et-1-Imid], [4188; 2-SMe-5-Pr-1-Imid], [4189; 2-SMe-5-iPr-1-Imid], [4190; 2-SMe-5-CF3-1-Imid], [4191; 2-SMe-5-NO2-1-Imid], [4192; 2-SMe-5-CHF2-1-Imid], [4193; 2-SMe-5-OMe-1-Imid], [4194; 2-SMe-5-OEt-1-Imid], [4195; 2-SMe-5-OCF3-1-Imid], [4196; 2-SMe-5-OCHF2-1-Imid], [4197; 2-SMe-5-CN-1-Imid], [4198; 2-SMe-5-SMe-1-Imid], [4199; 2-SMe-5-SEt-1-Imid], [4200; 2-SMe-5-cPr-1-Imid],

[4201; 4-F-1-Imid], [4202; 4-Cl-1-Imid], [4203; 4-Br-1-Imid], [4204; 4-I-1-Imid], [4205; 4-Me-1-Imid], [4206; 4-Et-1-Imid], [4207; 4-Pr-1-Imid], [4208; 4-iPr-1-Imid], [4209; 4-CF3-1-Imid], [4210; 4-NO2-1-Imid], [4211; 4-CHF2-1-Imid], [4212; 4-OMe-1-Imid], [4213; 4-OEt-1-Imid], [4214; 4-OCF3-1-Imid], [4215; 4-OCHF2-1-Imid], [4216; 2-F-4-F-1-Imid], [4217; 2-Cl-4-F-1-Imid], [4218; 2-Br-4-F-1-Imid], [4219; 2-I-4-F-1-Imid], [4220; 2-Me-4-F-1-Imid], [4221; 2-Et-4-F-1-Imid], [4222; 2-Pr-4-F-1-Imid], [4223; 2-iPr-4-F-1-Imid], [4224; 2-CF3-4-F-1-Imid], [4225; 2-NO2-4-F-1-Imid], [4226; 2-CHF2-4-F-1-Imid], [4227; 2-OMe-4-F-1-Imid], [4228; 2-OEt-4-F-1-Imid], [4229; 2-OCF3-4-F-1-Imid], [4230; 2-OCHF2-4-F-1-Imid], [4231; 2-CN-4-F-1-Imid], [4232; 2-SMe-4-F-1-Imid], [4233; 2-SEt-4-F-1-Imid], [4234; 2-cPr-4-F-1-Imid], [4235; 2-F-4-Cl-1-Imid], [4236; 2-Cl-4-Cl-1-Imid], [4237; 2-Br-4-Cl-1-Imid], [4238; 2-I-4-Cl-1-Imid], [4239; 2-Me-4-Cl-1-Imid], [4240; 2-Et-4-Cl-1-Imid], [4241; 2-Pr-4-Cl-1-Imid], [4242; 2-iPr-4-Cl-1-Imid], [4243; 2-CF3-4-Cl-1-Imid], [4244; 2-NO2-4-Cl-1-Imid], [4245; 2-CHF2-4-Cl-1-Imid], [4246; 2-OMe-4-Cl-1-Imid], [4247; 2-OEt-4-Cl-1-Imid], [4248; 2-OCF3-4-Cl-1-Imid], [4249; 2-OCHF2-4-Cl-1-Imid], [4250; 2-CN-4-Cl-1-Imid], [4251; 2-SMe-4-Cl-1-Imid], [4252; 2-SEt-4-Cl-1-Imid], [4253; 2-cPr-4-Cl-1-Imid], [4254; 2-F-4-Me-1-Imid], [4255; 2-Cl-4-Me-1-Imid], [4256; 2-Br-4-Me-1-Imid], [4257; 2-I-4-Me-1-Imid], [4258; 2-Me-4-Me-1-Imid], [4259; 2-Et-4-Me-1-Imid], [4260; 2-Pr-4-Me-1-Imid], [4261; 2-iPr-4-Me-1-Imid], [4262; 2-CF3-4-Me-1-Imid], [4263; 2-NO2-4-Me-1-Imid], [4264; 2-CHF2-4-Me-1-Imid], [4265; 2-OMe-4-Me-1-Imid], [4266; 2-OEt-4-Me-1-Imid], [4267; 2-OCF3-4-Me-1-Imid], [4268; 2-OCHF2-4-Me-1-Imid], [4269; 2-CN-4-Me-1-Imid], [4270; 2-SMe-4-Me-1-Imid], [4271; 2-SEt-4-Me-1-Imid], [4272; 2-cPr-4-Me-1-Imid], [4273; 2-F-4-Et-1-Imid], [4274; 2-Cl-4-Et-1-Imid], [4275; 2-Br-4-Et-1-Imid], [4276; 2-I-4-Et-1-Imid], [4277; 2-Me-4-Et-1-Imid], [4278; 2-Et-4-Et-1-Imid], [4279; 2-Pr-4-Et-1-Imid], [4280; 2-iPr-4-Et-1-Imid], [4281; 2-CF3-4-Et-1-Imid], [4282; 2-NO2-4-Et-1-Imid], [4283; 2-CHF2-4-Et-1-Imid], [4284; 2-OMe-4-Et-1-Imid], [4285; 2-OEt-4-Et-1-Imid], [4286; 2-OCF3-4-Et-1-Imid], [4287; 2-OCHF2-4-Et-1-Imid], [4288; 2-CN-4-Et-1-Imid], [4289; 2-SMe-4-Et-1-Imid], [4290; 2-SEt-4-Et-1-Imid], [4291; 2-cPr-4-Et-1-Imid], [4292; 2-F-4-CF3-1-Imid], [4293; 2-Cl-4-CF3-1-Imid], [4294; 2-Br-4-CF3-1-Imid], [4295; 2-I-4-CF3-1-Imid], [4296; 2-Me-4-CF3-1-Imid], [4297; 2-Et-4-CF3-1-Imid], [4298; 2-Pr-4-CF3-1-Imid], [4299; 2-iPr-4-CF3-1-Imid], [4300; 2-CF3-4-CF3-1-Imid],

[4301; 2-CHF2-4-CF3-1-Imid], [4302; 2-OMe-4-CF3-1-Imid], [4303; 2-OEt-4-CF3-1-Imid], [4304; 2-OCF3-4-CF3-1-Imid], [4305; 2-OCHF2-4-CF3-1-Imid], [4306; 2-CN-4-CF3-1-Imid], [4307; 2-SMe-4-CF3-1-Imid], [4308; 2-SEt-4-CF3-1-Imid], [4309; 2-cPr-4-CF3-1-Imid], [4310; 2-F-4-NO2-1-Imid], [4311; 2-Cl-4-N02-1-Imid], [4312; 2-Br-4-NO2-1-Imid], [4313; 2-I-4-NO2-1-Imid], [4314; 2-Me-4-NO2-1-Imid], [4315; 2-Et-4-NO2-1-Imid], [4316; 2-Pr-4-NO2-1-Imid], [4317; 2-iPr-4-NO2-1-Imid], [4318; 2-NO2-4-NO2-1-Imid], [4319; 2-CHF2-4-NO2-1-Imid], [4320; 2-OMe-4-NO2-1-Imid], [4321; 2-OEt-4-NO2-1-Imid], [4322; 2-OCF3-4-NO2-1-Imid], [4323; 2-OCHF2-4-NO2-1-Imid], [4324; 2-CN-4-N02-1-Imid], [4325; 2-SMe-4-NO2-1-Imid], [4326; 2-SEt-4-NO2-1-Imid], [4327; 2-cPr-4-NO2-1-Imid], [4328; 2-F-4-OMe-1-Imid], [4329; 2-Cl-4-OMe-1-Imid], [4330; 2-Br-4-OMe-1-Imid], [4331; 2-I-4-OMe-1-Imid], [4332; 2-Me-4-OMe-1-Imid], [433; 2-Et-4-OMe-1-Imid], [4334; 2-Pr-4-OMe-1-Imid], [4335; 2-iPr-4-OMe-1-Imid], [4336; 2-CF3-4-OMe-1-Imid], [4337; 2-NO2-4-OMe-1-Imid], [4338; 2-CHF2-4-OMe-1-Imid], [4339; 2-OMe-4-OMe-1-Imid], [4340; 2-OEt-4-OMe-1-Imid], [4341; 2-OCF3-4-OMe-1-Imid], [4342; 2-OCHF2-4-OMe-1-Imid], [4343; 2-CN-4-OMe-1-Imid], [4344; 2-SMe-4-OMe-1-Imid], [4345; 2-SEt-4-OMe-1-Imid], [4346; 2-cPr-4-OMe-1-Imid], [4347; 2-F-4-OEt-1-Imid], [4348; 2-Cl-4-OEt-1-Imid], [4349; 2-Br-4-OEt-1-Imid], [4350; 2-I-4-OEt-1-Imid], [4351; 2-Me-4-OEt-1-Imid], [4352; 2-Et-4-OEt-1-Imid], [4353; 2-Pr-4-OEt-1-Imid], [4354; 2-iPr-4-OEt-1-Imid], [4355; 2-CF3-4-OEt-1-Imid], [4356; 2-NO2-4-OEt-1-Imid], [4357; 2-CHF2-4-OEt-1-Imid], [4358; 2-OMe-4-OEt-1-Imid], [4359; 2-OEt-4-OEt-1-Imid], [4360; 2-OCF3-4-OEt-1-Imid], [4361; 2-OCHF2-4-OEt-1-Imid], [4362; 2-CN-4-OEt-1-Imid], [4363; 2-SMe-4-OEt-1-Imid], [4364; 2-SEt-4-OEt-1-Imid], [4365; 2-cPr-4-OEt-1-Imid], [4366; 2-F-4-SMe-1-Imid], [4367; 2-Cl-4-SMe-1-Imid],

[4368; 2-Br-4-SMe-1-Imid], [4369; 2-I-4-SMe-1-Imid], [4370; 2-Me-4-SMe-1-Imid], [4371; 2-Et-4-SMe-1-Imid], [4372; 2-Pr-4-SMe-1-Imid], [4373; 2-iPr-4-SMe-1-Imid], [4374; 2-CF3-4-SMe-1-Imid], [4375; 2-NO2-4-SMe-1-Imid], [4376; 2-CHF2-4-SMe-1-Imid], [4377; 2-OMe-4-SMe-1-Imid], [4378; 2-OEt-4-SMe-1-Imid], [4378; 2-OCF3-4-SMe-1-Imid], [4379; 2-OCHF2-4-SMe-1-Imid], [4380; 2-CN-4-SMe-1-Imid], [4381; 2-SMe-4-SMe-1-Imid], [4382; 2-SEt-4-SMe-1-Imid], [4383; 2-cPr-4-SMe-1-Imid], [4384; 4-F-5-F-1-Imid], [4385; 4-F-5-Cl-1-Imid], [4386; 4-F-5-Br-1-Imid], [4387; 4-F-5-I-1-Imid], [4388; 4-F-5-Me-1-Imid], [4389; 4-F-5-Et-1-Imid], [4390; 4-F-5-Pr-1-Imid], [4391; 4-F-5-iPr-1-Imid], [4392; 4-F-5-CF3-1-Imid], [4393; 4-F-5-NO2-1-Imid], [4394; 4-F-5-CHF2-1-Imid], [4395; 4-F-5-OMe-1-Imid], [4396; 4-F-5-OEt-1-Imid], [4397; 4-F-5-OCF3-1-Imid], [4398; 4-F-5-OCHF2-1-Imid], [4399; 4-F-5-CN-1-Imid], [4400; 4-F-5-SMe-1-Imid],

[4401; 4-F-5-SEt-1-Imid], [4402; 4-F-5-cPr-1-Imid], [4403; 4-Cl-5-F-1-Imid], [4404; 4-Cl-5-Cl-1-Imid], [4405; 4-Cl-5-Br-1-Imid], [4406; 4-Cl-5-I-1-Imid], [4407; 4-Cl-5-Me-1-Imid], [4408; 4-Cl-5-Et-1-Imid], [4409; 4-Cl-5-Pr-1-Imid], [4410; 4-Cl-5-iPr-1-Imid], [4411; 4-Cl-5-CF3-1-Imid], [4412; 4-Cl-5-N02-1-Imid], [4413; 4-Cl-5-CHF2-1-Imid], [4414; 4-Cl-5-OMe-1-Imid], [4415; 4-Cl-5-OEt-1-Imid], [4416; 4-Cl-5-OCF3-1-Imid], [4417; 4-Cl-5-OCHF2-1-Imid], [4418; 4-Cl-5-CN-1-Imid], [4419; 4-Cl-5-SMe-1-Imid], [4420; 4-Cl-5-SEt-1-Imid], [4421; 4-Cl-5-cPr-1-Imid], [4422; 4-Me-5-F-1-Imid], [4423; 4-Me-5-Cl-1-Imid], [4424; 4-Me-5-Br-1-Imid], [4425; 4-Me-5-I-1-Imid], [4426; 4-Me-5-Me-1-Imid], [4427; 4-Me-5-Et-1-Imid], [4428; 4-Me-5-Pr-1-Imid], [4429; 4-Me-5-iPr-1-Imid], [4430; 4-Me-5-CF3-1-Imid], [4431; 4-Me-5-NO2-1-Imid], [4432; 4-Me-5-CHF2-1-Imid], [4433; 4-Me-5-OMe-1-Imid], [4434; 4-Me-5-OEt-1-Imid], [4435; 4-Me-5-OCF3-1-Imid], [4436; 4-Me-5-OCHF2-1-Imid], [4437; 4-Me-5-CN-1-Imid], [4438; 4-Me-5-SMe-1-Imid], [4439; 4-Me-5-SEt-1-Imid], [4440; 4-Me-5-cPr-1-Imid], [4441; 4-Et-5-F-1-Imid], [4442; 4-Et-5-Cl-1-Imid], [4443; 4-Et-5-Br-1-Imid], [4444; 4-Et-5-I-1-Imid], [4445; 4-Et-5-Me-1-Imid], [4446; 4-Et-5-Et-1-Imid], [4447; 4-Et-5-Pr-1-Imid], [4448; 4-Et-5-iPr-1-Imid], [4449; 4-Et-5-CF3-1-Imid], [4450; 4-Et-5-NO2-1-Imid], [4451; 4-Et-5-CHF2-1-Imid], [4452; 4-Et-5-OMe-1-Imid], [4453; 4-Et-5-OEt-1-Imid], [4454; 4-Et-5-OCF3-1-Imid], [4455; 4-Et-5-OCHF2-1-Imid], [4456; 4-Et-5-CN-1-Imid], [4457; 4-Et-5-SMe-1-Imid], [4458; 4-Et-5-SEt-1-Imid], [4459; 4-Et-5-cPr-1-Imid], [4460; 4-CF3-5-F-1-Imid], [4461; 4-CF3-5-Cl-1-Imid], [4462; 4-CF3-5-Br-1-Imid], [4463; 4-CF3-5-I-1-Imid], [4464; 4-CF3-5-Me-1-Imid], [4465; 4-CF3-5-Et-1-Imid], [4466; 4-CF3-5-Pr-1-Imid], [4467; 4-CF3-5-iPr-1-Imid], [4468; 4-CF3-5-CF3-1-Imid], [4469; 4-CF3-5-CHF2-1-Imid], [4470; 4-CF3-5-OMe-1-Imid], [4471; 4-CF3-5-OEt-1-Imid], [4472; 4-CF3-5-OCF3-1-Imid], [4471; 4-CF3-5-OCHF2-1-Imid], [4472; 4-CF3-5-CN-1-Imid], [4473; 4-CF3-5-SMe-1-Imid], [4474; 4-CF3-5-SEt-1-Imid], [4475; 4-CF3-5-cPr-1-Imid], [4476; 4-NO2-5-F-1-Imid], [4477; 4-NO2-5-Cl-1-Imid], [4478; 4-NO2-5-Br-1-Imid], [4479; 4-NO2-5-I-1-Imid], [4480; 4-N02-5-Me-1-Imid], [4481; 4-NO2-5-Et-1-Imid], [4482; 4-NO2-5-Pr-1-Imid], [4483; 4-NO2-5-iPr-1-Imid], [4484; 4-NO2-5-NO2-1-Imid], [4485; 4-NO2-5-CHF2-1-Imid], [4486; 4-NO2-5-OMe-1-Imid], [4487; 4-NO2-5-OEt-1-Imid], [4488; 4-NO2-5-OCF3-1-Imid], [4489; 4-NO2-5-OCHF2-1-Imid], [4490; 4-NO2-5-CN-1-Imid], [4491; 4-NO2-5-SMe-1-Imid], [4492; 4-NO2-5-SEt-1-Imid], [4493; 4-NO2-5-cPr-1-Imid], [4494; 4-OMe-5-F-1-Imid], [4495; 4-OMe-5-Cl-1-Imid], [4496; 4-OMe-5-Br-1-Imid],

[4497; 4-OMe-5-I-1-Imid], [4498; 4-OMe-5-Me-1-Imid], [4499; 4-OMe-5-Et-1-Imid], [4500; 4-OMe-5-Pr-1-Imid], [4501; 4-OMe-5-iPr-1-Imid], [4502; 4-OMe-5-CF3-1-Imid], [4503; 4-OMe-5-NO2-1-Imid], [4504; 4-OMe-5-CHF2-1-Imid], [4505; 4-OMe-5-OMe-1-Imid], [4506; 4-OMe-5-OEt-1-Imid], [4507; 4-OMe-5-OCF3-1-Imid], [4508; 4-OMe-5-OCHF2-1-Imid], [4509; 4-OMe-5-CN-1-Imid], [4510; 4-OMe-5-SMe-1-Imid], [4511; 4-OMe-5-SEt-1-Imid], [4512; 4-OMe-5-cPr-1-Imid], [4513; 4-OEt-5-F-1-Imid], [4514; 4-OEt-5-Cl-1-Imid], [4515; 4-OEt-5-Br-1-Imid], [4516; 4-OEt-5-I-1-Imid], [4517; 4-OEt-5-Me-1-Imid], [4518; 4-OEt-5-Et-1-Imid], [4519; 4-OEt-5-Pr-1-Imid], [4520; 4-OEt-5-iPr-1-Imid], [4521; 4-OEt-5-CF3-1-Imid], [4522; 4-OEt-5-NO2-1-Imid], [4523; 4-OEt-5-CHF2-1-Imid], [4524; 4-OEt-5-OMe-1-Imid], [4525; 4-OEt-5-OEt-1-Imid], [4526; 4-OEt-5-OCF3-1-Imid], [4527; 4-OEt-5-OCHF2-1-Imid], [4528; 4-OEt-5-CN-1-Imid], [4529; 4-OEt-5-SMe-1-Imid], [4530; 4-OEt-5-SEt-1-Imid], [4531; 4-OEt-5-cPr-1-Imid], [4532; 4-SMe-5-F-1-Imid], [4533; 4-SMe-5-Cl-1-Imid], [4534; 4-SMe-5-Br-1-Imid], [4535; 4-SMe-5-I-1-Imid], [4536; 4-SMe-5-Me-1-Imid], [4537; 4-SMe-5-Et-1-Imid], [4538; 4-SMe-5-Pr-1-Imid], [4539; 4-SMe-5-iPr-1-Imid], [4540; 4-SMe-5-CF3-1-Imid], [4541; 4-SMe-5-NO2-1-Imid], [4542; 4-SMe-5-CHF2-1-Imid], [4543; 4-SMe-5-OMe-1-Imid], [4544; 4-SMe-5-OEt-1-Imid], [4545; 4-SMe-5-OCF3-1-Imid], [4546; 4-SMe-5-OCHF2-1-Imid], [4547; 4-SMe-5-CN-1-Imid], [4548; 4-SMe-5-SMe-1-Imid], [4549; 4-SMe-5-SEt-1-Imid], [4550; 4-SMe-5-cPr-1-Imid], [4551; 2-Me-4-Me-5-F-1-Imid], [4551; 2-Me-4-Me-5-Cl-1-Imid], [4552; 2-Me-4-Me-5-Br-1-Imid], [4553; 2-Me-4-Me-5-I-1-Imid], [4554; 2-Me-4-Me-5-Me-1-Imid], [4555; 2-Me-4-Me-5-Et-1-Imid], [4556; 2-Me-4-Me-5-Pr-1-Imid], [4557; 2-Me-4-Me-5-iPr-1-Imid], [4558; 2-Me-4-Me-5-CF3-1-Imid], [4559; 2-Me-4-Me-5-N02-1-Imid], [4560; 2-Me-4-Me-5-CHF2-1-Imid], [4561; 2-Me-4-Me-5-OMe-1-Imid], [4562; 2-Me-4-Me-5-OEt-1-Imid], [4563; 2-Me-4-Me-5-OCF3-1-Imid], [4564; 2-Me-4-Me-5-OCHF2-1-Imid], [4565; 2-Me-4-Me-5-CN-1-Imid], [4566; 2-Me-4-Me-5-SMe-1-Imid], [4567; 2-Me-4-Me-5-SEt-1-Imid], [4568; 2-Me-4-Me-5-cPr-1-Imid], [4569; 2-F-4-Me-5-Me-1-Imid], [4570; 2-Cl-4-Me-5-Me-1-Imid], [4571; 2-Br-4-Me-5-Me-1-Imid], [4572; 2-I-4-Me-5-Me-1-Imid], [4573; 2-Et-4-Me-5-Me-1-Imid], [4574; 2-Pr-4-Me-5-Me-1-Imid], [4575; 2-iPr-4-Me-5-Me-1-Imid], [4576; 2-CF3-4-Me-5-Me-1-Imid], [4577; 2-NO2-4-Me-5-Me-1-Imid], [4578; 2-CHF2-4-Me-5-Me-1-Imid], [4579; 2-OMe-4-Me-5-Me-1-Imid], [4580; 2-OEt-4-Me-5-Me-1-Imid], [4581; 2-OCF3-4-Me-5-Me-1-Imid], [4582; 2-OCHF2-4-Me-5-Me-1-Imid], [4583; 2-CN-4-Me-5-Me-1-Imid], [4584; 2-SMe-4-Me-5-Me-1-Imid], [4585; 2-SEt-4-Me-5-Me-1-Imid], [4586; 2-cPr-4-Me-5-Me-1-Imid], [4587; 2-Imid], [4588; 4-F-2-Imid], [4589; 4-Cl-2-Imid], [4590; 4-Br-2-Imid], [4591; 4-Me-2-Imid], [4592; 4-Et-2-Imid], [4593; 4-OMe-2-Imid], [4594; 4-SMe-2-Imid], [4595; 4-CF3-2-Imid], [4596; 4-NO2-2-Imid], [4597; 4-F-5-F-2-Imid], [4598; 4-F-5-Cl-2-Imid], [4599; 4-F-5-Br-2-Imid], [4600; 4-F-5-Me-2-Imid],

[4601; 4-F-5-Et-2-Imid], [4602; 4-F-5-OMe-2-Imid], [4603; 4-F-5-SMe-2-Imid], [4604; 4-F-5-CF3-2-Imid], [4605; 4-F-5-NO2-2-Imid], [4606; 4-Me-5-F-2-Imid], [4607; 4-Me-5-Cl-2-Imid], [4608; 4-Me-5-Br-2-Imid], [4609; 4-Me-5-Me-2-Imid], [4610; 4-Me-5-Et-2-Imid], [4611; 4-Me-5-OMe-2-Imid], [4612; 4-Me-5-SMe-2-Imid], [4613; 4-Me-5-CF3-2-Imid], [4614; 4-Me-5-NO2-2-Imid], [4615; 4-OMe-5-F-2-Imid], [4616; 4-OMe-5-Cl-2-Imid], [4617; 4-OMe-5-Br-2-Imid], [4618; 4-OMe-5-Me-2-Imid], [4619; 4-OMe-5-Et-2-Imid], [4620; 4-OMe-5-OMe-2-

Imid], [4621; 4-OMe-5-SMe-2-Imid], [4622; 4-OMe-5-CF3-2-Imid], [4623; 4-OMe-5-NO2-2-Imid], [4624; 1-Me-2-Imid], [4625; 1-Me-4-F-2-Imid], [4626; 1-Me-4-Cl-2-Imid], [4627; 1-Me-4-Br-2-Imid], [4628; 1-Me-4-Me-2-Imid], [4629; 1-Me-4-Et-2-Imid], [4630; 1-Me-4-OMe-2-Imid], [4631; 1-Me-4-SMe-2-Imid], [4632; 1-Me-4-CF3-2-Imid], [4633; 1-Me-4-NO2-2-Imid], [4634; 1-Me-4-F-5-F-2-Imid], [4635; 1-Me-4-F-5-Cl-2-Imid], [4636; 1-Me-4-F-5-Br-2-Imid], [4637; 1-Me-4-F-5-Me-2-Imid], [4638; 1-Me-4-F-5-Et-2-Imid], [4639; 1-Me-4-F-5-OMe-2-Imid], [4640; 1-Me-4-F-5-SMe-2-Imid], [4641; 1-Me-4-F-5-CF3-2-Imid], [4642; 1-Me-4-F-5-NO2-2-Imid], [4643; 1-Me-4-Me-5-F-2-Imid], [4644; 1-Me-4-Me-5-Cl-2-Imid], [4645; 1-Me-4-Me-5-Br-2-Imid], [4646; 1-Me-4-Me-5-Me-2-Imid], [4647; 1-Me-4-Me-5-Et-2-Imid], [4648; 1-Me-4-Me-5-OMe-2-Imid], [4649; 1-Me-4-Me-5-SMe-2-Imid], [4650; 1-Me-4-Me-5-CF3-2-Imid], [4651; 1-Me-4-Me-5-NO2-2-Imid], [4652; 1-Me-4-OMe-5-F-2-Imid], [4653; 1-Me-4-OMe-5-Cl-2-Imid], [4654; 1-Me-4-OMe-5-Br-2-Imid], [4655; 1-Me-4-OMe-5-Me-2-Imid], [4656; 1-Me-4-OMe-5-Et-2-Imid], [4657; 1-Me-4-OMe-5-OMe-2-Imid], [4658; 1-Me-4-OMe-5-SMe-2-Imid], [4659; 1-Me-4-OMe-5-CF3-2-Imid], [4660; 1-Me-4-OMe-5-NO2-2-Imid], [4661; 4-Imid], [4662; 2-F-4-Imid], [4663; 2-Cl-4-Imid], [4664; 2-Br-4-Imid], [4665; 2-Me-4-Imid], [4666; 2-Et-4-Imid], [4667; 2-OMe-4-Imid], [4668; 2-SMe-4-Imid], [4669; 2-CF3-4-Imid], [4670; 2-NO2-4-Imid], [4671; 2-F-5-F-4-Imid], [4672; 2-F-5-Cl-4-Imid], [4673; 2-F-5-Br-4-Imid], [4674; 2-F-5-Me-4-Imid], [4675; 2-F-5-Et-4-Imid], [4676; 2-F-5-OMe-4-Imid], [4677; 2-F-5-SMe-4-Imid], [4678; 2-F-5-CF3-4-Imid], [4679; 2-F-5-NO2-4-Imid], [4680; 2-Me-5-F-4-Imid], [4681; 2-Me-5-Cl-4-Imid], [4682; 2-Me-5-Br-4-Imid], [4683; 2-Me-5-Me-4-Imid], [4684; 2-Me-5-Et-4-Imid], [4685; 2-Me-5-OMe-4-Imid], [4686; 2-Me-5-SMe-4-Imid], [4687; 2-Me-5-CF3-4-Imid], [4688; 2-Me-5-NO2-4-Imid], [4689; 2-OMe-5-F-4-Imid], [4690; 2-OMe-5-Cl-4-Imid], [4691; 2-OMe-5-Br-4-Imid], [4692; 2-OMe-5-Me-4-Imid], [4693; 2-OMe-5-Et-4-Imid], [4694; 2-OMe-5-OMe-4-Imid], [4695; 2-OMe-5-SMe-4-Imid], [4696; 2-OMe-5-CF3-4-Imid], [4697; 2-OMe-5-NO2-4-Imid], [4698; 1-Me-4-Imid], [4699; 1-Me-2-F-4-Imid], [4700; 1-Me-2-Cl-4-Imid],

[4701; 1-Me-2-Br-4-Imid], [4702; 1-Me-2-Me-4-Imid], [4703; 1-Me-2-Et-4-Imid], [4704; 1-Me-2-OMe-4-Imid], [4705; 1-Me-2-SMe-4-Imid], [4706; 1-Me-2-CF3-4-Imid], [4707; 1-Me-2-NO2-4-Imid], [4708; 1-Me-2-F-5-F-4-Imid], [4709; 1-Me-2-F-5-Cl-4-Imid], [4710; 1-Me-2-F-5-Br-4-Imid], [4701; 1-Me-2-F-5-Me-4-Imid], [4702; 1-Me-2-F-5-Et-4-Imid], [4703; 1-Me-2-F-5-OMe-4-Imid], [4704; 1-Me-2-F-5-SMe-4-Imid], [4705; 1-Me-2-F-5-CF3-4-Imid], [4706; 1-Me-2-F-5-NO2-4-Imid], [4707; 1-Me-2-Me-5-F-4-Imid], [4708; 1-Me-2-Me-5-Cl-4-Imid], [4709; 1-Me-2-Me-5-Br-4-Imid], [4710; 1-Me-2-Me-5-Me-4-Imid], [4711; 1-Me-2-Me-5-Et-4-Imid], [4712; 1-Me-2-Me-5-OMe-4-Imid], [4713; 1-Me-2-Me-5-SMe-4-Imid], [4714; 1-Me-2-Me-5-CF3-4-Imid], [4715; 1-Me-2-Me-5-NO2-4-Imid], [4716; 1-Me-2-OMe-5-F-4-Imid], [4717; 1-Me-2-OMe-5-Cl-4-Imid], [4718; 1-Me-2-OMe-5-Br-4-Imid], [4719; 1-Me-2-OMe-5-Me-4-Imid], [4720; 1-Me-2-OMe-5-Et-4-Imid], [4721; 1-Me-2-OMe-5-OMe-4-Imid], [4722; 1-Me-2-OMe-5-SMe-4-Imid], [4723; 1-Me-2-OMe-5-CF3-4-Imid], [4724; 1-Me-2-OMe-5-NO2-4-Imid], [4725; 2-thiazolin-2-yl], [4726; 4-Me-2-thiazolin-2-yl], [4727; 5-Me-2-thiazolin-2-yl], [4728; 4,4-diMe-2-thiazolin-2-yl], [4729; 5,5-diMe-2-thiazolin-2-yl], [4730; 4-Me-5-Me-2-thiazolin-2-yl], [4731; 4,4,5-triMe-2-thiazolin-2-yl], [4732; 4,5,5-triMe-2-thiazolin-2-yl], [4733; 4,4,5,5-tetraMe-2-thi-azolin-2-yl], [4734; 2-oxazolin-2-yl], [4735; 4-Me-2-oxazolin-2-yl], [4736; 5-Me-2-oxazolin-2-yl], [4737; 4,4-diMe-2-oxazolin-2-yl], [4738; 5,5-diMe-2-oxazolin-2-yl], [4739; 4-Me-5-Me-2-oxazolin-2-yl], [4740; 4,4,5-triMe-2-oxazolin-2-yl], [4741; 4,5,5-triMe-2-oxazolin-2-yl], [4742; 4,4,5,5-tetraMe-2-oxazolin-2-yl], [4743; succinimide-1-yl], [4744; 3-Me-succinimide-1-yl], [4745; 4-Me-succinimide-1-yl], [4746; 3-Me-3-Me-succinimide-1-yl], [4747; 4,4-diMe-succinimide-1-yl], [4748; 3-Me-4-Me-succinimide-1-yl], [4749; 3,3,4-triMe-succinimide-1-yl], [4751; 3-Me-3-Me-4-Me-4-Me-succinimide-1-yl], [4752; maleimide-1-yl], [4753; 3-Me-maleimide-1-yl], [4754; 3-Me-4-Me-maleimide-1-yl], [4755; 1-Tria], [4756; 3-F-1-Tria], [4757; 3-Cl-1-Tria], [4758; 3-Br-1-Tria], [4759; 3-I-1-Tria], [4760; 3-Me-1-Tria], [4761; 3-Et-1-Tria], [4762; 3-Pr-1-Tria], [4763; 3-iPr-1-Tria], [4764; 3-CF3-1-Tria], [4765; 3-CHF2-1-Tria], [4766; 3-OMe-1-Tria], [4767; 3-OEt-1-Tria], [4768; 3-OCF3-1-Tria], [4769; 3-OCHF2-1-Tria], [4770; 3-CN-1-Tria], [4771; 3-SMe-1-Tria], [4772; 3-SEt-1-Tria], [4773; 3-cPr-1-Tria], [4774; 5-F-1-Tria], [4775; 5-Cl-1-Tria], [4776; 5-Br-1-Tria], [4777; 5-I-1-Tria], [4778; 5-Me-1-Tria], [4779; 5-Et-1-Tria], [4780; 5-Pr-1-Tria], [4781; 5-iPr-1-Tria], [4782; 5-CF3-1-Tria], [4783; 5-CHF2-1-Tria], [4784; 5-OMe-1-Tria], [4785; 5-OEt-1-Tria], [4786; 5-OCF3-1-Tria], [4787; 5-OCHF2-1-Tria], [4788; 5-CN-1-Tria], [4789; 5-SMe-1-Tria], [4790; 5-SEt-1-Tria], [4791; 5-cPr-1-Tria], [4792; 3-F-5-F-1-Tria], [4793; 3-F-5-Cl-1-Tria], [4794; 3-F-5-Br-1-Tria], [4795; 3-F-5-I-1-Tria], [4796; 3-F-5-Me-1-Tria], [4797; 3-F-5-Et-1-Tria], [4798; 3-F-5-Pr-1-Tria], [4799; 3-F-5-iPr-1-Tria], [4800; 3-F-5-CF3-1-Tria],

[4801; 3-F-5-CHF2-1-Tria], [4802; 3-F-5-OMe-1-Tria], [4803; 3-F-5-OEt-1-Tria], [4804; 3-F-5-OCF3-1-Tria], [4805; 3-F-5-OCHF2-1-Tria], [4806; 3-F-5-CN-1-Tria], [4807; 3-F-5-SMe-1-Tria], [4808; 3-F-5-SEt-1-Tria], [4809; 3-F-5-cPr-1-Tria], [4810; 3-Cl-5-F-1-Tria], [4811; 3-Cl-5-Cl-1-Tria], [4812; 3-Cl-5-Br-1-Tria], [4813; 3-Cl-5-I-1-Tria], [4814; 3-Cl-5-Me-1-Tria], [4815; 3-Cl-5-Et-1-Tria], [4816; 3-Cl-5-Pr-1-Tria], [4817; 3-Cl-5-iPr-1-Tria], [4818; 3-Cl-5-CF3-1-Tria], [4819; 3-Cl-5-CHF2-1-Tria], [4820; 3-Cl-5-OMe-1-Tria], [4821; 3-Cl-5-OEt-1-Tria], [4822; 3-Cl-5-OCF3-1-Tria], [4823; 3-Cl-5-OCHF2-1-Tria], [4824; 3-Cl-5-CN-1-Tria], [4825; 3-Cl-5-SMe-1-Tria], [4826; 3-Cl-5-SEt-1-Tria], [4827; 3-Cl-5-cPr-1-Tria], [4828; 3-Me-5-F-1-Tria], [4829; 3-Me-5-Cl-1-Tria], [4830; 3-Me-5-Br-1-Tria], [4831; 3-Me-5-I-1-Tria], [4832; 3-Me-5-Me-1-Tria], [4833; 3-Me-5-Et-1-Tria], [4834; 3-Me-5-Pr-1-Tria], [4835; 3-Me-5-iPr-1-Tria], [4836; 3-Me-5-CF3-1-Tria], [4837; 3-Me-5-CHF2-1-Tria], [4838; 3-Me-5-OMe-1-Tria], [4839; 3-Me-5-OEt-1-Tria], [4840; 3-Me-5-OCF3-1-Tria], [4841; 3-Me-5-OCHF2-1-Tria], [4842; 3-Me-5-CN-1-Tria], [4843; 3-Me-5-SMe-1-Tria], [4844; 3-Me-5-SEt-1-Tria], [4845; 3-Me-5-cPr-1-Tria], [4846; 3-Et-5-F-1-Tria], [4847; 3-Et-5-Cl-1-Tria], [4848; 3-Et-5-Br-1-Tria], [4849; 3-Et-5-I-1-Tria], [4850; 3-Et-5-Me-1-Tria], [4851; 3-Et-5-Et-1-Tria], [4852; 3-Et-5-Pr-1-Tria], [4853; 3-Et-5-iPr-1-Tria], [4854; 3-Et-5-CF3-1-Tria], [4855; 3-Et-5-CHF2-1-Tria], [4856; 3-Et-5-OMe-1-Tria], [4857; 3-Et-5-OEt-1-Tria], [4858; 3-Et-5-OCF3-1-Tria], [4859; 3-Et-5-OCHF2-1-Tria], [4860; 3-Et-5-CN-1-Tria], [4861; 3-Et-5-SMe-1-Tria], [4862; 3-Et-5-SEt-1-Tria], [4863; 3-Et-5-cPr-1-Tria], [4864; 3-CF3-5-F-1-Tria], [4865; 3-CF3-5-Cl-1-Tria], [4866; 3-CF3-5-Br-1-Tria], [4867; 3-CF3-5-I-1-Tria], [4868; 3-CF3-5-Me-1-Tria], [4869; 3-CF3-5-Et-1-Tria], [4870; 3-CF3-5-Pr-1-Tria], [4871; 3-CF3-5-iPr-1-Tria], [4872; 3-CF3-5-CF3-1-Tria], [4873; 3-CF3-5-CHF2-1-Tria], [4874; 3-CF3-5-OMe-1-Tria], [4875; 3-CF3-5-OEt- 1-Tria], [4876; 3-CF3-5-OCF3-1-Tria], [4877; 3-CF3-5-OCHF2-1-Tria], [4878; 3-CF3-5-CN-1-Tria], [4879; 3-CF3-5-SMe-1-Tria], [4880; 3-CF3-5-SEt-1-Tria], [4881; 3-CF3-5-cPr-1-Tria], [4882; 3-OMe-5-F-1-Tria], [4883; 3-OMe-5-Cl-1-Tria], [4884; 3-OMe-5-Br-1-Tria], [4885; 3-OMe-5-I-1-Tria], [4886; 3-OMe-5-Me-1-Tria], [4887; 3-OMe-5-Et-1-Tria], [4888; 3-OMe-5-Pr-1-Tria], [4889; 3-OMe-5-iPr-1-Tria], [4890; 3-OMe-5-CF3-1-Tria], [4891; 3-OMe-5-CHF2-1-Tria], [4892; 3-OMe-5-OMe-1-Tria], [4893; 3-OMe-5-OEt-1-Tria], [4894; 3-OMe-5-OCF3-1-Tria], [4895; 3-OMe-5-OCHF2-1-Tria], [4896; 3-OMe-5-CN-1-Tria], [4897; 3-OMe-5-SMe-1-Tria], [4898; 3-OMe-5-SEt-1-Tria], [4899; 3-OMe-5-cPr-1-Tria], [4900; 3-OEt-5-F-1-Tria],

[4901; 3-OEt-5-Cl-1-Tria], [4902; 3-OEt-5-Br-1-Tria], [4903; 3-OEt-5-I-1-Tria], [4904; 3-OEt-5-Me-1-Tria], [4905; 3-OEt-5-Et-1-Tria], [4906; 3-OEt-5-Pr-1-Tria], [4907; 3-OEt-5-iPr-1-Tria], [4908; 3-OEt-5-CF3-1-Tria], [4909; 3-OEt-5-CHF2-1-Tria], [4910; 3-OEt-5-OMe-1-Tria], [4911; 3-OEt-5-OEt-1-Tria], [4912; 3-OEt-5-OCF3-1-Tria], [4913; 3-OEt-5-OCHF2-1-Tria], [4914; 3-OEt-5-CN-1-Tria], [4915; 3-OEt-5-SMe-1-Tria], [4916; 3-OEt-5-SEt-1-Tria], [4917; 3-OEt-5-cPr-1-Tria], [4918; 3-SMe-5-F-1-Tria], [4919; 3-SMe-5-Cl-1-Tria], [4920; 3-SMe-5-Br-1-Tria], [4921; 3-SMe-5-I-1-Tria], [4922; 3-SMe-5-Me-1-Tria], [4923; 3-SMe-5-Et-1-Tria], [4924; 3-SMe-5-Pr-1-Tria], [4925; 3-SMe-5-iPr-1-Tria], [4926; 3-SMe-5-CF3-1-Tria], [4927; 3-SMe-5-CHF2-1-Tria], [4928; 3-SMe-5-OMe-1-Tria], [4929; 3-SMe-5-OEt-1-Tria], [4930; 3-SMe-5-OCF3-1-Tria], [4931; 3-SMe-5-OCHF2-1-Tria], [4932; 3-SMe-5-CN-1-Tria], [4933; 3-SMe-5-SMe-1-Tria], [4934; 3-SMe-5-SEt-1-Tria], [4935; 3-SMe-5-cPr-1-Trial], [4936; 3-Tria], [4937; 1-Me-3-Tria], [4938; 5-F-3-Tria], [4939; 5-Cl-3-Tria], [4940; 5-Br-3-Tria], [4941; 5-I-3-Tria], [4942; 5-Me-3-Tria], [4943; 5-Et-3-Tria], [4944; 5-Pr-3-Tria], [4945; 5-iPr-3-Tria], [4946; 5-CF3-3-Tria], [4947; 5-CHF2-3-Tria], [4948; 5-OMe-3-Tria], [4949; 5-OEt-3-Tria], [4950; 5-OCF3-3-Tria], [4951; 5-OCHF2-3-Tria], [4952; 5-CN-3-Tria], [4953; 5-SMe-3-Tria], [4954; 5-SEt-3-Tria], [4955; 5-cPr-3-Tria], [4956; 1-Me-5-F-3-Tria], [4957; 1-Me-5-Cl-3-Tria], [4958; 1-Me-5-Br-3-Tria], [4959; 1-Me-5-I-3-Tria], [4960; 1-Me-5-Me-3-Tria], [4961; 1-Me-5-Et-3-Tria], [4962; 1-Me-5-Pr-3-Tria], [4963; 1-Me-5-iPr-3-Tria], [4964; 1-Me-5-CF3-3-Tria], [4965; 1-Me-5-CHF2-3-Tria], [4966; 1-Me-5-OMe-3-Tria], [4967; 1-Me-5-OEt-3-Tria], [4968; 1-Me-5-OCF3-3-Tria], [4969; 1-Me-5-OCHF2-3-Tria], [4970; 1-Me-5-CN-3-Tria], [4971; 1-Me-5-SMe-3-Tria], [4972; 1-Me-5-SEt-3-Tria], [4973; 1-Me-5-cPr-3-Tria], [4974; 1-Me-5-NO2-3-Tria], [4975; 5-NO2-3-Tria], [4976; 3-NO2-1-Tria], [4977; 3-NO2-5-F-1-Tria], [4978; 3-N02-5-Cl-1-Tria], [4979; 3-NO2-5-Br-1-Tria], [4980; 3-NO2-5-I-1-Tria], [4981; 3-NO2-5-Me-1-Tria], [4982; 3-NO2-5-Et-1-Tria], [4983; 3-NO2-5-Pr-1-Tria], [4984; 3-NO2-5-iPr-1-Tria], [4985; 3-NO2-5-CF3-1-Tria], [4986; 3-NO2-5-CHF2-1-Tria], [4987; 3-N02-5-OMe-1-Tria], [4988; 3-NO2-5-OEt-1-Tria], [4989; 3-NO2-5-OCF3-1-Tria], [4990; 3-NO2-5-OCHF2-1-Tria], [4991; 3-NO2-5-CN-1-Tria], [4992; 3-NO2-5-SMe-1-Tria], [4993; 3-NO2-5-SEt-1-Tria], [4994; 3-NO2-5-cPr-1-Tria], [4995; 5-NO2-1-Tria], [4996; 3-NO2-5-NO2-2-Tria], [4997; Diox], [4998; 5-Me-Diox], [4998; 5,5-diMe-Diox], [4999; Oxa], [5000; 4-Me-Oxa],

[5001; 5-Me-Oxa], [5002; 4,4-diMe-Oxa], [5003; 5,5-diMe-Oxa], [5004; 4-Me-5-Me-Oxa], [5005; 4,4,5-triMe-Oxa], [5006; 4,5,5-triMe-Oxa], [5006; 4,4,5,5-tetraMe-Oxa], [5007; Dihy], [5008; 3-Me-Dihy], [5009; 4-Me-Dihy], [5010; 5-Me-Dihy], [5011; 4,4-diMe-Dihy], [5012; 5,5-diMe-Dihy], [5013; 4-Me-5-Me-Dihy], [5014; 3-Me-4-Me-5-Me-Dihy], [5015; 4,4,5-triMe-Dihy], [5016; 3,5,5-triMe-Dihy], [5017; 4,5,5-triMe-Dihy], [5018; 4,4,5,5-tetraMe-Dihy], [5019; 3,4,4,5-tetraMe-Dihy], [5020; 3,4,5,5-tetraMe-Dihy], [5021; 3,4,4,5,5-pentaMe-Dihy], [5022; Imida], [5000; 4-Me-Imida], [5023; 5-Me-Imida], [5024; 4,4-diMe-Imida], [5025; 5,5-diMe-Imida], [5026; 4-Me-5-Me-Imida], [5027; 4,4,5-triMe-Imida], [5028; 4,5,5-triMe-Imida], [5029; 4,4,5,5-tetraMe-Imida]

Formulation Examples will be shown below. Parts are by weight.

FORMULATION EXAMPLE 1

Fifty parts (50 parts) of any one of the present compounds 1 to 58, 3 parts of calcium lignosulfonate, 2 parts of magnesium lauryl sulfate, and 45 parts of synthetic hydrated silicon oxide are thoroughly ground and mixed to obtain each formulation.

FORMULATION EXAMPLE 2

Twenty parts (20 parts) of any one of the present compounds 1 to 58 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

FORMULATION EXAMPLE 3

Two parts (2 parts) of any one of the present compounds 1 to 58, 88 parts of kaolin clay, and 10 parts of talc are thoroughly ground and mixed to obtain each formulation.

FORMULATION EXAMPLE 4

Five parts (5 parts) of any one of the present compounds 1 to 58, 14 parts of polyoxyethylene styryl phenyl ether, 6 parts of calcium dodecylbenzenesulfonate, and 75 parts of xylene are thoroughly ground and mixed to obtain each formulation.

FORMULATION EXAMPLE 5

Two parts (2 parts) of any one of the present compounds 1 to 58, 1 part of synthetic hydrated silicon oxide, 2 parts of calcium lignosulfonate, 30 parts of bentonite, and 65 parts of kaolin clay are thoroughly ground and mixed. After the addition of water, the mixture is thoroughly kneaded and further granulated and dried to obtain each formulation.

FORMULATION EXAMPLE 6

Ten parts (10 parts) of any one of the present compounds 1 to 58, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion spots on each of test plants at the time of investigation, and comparing the area of lesion spots on a plant treated with the present compound with that on an untreated plant.

TEST EXAMPLE 1

Each of plastic pots was filled with sandy loam and barley (cultivar: MIKAMO GOLDEN) was sowed and grown in a greenhouse for 7 days. Then, each water dilution prepared by adjusting so as to contain a predetermined concentration (500 ppm) of any one compound of the present compounds 1, 2, 3, 4, 5, 6, 7, 8, 9, 11, 13, 14, 15, 17, 18, 23, 24, 25, 26, 27, 28, 29, 32, 33, 34, 35, 38, 39, 40, 41, 42, 43, 44, 45, 47, 48, 55, 57, 60, 61, 62, and 63 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with of the present compound 1, 2, 3, 4, 5, 6, 7, 8, 9, 11, 13, 14, 15, 17, 18, 23, 24, 25, 26, 27, 28, 29, 32, 33, 34, 35, 38, 39, 40, 41, 42, 43, 44, 45, 47, 48, 55, 57, 60, 61, 62, or 63 was 30% or less of that on an untreated plant.

TEST EXAMPLE 2

Each of plastic pots was filled with sandy loam and wheat (cultivar: SHIROGANE) was sowed and grown in a greenhouse for 9 days. Then, each water dilution prepared by adjusting so as to contain a predetermined concentration (500 ppm) of the present compounds 3, 32, 38, and 47 was sprayed over stems and leaves of the wheat so that it sufficiently adhered to the surface of the leaves of the wheat. After spraying, the plant was air-dried so as to dry the dilution on the surface of the leaves. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with the present compound 3, 32, 38, or 47 was 30% or less of that on an untreated plant.

TEST EXAMPLE 3

Each of plastic pots was filled with sandy loam and rice (cultivar: NIHONBARE) was sowed and grown in a greenhouse for 20 days. Then, each water dilution prepared by adjusting so as to contain a predetermined concentration (500 ppm) of any one compound of the present compounds 1, 3, 25, 27, 28, 32, 33, 37, 38, 41, 42, 47, 57, and 61 was sprayed over stems and leaves so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compound 1, 3, 25, 27, 28, 32, 33, 37, 38, 41, 42, 47, 57, or 61 were 30% or less with respect to the lesion area on the non-treated plant.

TEST EXAMPLE 4

Each of plastic pots was filled with sandy loam and kidney bean (cultivar: NAGAUZURA SAITOU) was sowed and grown in a greenhouse for 8 days. Then, each water dilution prepared by adjusting so as to contain a predetermined concentration (500 ppm) of any one compound of the present compounds 1, 2, 3, 4, 5, 6, 9, 11, 13, 15, 17, 18, 23, 24, 27, 28, 29, 30, 31, 32, 33, 34, 35, 37, 38, 39, 41, 42, 43, 44, 47, 48, 55, 60, 61, and 63 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 1, 2, 3, 4, 5, 6, 9, 11, 13, 15, 17, 18, 23, 24, 27, 28, 29, 30, 31, 32, 33, 34, 35, 37, 38, 39, 41, 42, 43, 44, 47, 48, 55, 60, 61, or 63 was 30% or less of that on an untreated plant.

TEST EXAMPLE 5

Each of plastic pots was filled with sandy loam and wheat (cultivar: APOGEE) was sowed and grown in a greenhouse for 10 days. Then, each water dilution prepared by adjusting so as to contain a predetermined concentration (500 ppm) of any one compound of the present compounds 1, 2, 3, 6, 9, 11, 12, 13, 23, 24, 25, 27, 28, 29, 30, 31, 32, 33, 34, 35, 38, 41, 42, 47, 48, 55, 57, 61, and 63 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound 1, 2, 3, 6, 9, 11, 12, 13, 23, 24, 25, 27, 28, 29, 30, 31, 32, 33, 34, 35, 38, 41, 42, 47, 48, 55, 57, 61, or 63 was 30% or less of that on an untreated plant.

TEST EXAMPLE 6

Each of plastic pots was filled with sandy loam and cucumber (cultivar: SAGAMI HANJIRO) was sowed and grown in a greenhouse for 12 days. Then, each water dilution prepared by adjusting so as to contain a predetermined concentration (500 ppm) of any one compound of the present compounds 1, 3, 4, 5, 6, 7, 8, 9, 11, 12, 13, 14, 15, 17, 23, 24, 25, 26, 27, 29, 31, 32, 33, 34, 35, 37, 38, 39, 40, 41, 42, 43, 44, 45, 47, 48, 55, 60, and 63 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with the present compound 1, 3, 4, 5, 6, 7, 8, 9, 11, 12, 13, 14, 15, 17, 23, 24, 25, 26, 27, 29, 31, 32, 33, 34, 35, 37, 38, 39, 40, 41, 42, 43, 44, 45, 47, 48, 55, 60, or 63 was 30% or less of that on an untreated plant.

TEST EXAMPLE 7

Each of plastic pots was filled with sandy loam and soybean (cultivar: KUROSENGOKU) was sowed and grown in a greenhouse for 13 days. Then, each water dilution prepared by adjusting so as to contain a predetermined concentration (500 ppm) of any one compound of the present compounds 3, 6, 23, 28, 29, 33, 34, 35, 38, 41, 42, 44, and 59 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion spots was investigated. As a result, it has been found that the area of lesion spots on the plant treated with the present compound 3, 6, 23, 28, 29, 33, 34, 35, 38, 41, 42, 44, or 59 was 30% or less of that on an untreated plant.

TEST EXAMPLE 8

Each of plastic pots was filled with sandy loam and barley (cultivar: MIKAMO GOLDEN) was sowed and grown in a greenhouse for 7 days. Then, each water dilution prepared by adjusting so as to contain a predetermined concentration (500 ppm) of any one compound of the present compounds 1, 2, 3, 5, 6, 8, 9, 10, 11, 12, 13, 14, 15, 16, 17, 18, 19, 20, 22, 23, 24, 25, 26, 27, 28, 29, 30, 31, 32, 33, 34, 35, 37, 38, 39, 40, 42, 43, 44, 45, 47, 48, 49, 55, 57, 60, and 61 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, it has been found that the area of lesion spots on the plant treated with of the present compound 1, 2, 3, 5, 6, 8, 9, 10, 11, 12, 13, 14, 15, 16, 17, 18, 19, 20, 22, 23, 24, 25, 26, 27, 28, 29, 30, 31, 32, 33, 34, 35, 37, 38, 39, 40, 42, 43, 44, 45, 47, 48, 49, 55, 57, 60, or 61 was 30% or less of that on an untreated plant.

TEST EXAMPLE 9

Each of plastic pots was filled with sandy loam and cucumber (cultivar: SAGAMI HANJIRO) was sowed and grown in a greenhouse for 19 days. Then, each water dilution prepared by adjusting so as to contain a predetermined concentration (500 ppm) of any one compound of the present compounds 29, 41, 42, 47, 55, 59, 60, 61, and 63 was sprayed over stems and leaves of the cucumber so that it sufficiently adhered to the surface of the leaves of the cucumber. After spraying, the plant was air-dried. After one day, the plant was inoculated by sprinkling with spores of cucumber *corynespora* leaf spot fungus (*Corynespora cassicola*). After the inoculation, the plant was cultivated in a greenhouse at 24° C. in the daytime and 20° C. at night for 7 days, and then the area of lesion spots was investigated. As a result, the area of lesion spots on the plant treated with the present compound 29, 41, 42, 47, 55, 59, 60, 61, or 63 was 30% or less of that on an untreated plant.

TEST EXAMPLE 10

Each of plastic pots was filled with sandy loam and cucumber (cultivar: SAGAMI HANJIRO) was sowed and grown in a greenhouse for 19 days. Then, each water dilution prepared by adjusting so as to contain a predetermined concentration (500 ppm) of any one compound of the present compounds 1, 2, 3, 4, 5, 6, 7, 9, 10, 11, 12, 13, 15, 23, 24, 25, 26, 27, 28, 37, 38, 48, 49, 50, and 63 was sprayed over stems and leaves of the cucumber so that it sufficiently adhered to the surface of the leaves of the cucumber. After spraying, the plant was air-dried. After one day, the plant was inoculated by sprinkling with spores of cucumber anthracnose fungus (*Colletotrichum* lagenarium). After the inoculation, the plant was at first left to stand at 23° C. under high humidity condition for one day and cultivated in a greenhouse at 24° C. in the daytime and 20° C. at night for 6 days, and then the area of lesion spots was investigated. As a result, the area of lesion spots on the plant treated with the present compound 1, 2, 3, 4, 5, 6, 7, 9, 10, 11, 12, 13, 15, 23, 24, 25, 26, 27, 28, 37, 38, 48, 49, 50, or 63 was 30% or less of that on an untreated plant.

TEST EXAMPLE 11

In the present Test Example, a water dilution (test chemical solution) prepared by adjusting so as to contain a predetermined concentration (500 ppm) of any one compound of the present compounds 34 and 11 was used as a test chemical solution. Thirty (30) heads of cotton aphid (*Aphis gossypii*) (including adults and larvae) were released on the leaves of cucumber (cultivar: SAGAMI HANJIRO FUSHINARI) grown in a polyethylene cup until the first true leaf was developed. Next day, 20 mL of the above test chemical solution was sprayed. After 6 days, the number of the surviving insects was counted and the control value was calculated by the following equation.

Control value (%)={1−($Cb$×$Tai$)/($Cai$×$Tb$)}×100 wherein symbols in the equation represent the followings:
Cb: Number of insects before spraying chemical solution in untreated area;
Cai: Number of surviving insects in untreated area;
Tb: Number of insects before spraying chemical solution in treated area; and
Tai: Number of surviving insects in treated area.
As a result, the present compound 34 or 11 showed 90% or more of the control value.

Comparative Test Example

Each of plastic pots was filled with sandy loam and cucumber (cultivar: SAGAMI HANJIRO) was sowed and grown in a greenhouse for 12 days. Then, each water dilution prepared by adjusting so as to contain a predetermined concentration (500 ppm) of 1-{[2-[2-methyl-4-(thiophen-2-yl)phenoxy]methyl]phenyl}-4-methyl-1,4-dihydrotetrazol-5-one was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with 1-{[2-[2-methyl-4-(thiophen-2-yl)phenoxy]methyl]phenyl}-4-methyl-1,4-dihydrotetrazol-5-one was 70% or more of that on an untreated plant.

The present compound has control activity against pests and is useful as an active ingredient of a pest control agent.

The invention claimed is:

1. A tetrazolinone compound represented by formula (1):

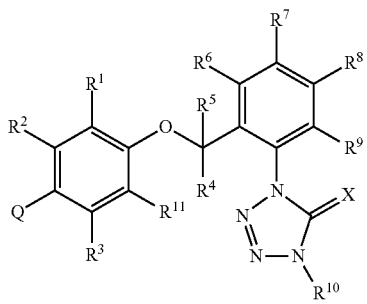

wherein $R^1$, $R^2$, $R^3$, and $R^{11}$ each independently represents a C1-C6 alkyl group optionally having one or more atoms or groups selected from Group $P^3$, a C3-C6 cycloalkyl group optionally having one or more atoms or groups selected from Group $P^3$, a halogen atom, a hydrogen atom, a C1-C6 alkoxy group optionally having one or more halogen atoms, a cyano group, a nitro group, an amino group, a hydroxy group, a sulfanyl group, a C2-C6 alkenyl group optionally having one or more halogen atoms, a C2-C6 alkynyl group optionally having one or more halogen atoms, a C1-C8 alkylamino group optionally having one or more halogen atoms, a C1-C6 alkylthio group optionally having one or more halogen atoms, a C1-C6 alkylsulfinyl group optionally having one or more halogen atoms, a C1-C6 alkylsulfonyl group optionally having one or more halogen atoms, a pentafluorosulfanyl group, a C3-C9 trialkylsilyl group, a C2-C6 alkylcarbonyl group, a C2-C6 alkoxycarbonyl group, or an aminocarbonyl group optionally having one or more C1-C6 alkyl groups;

$R^4$ and $R^5$ each independently represents a hydrogen atom, a halogen atom, or a C1-C3 alkyl group;

$R^6$ represents a C1-C6 alkyl group optionally having one or more halogen atoms, a C3-C6 cycloalkyl group optionally having one or more halogen atoms, a halogen atom, a C2-C6 alkenyl group optionally having one or more halogen atoms, a C1-C6 alkoxy group optionally having one or more halogen atoms, a C1-C6 alkylthio group optionally having one or more halogen atoms, a C2-C6 alkynyl group optionally having one or more halogen atoms, a nitro group, a cyano group, an aminocarbonyl group optionally having one or more C1-C6 alkyl groups, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group, a C2-C6 alkylcarbonylthio group, a C2-C6 alkoxycarbonyl group, a hydroxy group, a sulfanyl group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group optionally having one or more halogen atoms, a C1-C4 alkylsulfinyl group optionally having one or more halogen atoms, a C2-C5 alkoxyalkyl group, or a C2-C5 alkylthioalkyl group;

$R^7$, $R^8$, and $R^9$ each independently represents a hydrogen atom, a halogen atom, a C1-C3 alkyl group optionally having one or more halogen atoms, a C2-C3 alkenyl group optionally having one or more halogen atoms, or a C1-C3 alkoxy group optionally having one or more halogen atoms;

$R^{10}$ represents a C1-C3 alkyl group optionally having one or more halogen atoms, a C2-C3 alkenyl group optionally having one or more halogen atoms, a C2-C3 alkynyl group optionally having one or more halogen atoms, or a C3-C5 cycloalkyl group optionally having one or more halogen atoms;

Q represents any one group selected from Group $P^2$, wherein the group optionally has one or more atoms or groups selected from Group $P^1$; and X represents an oxygen atom or a sulfur atom;

Group $P^1$ is selected from the group consisting of a C1-C6 alkyl group optionally having one or more halogen atoms, a halogen atom, a C2-C6 alkenyl group optionally having one or more halogen atoms, a C2-C6 alkynyl group optionally having one or more halogen atoms, a C3-C6 cycloalkyl group optionally having one or more halogen atoms, a C1-C6 alkoxy group optionally having one or more halogen atoms, a C1-C6 alkylthio group optionally having one or more halogen atoms, a C3-C6 cycloalkyloxy group optionally having one or more halogen atoms, a C3-C6 cycloalkylthio group optionally having one or more halogen atoms, a C3-C6 alkenyloxy group optionally having one or more halogen atoms, a C3-C6 alkynyloxy group optionally having one or more halogen atoms, a C3-C6 alkenylthio group optionally having one or more halogen atoms, a C3-C6 alkynylthio group optionally having one or more halogen atoms, a C2-C6 alkylcarbonyl group optionally having one or more halogen atoms, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C6-C16 aryl group optionally having one or more halogen atoms, a C6-C16 aryloxy group optionally having one or more halogen atoms, a C6-C16 arylthio group optionally having one or more halogen atoms, a C7-C18 aralkyl group optionally having one or more halogen atoms, a C7-C18 arylalkoxy group optionally having one or more halogen atoms, a sulfanyl group, a pentafluorosulfanyl group, a C3-C12 trialkylsilyl group, a C5-C14 trialkylsilylethynyl group, a C1-C6 alkylsulfonyl group optionally having one or more halogen atoms, a C6-C16 arylsulfonyl group optionally having one or more halogen atoms, a C1-C6 alkylsulfinyl group optionally having one or more halogen atoms, a C6-C16 arylsulfinyl group optionally having one or more halogen atoms, an aminosulfonyl group optionally having a C1-C6 alkyl group and/or a C6-C12 aryl group, and an aminocarbonyl group optionally having one or more C1-C6 alkyl groups;

Group $P^2$ is selected from the group consisting of a thiazolyl group, a Thiazolinyl group, an oxazolyl group, an oxazolinyl group, a triazolyl group, a tetrazolyl group, a furyl group, a thienyl group, a thiadiazolyl group, an oxadiazolyl group, an isoxazolyl group, an isothiazolyl group, a tetrahydrofuryl group, a butenolidyl group, a γ-butyrolactonyl group, a tetrahydrothienyl group, a pyrrolyl group, a pyrrolinyl group, a pyrrolidinyl group, a pyrrolidonyl group, an oxazolidinyl group, an oxazolidonyl group, a thiazolidinyl group, a thiazolidonyl group, an isoxazolinyl group, an isoxazolidinyl group, an isoxazolidonyl group, an isothiazolinyl group, an isothiazolidinyl group, an isothiazolidonyl group, a dioxolanyl group, a floxanil group, a tetrazolinyl group, a tetrazolidinyl group, a tetrazolinonyl group, a triazolinyl group, a triazolidinyl group, a triazolinonyl group, a urazolyl group, an imidazolyl group, an imidazolinyl group, an imidazolidinyl group, an imidazolidonyl group, a hydantoinyl group, a thiohydantoinyl group, a dithiohydantoinyl group, a pyrazolinyl group, a pyrazolidinyl group, a pyrazolidonyl group, a pyrazolonyl group, a succinimidyl group, a maleimidyl group, and a dioxazolyl group; and Group $P^3$ is selected from the group consisting of a halogen atom, a cyano group, a C3-C6 cycloalkyl group optionally having one or more halogen atoms, a C1-C4 alkoxy group optionally having one or more halogen atoms, and a C1-C4 alkylthio group optionally having one or more halogen atoms.

2. The tetrazolinone compound according to claim 1, Wherein $R^1$ is a C1-C3 alkyl group optionally having one or more halogen atoms, a halogen atom, a C3-C5 cycloalkyl group optionally having one or more halogen atoms, a hydrogen atom, a C1-C3 alkoxy group optionally having one or more halogen atoms, a C2-C4 alkenyl group optionally having one or more halogen atoms, a C2-C4 alkynyl group optionally having one or more halogen atoms, or a C1-C3 alkylthio group optionally having one or more halogen atoms;

$R^2$, $R^4$, $R^5$, $R^7$, $R^8$, $R^9$, and $R^{11}$ are hydrogen atoms;

$R^3$ is a hydrogen atom, a halogen atom, or a C1-C3 alkyl group optionally having one or more halogen atoms;

$R^6$ is a C1-C3 alkyl group optionally having one or more halogen atoms, a halogen atom, a C3-C5 cycloalkyl group optionally having one or more halogen atoms, a C1-C3 alkoxy group optionally having one or more halogen atoms, a C2-C4 alkenyl group optionally having one or more halogen atoms, or a C2-C4 alkynyl group optionally having one or more halogen atoms; and $R^{10}$ is a C1-C3 alkyl group; and X is an oxygen atom.

3. The tetrazolinone compound according to claim 1, wherein $R^1$ is a C1-C3 alkyl group optionally having one or more halogen atoms, a halogen atom, a C2-C3 alkenyl group optionally having one or more halogen atoms, a C3-C5 cycloalkyl group optionally having one or more halogen atoms, or a C1-C3 alkoxy group optionally having one or more halogen atoms;

$R^3$ is a hydrogen atom or a methyl group;

Q is any one group selected from Group $P^8$, wherein the group optionally has one or more atoms or groups selected from Group $P^4$;

Group $P^4$ is selected from the group consisting of a C1-C3 alkyl group optionally having one or more halogen atoms, a halogen atom, a cyano group, a nitro group, a C3-C6 cycloalkyl group optionally having one or more halogen atoms, a C2-C3 alkenyl group optionally having one or more halogen atoms, a C1-C4 alkoxy group optionally having one or more halogen atoms, and a C1-C4 alkylthio group optionally having one or more halogen atoms; and Group $P^8$ is selected from the group consisting of a thiazolyl group, an oxazolyl group, a thiazolinyl group, an oxazolinyl group, a furyl group, a thienyl group, a 1,3,4-thiadiazolyl group, a 1,3,4-oxadiazolyl group, a 1,2,3-triazolyl group, a tetrazolyl group, a dioxolanyl group, a tetrahydrofuryl group, a pyrazolonyl group, a pyrrolyl group, an imidazolyl group, and a 1,2,4-triazolyl group.

4. The tetrazolinone compound according to claim 1, wherein $R^1$ is a C1-C3 alkyl group optionally having one or more halogen atoms;

$R^3$ is a hydrogen atom or a methyl group;

$R^6$ is a C1-C3 alkyl group optionally having one or more halogen atoms, a halogen atom, a C3-C5 cycloalkyl group optionally having one or more halogen atoms, or a C1-C3 alkoxy group optionally having one or more halogen atoms; and Q is any one group selected from Group $P^9$, wherein the group optionally has one or more atoms or groups selected from Group $P^{11}$;

Group $P^9$ is selected from the group consisting of a thiazolyl group, and oxazolyl group, a thiazolinyl group, an oxazolinyl group, a furyl group, a thienyl group, a 1,3,4-oxadiazolyl group, a 1,2,3-triazolyl group, a dioxolanyl group, a tetrahydrofuryl group, a pyrrolyl group, an imidazolyl group, a 1,2,4-triazolyl group, a 1,2,4-thiadiazolyl group, an isothiazolyl group, a pyrrolidinyl group, and a pyrrolidonyl group; and Group $P^{11}$ is selected from the group consisting of a C1-C3 alkyl group optionally having one or more halogen atoms, a halogen atom, a cyano group, a C1-C4 alkoxy group optionally having one or more halogen atoms, a C1-C4 alkylthio group optionally having one or more halogen atoms, a C2-C6 alkylcarbonyl group optionally having one or more halogen atoms, and a C2-C6 alkylcarbonyloxy group.

5. The tetrazolinone compound according to claim 4, wherein Q is any one group selected from Group $P^{10}$, wherein the group optionally has one or more atoms or groups selected from Group $P^{11}$;

Group $P^{10}$ is selected from the group consisting of a thiazolyl group, an oxazolyl group, a thiazolinyl group, an oxazolinyl group, a furyl group, and a thienyl group.

6. The tetrazolinone compound according to claim 5, wherein Q is any one group selected from Group $P^{10}$, wherein the group optionally has one or more atoms or groups selected from Group $P^{12}$;

Group $P^{12}$ is selected from the group consisting of a halogen atom, a cyano group, and a C1-C3 alkyl group optionally having one or more halogen atoms.

7. The tetrazolinone compound according to claim 4, wherein Q is a thiazolyl or thienyl group optionally having one or more atoms or groups selected from Group $P^{11}$.

8. The tetrazolinone compound according to claim 6, wherein Q is a thiazolyl or thienyl group optionally having one or more atoms or groups selected from Group $P^{12}$.

9. The tetrazolinone compound according to claim 4, wherein Q is a thiazolyl group optionally having one or more atoms or groups selected from Group $P^{11}$.

10. The tetrazolinone compound according to claim 6, wherein Q is a thienyl group optionally having one or more atoms or groups selected from Group $P^{12}$.

11. A pest control agent comprising the tetrazolinone compound according to claim 1.

12. A method for controlling pests, which comprises treating plants or soil with an effective amount of the tetrazolinone compound according to claim 1.

* * * * *